US008338452B2

(12) United States Patent
Ahrendt et al.

(10) Patent No.: US 8,338,452 B2
(45) Date of Patent: Dec. 25, 2012

(54) RAF INHIBITOR COMPOUNDS AND METHODS OF USE THEREOF

(75) Inventors: Kateri A. Ahrendt, Boulder, CO (US); Alexandre J. Buckmelter, Boulder, CO (US); Jonas Grina, Boulder, CO (US); Joshua D. Hansen, Boulder, CO (US); Ellen R. Laird, Boulder, CO (US); David Moreno, Boulder, CO (US); Brad Newhouse, Boulder, CO (US); Li Ren, Boulder, CO (US); Steven M. Wenglowsky, Boulder, CO (US); Bainian Feng, South San Francisco, CA (US); Janet Gunzner, South San Francisco, CA (US); Kim Malesky, South San Francisco, CA (US); Simon Mathieu, South San Francisco, CA (US); Joachim Rudolph, South San Francisco, CA (US); Zhaoyang Wen, South San Francisco, CA (US); Wendy B. Young, South San Francisco, CA (US)

(73) Assignees: Array BioPharma Inc., Boulder, CO (US); Genentech, Inc., South San Francisco, CA (US)

( * ) Notice: Subject to any disclaimer, the term of this patent is extended or adjusted under 35 U.S.C. 154(b) by 289 days.

(21) Appl. No.: 12/920,045

(22) PCT Filed: Feb. 27, 2009

(86) PCT No.: PCT/US2009/035380
§ 371 (c)(1),
(2), (4) Date: Aug. 27, 2010

(87) PCT Pub. No.: WO2009/111278
PCT Pub. Date: Sep. 11, 2009

(65) Prior Publication Data
US 2011/0110889 A1 May 12, 2011

Related U.S. Application Data

(60) Provisional application No. 61/032,839, filed on Feb. 29, 2008.

(51) Int. Cl.
A01N 43/42 (2006.01)
A61K 31/44 (2006.01)
C07D 471/02 (2006.01)
C07D 491/02 (2006.01)
(52) U.S. Cl. ........................ 514/300; 546/113
(58) Field of Classification Search .................. 546/113; 514/300
See application file for complete search history.

(56) References Cited

U.S. PATENT DOCUMENTS

| 4,328,155 | A | 5/1982 | Masaru et al. |
|---|---|---|---|
| 6,335,342 | B1 * | 1/2002 | Longo et al. ............. 514/254.09 |
| 7,235,576 | B1 | 6/2007 | Riedl et al. |
| 7,351,834 | B1 | 4/2008 | Riedl et al. |
| 2001/0011135 | A1 | 8/2001 | Riedl et al. |
| 2002/0137774 | A1 | 9/2002 | Riedl et al. |
| 2002/0165394 | A1 | 11/2002 | Dumas et al. |
| 2003/0105091 | A1 | 6/2003 | Riedl et al. |
| 2003/0139605 | A1 | 7/2003 | Riedl et al. |
| 2003/0181442 | A1 | 9/2003 | Riedl et al. |
| 2003/0207914 | A1 | 11/2003 | Dumas et al. |
| 2004/0087626 | A1 | 5/2004 | Renhowe et al. |
| 2005/0085482 | A1 | 4/2005 | Ramurthy et al. |
| 2005/0187230 | A1 | 8/2005 | Ding et al. |
| 2005/0192287 | A1 | 9/2005 | Costales et al. |
| 2006/0189627 | A1 | 8/2006 | Laird et al. |
| 2006/0281751 | A1 | 12/2006 | Laird et al. |
| 2006/0281762 | A1 | 12/2006 | Staehle et al. |
| 2006/0293340 | A1 | 12/2006 | Batt et al. |
| 2007/0010560 | A1 | 1/2007 | Buchstaller et al. |
| 2007/0021456 | A1 | 1/2007 | Mitjans et al. |
| 2007/0032519 | A1 | 2/2007 | Zhang et al. |
| 2007/0049603 | A1 | 3/2007 | Miknis et al. |

(Continued)

FOREIGN PATENT DOCUMENTS

DE 28 03 651 A1 8/1978

(Continued)

OTHER PUBLICATIONS

Li et al., "B-Raf Kinase Inhibitors for Cancer Treatment", *Current Opinion in Investigational Drugs*, vol. 8, No. 6, 452-456 (2007).

(Continued)

*Primary Examiner* — D M Seaman
*Assistant Examiner* — Niloofar Rahmani
(74) *Attorney, Agent, or Firm* — Viksnins Harris & Padys PLLP

(57) ABSTRACT

Compounds of Formula (I) are useful for inhibition of Raf kinases. Methods of using compounds of Formula (I) and stereoisomers, tautomers, prodrugs and pharmaceutically acceptable salts thereof, for in vitro, in situ, and in vivo diagnosis, prevention or treatment of such disorders in mammalian cells, or associated pathological conditions are disclosed.

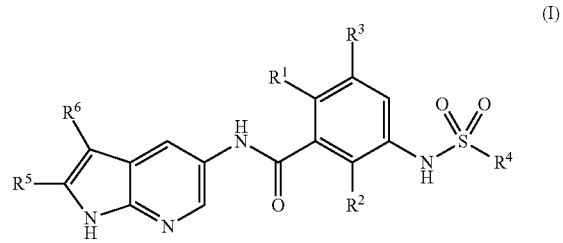

49 Claims, No Drawings

U.S. PATENT DOCUMENTS

| | | |
|---|---|---|
| 2007/0049615 A1 | 3/2007 | Ibrahim et al. |
| 2007/0054916 A1 | 3/2007 | Patel et al. |
| 2007/0060607 A1 | 3/2007 | Bartkovitz et al. |
| 2007/0078121 A1 | 4/2007 | Flynn et al. |
| 2007/0093532 A1 | 4/2007 | Buchstaller et al. |
| 2007/0142440 A1 | 6/2007 | Burgdorf et al. |
| 2007/0149533 A1 | 6/2007 | Calderwood et al. |
| 2007/0155746 A1 | 7/2007 | Lang et al. |
| 2007/0155764 A1 | 7/2007 | Lang et al. |
| 2007/0259849 A1 | 11/2007 | Aquila et al. |
| 2007/0287838 A1 | 12/2007 | Niculescu-Duvaz et al. |
| 2008/0114006 A1 | 5/2008 | Flynn et al. |
| 2008/0146570 A1 | 6/2008 | Aquila et al. |
| 2008/0167338 A1 | 7/2008 | Spevak et al. |
| 2008/0188514 A1 | 8/2008 | Wu et al. |
| 2008/0207616 A1 | 8/2008 | Aquila et al. |
| 2008/0221148 A1 | 9/2008 | Ibrahim et al. |
| 2008/0255184 A1 | 10/2008 | Tang |
| 2008/0300246 A1 | 12/2008 | Xie et al. |
| 2008/0306096 A1 | 12/2008 | Aquila et al. |
| 2009/0054469 A1 | 2/2009 | Aquila et al. |
| 2009/0099190 A1 | 4/2009 | Flynn et al. |
| 2009/0105250 A1 | 4/2009 | Sim et al. |
| 2009/0118261 A1 | 5/2009 | Aquila et al. |
| 2009/0118273 A1 | 5/2009 | Nagle et al. |
| 2009/0149484 A1 | 6/2009 | Aquila et al. |
| 2009/0163525 A1 | 6/2009 | Aquila et al. |
| 2009/0170849 A1 | 7/2009 | Aquila et al. |
| 2009/0286782 A1 | 11/2009 | Ibrahim et al. |
| 2009/0286783 A1 | 11/2009 | Ibrahim et al. |
| 2009/0298815 A1 | 12/2009 | Adams et al. |
| 2009/0306086 A1 | 12/2009 | Ibrahim et al. |
| 2009/0306087 A1 | 12/2009 | Ibrahim et al. |
| 2009/0306107 A1 | 12/2009 | Perez et al. |
| 2009/0318428 A1 | 12/2009 | Honold et al. |
| 2010/0029605 A1 | 2/2010 | Albaugh et al. |
| 2010/0184765 A1 | 7/2010 | Huang et al. |
| 2010/0190777 A1 | 7/2010 | Wu et al. |
| 2010/0249119 A1 | 9/2010 | Hirose et al. |
| 2011/0003809 A1 | 1/2011 | Ahrendt |
| 2011/0003859 A1 | 1/2011 | Ahrendt |
| 2011/0053932 A1 | 3/2011 | Sim et al. |
| 2011/0053946 A1 | 3/2011 | Niculescu-Duvaz et al. |
| 2011/0092479 A1 | 4/2011 | Ahrendt et al. |
| 2011/0118245 A1 | 5/2011 | Abraham et al. |
| 2011/0172245 A1 | 7/2011 | Hirose et al. |
| 2011/0201594 A1 | 8/2011 | Murthi et al. |
| 2012/0130069 A1 | 5/2012 | Sim et al. |

FOREIGN PATENT DOCUMENTS

| | | | |
|---|---|---|---|
| WO | WO 99/32106 A1 | 7/1999 | |
| WO | WO 99/32436 A1 | 7/1999 | |
| WO | WO 99/32455 A1 | 7/1999 | |
| WO | WO 01/98299 A1 | 12/2001 | |
| WO | WO 03/068773 A1 | 8/2003 | |
| WO | WO 2004/024897 A2 | 3/2004 | |
| WO | WO 2004/054974 A2 | 7/2004 | |
| WO | WO 2004/108133 A2 | 12/2004 | |
| WO | WO 2005/030709 A1 | 4/2005 | |
| WO | WO 2005/062795 A2 | 7/2005 | |
| WO | WO 2006/066913 A2 | 6/2006 | |
| WO | WO 2006/067446 A1 | 6/2006 | |
| WO | WO 2006/124731 A3 | 11/2006 | |
| WO | WO 2006/124780 A2 | 11/2006 | |
| WO | WO 2007/002325 A1 | 1/2007 | |
| WO | WO 2007/002433 A1 | 1/2007 | |
| WO | WO 2007/013896 A2 | 2/2007 | |
| WO | WO 2007/017143 A1 | 2/2007 | |
| WO | WO 2007/076460 A2 | 7/2007 | |
| WO | WO 2008/028617 A1 | 3/2008 | |
| WO | WO 2008/044688 A1 | 4/2008 | |
| WO | WO 2008/079906 A1 | 7/2008 | |
| WO | WO 2008/079909 A1 | 7/2008 | |
| WO | WO 2008/112695 A2 | 9/2008 | |
| WO | WO 2008/124393 A1 | 10/2008 | |
| WO | WO 2008/144253 A1 | 11/2008 | |
| WO | WO 2009/012283 A1 | 1/2009 | |

OTHER PUBLICATIONS

Patent Cooperation Treaty, International Search Report and Written Opinion for PCT/US2009/035380, 18 pages, dated May 20, 2010.

Perzanowski et al., "Carbon-13 and Nitrogen-15 NMR Spectral Study of Some Dimethanesulfonanilides", *Canadian Journal of Analytical Sciences and Spectroscopy*, vol. 42, No. 1 (1997).

Yagupol et al., "N,N-Bis(trifluoromethylsulfonyl)arylamines and .Sigma.-Constants of the bis(Trifluoromethylsulfonyl)amino Group", *Zhurnal Organicheskoi Khimii*, vol. 10, No. 4 (1974).

Smith et al., "Recent Advances in the Research and Development of RAF Kinase Inhibitors", Current Topics in Medicinal Chemistry. vol. 6, No. 11, 1071-1089 (2006).

\* cited by examiner

RAF INHIBITOR COMPOUNDS AND METHODS OF USE THEREOF

RELATED APPLICATIONS

This application claims priority to U.S. Provisional Application No. 61/032,839 that was filed on Feb. 29, 2008.

BACKGROUND OF THE INVENTION

1. Field of the Invention

The present invention relates to novel compounds, to pharmaceutical compositions comprising the compounds, to a process for making the compounds and to the use of the compounds in therapy. More particularly, it relates to certain substituted 1H-pyrrolo[2,3-b]pyridine compounds useful for inhibiting Raf kinase and for treating disorders mediated thereby.

2. Description of the State of the Art

The Raf/MEK/ERK pathway is critical for cell survival, growth, proliferation and tumorigenesis. Li, Nanxin, et al. "B-Raf kinase inhibitors for cancer treatment." *Current Opinion in Investigational Drugs*. Vol. 8, No. 6 (2007): 452-456. Raf kinases exist as three isoforms, A-Raf, B-Raf and C-Raf. Among the three isoforms, studies have shown that B-Raf functions as the primary MEK activator. B-Raf is one of the most frequently mutated genes in human cancers. B-Raf kinase represents an excellent target for anticancer therapy based on preclinical target validation, epidemiology and drugability.

Small molecule inhibitors of B-Raf are being developed for anticancer therapy. Nexavar® (sorafenib tosylate) is a multi-kinase inhibitor, which includes inhibition of B-Raf, and is approved for the treatment of patients with advanced renal cell carcinoma and unresectable hepatocellular carcinoma. Other Raf inhibitors have also been disclosed or have entered clinical trials, for example SB-590885, RAF-265, PLX-4032 and XL-281. Other B-Raf inhibitors are also known, see for example, U.S. Patent Application Publication 2006/0189627, U.S. Patent Application Publication 2006/0281751, U.S. Patent Application Publication 2007/0049603, International Patent Application Publication WO 2007/002325 and International Patent Application Publication WO 2007/002433.

Pyrrolopyridines are known, see for example, International Patent Application Publication WO 2005/062795 and International Patent Application Publication WO 2007/013896.

International Patent Application Publication WO 2008/079906 and International Patent Application Publication WO 2008/079909 also disclose pyrrolopyridines.

International Patent Application Publication WO 2006/066913, International Patent Application Publication WO 2008/028617 and International Patent Application Publication WO 2009/012283 also disclose kinase inhibitors.

SUMMARY OF THE INVENTION

In one aspect, the invention relates to compounds that are inhibitors of Raf kinases, particularly B-Raf inhibitors. Certain hyperproliferative disorders are characterized by the overactivation of Raf kinase function, for example by mutations or overexpression of the protein. Accordingly, the compounds of the invention are useful in the treatment of hyperproliferative disorders, such as cancer.

More specifically, one aspect of the present invention provides compounds of Formula I:

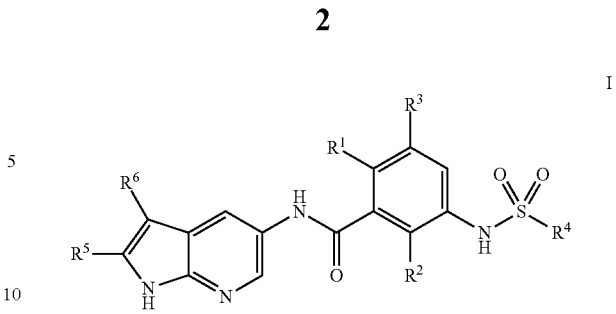

and stereoisomers, tautomers, prodrugs and pharmaceutically acceptable salts thereof, wherein $R^1$, $R^2$, $R^3$, $R^4$, $R^5$ and $R^6$ are as defined herein.

More specifically, one aspect of the present invention provides compounds of Formula I:

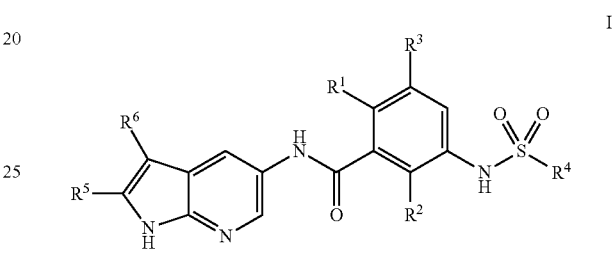

and stereoisomers, tautomers and pharmaceutically acceptable salts thereof, wherein $R^1$, $R^2$, $R^3$, $R^4$, $R^5$ and $R^6$ are as defined herein.

Another aspect of the present invention provides intermediate compounds of Formula III:

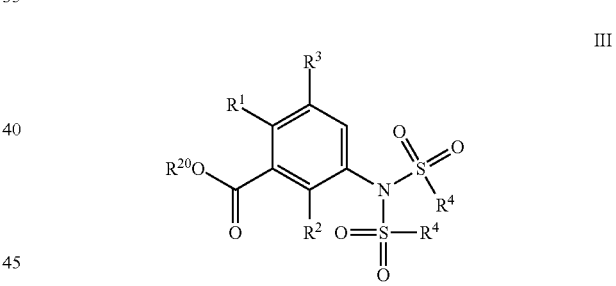

wherein $R^1$, $R^2$, $R^3$, $R^4$ and $R^{20}$ are as defined herein.

Another aspect of the present invention provides methods of preventing or treating a disease or disorder modulated by B-Raf, comprising administering to a mammal in need of such treatment an effective amount of a compound of this invention or a stereoisomer, prodrug or pharmaceutically acceptable salt thereof. Examples of such diseases and disorders include, but are not limited to, hyperproliferative disorders (such as cancer, including melanoma and other cancers of the skin), neurodegeneration, cardiac hypertrophy, pain, migraine and neurotraumatic disease.

Another aspect of the present invention provides methods of preventing or treating a disease or disorder modulated by B-Raf, comprising administering to a mammal in need of such treatment an effective amount of a compound of this invention or a stereoisomer or pharmaceutically acceptable salt thereof. Examples of such diseases and disorders include, but are not limited to, hyperproliferative disorders (such as cancer, including melanoma and other cancers of the skin), neurodegeneration, cardiac hypertrophy, pain, migraine and neurotraumatic disease.

Another aspect of the present invention provides methods of preventing or treating cancer, comprising administering to a mammal in need of such treatment an effective amount of a compound of this invention, or a stereoisomer, prodrug or pharmaceutically acceptable salt thereof, alone or in combination with one or more additional compounds having anti-cancer properties.

Another aspect of the present invention provides methods of preventing or treating cancer, comprising administering to a mammal in need of such treatment an effective amount of a compound of this invention, or a stereoisomer or pharmaceutically acceptable salt thereof, alone or in combination with one or more additional compounds having anti-cancer properties.

Another aspect of the present invention provides a method of treating a hyperproliferative disease in a mammal comprising administering a therapeutically effective amount of a compound of this invention to the mammal.

Another aspect of the present invention provides methods of preventing or treating kidney disease, comprising administering to a mammal in need of such treatment an effective amount of a compound of this invention, or a stereoisomer, prodrug or pharmaceutically acceptable salt thereof, alone or in combination with one or more additional compounds.

Another aspect of the present invention provides methods of preventing or treating polycystic kidney disease, comprising administering to a mammal in need of such treatment an effective amount of a compound of this invention, or a stereoisomer, prodrug or pharmaceutically acceptable salt thereof, alone or in combination with one or more additional compounds.

Another aspect of the present invention provides the compounds of the present invention for use in therapy.

Another aspect of the present invention provides the compounds of the present invention for use in the treatment of a hyperproliferative disease. In a further embodiment, the hyperproliferative disease may be cancer (or still further, a specific cancer as defined herein).

Another aspect of the present invention provides the compounds of the present invention for use in the treatment of a kidney disease. In a further embodiment, the kidney disease may be polycystic kidney disease.

Another aspect of the present invention provides the use of a compound of this invention in the manufacture of a medicament for the treatment of a hyperproliferative disease. In a further embodiment, the hyperproliferative disease may be cancer (or still further, a specific cancer as defined herein).

Another aspect of the present invention provides the use of a compound of this invention in the manufacture of a medicament for the treatment of a kidney disease. In a further embodiment, the kidney disease may be polycystic kidney disease.

Another aspect of the present invention provides the use of a compound of the present invention in the manufacture of a medicament, for use as a B-Raf inhibitor in the treatment of a patient undergoing cancer therapy.

Another aspect of the present invention provides the use of a compound of the present invention in the manufacture of a medicament, for use as a B-Raf inhibitor in the treatment of a patient undergoing polycystic kidney disease therapy.

Another aspect of the present invention provides a pharmaceutical composition comprising a compound of the present invention for use in the treatment of a hyperproliferative disease.

Another aspect of the present invention provides a pharmaceutical composition comprising a compound of the present invention for use in the treatment of cancer.

Another aspect of the present invention provides a pharmaceutical composition comprising a compound of the present invention for use in the treatment of polycystic kidney disease.

Another aspect of the present invention provides a pharmaceutical composition comprising a compound of this invention, a stereoisomer, prodrug or a pharmaceutically acceptable salt thereof, and a pharmaceutically acceptable carrier or excipient.

Another aspect of the present invention provides a pharmaceutical composition comprising a compound of this invention or a pharmaceutically acceptable salt thereof, and a pharmaceutically acceptable carrier or excipient.

Another aspect of the present invention provides intermediates for preparing compounds of Formula I. Certain compounds of Formula I may be used as intermediates for other compounds of Formula I.

Another aspect of the present invention includes methods of preparing, methods of separation, and methods of purification of the compounds of this invention.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

DEFINITIONS

The term "alkyl" includes linear or branched-chain radicals of carbon atoms. In one example, the alkyl radical is one to six carbon atoms ($C_1$-$C_6$). In other examples, the alkyl radical is $C_1$-$C_5$, $C_1$-$C_4$ or $C_1$-$C_3$. Some alkyl moieties have been abbreviated, for example, methyl ("Me"), ethyl ("Et"), propyl ("Pr") and butyl ("Bu"), and further abbreviations are used to designate specific isomers of compounds, for example, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu") and the like. Other examples of alkyl groups include 1-pentyl (n-pentyl, —$CH_2CH_2CH_2CH_2CH_3$), 2-pentyl (—$CH(CH_3)$ $CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH$ $(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)$ $CH_2CH_2CH_2CH_3$), 3-hexyl (—$CH(CH_2CH_3)$ $(CH_2CH_2CH_3)$), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$) and 3,3-dimethyl-2-butyl (—CH(CH$_3$)C(CH$_3$)$_3$. The abbreviations are sometimes used in conjunction with elemental abbreviations and chemical structures, for example, methanol ("MeOH") or ethanol ("EtOH").

Additional abbreviations used throughout the application include, for example, benzyl ("Bn"), phenyl ("Ph") and acetyl ("Ac").

The term dimethylsulfoxide is abbreviated ("DMSO").

The term "alkenyl" refers to linear or branched-chain monovalent hydrocarbon radical with at least one site of unsaturation, i.e., a carbon-carbon double bond, wherein the alkenyl radical may be optionally substituted independently with one or more substituents described herein, and includes radicals having "cis" and "trans" orientations, or alternatively, "E" and "Z" orientations. In one example, the alkenyl radical is two to six carbon atoms (C$_2$-C$_6$). In other examples, the alkenyl radical is C$_2$-C$_3$. Examples include, but are not limited to, ethenyl or vinyl (—CH=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, hexa-1,3-dienyl.

The term "alkynyl" refers to a linear or branched monovalent hydrocarbon radical with at least one site of unsaturation, i.e., a carbon-carbon, triple bond, wherein the alkynyl radical may be optionally substituted independently with one or more substituents described herein. In one example, the alkynyl radical is two to eighteen carbon atoms (C$_2$-C$_6$). In other examples, the alkynyl radical is C$_2$-C$_3$. Examples include, but are not limited to, ethynyl (—C≡CH), prop-1-ynyl (—C≡CCH$_3$), prop-2-ynyl (propargyl, CH$_2$C≡CH), but-1-ynyl, but-2-ynyl and but-3-ynyl.

The terms "alkenyl" and "alkynyl" also include linear or branched-chain radicals of carbon atoms containing at least one unsaturated bond.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 6 carbon atoms (C$_3$-C$_6$). In other examples, cycloalkyl is C$_3$-C$_4$ or C$_3$-C$_5$. In other examples, the cycloalkyl group, as a monocycle, is C$_3$-C$_6$ or C$_5$-C$_6$. In another example, the cycloalkyl group, as a bicycle, is C$_7$-C$_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane, and bicyclo[3.2.2]nonane.

The terms "heterocyclic" or "heterocycle" or "heterocyclyl" refers to a saturated or a partially unsaturated (i.e., having one or more double and/or triple bonds within the ring) cyclic group in which at least one ring atom is a heteroatom independently selected from nitrogen, oxygen, and sulfur, the remaining ring atoms being carbon. In one embodiment, heterocyclyl includes saturated or partially unsaturated 4-6 membered heterocyclyl groups. The heterocyclyl group may be optionally substituted with one or more substituents described herein. Exemplary heterocyclyl groups include, but are not limited to, oxiranyl, aziridinyl, thiiranyl, azetidinyl, oxetanyl, thietanyl, 1,2-dithietanyl, 1,3-dithietanyl, pyrrolidinyl, piperidinyl, dihydropyridinyl, tetrahydropyridinyl, morpholinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, imidazolidinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Heterocycles include 4 to 6 membered rings containing one or two heteroatoms selected from oxygen, nitrogen and sulfur.

The term "heteroaryl" refers to an aromatic cyclic group in which at least one ring atom is a heteroatom independently selected from nitrogen, oxygen and sulfur, the remaining ring atoms being carbon. Heteroaryl groups may be optionally substituted with one or more substituents described herein. In one example, heteroaryl includes 5-6 membered heteroaryl groups. Other examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, and furopyridinyl. Heteroaryls includes 5 to 6 membered aromatic rings containing one, two or three heteroatoms selected from oxygen, nitrogen and sulfur.

"Halogen" refers to F, Cl, Br or I.

The abbreviation "TLC" stands for thin layer chromatography.

The terms "treat" or "treatment" refer to therapeutic, prophylactic, palliative or preventative measures. In one example, treatment includes therapeutic and palliative treatment. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

The phrases "therapeutically effective amount" or "effective amount" mean an amount of a compound of the present invention that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "cancer" and "cancerous" refer to or describe the physiological condition in mammals that is typically characterized by abnormal or unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term cancer may be used generically to include various types of cancer or specifically (as listed above).

The phrase "pharmaceutically acceptable" indicates that the substance or composition is compatible chemically and/or toxicologically, with the other ingredients comprising a formulation, and/or the mammal being treated therewith.

The phrase "pharmaceutically acceptable salt," as used herein, refers to pharmaceutically acceptable organic or inorganic salts of a compound of the invention.

The compounds of this invention also include other salts of such compounds which are not necessarily pharmaceutically acceptable salts, and which may be useful as intermediates for preparing and/or purifying compounds of this invention and/or for separating enantiomers of compounds of this invention.

The term "mammal" means a warm-blooded animal that has or is at risk of developing a disease described herein and includes, but is not limited to, guinea pigs, dogs, cats, rats, mice, hamsters, and primates, including humans.

B-Raf Inhibitor Compounds

The present invention provides compounds, and pharmaceutical formulations thereof, that are potentially useful in the treatment of diseases, conditions and/or disorders modulated by B-Raf.

One embodiment of this invention provides compounds of Formula I:

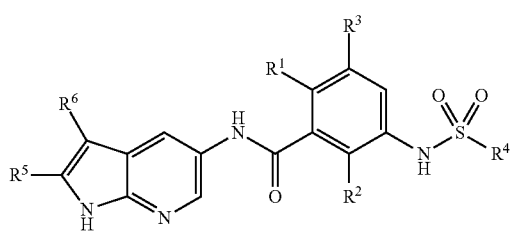

I and stereoisomers, tautomers, prodrugs and pharmaceutically acceptable salts thereof, wherein:

$R^1$ and $R^2$ are independently selected from hydrogen, halogen, CN, $C_1$-$C_3$ alkyl and $C_1$-$C_3$ alkoxy;

$R^3$ is hydrogen, halogen or $C_1$-$C_3$ alkyl;

$R^4$ is $C_3$-$C_5$ cycloalkyl, $C_1$-$C_6$ alkyl, $C_2$-$C_6$ alkenyl, $C_2$-$C_6$ alkynyl, phenyl, a 5-6 membered heteroaryl, or $NR^nR^o$, wherein the cycloalkyl, alkyl, alkenyl, alkynyl, phenyl and heteroaryl are optionally substituted with $OR^g$, halogen, phenyl, $C_3$-$C_4$ cycloalkyl, or $C_1$-$C_4$ alkyl optionally substituted with halogen;

$R^5$ is:
hydrogen,
halogen,
CN,
$NR^kR^l$,
$C_1$-$C_6$ alkyl optionally substituted with halogen, oxo, $OR^g$ or $NR^gR^h$,
$C_2$-$C_6$ alkenyl optionally substituted with halogen, $OR^g$ or $NR^gR^h$,
$C_2$-$C_6$ alkynyl optionally substituted with halogen, $OR^g$ or $NR^gR^h$,
a saturated or partially unsaturated $C_3$-$C_6$ cycloalkyl optionally substituted with halogen or $C_1$-$C_4$ alkyl,
a saturated or partially unsaturated 4-6 membered heterocyclyl optionally substituted with $C_1$-$C_4$ alkyl,
a 5-6 membered heteroaryl optionally substituted with $R^c$,
a 9-10 membered bicyclic heterocyclyl optionally substituted with $C_1$-$C_4$ alkyl,
a 9-10 membered bicyclic heteroaryl optionally substituted with $C_1$-$C_4$ alkyl, or
phenyl optionally substituted with $R^d$;

$R^6$ is:
hydrogen,
halogen,
CN,
$NR^kR^l$,
$OR^m$,
a saturated or partially unsaturated $C_3$-$C_6$ cycloalkyl optionally substituted with halogen or $C_1$-$C_4$ alkyl,
a saturated or partially unsaturated 4-6 membered heterocyclyl optionally substituted with $C_1$-$C_4$ alkyl,
phenyl optionally substituted with one to three $R^a$ groups,
a 5-6 membered heteroaryl optionally substituted with $C_1$-$C_4$ alkyl or benzyl,
$C_2$-$C_6$ alkenyl optionally substituted with halogen, $OR^g$ or $NR^gR^h$,
$C_2$-$C_6$ alkynyl optionally substituted with halogen, $OR^g$ or $NR^gR^h$, or
$C_1$-$C_6$ alkyl optionally substituted with one to three $R^b$ groups;

each $R^a$ is independently selected from halogen, CN, $CF_3$, OH, —O($C_1$-$C_4$ alkyl), a 5-6 membered heterocyclyl, or $C_1$-$C_4$ alkyl optionally substituted with $NR^gR^h$ or a 5-6 membered heterocyclyl;

each $R^b$ is independently selected from halogen, OH, $OCH_3$, oxo, —$NR^eR^f$, phenyl optionally substituted with a halogen, $C_3$-$C_6$ cycloalkyl, and a 5-6 membered heterocyclyl optionally substituted with halogen;

$R^c$ is —$NR^hR^j$, $C_1$-$C_4$ alkyl, or a 5-6 membered heterocyclyl optionally substituted by $C_1$-$C_4$ alkyl or —$(CH_2)_pC_3$-$C_6$ cycloalkyl;

$R^d$ is halogen, CN, $NR^gR^h$, phenyl, a 5-6 membered heterocyclyl, —O($C_1$-$C_4$ alkyl) or $C_1$-$C_4$ alkyl, wherein the alkyl or alkoxy are optionally substituted with halogen, OH, oxo, —O($C_1$-$C_3$ alkyl), $NR^gR^h$, or a 5-6 membered heterocyclyl optionally substituted with $C_1$-$C_3$ alkyl;

each $R^e$ and $R^f$ are independently selected from hydrogen, $C_1$-$C_4$ alkyl and phenyl;

each $R^g$ and $R^h$ are independently selected from hydrogen and $C_1$-$C_4$ alkyl;

$R^j$ is hydrogen or $C_1$-$C_4$ alkyl optionally substituted with a 5-6 membered heterocyclyl;

each $R^k$ and $R^l$ are independently selected from hydrogen and $C_1$-$C_4$ alkyl;

$R^m$ is selected from hydrogen and $C_1$-$C_4$ alkyl;

$R^n$ and $R^o$ are independently selected from hydrogen and $C_1$-$C_5$ alkyl, or $R^n$ and $R^o$ together with the nitrogen to which they are attached form a 4 to 6 membered heterocyclic ring; and p is 0 or 1.

Compounds of Formula I include compounds wherein:

$R^1$, $R^2$ and $R^3$ are independently selected from hydrogen, halogen or $C_1$-$C_3$ alkyl;

$R^4$ is $C_3$-$C_4$ cycloalkyl; $C_1$-$C_6$ alkyl optionally substituted with halogen or $C_3$-$C_4$ cycloalkyl; or $NR''R^o$;

$R^5$ is hydrogen, halogen, CN, $NR^kR^l$, $C_1$-$C_6$ alkyl optionally substituted with halogen, oxo, $OR^g$ or $NR^gR^h$, $C_2$-$C_6$ alkynyl optionally substituted with $OR^g$ or $NR^gR^h$, a saturated $C_3$-$C_6$ cycloalkyl, a saturated or partially unsaturated 4-6 membered heterocyclyl optionally substituted with $C_1$-$C_4$ alkyl, a 5-6 membered heteroaryl optionally substituted with $R^c$, a 9-10 membered bicyclic heterocyclyl, a 9-10 membered bicyclic heteroaryl optionally substituted with $C_1$-$C_4$ alkyl, or phenyl optionally substituted with $R^d$;

$R^6$ is hydrogen, halogen, CN, $NR^kR^l$, $OR^m$, a saturated or partially unsaturated $C_3$-$C_6$ cycloalkyl, a saturated 4-6 membered heterocyclyl, phenyl optionally substituted with one to three $R^a$ groups, a 5-6 membered heteroaryl optionally substituted with $C_1$-$C_4$ alkyl or benzyl, $C_2$-$C_6$ alkenyl, $C_2$-$C_6$ alkynyl optionally substituted with $OR^g$, or $C_1$-$C_6$ alkyl optionally substituted with one to three $R^b$ groups;

each $R^a$ is independently selected from halogen, $CF_3$, —$O(C_1$-$C_4$ alkyl), a 5-6 membered heterocyclyl, or $C_1$-$C_4$ alkyl optionally substituted with $NR^gR^h$ or a 5-6 membered heterocyclyl;

each $R^b$ is independently selected from OH, $OCH_3$, oxo, —$NR^eR^f$, phenyl optionally substituted with a halogen, $C_3$-$C_6$ cycloalkyl, and a 5-6 membered heterocyclyl optionally substituted with halogen;

$R^c$ is —$NR^hR^j$, $C_1$-$C_4$ alkyl, or a 5-6 membered heterocyclyl optionally substituted by $C_1$-$C_4$ alkyl or —$(CH_2)_p C_3$-$C_6$ cycloalkyl;

$R^d$ is halogen, $NR^gR^h$, phenyl, a 5-6 membered heterocyclyl, —$O(C_1$-$C_4$ alkyl) or $C_1$-$C_4$ alkyl, wherein the alkyl or alkoxy are optionally substituted with OH, oxo, —$O(C_1$-$C_3$ alkyl), $NR^gR^h$, or a 5-6 membered heterocyclyl optionally substituted with $C_1$-$C_3$ alkyl;

each $R^e$ and $R^f$ are independently selected from $C_1$-$C_4$ alkyl and phenyl;

each $R^g$ and $R^h$ are independently selected from hydrogen and $C_1$-$C_4$ alkyl;

$R^j$ is hydrogen or $C_1$-$C_4$ alkyl optionally substituted with a 5-6 membered heterocyclyl;

each $R^k$ and $R^l$ are independently $C_1$-$C_4$ alkyl;

$R^m$ is $C_1$-$C_4$ alkyl;

$R^n$ and $R^o$ are independently selected from hydrogen and $C_1$-$C_5$ alkyl, or $R^n$ and $R^o$ together with the nitrogen to which they are attached form a 4 to 6 membered heterocyclic ring; and p is 1.

One embodiment of this invention provides compounds of Formula I:

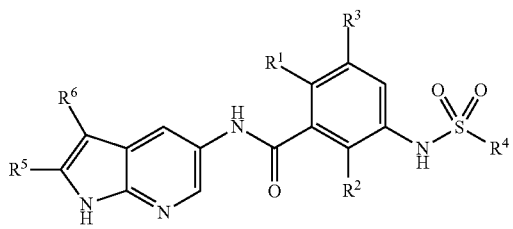

and stereoisomers, tautomers and pharmaceutically acceptable salts thereof, wherein:

$R^1$ and $R^2$ are independently selected from hydrogen, halogen, CN, $C_1$-$C_3$ alkyl and $C_1$-$C_3$ alkoxy;

$R^3$ is hydrogen, halogen or $C_1$-$C_3$ alkyl;

$R^4$ is $C_3$-$C_5$ cycloalkyl, $C_1$-$C_6$ alkyl, $C_2$-$C_6$ alkenyl, or $C_2$-$C_6$ alkynyl, wherein the cycloalkyl, alkyl, alkenyl and alkynyl are optionally substituted with $OR^g$, halogen or $C_3$-$C_4$ cycloalkyl;

$R^5$ is hydrogen, halogen, CN, $C_1$-$C_4$ alkyl optionally substituted with $OR^g$ or $NR^gR^h$, $C_3$-$C_6$ alkynyl optionally substituted with $OR^g$ or $NR^gR^h$, a saturated or partially unsaturated $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, a 5-6 membered heteroaryl optionally substituted with $R^c$, a 9-10 membered bicyclic heterocyclyl optionally substituted with $C_1$-$C_4$ alkyl, a 9-10 membered bicyclic heteroaryl optionally substituted with $C_1$-$C_4$ alkyl, or phenyl optionally substituted with $R^d$;

$R^6$ is hydrogen, halogen, CN, a saturated or partially unsaturated $C_3$-$C_6$ cycloalkyl optionally substituted with halogen or $C_1$-$C_4$ alkyl, a saturated or partially unsaturated 4-6 membered heterocyclyl, —$O(CH_2)_m$ 4-6 membered heterocyclyl optionally substituted with $C_1$-$C_3$ alkyl, phenyl optionally substituted with one to three $R^a$ groups, a 5-6 membered heteroaryl optionally substituted with $C_1$-$C_4$ alkyl or benzyl, $C_1$-$C_4$ alkenyl optionally substituted with $OR^g$, $C_3$-$C_6$ alkynyl optionally substituted with $OR^g$, or $C_1$-$C_4$ alkyl optionally substituted with one to three $R^b$ groups;

each $R^a$ is independently selected from halogen, CN, $CF_3$, OH, —$O(C_1$-$C_4$ alkyl), a 5-6 membered heterocyclyl, or $C_1$-$C_4$ alkyl optionally substituted with $NR^gR^h$ or a 5-6 membered heterocyclyl;

each $R^b$ is independently selected from halogen, OH, $OCH_3$, oxo, —$NR^eR^f$, phenyl optionally substituted with a halogen, $C_3$-$C_6$ cycloalkyl, or a 5-6 membered heterocyclyl optionally substituted with halogen;

is —$NR^hR^j$, $C_1$-$C_4$ alkyl, or a 5-6 membered heterocyclyl optionally substituted by $C_1$-$C_4$ alkyl or —$(CH_2)_p C_3$-$C_6$ cycloalkyl;

$R^d$ is halogen, CN, $NR^gR^h$, phenyl, a 5-6 membered heterocyclyl, —$O(C_1$-$C_4$ alkyl) or $C_1$-$C_4$ alkyl, wherein the alkyl or alkoxy are optionally substituted with halogen, OH, oxo, —$O(C_1$-$C_3$ alkyl), $NR^gR^h$, or a 5-6 membered heterocyclyl optionally substituted with $C_1$-$C_3$ alkyl;

$R^e$ and $R^f$ are independently selected from $C_1$-$C_4$ alkyl and phenyl;

each $R^g$ and $R^h$ are independently selected from hydrogen and $C_1$-$C_4$ alkyl;

$R^j$ is hydrogen or $C_1$-$C_4$ alkyl optionally substituted with a 5-6 membered heterocyclyl;

m is 0, 1, 2, or 3; and p is 0 or 1.

Compounds of Formula I include compounds wherein:

$R^1$, $R^2$ and $R^3$ are independently selected from hydrogen, halogen or $C_1$-$C_3$ alkyl;

$R^4$ is $C_3$-$C_4$ cycloalkyl, or $C_1$-$C_6$ alkyl optionally substituted with OH, halogen or $C_3$-$C_4$ cycloalkyl;

$R^5$ is hydrogen, halogen, CN, $C_1$-$C_4$ alkyl optionally substituted with OH or $NR^gR^h$, $C_3$-$C_6$ alkynyl optionally substituted with OH or $NR^gR^h$, a saturated or partially unsaturated $C_3$-$C_6$ cycloalkyl, a saturated or partially unsaturated 4-6 membered heterocyclyl optionally substituted with $C_1$-$C_4$ alkyl, a 5-6 membered heteroaryl optionally substituted with $R^c$, a 9-10 membered bicyclic heterocyclyl, a 9-10 membered bicyclic heteroaryl optionally substituted with $C_1$-$C_4$ alkyl, or phenyl optionally substituted with $R^d$;

$R^6$ is hydrogen, halogen, CN, a saturated or partially unsaturated $C_3$-$C_6$ cycloalkyl, (2,2-dimethyl-1,3-dioxolan-4-yl) methoxy, phenyl optionally substituted with one to three $R^a$, groups, a 5-6 membered heteroaryl optionally substituted with $C_1$-$C_4$ alkyl or benzyl, $C_1$-$C_4$ alkenyl, $C_3$-$C_6$ alkynyl optionally substituted with $OR^g$, or $C_1$-$C_4$ alkyl optionally substituted with one to three $R^b$ groups;

each $R^a$ is independently selected from halogen, CN, $CF_3$, —O($C_1$-$C_4$ alkyl), a 5-6 membered heterocyclyl, or $C_1$-$C_4$ alkyl optionally substituted with $NR^gR^h$ or a 5-6 membered heterocyclyl;

each $R^b$ is independently selected from halogen, OH, $OCH_3$, oxo, —$NR^eR^f$, phenyl optionally substituted with a halogen, $C_3$-$C_6$ cycloalkyl, or a 5-6 membered heterocyclyl optionally substituted with halogen;

$R^c$ is —$NR^hR^j$, $C_1$-$C_4$ alkyl, or a 5-6 membered heterocyclyl optionally substituted by $C_1$-$C_4$ alkyl or —$(CH_2)_pC_3$-$C_6$ cycloalkyl;

$R^d$ is halogen, CN, $NR^gR^h$, phenyl, a 5-6 membered heterocyclyl, —O($C_1$-$C_4$ alkyl) or $C_1$-$C_4$ alkyl, wherein the alkyl or alkoxy are optionally substituted with halogen, OH, oxo, —O($C_1$-$C_3$ alkyl), $NR^gR^h$, or a 5-6 membered heterocyclyl optionally substituted with $C_1$-$C_3$ alkyl;

$R^e$ and $R^f$ are independently selected from hydrogen, $C_1$-$C_4$ alkyl and phenyl;

each $R^g$ and $R^h$ are independently selected from hydrogen and $C_1$-$C_4$ alkyl;

$R^j$ is hydrogen or $C_1$-$C_4$ alkyl optionally substituted with a 5-6 membered heterocyclyl; and p is 0 or 1.

In certain embodiments, $R^1$ and $R^2$ are independently selected from hydrogen, halogen, CN, $C_1$-$C_3$ alkyl or $C_1$-$C_3$ alkoxy.

In certain embodiments, $R^1$, $R^2$ and $R^3$ are independently selected from hydrogen, halogen or $C_1$-$C_3$ alkyl.

In certain embodiments, $R^1$, $R^2$ and $R^3$ are independently selected from hydrogen, F, Cl or methyl.

In certain embodiments, $R^1$ is hydrogen, halogen, CN, $C_1$-$C_3$ alkyl or $C_1$-$C_3$ alkoxy.

In certain embodiments, $R^1$ is hydrogen.

In certain embodiments, $R^1$ is halogen. In certain embodiments, $R^1$ is F or Cl.

In certain embodiments, $R^1$ is $C_1$-$C_3$ alkyl. In certain embodiments, $R^1$ is methyl.

In certain embodiments, $R^2$ is hydrogen, halogen, CN, $C_1$-$C_3$ alkyl or $C_1$-$C_3$ alkoxy.

In certain embodiments, $R^2$ is hydrogen.

In certain embodiments, $R^2$ is halogen. In certain embodiments, $R^2$ is F or Cl.

In certain embodiments, $R^2$ is $C_1$-$C_3$ alkyl. In certain embodiments, $R^2$ is methyl.

In certain embodiments of Formula I, $R^2$ is Cl.

In certain embodiments of Formula I, $R^2$ is hydrogen.

In certain embodiments, $R^3$ is hydrogen, halogen or $C_1$-$C_3$ alkyl.

In certain embodiments, $R^3$ is hydrogen.

In certain embodiments, $R^3$ is halogen. In certain embodiments, $R^3$ is F or Cl.

In certain embodiments, $R^1$ and $R^2$ are F and $R^3$ is hydrogen.

In certain embodiments, $R^1$ is F and $R^2$ is Cl and $R^3$ is hydrogen.

In certain embodiments, $R^1$ is Cl and $R^2$ is F and $R^3$ is hydrogen.

In certain embodiments, $R^1$ is F and $R^2$ and $R^3$ are hydrogen.

In certain embodiments, $R^1$ and $R^3$ are hydrogen and $R^2$ is F.

In certain embodiments, $R^2$ and $R^3$ are F and $R^1$ is hydrogen.

In certain embodiments, $R^1$ is Cl and $R^2$ and $R^3$ are hydrogen.

In certain embodiments, $R^1$, $R^2$ and $R^3$ are F.

In certain embodiments, $R^1$ is F and $R^2$ is methyl and $R^3$ is hydrogen.

In certain embodiments, $R^1$ is methyl and $R^2$ is F and $R^3$ is hydrogen.

In certain embodiments, $R^1$ is F and $R^2$ and $R^3$ are hydrogen.

In certain embodiments, $R^1$ is Cl and $R^2$ and $R^3$ are hydrogen.

In certain embodiments, $R^2$ is F and $R^1$ and $R^3$ are hydrogen.

In certain embodiments, the residue:

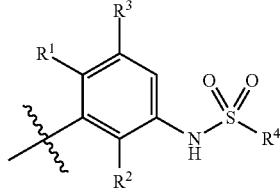

of Formula I, wherein the wavy line represents the point of attachment of the residue in Formula I, is selected from:

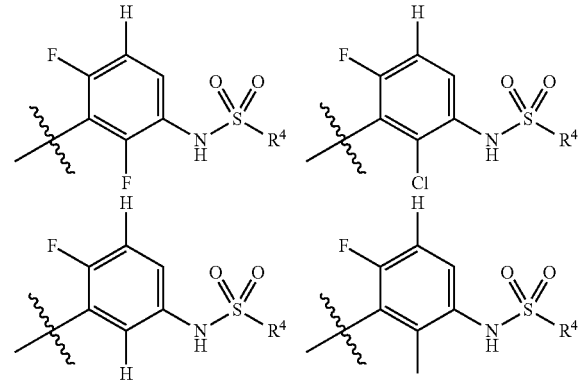

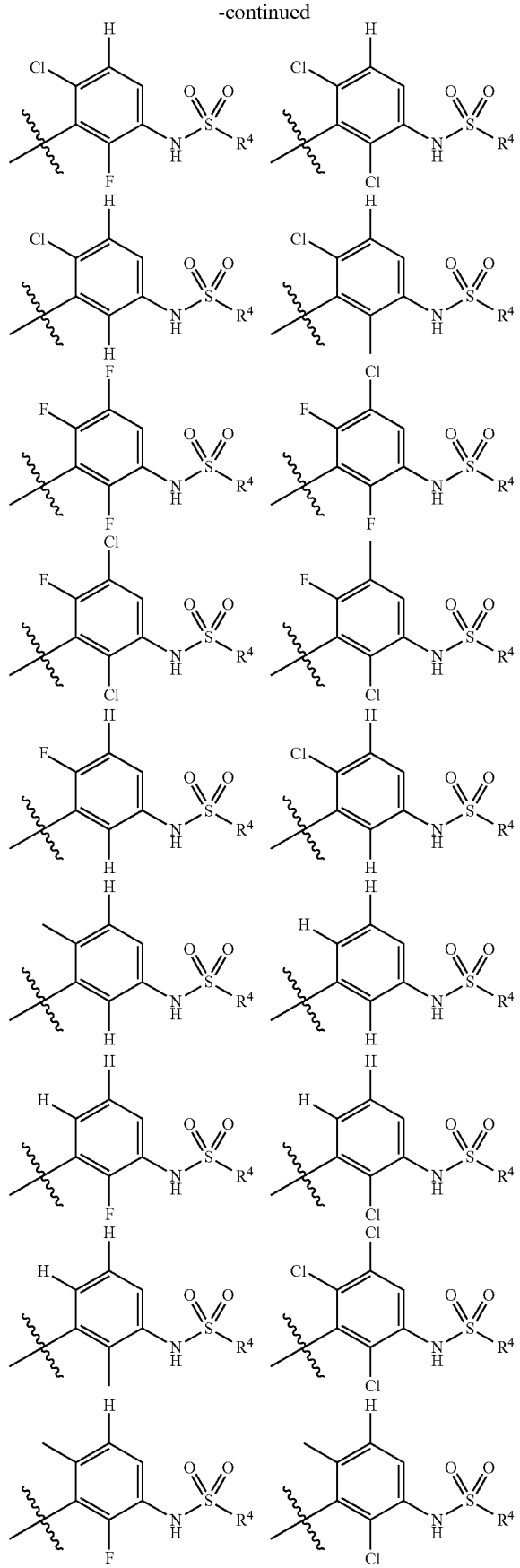

In certain embodiments, $R^4$ is $C_3$-$C_5$ cycloalkyl, $C_1$-$C_6$ alkyl, $C_2$-$C_6$ alkenyl, $C_2$-$C_6$ alkynyl, phenyl, a 5-6 membered heteroaryl, or $NR''R^o$, wherein the cycloalkyl, alkyl, alkenyl, alkynyl, phenyl and heteroaryl are optionally substituted with $OR^g$, halogen, phenyl, $C_3$-$C_4$ cycloalkyl, or $C_1$-$C_4$ alkyl optionally substituted with halogen.

In certain embodiments, $R^4$ is $C_3$-$C_4$ cycloalkyl; $C_1$-$C_6$ alkyl optionally substituted with halogen or $C_3$-$C_4$ cycloalkyl; or $NR''R^o$. In certain embodiments, $R''$ and $R^o$ are independently selected from hydrogen and $C_1$-$C_5$ alkyl.

In certain embodiments, $R^4$ is $C_3$-$C_5$ cycloalkyl, $C_1$-$C_6$ alkyl, $C_2$-$C_6$ alkenyl, or $C_2$-$C_6$ alkynyl, wherein the cycloalkyl, alkyl, alkenyl and alkynyl are optionally substituted with $OR^g$, halogen or $C_3$-$C_4$ cycloalkyl.

In certain embodiments, $R^4$ is cyclopropyl, ethyl, propyl, butyl, isobutyl, —$CH_2Cl$, —$CH_2CF_3$, —$CH_2CH_2CH_2F$, —$CH_2CH_2CF_3$, phenylmethyl, cyclopropylmethyl, phenyl, 2-fluorophenyl, 3-fluorophenyl, 4-fluorophenyl, 2,5-difluorophenyl, 4-chloro-3-trifluoromethylphenyl, 1-methyl-1H-imidazol-4-yl, furan-2-yl, pyridin-2-yl, pyridin-3-yl, thiophen-2-yl, —$NHCH_2CH_3$, —$NHCH_2CH_2CH_3$, —$N(CH_3)CH_2CH_3$, —$N(CH_3)_2$, or pyrrolidine.

In certain embodiments, $R^4$ is cyclopropyl, propyl, butyl, isobutyl, —$CH_2Cl$, —$CH_2CF_3$, —$CH_2CH_2CH_2F$, —$CH_2CH_2CF_3$, cyclopropylmethyl, —$NHCH_2CH_2CH_3$, —$N(CH_3)CH_2CH_3$, —$N(CH_3)_2$, or pyrrolidine.

In certain embodiments, $R^4$ is cyclopropyl, propyl, butyl, isobutyl, —$CH_2Cl$, —$CH_2CF_3$, —$CH_2CH_2CH_2F$, —$CH_2CH_2CF_3$, cyclopropylmethyl or —$NHCH_2CH_2CH_3$.

In certain embodiments, $R^4$ is propyl, butyl, isobutyl, —$CH_2CH_2CH_2F$, —$CH_2CH_2CF_3$ or cyclopropylmethyl.

In certain embodiments, $R^4$ is $C_3$-$C_5$ cycloalkyl or $C_1$-$C_6$ alkyl optionally substituted with OH, halogen or $C_3$-$C_4$ cycloalkyl.

In certain embodiments, $R^4$ is $C_3$-$C_5$ cycloalkyl. In certain embodiments, $R^4$ is $C_3$-$C_4$ cycloalkyl. In certain embodiments, $R^4$ is cyclopropyl or cyclobutyl.

In certain embodiments, $R^4$ is $C_3$-$C_5$ cycloalkyl. In certain embodiments, $R^4$ is $C_3$-$C_4$ cycloalkyl. In certain embodiments, $R^4$ is cyclopropyl.

In certain embodiments, $R^4$ is $C_1$-$C_6$ alkyl. In certain embodiments, $R^4$ is ethyl, propyl, butyl or isobutyl.

In certain embodiments, $R^4$ is $C_1$-$C_6$ alkyl. In certain embodiments, $R^4$ is propyl, butyl or isobutyl.

In certain embodiments, $R^4$ is $C_1$-$C_6$ alkyl optionally substituted with halogen. In certain embodiments, $R^4$ is —$CF_3$, —$CH_2Cl$, —$CH_2CF_3$, —$CH_2CH_2CH_2F$, —$CH_2CH_2CF_3$, —$CF_2CF_3$ or —$CF_2CF_2CF_3$.

In certain embodiments, $R^4$ is $C_1$-$C_6$ alkyl optionally substituted with halogen. In certain embodiments, $R^4$ is —$CF_3$, —$CH_2CF_3$, —$CH_2CH_2CH_2F$, —$CH_2CH_2CF_3$, —$CF_2CF_3$ or —$CF_2CF_2CF_3$. In certain embodiments, $R^4$ is —$CH_2CH_2CH_2F$ or —$CH_2CH_2CF_3$.

In certain embodiments, $R^4$ is $C_1$-$C_6$ alkyl optionally substituted with OH, halogen or $C_3$-$C_4$ cycloalkyl. In certain embodiments, $R^4$ is cyclopropylmethyl (—$CH_2$-cyclopropyl)

or cyclobutylmethyl (—CH$_2$-cyclobutyl). In certain embodiments, R$^4$ is cyclopropylmethyl (—CH$_2$-cyclopropyl).

In certain embodiments, R$^4$ is C$_1$-C$_6$ alkyl optionally substituted with phenyl. In certain embodiments, R$^4$ is phenylmethyl.

In certain embodiments, R$^4$ is phenyl optionally substituted with OR$^g$, halogen, C$_3$-C$_4$ cycloalkyl, or C$_1$-C$_4$ alkyl optionally substituted with halogen. In certain embodiments, R$^4$ is phenyl optionally substituted with halogen. In certain embodiments, R$^4$ is phenyl optionally substituted with C$_1$-C$_4$ alkyl optionally substituted with halogen. In certain embodiments, R$^4$ is phenyl optionally substituted with halogen and C$_1$-C$_4$ alkyl optionally substituted with halogen. In certain embodiments, R$^4$ is phenyl. In certain embodiments, R$^4$ is phenyl, 2-fluorophenyl, 3-fluorophenyl, 4-fluorophenyl, 2,5-difluorophenyl or 4-chloro-3-trifluoromethylphenyl.

In certain embodiments, R$^4$ is a 5-6 membered heteroaryl optionally substituted with OR$^g$, halogen, C$_3$-C$_4$ cycloalkyl or C$_1$-C$_4$ alkyl optionally substituted with halogen. In certain embodiments, R$^4$ is a 5-6 membered heteroaryl optionally substituted with C$_1$-C$_4$ alkyl. In certain embodiments, R$^4$ is a 5-6 membered heteroaryl, wherein the heteroaryl contains one or two heteroatoms selected from the group consisting of oxygen, nitrogen and sulfur. In certain embodiments, R$^4$ is a 5-6 membered heteroaryl, wherein the heteroaryl is imidazolyl, furanyl, pyridinyl or thiophenyl. In certain embodiments, R$^4$ is 1-methyl-1H-imidazol-4-yl, furan-2-yl, pyridin-2-yl, pyridin-3-yl or thiophen-2-yl.

In certain embodiments, R$^4$ is NR″R$^o$. In certain embodiments, R″ and R$^o$ are independently selected from hydrogen and C$_1$-C$_5$ alkyl. In certain embodiments, R$^o$ is hydrogen. In certain embodiments, R″ is C$_1$-C$_5$ alkyl. In certain embodiments, R″ is ethyl or propyl. In certain embodiments, R$^4$ is selected from the group consisting of —NHCH$_2$CH$_3$, —NHCH$_2$CH$_2$CH$_3$, —N(CH$_3$)CH$_2$CH$_3$ and —N(CH$_3$)$_2$.

In certain embodiments, R″ and R$^o$ together with the nitrogen to which they are attached form a 4 to 6 membered heterocyclic ring. In certain embodiments, R″ and R$^o$ together with the nitrogen to which they are attached form a 4 to 6 membered heterocyclic ring, wherein the heterocyclic ring contains one nitrogen heteroatom. In certain embodiments, R$^4$ is pyrrolidine.

In certain embodiments, R$^4$ is selected from propyl, cyclopropylmethyl, —CH$_2$CH$_2$CH$_2$F and phenyl. In a further embodiment, R$^4$ is selected from propyl, cyclopropylmethyl and —CH$_2$CH$_2$CH$_2$F.

In certain embodiments of Formula I, R$^1$ and R$^2$ are F, R$^3$ is hydrogen and R$^4$ is propyl, such that the compounds have the structure of Formula Ia:

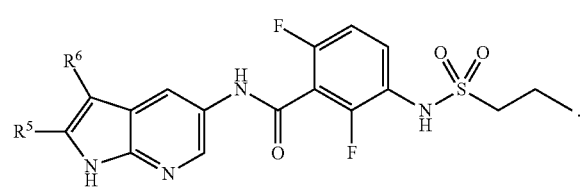

Ia

In certain embodiments of Formula I, R$^1$ is Cl and R$^2$ is F, R$^3$ is hydrogen and R$^4$ is propyl, such that the compounds have the structure of Formula Ia1:

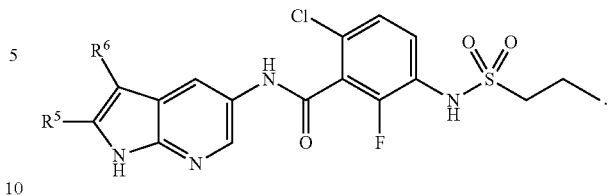

Ia1

In certain embodiments of Formula I, R$^1$ is F and R$^2$ is Cl, R$^3$ is hydrogen and R$^4$ is propyl, such that the compounds have the structure of Formula Ia2:

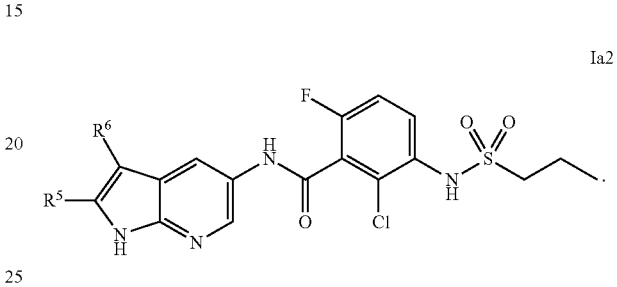

Ia2

In certain embodiments, R$^6$ is hydrogen, halogen, CN, NR$^k$R$^l$, OR$^m$, a saturated or partially unsaturated C$_3$-C$_6$ cycloalkyl optionally substituted with halogen or C$_1$-C$_4$ alkyl, a saturated or partially unsaturated 4-6 membered heterocyclyl optionally substituted with C$_1$-C$_4$ alkyl, —O(CH$_2$)$_m$4-6 membered heterocyclyl optionally substituted with C$_1$-C$_4$ alkyl, phenyl optionally substituted with one to three R$^a$ groups, a 5-6 membered heteroaryl optionally substituted with C$_1$-C$_4$ alkyl or benzyl, C$_2$-C$_6$ alkenyl optionally substituted with halogen, OR$^g$ or NR$^g$R$^h$, C$_2$-C$_6$ alkynyl optionally substituted with halogen, OR$^g$ or NR$^g$R$^h$, or C$_1$-C$_6$ alkyl optionally substituted with one to three R$^b$ groups. In certain embodiments, m is 0, 1, 2, or 3.

In certain embodiments, R$^6$ is hydrogen, halogen, CN, a saturated or partially unsaturated C$_3$-C$_6$ cycloalkyl optionally substituted with halogen or C$_1$-C$_4$ alkyl, a saturated or partially unsaturated 4-6 membered heterocyclyl, —O(CH$_2$)$_m$4-6 membered heterocyclyl optionally substituted with C$_1$-C$_3$ alkyl, phenyl optionally substituted with one to three R$^a$ groups, a 5-6 membered heteroaryl optionally substituted with C$_1$-C$_4$ alkyl or benzyl, C$_1$-C$_4$ alkenyl optionally substituted with OR$^g$, C$_3$-C$_6$ alkynyl optionally substituted with OR$^g$, or C$_1$-C$_4$ alkyl optionally substituted with one to three R$^b$ groups. In certain embodiments, m is 0, 1, 2, or 3.

In certain embodiments, R$^6$ is hydrogen, CN, NR$^k$R$^l$, OR$^m$, a saturated or partially unsaturated C$_3$-C$_6$ cycloalkyl optionally substituted with halogen or C$_1$-C$_4$ alkyl, a saturated or partially unsaturated 4-6 membered heterocyclyl optionally substituted with C$_1$-C$_4$ alkyl, —O(CH$_2$)$_m$4-6 membered heterocyclyl optionally substituted with C$_1$-C$_4$ alkyl, phenyl optionally substituted with one to three R$^a$ groups, a 5-6 membered heteroaryl optionally substituted with C$_1$-C$_4$ alkyl or benzyl, C$_2$-C$_6$ alkenyl optionally substituted with halogen, OR$^g$ or NR$^g$R$^h$, C$_2$-C$_6$ alkynyl optionally substituted with halogen, OR$^g$ or NR$^g$R$^h$, or C$_1$-C$_6$ alkyl optionally substituted with one to three R$^b$ groups. In certain embodiments, m is 0, 1, 2, or 3.

In certain embodiments, R$^6$ is hydrogen, CN, a saturated or partially unsaturated C$_3$-C$_6$ cycloalkyl optionally substituted with halogen or C$_1$-C$_4$ alkyl, a saturated or partially unsaturated 4-6 membered heterocyclyl, —O(CH$_2$)$_m$4-6 membered heterocyclyl optionally substituted with $C_1$-$C_3$ alkyl, phenyl optionally substituted with one to three $R^a$ groups, a 5-6 membered heteroaryl optionally substituted with $C_1$-$C_4$ alkyl or benzyl, $C_1$-$C_4$ alkenyl optionally substituted with $OR^g$, $C_3$-$C_6$ alkynyl optionally substituted with $OR^g$, or $C_1$-$C_4$ alkyl optionally substituted with one to three $R^b$ groups. In certain embodiments, m is 0, 1, 2, or 3.

In certain embodiments, $R^6$ is CN, $NR^kR^l$, $OR^m$, a saturated or partially unsaturated $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, $-O(CH_2)_m$4-6 membered heterocyclyl optionally substituted with $C_1$-$C_4$ alkyl, phenyl optionally substituted with one to three $R^a$ groups, a 5-6 membered heteroaryl optionally substituted with $C_1$-$C_4$ alkyl or benzyl, $C_2$-$C_6$ alkenyl optionally substituted with halogen, $OR^g$ or $NR^gR^h$, $C_2$-$C_6$ alkynyl optionally substituted with halogen, $OR^g$ or $NR^gR^h$, or $C_1$-$C_6$ alkyl optionally substituted with one to three $R^b$ groups. In certain embodiments, m is 0, 1, 2, or 3.

In certain embodiments, $R^6$ is CN, a saturated or partially unsaturated $C_3$-$C_6$ cycloalkyl optionally substituted with halogen or $C_1$-$C_4$ alkyl, a saturated or partially unsaturated 4-6 membered heterocyclyl, $-O(CH_2)_m$4-6 membered heterocyclyl optionally substituted with $C_1$-$C_3$ alkyl, phenyl optionally substituted with one to three $R^a$ groups, a 5-6 membered heteroaryl optionally substituted with $C_1$-$C_4$ alkyl or benzyl, $C_1$-$C_4$ alkenyl optionally substituted with $OR^g$, $C_3$-$C_6$ alkynyl optionally substituted with $OR^g$, or $C_1$-$C_4$ alkyl optionally substituted with one to three $R^b$ groups. In certain embodiments, m is 0, 1, 2, or 3.

In certain embodiments, each $R^a$ is independently selected from halogen, CN, $CF_3$, OH, $-O(C_1$-$C_4$ alkyl), a 5-6 membered heterocyclyl, or $C_1$-$C_4$ alkyl optionally substituted with $NR^gR^h$, and a 5-6 membered heterocyclyl.

In certain embodiments, each $R^a$ is independently selected from halogen, CN, $CF_3$, OH, $-O(C_1$-$C_4$ alkyl), a 5-6 membered heterocyclyl, or $C_1$-$C_4$ alkyl optionally substituted with $NR^gR^h$ or a 5-6 membered heterocyclyl.

In certain embodiments, each $R^b$ is independently selected from halogen, OH, $-OCH_3$, oxo, $-NR^eR^f$, phenyl optionally substituted with a halogen, $C_3$-$C_6$ cycloalkyl, and a 5-6 membered heterocyclyl optionally substituted with halogen.

In certain embodiments, each $R^b$ is independently selected from halogen, OH, $-OCH_3$, oxo, $-NR^eR^f$, phenyl optionally substituted with a halogen, $C_3$-$C_6$ cycloalkyl, or a 5-6 membered heterocyclyl optionally substituted with halogen.

In certain embodiments, each $R^b$ is independently selected from halogen, OH, $-OCH_3$, $-NR^eR^f$, phenyl optionally substituted with a halogen, $C_3$-$C_6$ cycloalkyl, or a 5-6 membered heterocyclyl optionally substituted with halogen.

In certain embodiments, $R^e$ is hydrogen, $C_1$-$C_4$ alkyl or phenyl.

In certain embodiments, $R^f$ is hydrogen, $C_1$-$C_4$ alkyl or phenyl.

In certain embodiments, $R^g$ is hydrogen or $C_1$-$C_4$ alkyl.
In certain embodiments, $R^h$ is hydrogen or $C_1$-$C_4$ alkyl.
In certain embodiments, $R^k$ is hydrogen or $C_1$-$C_4$ alkyl.
In certain embodiments, $R^l$ is hydrogen or $C_1$-$C_4$ alkyl.
In certain embodiments, $R^m$ is hydrogen or $C_1$-$C_4$ alkyl.

In certain embodiments, $R^6$ is hydrogen, halogen, CN, $NR^kR^l$, $OR^m$, a saturated or partially unsaturated $C_3$-$C_6$ cycloalkyl, a saturated 4-6 membered heterocyclyl, phenyl optionally substituted with one to three $R^a$ groups, a 5-6 membered heteroaryl optionally substituted with $C_1$-$C_4$ alkyl or benzyl, $C_2$-$C_6$ alkenyl, $C_2$-$C_6$ alkynyl optionally substituted with $OR^g$, or $C_1$-$C_6$ alkyl optionally substituted with one to three $R^b$ groups.

In certain embodiments, $R^6$ is hydrogen, halogen, CN, a saturated or partially unsaturated $C_3$-$C_6$ cycloalkyl, (2,2-dimethyl-1,3-dioxolan-4-yl)methoxy, phenyl optionally substituted with one to three $R^a$ groups, a 5-6 membered heteroaryl optionally substituted with $C_1$-$C_4$ alkyl or benzyl, $C_1$-$C_4$ alkenyl, $C_3$-$C_6$ alkynyl optionally substituted with $OR^g$, or $C_1$-$C_4$ alkyl optionally substituted with one to three $R^b$ groups.

In certain embodiments, $R^6$ is hydrogen, CN, $NR^kR^l$, $OR^m$, a saturated or partially unsaturated $C_3$-$C_6$ cycloalkyl, a saturated 4-6 membered heterocyclyl, phenyl optionally substituted with one to three $R^a$ groups, a 5-6 membered heteroaryl optionally substituted with $C_1$-$C_4$ alkyl or benzyl, $C_2$-$C_6$ alkenyl, $C_2$-$C_6$ alkynyl optionally substituted with $OR^g$, or $C_1$-$C_6$ alkyl optionally substituted with one to three $R^b$ groups.

In certain embodiments, $R^6$ is hydrogen, CN, a saturated or partially unsaturated $C_3$-$C_6$ cycloalkyl, (2,2-dimethyl-1,3-dioxolan-4-yl)methoxy, phenyl optionally substituted with one to three $R^a$ groups, a 5-6 membered heteroaryl optionally substituted with $C_1$-$C_4$ alkyl or benzyl, $C_1$-$C_4$ alkenyl, $C_3$-$C_6$ alkynyl optionally substituted with $OR^g$, or $C_1$-$C_4$ alkyl optionally substituted with one to three $R^b$ groups.

In certain embodiments, $R^6$ is CN, $NR^kR^l$, $OR^m$, a saturated or partially unsaturated $C_3$-$C_6$ cycloalkyl, a saturated 4-6 membered heterocyclyl, phenyl optionally substituted with one to three $R^a$ groups, a 5-6 membered heteroaryl optionally substituted with $C_1$-$C_4$ alkyl or benzyl, $C_2$-$C_6$ alkenyl, $C_2$-$C_6$ alkynyl optionally substituted with $OR^g$, or $C_1$-$C_6$ alkyl optionally substituted with one to three $R^b$ groups.

In certain embodiments, $R^6$ is CN, a saturated or partially unsaturated $C_3$-$C_6$ cycloalkyl, (2,2-dimethyl-1,3-dioxolan-4-yl)methoxy, phenyl optionally substituted with one to three $R^a$ groups, a 5-6 membered heteroaryl optionally substituted with $C_1$-$C_4$ alkyl or benzyl, $C_1$-$C_4$ alkenyl, $C_3$-$C_6$ alkynyl optionally substituted with $OR^g$, or $C_1$-$C_4$ alkyl optionally substituted with one to three $R^b$ groups.

In certain embodiments, each $R^a$ is independently selected from halogen, CN, $CF_3$, $-O(C_1$-$C_4$ alkyl), a 5-6 membered heterocyclyl, or $C_1$-$C_4$ alkyl optionally substituted with $NR^gR^h$ or a 5-6 membered heterocyclyl.

In certain embodiments, $R^6$ is hydrogen, Cl, Br, F, I, CN, dimethylamino, ethoxy, cyclohexyl, cyclopentyl, cyclobutyl, cyclopropyl, cyclopentenyl, morpholino, phenyl, 2-fluorophenyl, 3-fluorophenyl, 4-fluorophenyl, 3-chlorophenyl, 4-chlorophenyl, 3-methylphenyl, 3-methoxyphenyl, 3-isopropylphenyl, 3-isopropoxyphenyl, 3-trifluoromethylphenyl, 4-trifluoromethylphenyl, 3-morpholinophenyl, 2,5-difluorophenyl, 3,4-difluorophenyl, 3-chloro-4-fluorophenyl, 3,5-difluorophenyl, 3-((dimethylamino)methyl)phenyl, 3-(morpholinomethyl)phenyl, pyridin-3-yl, furan-3-yl, thiopheny-3-yl, 2-methylthiazol-4-yl, 1-methyl-1H-pyrazol-4-yl, 1H-pyrazol-5-yl, 1-benzyl-1H-pyrazol-4-yl, $-CH=CH_2$, $-C\equiv CCH_2OH$, $-C\equiv CCH_2OCH_3$, methyl, ethyl, tert-butyl, cyclopropylmethyl, $-CH_2CH_2CH_2OCH_3$, $-CH_2CH_2CH_2OH$, $-CH_2$-4-chlorophenyl, $-C(=O)CH_3$, $-C(=O)CH_2N(CH_3)_2$, $-C(=O)NH(phenyl)$, $-C(=O)NH(CH_3)$, $-C(=O)N(CH_3)_2$, $-C(=O)$cyclopropyl, $-CH(OH)$-4-chlorophenyl, $-C(=O)$-4-chlorophenyl, $-C(=O)$-3,4-dichlorophenyl, $-C(=O)CH_2$-piperidin-1-yl, $-C(=O)CH_2$-3-fluoropiperidin-1-yl, $-C(=O)OCH_3$, $CF_3$, isobutyryl, $-C(=O)$-cyclobutyl or $-C(=O)$-cyclopentyl.

In certain embodiments, $R^6$ is hydrogen, Cl, Br, I, CN, cyclohexyl, cyclopentyl, cyclobutyl, cyclopropyl, cyclopentenyl, (2,2-dimethyl-1,3-dioxolan-4-yl)methoxy, phenyl, 2-fluorophenyl, 3-fluorophenyl, 4-fluorophenyl, 3-chlorophenyl, 4-chlorophenyl, 3-methylphenyl, 3-methoxyphenyl, 3-isopropylphenyl, 3-isopropoxyphenyl, 3-trifluoromethylphenyl, 4-trifluoromethylphenyl, 3-morpholinophenyl, 2,5-difluorophenyl, 3,4-difluorophenyl, 3-chloro-4-fluorophenyl, 3,5-difluorophenyl, 3-((dimethylamino)methyl) phenyl, 3-(morpholinomethyl)phenyl, pyridin-3-yl, furan-3-yl, thiopheny-3-yl, 2-methylthiazol-4-yl, 1-methyl-1H-pyrazol-4-yl, 1H-pyrazol-5-yl, 1-benzyl-1H-pyrazol-4-yl, —CH=CH$_2$, —C≡CCH$_2$OH, —C≡CCH$_2$OCH$_3$, methyl, ethyl, tert-butyl, cyclopropylmethyl, —CH$_2$CH$_2$CH$_2$OCH$_3$, —CH$_2$CH$_2$CH$_2$OH, —CH$_2$-4-chlorophenyl, —C(=O)CH$_3$, —C(=O)CH$_2$N(CH$_3$)$_2$, —C(=O)NH(phenyl), —C(=O)NH(CH$_3$), —C(=O)N(CH$_3$)$_2$, —C(=O)cyclopropyl, —CH(OH)-4-chlorophenyl, —C(=O)-4-chlorophenyl, —C(=O)-3,4-dichlorophenyl, —C(=O)CH$_2$-piperidin-1-yl, —C(=O)CH$_2$-3-fluoropiperidin-1-yl, —C(=O)OCH$_3$ or CF$_3$.

In certain embodiments, $R^6$ is hydrogen, Cl, Br, I, CN, cyclohexyl, cyclopentyl, cyclobutyl, cyclopropyl, cyclopentenyl, phenyl, 2-fluorophenyl, 3-fluorophenyl, 4-fluorophenyl, 3-chlorophenyl, 4-chlorophenyl, 3-methylphenyl, 3-methoxyphenyl, 3-isopropylphenyl, 3-isopropoxyphenyl, 3-trifluoromethylphenyl, 4-trifluoromethylphenyl, 3-morpholinophenyl, 2,5-difluorophenyl, 3,4-difluorophenyl, 3-chloro-4-fluorophenyl, 3,5-difluorophenyl, 3-((dimethylamino)methyl)phenyl, 3-(morpholinomethyl)phenyl, pyridin-3-yl, furan-3-yl, thiopheny-3-yl, 2-methylthiazol-4-yl, 1-methyl-1H-pyrazol-4-yl, 1H-pyrazol-5-yl, 1-benzyl-1H-pyrazol-4-yl, —CH=CH$_2$, —C≡CCH$_2$OH, —C≡CCH$_2$OCH$_3$, methyl, ethyl, tert-butyl, cyclopropylmethyl, —CH$_2$CH$_2$CH$_2$OCH$_3$, —CH$_2$CH$_2$CH$_2$OH, —CH$_2$-4-chlorophenyl, —C(=O)CH$_3$, —C(=O)CH$_2$N(CH$_3$)$_2$, —C(=O)NH(phenyl), —C(=O)NH(CH$_3$), —C(=O)N(CH$_3$)$_2$, —C(=O)cyclopropyl, —CH(OH)-4-chlorophenyl, —C(=O)-4-chlorophenyl, —C(=O)-3,4-dichlorophenyl, —C(=O)CH$_2$-piperidin-1-yl, —C(=O)CH$_2$-3-fluoropiperidin-1-yl, —C(=O)OCH$_3$ or CF$_3$.

In certain embodiments, $R^6$ is hydrogen.

In certain embodiments, $R^6$ is halogen. In certain embodiments, $R^6$ is Cl, Br, F or I.

In certain embodiments, $R^6$ is halogen. In certain embodiments, $R^6$ is Cl, Br or I.

In certain embodiments, $R^6$ is CN.

In certain embodiments, $R^6$ is $NR^kR^l$. In certain embodiments, $R^k$ and $R^l$ are independently selected from hydrogen and $C_1$-$C_4$ alkyl. In certain embodiments, $R^6$ is dimethylamino.

In certain embodiments, $R^6$ is $OR^m$. In certain embodiments, $R^m$ is hydrogen or $C_1$-$C_4$ alkyl. In certain embodiments, $R^6$ is ethoxy.

In certain embodiments, $R^6$ is a saturated or partially unsaturated $C_3$-$C_6$ cycloalkyl optionally substituted with halogen or $C_1$-$C_4$ alkyl. In certain embodiments, $R^6$ is a saturated or partially unsaturated $C_3$-$C_6$ cycloalkyl. In certain embodiments, $R^6$ is selected from cyclopropyl, cyclobutyl, cyclopentyl, cyclopentenyl, cyclohexyl and cyclohexenyl.

In certain embodiments, $R^6$ is a saturated $C_3$-$C_6$ cycloalkyl optionally substituted with halogen or $C_1$-$C_4$ alkyl. In certain embodiments, $R^6$ is a saturated $C_3$-$C_6$ cycloalkyl. In certain embodiments, $R^6$ is cyclohexyl, cyclopentyl, cyclobutyl or cyclopropyl.

In certain embodiments, $R^6$ is a partially unsaturated $C_3$-$C_6$ cycloalkyl optionally substituted with halogen or $C_1$-$C_4$ alkyl. In certain embodiments, $R^6$ is a partially unsaturated $C_3$-$C_6$ cycloalkyl. In certain embodiments, $R^6$ is cyclopentenyl.

In certain embodiments, $R^6$ is a saturated or partially unsaturated 4-6 membered heterocyclyl optionally substituted with $C_1$-$C_4$ alkyl. In certain embodiments, $R^6$ is a saturated or partially unsaturated 4-6 membered heterocyclyl optionally substituted with $C_1$-$C_4$ alkyl, wherein the heterocyclyl contains one or two heteroatoms selected from nitrogen and oxygen. In certain embodiments, $R^6$ is a saturated or partially unsaturated 4-6 membered heterocyclyl optionally substituted with $C_1$-$C_4$ alkyl, wherein the heterocyclyl contains two heteroatoms selected from nitrogen and oxygen. In certain embodiments, $R^6$ is a saturated or partially unsaturated 4-6 membered heterocyclyl optionally substituted with $C_1$-$C_4$ alkyl, wherein the heterocyclyl is morpholino. In certain embodiments, $R^6$ is morpholino.

In certain embodiments, $R^6$ is a saturated or partially unsaturated 4-6 membered heterocyclyl.

In certain embodiments, $R^6$ is —O(CH$_2$)$_m$4-6 membered heterocyclyl optionally substituted with $C_1$-$C_3$ alkyl. In certain embodiments, $R^6$ is —O(CH$_2$)$_m$4-6 membered heterocyclyl optionally substituted with $C_1$-$C_3$ alkyl, wherein the heterocyclyl is 1,3-dioxolane. In certain embodiments, m is 0, 1, 2, or 3. In certain embodiments, m is 1. In certain embodiments, $R^6$ is (2,2-dimethyl-1,3-dioxolan-4-yl)methoxy.

In certain embodiments, $R^6$ is phenyl.

In certain embodiments, $R^6$ is phenyl optionally substituted with one to three $R^a$ groups. In certain embodiments, each $R^a$ is independently selected from halogen, CN, CF$_3$, OH, —O(C$_1$-C$_4$ alkyl), a 5-6 membered heterocyclyl, or C$_1$-C$_4$ alkyl optionally substituted with $NR^gR^h$ or a 5-6 membered heterocyclyl. In certain embodiments, each $R^a$ is independently selected from halogen, CN, CF$_3$, —O(C$_1$-C$_4$ alkyl), a 5-6 membered heterocyclyl, or C$_1$-C$_4$ alkyl optionally substituted with $NR^gR^h$ or a 5-6 membered heterocyclyl. In certain embodiments, $R^a$ is a 5-6 membered heterocyclyl, wherein the heterocyclyl is morpholinyl. In certain embodiments, $R^a$ is C$_1$-C$_4$ alkyl optionally substituted with a 5-6 membered heterocyclyl, wherein the heterocyclyl is morpholinyl. In certain embodiments, $R^6$ is phenyl, 2-fluorophenyl, 3-fluorophenyl, 4-fluorophenyl, 3-chlorophenyl, 4-chlorophenyl, 3-methylphenyl, 3-methoxyphenyl, 3-isopropylphenyl, 3-isopropoxyphenyl, 3-trifluoromethylphenyl, 4-trifluoromethylphenyl, 3-morpholinophenyl, 2,5-difluorophenyl, 3,4-difluorophenyl, 3-chloro-4-fluorophenyl, 3,5-difluorophenyl, 3-((dimethylamino)methyl)phenyl or 3-(morpholinomethyl)phenyl.

In certain embodiments, $R^6$ is phenyl optionally substituted with one to three $R^a$ groups. In certain embodiments, $R^6$ is phenyl substituted with one or two $R^a$ groups. In certain embodiments, each $R^a$ is independently selected from halogen, CN, CF$_3$, OH, —O(C$_1$-C$_4$ alkyl), a 5-6 membered heterocyclyl, or C$_1$-C$_4$ alkyl optionally substituted with $NR^gR^h$ or a 5-6 membered heterocyclyl. In certain embodiments, each $R^a$ is independently selected from halogen, CN, CF$_3$, —O(C$_1$-C$_4$ alkyl), a 5-6 membered heterocyclyl, or C$_1$-C$_4$ alkyl optionally substituted with $NR^gR^h$ or a 5-6 membered heterocyclyl. In certain embodiments, $R^a$ is F or Cl. In certain embodiments, $R^a$ is —OCH$_3$ or —OCH(CH$_3$)$_2$. In certain embodiments, $R^a$ is methyl or isopropyl. In certain embodiments, $R^a$ is a 5-6 membered heterocyclyl, wherein the heterocyclyl is morpholinyl. In certain embodiments, $R^a$ is C$_1$-C$_4$ alkyl optionally substituted with a 5-6 membered heterocyclyl, wherein the heterocyclyl is morpholinyl. In certain embodiments, $R^6$ is 2-fluorophenyl, 3-fluorophenyl, 4-fluorophenyl, 3-chlorophenyl, 4-chlorophenyl, 3-methylphenyl, 3-methoxyphenyl, 3-isopropylphenyl, 3-isopropoxyphenyl, 3-trifluoromethylphenyl, 4-trifluoromethylphenyl, 3-morpholinophenyl, 2,5-difluorophenyl, 3,4-difluorophenyl, 3-chloro-4-fluorophenyl, 3,5-difluorophenyl, 3-((dimethylamino)methyl)phenyl or 3-(morpholinomethyl)phenyl.

In certain embodiments, $R^6$ is a 5-6 membered heteroaryl optionally substituted with $C_1$-$C_4$ alkyl or benzyl. In certain embodiments, $R^6$ is a 5-6 membered heteroaryl optionally substituted with $C_1$-$C_4$ alkyl or benzyl, wherein the heteroaryl contains one or two heteroatoms selected from nitrogen, oxygen and sulfur. In certain embodiments, $R^6$ is a 5-6 membered heteroaryl optionally substituted with $C_1$-$C_4$ alkyl or benzyl, wherein the heteroaryl is selected from furan, thiophene, thiazole, pyrazole and pyridine. In certain embodiments, $R^6$ is furan-3-yl, thiopheny-3-yl, 2-methylthiazol-4-yl, 1-methyl-1H-pyrazol-4-yl, 1H-pyrazol-5-yl, 1-benzyl-1H-pyrazol-4-yl or pyridin-3-yl.

In certain embodiments, $R^6$ is a 5-6 membered heteroaryl optionally substituted with $C_1$-$C_4$ alkyl or benzyl. In certain embodiments, $R^6$ is a 6 membered heteroaryl. In certain embodiments, $R^6$ is pyridinyl. In certain embodiments, $R^6$ is pyridin-3-yl.

In certain embodiments, $R^6$ is a 5-6 membered heteroaryl optionally substituted with $C_1$-$C_4$ alkyl or benzyl. In certain embodiments, $R^6$ is a 5 membered heteroaryl optionally substituted with $C_1$-$C_4$ alkyl or benzyl. In certain embodiments, $R^6$ is a 5 membered heteroaryl optionally substituted with methyl. In certain embodiments, $R^6$ is a 5 membered heteroaryl optionally substituted with benzyl. In certain embodiments, $R^6$ is a 5 membered heteroaryl selected from furanyl, thiophenyl, thiazolyl and pyrazolyl. In certain embodiments, $R^6$ is furan-3-yl, thiopheny-3-yl, 2-methylthiazol-4-yl, 1-methyl-1H-pyrazol-4-yl, 1H-pyrazol-5-yl or 1-benzyl-1H-pyrazol-4-yl.

In certain embodiments, $R^6$ is $C_2$-$C_6$ alkenyl optionally substituted with halogen, $OR^g$ or $NR^gR^h$. In certain embodiments, $R^6$ is $C_2$-$C_4$ alkenyl optionally substituted with halogen, $OR^g$ or $NR^gR^h$. In certain embodiments, $R^6$ is $C_2$-$C_4$ alkenyl. In certain embodiments, $R^6$ is —CH=CH$_2$ (vinyl).

In certain embodiments, $R^6$ is $C_1$-$C_4$ alkenyl optionally substituted with $OR^g$. In certain embodiments, $R^6$ is $C_1$-$C_4$ alkenyl. In certain embodiments, $R^6$ is —CH=CH$_2$ (vinyl).

In certain embodiments, $R^6$ is $C_2$-$C_6$ alkynyl optionally substituted with halogen, $OR^g$ or $NR^gR^h$. In certain embodiments, $R^6$ is $C_2$-$C_6$ alkynyl optionally substituted with $OR^g$. In certain embodiments, $R^6$ is $C_2$-$C_4$ alkynyl optionally substituted with halogen, $OR^g$ or $NR^gR^h$. In certain embodiments, $R^g$ is hydrogen or $C_1$-$C_4$ alkyl. In certain embodiments $R^g$ is hydrogen or methyl. In certain embodiments, $R^6$ is —C≡CCH$_2$OH or —C≡CCH$_2$OCH$_3$.

In certain embodiments, $R^6$ is $C_3$-$C_6$ alkynyl optionally substituted with $OR^g$. In certain embodiments, $R^g$ is hydrogen or $C_1$-$C_4$ alkyl. In certain embodiments $R^g$ is hydrogen or methyl. In certain embodiments, $R^6$ is C≡CCH$_2$OH or C≡CCH$_2$OCH$_3$.

In certain embodiments, $R^6$ is $C_1$-$C_6$ alkyl optionally substituted with one to three $R^b$ groups. In certain embodiments, each $R^b$ is independently selected from halogen, OH, OCH$_3$, oxo, —NR$^e$R$^f$, phenyl optionally substituted with a halogen, $C_3$-$C_6$ cycloalkyl, and a 5-6 membered heterocyclyl optionally substituted with halogen. In certain embodiments, $R^b$ is a 5-6 membered heterocyclyl optionally substituted with halogen, wherein the heterocyclyl contains one or two heteroatoms selected from oxygen, nitrogen and sulfur. In certain embodiments, $R^b$ is a 5-6 membered heterocyclyl optionally substituted with halogen, wherein the heterocyclyl is piperidinyl. In certain embodiments, $R^6$ is methyl, ethyl, tert-butyl, cyclopropylmethyl, —CH$_2$CH$_2$CH$_2$OCH$_3$, —CH$_2$CH$_2$CH$_2$OH, —CH$_2$-4-chlorophenyl, —C(=O)CH$_3$, —C(=O)CH$_2$N(CH$_3$)$_2$, —C(=O)NH(phenyl), —C(=O)NH(CH$_3$), —C(=O)N(CH$_3$)$_2$, —C(=O)cyclopropyl, —CH(OH)-4-chlorophenyl, —C(=O)-4-chlorophenyl, —C(=O)-3,4-dichlorophenyl, —C(=O)CH$_2$-piperidin-1-yl, —C(=O)CH$_2$-3-fluoropiperidin-1-yl, —C(=O)OCH$_3$, CF$_3$, isobutyryl (—C(=O)CH(CH$_3$)$_2$), —C(=O)-cyclobutyl or —C(=O)-cyclopentyl.

In certain embodiments, $R^6$ is $C_1$-$C_4$ alkyl optionally substituted with one to three $R^b$ groups. In certain embodiments, each $R^b$ is independently selected from halogen, OH, OCH$_3$, oxo, —NR$^e$R$^f$, phenyl optionally substituted with a halogen, $C_3$-$C_6$ cycloalkyl, and a 5-6 membered heterocyclyl optionally substituted with halogen. In certain embodiments, $R^6$ is methyl, ethyl, tert-butyl, cyclopropylmethyl, —CH$_2$CH$_2$CH$_2$OCH$_3$, —CH$_2$CH$_2$CH$_2$OH, —CH$_2$-4-chlorophenyl, —C(=O)CH$_3$, —C(=O)CH$_2$N(CH$_3$)$_2$, —C(=O)NH(phenyl), —C(=O)NH(CH$_3$), —C(=O)N(CH$_3$)$_2$, —C(=O)cyclopropyl, —CH(OH)-4-chlorophenyl, —C(=O)-4-chlorophenyl, —C(=O)-3,4-dichlorophenyl, —C(=O)CH$_2$-piperidin-1-yl, —C(=O)CH$_2$-3-fluoropiperidin-1-yl, —C(=O)OCH$_3$ or CF$_3$.

In certain embodiments, $R^6$ is $C_1$-$C_4$ alkyl optionally substituted with one to three $R^b$ groups. In certain embodiments, each $R^b$ is independently selected from halogen, OH, OCH$_3$, —NR$^e$R$^f$, phenyl optionally substituted with a halogen, $C_3$-$C_6$ cycloalkyl, and a 5-6 membered heterocyclyl optionally substituted with halogen. In certain embodiments, $R^6$ is methyl, ethyl, tert-butyl, cyclopropylmethyl, —CH$_2$CH$_2$CH$_2$OCH$_3$, —CH$_2$CH$_2$CH$_2$OH, —CH$_2$-4-chlorophenyl, —CH(OH)-4-chlorophenyl, or CF$_3$.

In certain embodiments, $R^6$ is $C_1$-$C_6$ alkyl. In certain embodiments, $R^6$ is methyl, ethyl or tert-butyl.

In certain embodiments, $R^6$ is $C_1$-$C_4$ alkyl. In certain embodiments, $R^6$ is methyl, ethyl or tert-butyl.

In certain embodiments, $R^6$ is $C_1$-$C_6$ alkyl substituted with one $R^b$ group. In certain embodiments, $R^b$ is OH, OCH$_3$, $C_3$-$C_6$ cycloalkyl, oxo or phenyl optionally substituted with a halogen. In certain embodiments, $R^6$ is —CH$_2$CH$_2$CH$_2$OCH$_3$, —CH$_2$CH$_2$CH$_2$OH, —CH$_2$-4-chlorophenyl, cyclopropylmethyl, —C(=O)CH$_3$ or isobutyryl.

In certain embodiments, $R^6$ is $C_1$-$C_4$ alkyl substituted with one $R^b$ group. In certain embodiments, $R^b$ is OH or OCH$_3$. In certain embodiments, $R^6$ is —CH$_2$CH$_2$CH$_2$OCH$_3$ or —CH$_2$CH$_2$CH$_2$OH.

In certain embodiments, $R^6$ is $C_1$-$C_4$ alkyl substituted with one $R^b$ group. In certain embodiments, $R^b$ is phenyl optionally substituted with a halogen. In certain embodiments, $R^b$ is phenyl substituted with Cl. In certain embodiments, $R^6$ is —CH$_2$-4-chlorophenyl.

In certain embodiments, $R^6$ is $C_1$-$C_4$ alkyl substituted with one $R^b$ group. In certain embodiments, $R^b$ is $C_3$-$C_6$ cycloalkyl. In certain embodiments, $R^6$ is cyclopropylmethyl.

In certain embodiments, $R^6$ is $C_1$-$C_6$ alkyl substituted with one $R^b$ group. In certain embodiments, $R^6$ is $C_1$-$C_4$ alkyl substituted with one $R^b$ group. In certain embodiments, $R^b$ is oxo. In certain embodiments, $R^6$ is —C(=O)CH$_3$ or isobutyryl.

In certain embodiments, $R^6$ is $C_1$-$C_4$ alkyl substituted with one $R^b$ group. In certain embodiments, $R^b$ is oxo. In certain embodiments, $R^6$ is —C(=O)CH$_3$.

In certain embodiments, $R^6$ is $C_1$-$C_6$ alkyl substituted with one to three $R^b$ groups. In certain embodiments, each $R^b$ is independently selected from oxo, —NR$^e$R$^f$, OH, OCH$_3$, $C_3$-$C_6$ cycloalkyl, phenyl optionally substituted with a halogen, or a 5-6 membered heterocyclyl optionally substituted with halogen. In certain embodiments, each $R^e$ and $R^f$ are independently selected from H, $C_1$-$C_4$ alkyl and phenyl. In certain embodiments, $R^6$ is $C_1$-$C_4$ alkyl substituted with two $R^b$ groups. In certain embodiments, $R^6$ is —C(=O)CH$_2$N(CH$_3$)$_2$, —C(=O)NH(phenyl), —C(=O)NH(CH$_3$), —C(═O)N(CH$_3$)$_2$, —CH(OH)-4-chlorophenyl, —C(═O)-4-chlorophenyl, —C(═O)-3,4-dichlorophenyl, —C(═O)CH$_2$-piperidin-1-yl, —C(═O)CH$_2$-3-fluoropiperidin-1-yl, —C(═O)OCH$_3$, —C(═O)-cyclopropyl, —C(═O)-cyclobutyl or —C(═O)-cyclopentyl.

In certain embodiments, $R^6$ is $C_1$-$C_4$ alkyl substituted with one to three $R^b$ groups. In certain embodiments, each $R^b$ is independently selected from oxo or —NR$^e$R$^f$. In certain embodiments, $R^d$ and $R^e$ are independently selected from H, $C_1$-$C_4$ alkyl or phenyl. In certain embodiments, $R^6$ is $C_1$-$C_4$ alkyl substituted with two $R^b$ groups. In certain embodiments, $R^6$ is —C(═O)CH$_2$N(CH$_3$)$_2$, —C(═O)NH(phenyl), —C(═O)NH(CH$_3$) or —C(═O)N(CH$_3$)$_2$.

In certain embodiments, $R^6$ is $C_1$-$C_4$ alkyl substituted with one to three $R^b$ groups. In certain embodiments, each $R^b$ is independently selected from OH or phenyl optionally substituted with a halogen. In certain embodiments, $R^b$ is phenyl substituted with Cl. In certain embodiments, $R^6$ is $C_1$-$C_4$ alkyl substituted with two $R^b$ groups. In certain embodiments, —CH(OH)-4-chlorophenyl.

In certain embodiments, $R^6$ is $C_1$-$C_4$ alkyl optionally substituted with one to three $R^b$ groups. In certain embodiments, each $R^b$ is selected from oxo and phenyl optionally substituted with halogen. In certain embodiments, $R^b$ is 4-chlorophenyl or 3,4-dichlorophenyl. In certain embodiments, $R^6$ is $C_1$-$C_4$ alkyl substituted with two $R^b$ groups. In certain embodiments, $R^6$ is —C(═O)-4-chlorophenyl or —C(═O)-3,4-dichlorophenyl.

In certain embodiments, $R^6$ is $C_1$-$C_4$ alkyl optionally substituted with one to three $R^b$ groups. In certain embodiments, each $R^b$ is selected from oxo and a 5-6 membered heterocyclyl optionally substituted with halogen. In certain embodiments, $R^b$ is piperidinyl optionally substituted with a halogen. In certain embodiments, $R^6$ is $C_1$-$C_4$ alkyl substituted with two $R^b$ groups. In certain embodiments, $R^6$ is —C(═O)CH$_2$-piperidin-1-yl or —C(═O)CH$_2$-3-fluoropiperidin-1-yl.

In certain embodiments, $R^6$ is $C_1$-$C_4$ alkyl substituted with one to three $R^b$ groups. In certain embodiments, each $R^b$ is independently selected from oxo or OCH$_3$. In certain embodiments, $R^6$ is $C_1$-$C_4$ alkyl substituted with two $R^b$ groups. In certain embodiments, $R^6$ is —C(═O)OCH$_3$.

In certain embodiments, $R^6$ is $C_1$-$C_6$ alkyl substituted with one to three $R^b$ groups. In certain embodiments, each $R^b$ is independently selected from oxo and $C_3$-$C_6$ cycloalkyl. In certain embodiments, each $R^b$ is independently selected from oxo and $C_3$-$C_6$ cycloalkyl, wherein the cycloalkyl is selected from cyclopropyl, cyclobutyl and cyclopentyl. In certain embodiments, $R^6$ is $C_1$-$C_4$ alkyl substituted with two $R^b$ groups. In certain embodiments, $R^6$ is —C(═O)-cyclopropyl, —C(═O)-cyclobutyl or —C(═O)-cyclopentyl.

In certain embodiments, $R^6$ is $C_1$-$C_6$ alkyl substituted with at least one $R^b$ group. In certain embodiments, $R^6$ is $C_1$-$C_6$ alkyl substituted with oxo. In certain embodiments, $R^6$ is —C(═O)($C_1$-$C_5$ alkyl), wherein the alkyl is optionally substituted with one or two $R^{b1}$ groups, wherein $R^{b1}$ is independently selected from halogen, OH, —OCH$_3$, —NR$^e$R$^f$, phenyl optionally substituted with a halogen, $C_3$-$C_6$ cycloalkyl, or a 5-6 membered heterocyclyl optionally substituted with halogen. In certain embodiments, $R^6$ is —C(═O)CH$_3$, isobutyryl, —C(═O)CH$_2$N(CH$_3$)$_2$, —C(═O)NH(phenyl), —C(═O)NH(CH$_3$), —C(═O)N(CH$_3$)$_2$, —C(═O)cyclopropyl, —C(═O)-4-chlorophenyl, —C(═O)-3,4-dichlorophenyl, —C(═O)CH$_2$-piperidin-1-yl, —C(═O)CH$_2$-3-fluoropiperidin-1-yl, —C(═O)OCH$_3$, —C(═O)-cyclobutyl or —C(═O)-cyclopentyl.

In certain embodiments, $R^6$ is $C_1$-$C_4$ alkyl substituted with at least one $R^b$ group. In certain embodiments, $R^6$ is $C_1$-$C_4$ alkyl substituted with oxo. In certain embodiments, $R^6$ is —C(═O)$C_1$-$C_3$ alkyl optionally substituted with one or two $R^{b1}$ groups, wherein $R^{b1}$ is independently selected from halogen, OH, —OCH$_3$, —NR$^e$R$^f$, phenyl optionally substituted with a halogen, $C_3$-$C_6$ cycloalkyl, or a 5-6 membered heterocyclyl optionally substituted with halogen. In certain embodiments, $R^6$ is —C(═O)CH$_3$, —C(═O)CH$_2$N(CH$_3$)$_2$, —C(═O)NH(phenyl), —C(═O)NH(CH$_3$), —C(═O)N(CH$_3$)$_2$, —C(═O)cyclopropyl, —C(═O)-4-chlorophenyl, —C(═O)-3,4-dichlorophenyl, —C(═O)CH$_2$-piperidin-1-yl, —C(═O)CH$_2$-3-fluoropiperidin-1-yl or —C(═O)OCH$_3$.

In certain embodiments, $R^6$ is $C_1$-$C_4$ alkyl substituted with one to three $R^b$ groups. In certain embodiments, each $R^b$ is halogen. In certain embodiments, $R^6$ is $C_1$-$C_4$ alkyl substituted with three $R^b$ groups. In certain embodiments, $R^b$ is F. In certain embodiments, $R^6$ is CF$_3$.

In certain embodiments, $R^6$ is $C_1$-$C_2$ alkyl optionally substituted by one to three F, $C_1$-$C_2$ alkyl optionally substituted by oxo and —NR$^e$R$^f$ $C_1$-$C_2$ alkyl optionally substituted by oxo and phenyl optionally substituted by halogen, $C_1$-$C_2$ alkyl optionally substituted by oxo and —OCH$_3$, $C_1$-$C_2$ alkyl optionally substituted by OH and phenyl optionally substituted by halogen, $C_1$-$C_2$ alkyl optionally substituted by oxo and a 5-6 membered heterocyclyl optionally substituted with halogen, or $C_1$-$C_3$ alkyl optionally substituted by —OCH$_3$ or OH.

In certain embodiments, $R^5$ is hydrogen, halogen, CN, NR$^k$R$^l$, $C_1$-$C_6$ alkyl optionally substituted with halogen, OR$^g$ or NR$^g$R$^h$, $C_2$-$C_6$ alkenyl optionally substituted with halogen, OR$^g$ or NR$^g$R$^h$, $C_2$-$C_6$ alkynyl optionally substituted with halogen, OR$^g$ or NR$^g$R$^h$, a saturated or partially unsaturated $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, a 5-6 membered heteroaryl optionally substituted with R$^c$, a 9-10 membered bicyclic heterocyclyl optionally substituted with $C_1$-$C_4$ alkyl, a 9-10 membered bicyclic heteroaryl optionally substituted with $C_1$-$C_4$ alkyl, or phenyl optionally substituted with R$^d$.

In certain embodiments, $R^5$ is hydrogen, halogen, CN, $C_1$-$C_4$ alkyl optionally substituted with OR$^g$ or NR$^g$R$^h$, $C_3$-$C_6$ alkynyl optionally substituted with OR$^g$ or NR$^g$R$^h$, a saturated or partially unsaturated $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, a 5-6 membered heteroaryl optionally substituted with R$^c$, a 9-10 membered bicyclic heterocyclyl, a 9-10 membered bicyclic heteroaryl optionally substituted with $C_1$-$C_4$ alkyl, or phenyl optionally substituted with R$^d$.

In certain embodiments, $R^5$ is hydrogen, CN, NR$^k$R$^l$, $C_1$-$C_6$ alkyl optionally substituted with halogen, oxo, OR$^g$ or NR$^g$R$^h$, $C_2$-$C_6$ alkenyl optionally substituted with halogen, OR$^g$ or NR$^g$R$^h$, $C_2$-$C_6$ alkynyl optionally substituted with halogen, OR$^g$ or NR$^g$R$^h$, a saturated or partially unsaturated $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, a 5-6 membered heteroaryl optionally substituted with R$^c$, a 9-10 membered bicyclic heterocyclyl optionally substituted with $C_1$-$C_4$ alkyl, a 9-10 membered bicyclic heteroaryl optionally substituted with $C_1$-$C_4$ alkyl, or phenyl optionally substituted with R$^d$.

In certain embodiments, $R^5$ is hydrogen, CN, $C_1$-$C_4$ alkyl optionally substituted with OR$^g$ or NR$^g$R$^h$, $C_3$-$C_6$ alkynyl optionally substituted with OR$^g$ or NR$^g$R$^h$, a saturated or partially unsaturated $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, a 5-6 membered heteroaryl optionally substituted with $R^c$, a 9-10 membered bicyclic heterocyclyl, a 9-10 membered bicyclic heteroaryl optionally substituted with $C_1$-$C_4$ alkyl, or phenyl optionally substituted with $R^d$.

In certain embodiments, $R^5$ is CN, $NR^kR^l$, $C_1$-$C_6$ alkyl optionally substituted with halogen, oxo, $OR^g$ or $NR^gR^h$, $C_2$-$C_6$ alkenyl optionally substituted with halogen, $OR^g$ or $NR^gR^h$, $C_2$-$C_6$ alkynyl optionally substituted with halogen, $OR^g$ or $NR^gR^h$, a saturated or partially unsaturated $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, a 5-6 membered heteroaryl optionally substituted with $R^c$, a 9-10 membered bicyclic heterocyclyl optionally substituted with $C_1$-$C_4$ alkyl, a 9-10 membered bicyclic heteroaryl optionally substituted with $C_1$-$C_4$ alkyl, or phenyl optionally substituted with $R^d$.

In certain embodiments, $R^5$ is CN, $C_1$-$C_4$ alkyl optionally substituted with $OR^g$ or $NR^gR^h$, $C_3$-$C_6$ alkynyl optionally substituted with $OR^g$ or $NR^gR^h$, a saturated or partially unsaturated $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, a 5-6 membered heteroaryl optionally substituted with $R^c$, a 9-10 membered bicyclic heterocyclyl, a 9-10 membered bicyclic heteroaryl optionally substituted with $C_1$-$C_4$ alkyl, or phenyl optionally substituted with $R^d$.

In certain embodiments, $R^c$ is —$NR^hR^j$, $C_1$-$C_4$ alkyl, or a 5-6 membered heterocyclyl optionally substituted by $C_1$-$C_4$ alkyl or —$(CH_2)_pC_3$-$C_6$ cycloalkyl. In certain embodiments, p is 0 or 1.

In certain embodiments, $R^d$ is halogen, CN, $NR^gR^h$, phenyl, a 5-6 membered heterocyclyl, —$O(C_1$-$C_4$ alkyl) or $C_1$-$C_4$ alkyl, wherein the alkyl or alkoxy are optionally substituted with halogen, OH, oxo, —$O(C_1$-$C_3$ alkyl), $NR^gR^h$, or a 5-6 membered heterocyclyl optionally substituted with $C_1$-$C_3$ alkyl.

In certain embodiments, $R^g$ is hydrogen or $C_1$-$C_4$ alkyl.
In certain embodiments, $R^h$ is hydrogen or $C_1$-$C_4$ alkyl.
In certain embodiments, $R^j$ is hydrogen or $C_1$-$C_4$ alkyl optionally substituted with a 5-6 membered heterocyclyl.
In certain embodiments, $R^k$ is hydrogen or $C_1$-$C_4$ alkyl.
In certain embodiments, $R^l$ is hydrogen or $C_1$-$C_4$ alkyl.

In certain embodiments, $R^5$ is hydrogen, halogen, CN, $NR^kR^l$, $C_1$-$C_6$ alkyl optionally substituted with halogen, oxo, $OR^g$ or $NR^gR^h$, $C_2$-$C_6$ alkynyl optionally substituted with $OR^g$ or $NR^gR^h$, a saturated $C_3$-$C_6$ cycloalkyl, a saturated or partially unsaturated 4-6 membered heterocyclyl optionally substituted with $C_1$-$C_4$ alkyl, a 5-6 membered heteroaryl optionally substituted with $R^c$, a 9-10 membered bicyclic heterocyclyl, a 9-10 membered bicyclic heteroaryl optionally substituted with $C_1$-$C_4$ alkyl, or phenyl optionally substituted with $R^d$.

In certain embodiments, $R^5$ is hydrogen, halogen, CN, $C_1$-$C_4$ alkyl optionally substituted with OH or $NR^gR^h$, $C_3$-$C_6$ alkynyl optionally substituted with OH or $NR^gR^h$, a saturated or partially unsaturated $C_3$-$C_6$ cycloalkyl, a saturated or partially unsaturated 4-6 membered heterocyclyl optionally substituted with $C_1$-$C_4$ alkyl, a 5-6 membered heteroaryl optionally substituted with $R^c$, a 9-10 membered bicyclic heterocyclyl, a 9-10 membered bicyclic heteroaryl optionally substituted with $C_1$-$C_4$ alkyl, or phenyl optionally substituted with $R^d$.

In certain embodiments, $R^5$ is CN, $NR^kR^l$, $C_1$-$C_6$ alkyl optionally substituted with halogen, oxo, $OR^g$ or $NR^gR^h$, $C_2$-$C_6$ alkynyl optionally substituted with $OR^g$ or $NR^gR^h$, a saturated $C_3$-$C_6$ cycloalkyl, a saturated or partially unsaturated 4-6 membered heterocyclyl optionally substituted with $C_1$-$C_4$ alkyl, a 5-6 membered heteroaryl optionally substituted with $R^c$, a 9-10 membered bicyclic heterocyclyl, a 9-10 membered bicyclic heteroaryl optionally substituted with $C_1$-$C_4$ alkyl, or phenyl optionally substituted with $R^d$.

In certain embodiments, $R^5$ is hydrogen, CN, $C_1$-$C_4$ alkyl optionally substituted with OH or $NR^gR^h$, $C_3$-$C_6$ alkynyl optionally substituted with OH or $NR^gR^h$, a saturated or partially unsaturated $C_3$-$C_6$ cycloalkyl, a saturated or partially unsaturated 4-6 membered heterocyclyl optionally substituted with $C_1$-$C_4$ alkyl, a 5-6 membered heteroaryl optionally substituted with $R^c$, a 9-10 membered bicyclic heterocyclyl, a 9-10 membered bicyclic heteroaryl optionally substituted with $C_1$-$C_4$ alkyl, or phenyl optionally substituted with $R^d$.

In certain embodiments, $R^5$ is CN, $NR^kR^l$, $C_1$-$C_6$ alkyl optionally substituted with halogen, oxo, $OR^g$ or $NR^gR^h$, $C_2$-$C_6$ alkynyl optionally substituted with $OR^g$ or $NR^gR^h$, a saturated $C_3$-$C_6$ cycloalkyl, a saturated or partially unsaturated 4-6 membered heterocyclyl optionally substituted with $C_1$-$C_4$ alkyl, a 5-6 membered heteroaryl optionally substituted with $R^c$, a 9-10 membered bicyclic heterocyclyl, a 9-10 membered bicyclic heteroaryl optionally substituted with $C_1$-$C_4$ alkyl, or phenyl optionally substituted with $R^d$.

In certain embodiments, $R^5$ is CN, $C_1$-$C_4$ alkyl optionally substituted with OH or $NR^gR^h$, $C_3$-$C_6$ alkynyl optionally substituted with OH or $NR^gR^h$, a saturated or partially unsaturated $C_3$-$C_6$ cycloalkyl, a saturated or partially unsaturated 4-6 membered heterocyclyl optionally substituted with $C_1$-$C_4$ alkyl, a 5-6 membered heteroaryl optionally substituted with $R^c$, a 9-10 membered bicyclic heterocyclyl, a 9-10 membered bicyclic heteroaryl optionally substituted with $C_1$-$C_4$ alkyl, or phenyl optionally substituted with $R^d$.

In certain embodiments, $R^5$ is hydrogen, Br, I, CN, dimethylamino, methyl, ethyl, difluoromethyl, trifluoromethyl, —$CH_2OH$, —$CH_2OCH_3$, —$CH_2CH_2CH_2OH$, —$CH_2CH_2CH_2N(CH_3)_2$, —$CH_2N(CH_3)_2$, —$CH(OH)CH_3$, —C(=O)$CH_3$, —C≡CH, —C≡$CCH_2OH$, —C≡$CCH_2N(CH_3)_2$, cyclopropyl, 1-methyl-1,2,3,6-tetrahydropyridin-4-yl, 1-methylpiperidin-4-yl, 1-methyl-1H-imidazol-5-yl, pyridin-2-yl, pyridin-3-yl, 6-(dimethylamino)pyridin-3-yl, 6-(piperazin-1-yl)pyridin-3-yl, 6-(4-methylpiperazin-1-yl) pyridin-3-yl, 2-(4-methylpiperazin-1-yl)pyridin-4-yl, 6-aminopyridin-3-yl, 6-(2-morpholinoethylamino)pyridin-3-yl, 6-(4-isopropylpiperazin-1-yl)pyridin-3-yl, 6-(4-(cyclopropylmethyl)piperazin-1-yl)pyridin-3-yl, 1H-pyrazol-4-yl, 1-methyl-1H-pyrazol-4-yl, 6-morpholinopyridin-3-yl, 2,3-dihydrobenzofuran-5-yl, 1H-indol-5-yl, 1-methyl-1H-indol-5-yl, phenyl, 2-fluorophenyl, 3-fluorophenyl, 4-fluorophenyl, 2-chlorophenyl, 3-chlorophenyl, 4-chlorophenyl, 3-(dimethylamino)phenyl, 3-(OCH$_2$CH$_2$OCH$_2$CH$_3$)phenyl, 3-(OCH$_2$CH(OH)CH$_2$OH)phenyl, 3-((2,2-dimethyl-1,3-dioxolan-4-yl)methoxy)phenyl, 3-(OCH$_2$CH$_2$N(CH$_3$)$_2$)phenyl, 4-(OCH$_2$CH$_2$N(CH$_3$)$_2$)phenyl, 4-morpholinophenyl, 3-((dimethylamino)methyl)phenyl, 4-acetylphenyl, biphenyl-4-yl, 4-(4-methylpiperazine-1-carbonyl)phenyl or 4-(dimethylamino)phenyl.

In certain embodiments, $R^5$ is hydrogen, I, CN, methyl, —CH$_2$CH$_2$CH$_2$OH, —CH$_2$CH$_2$CH$_2$N(CH$_3$)$_2$, —C≡CCH$_2$OH, —C≡CCH$_2$N(CH$_3$)$_2$, cyclopropyl, 1-methyl-1,2,3,6-tetrahydropyridin-4-yl, 1-methyl-1H-imidazol-5-yl, pyridin-2-yl, pyridin-3-yl, 6-(dimethylamino)pyridin-3-yl, 6-(piperazin-1-yl)pyridin-3-yl, 6-(4-methylpiperazin-1-yl)pyridin-3-yl, 2-(4-methylpiperazin-1-yl)pyridin-4-yl, 6-aminopyridin-3-yl, 6-(2-morpholinoethylamino)pyridin- 3-yl, 6-(4-isopropylpiperazin-1-yl)pyridin-3-yl, 6-(4-(cyclopropylmethyl)piperazin-1-yl)pyridin-3-yl, 1H-pyrazol-4-yl, 1-methyl-1H-pyrazol-4-yl, 2,3-dihydrobenzofuran-5-yl, 1H-indol-5-yl, 1-methyl-1H-indol-5-yl, phenyl, 2-fluorophenyl, 3-fluorophenyl, 4-fluorophenyl, 2-chlorophenyl, 3-chlorophenyl, 4-chlorophenyl, 3-(dimethylamino)phenyl, 3-(OCH$_2$CH$_2$OCH$_2$CH$_3$)phenyl, 3-(OCH$_2$CH(OH)CH$_2$OH) phenyl, 3-(OCH$_2$CH$_2$N(CH$_3$)$_2$)phenyl, 4-(OCH$_2$CH$_2$N (CH$_3$)$_2$)phenyl, 4-morpholinophenyl, 3-((dimethylamino) methyl)phenyl, 3-cyanophenyl, 4-acetylphenyl, biphenyl-4-yl or 4-(4-methylpiperazine-1-carbonyl)phenyl.

In certain embodiments, $R^5$ is hydrogen.

In certain embodiments, $R^5$ is halogen. In certain embodiments, $R^5$ is selected from F, Cl, Br and I. In certain embodiments, $R^5$ is halogen. In certain embodiments, $R^5$ is selected from Br and I.

In certain embodiments, $R^5$ is halogen. In certain embodiments, $R^5$ is I.

In certain embodiments, $R^5$ is CN.

In certain embodiments, $R^5$ is $NR^kR^l$. In certain embodiments, each $R^k$ and $R^l$ are independently selected from hydrogen and $C_1$-$C_4$ alkyl. In certain embodiments, $R^5$ is dimethylamino.

In certain embodiments, $R^5$ is $C_1$-$C_6$ alkyl optionally substituted with halogen, oxo, $OR^g$ or $NR^gR^h$. In certain embodiments, each $R^g$ and $R^h$ are independently selected from hydrogen and $C_1$-$C_4$ alkyl. In certain embodiments, $R^g$ and $R^h$ are hydrogen or methyl. In certain embodiments, $R^5$ is methyl, ethyl, difluoromethyl, trifluoromethyl, —CH$_2$OH, —CH$_2$OCH$_3$, —CH$_2$CH$_2$CH$_2$OH, —CH$_2$CH$_2$CH$_2$N(CH$_3$)$_2$, —CH$_2$N(CH$_3$)$_2$, —CH(OH)CH$_3$, or —C(=O)CH$_3$.

In certain embodiments, $R^5$ is $C_1$-$C_4$ alkyl optionally substituted with $OR^g$ or $NR^gR^h$. In certain embodiments, $R^5$ is $C_1$-$C_4$ alkyl optionally substituted with OH or $NR^gR^h$. In certain embodiments, $R^g$ and $R^h$ are independently selected from hydrogen or $C_1$-$C_4$ alkyl. In certain embodiments, $R^g$ and $R^h$ are methyl. In certain embodiments, $R^5$ is methyl, —CH$_2$CH$_2$CH$_2$OH or —CH$_2$CH$_2$CH$_2$N(CH$_3$)$_2$.

In certain embodiments, $R^5$ is $C_2$-$C_6$ alkenyl optionally substituted with halogen, $OR^g$ or $NR^gR^h$.

In certain embodiments, $R^5$ is $C_2$-$C_6$ alkynyl optionally substituted with halogen, $OR^g$ or $NR^gR^h$. In certain embodiments, $R^5$ is $C_2$-$C_6$ alkynyl optionally substituted with $OR^g$ or $NR^gR^h$. In certain embodiments, $R^5$ is $C_2$-$C_6$ alkynyl optionally substituted with OH or $NR^gR^h$. In certain embodiments, each $R^g$ and $R^h$ are independently selected from hydrogen and $C_1$-$C_4$ alkyl. In certain embodiments, $R^5$ is —C≡CH, —C≡CCH$_2$OH or —C≡CCH$_2$N(CH$_3$)$_2$.

In certain embodiments, $R^5$ is $C_3$-$C_6$ alkynyl optionally substituted with $OR^g$ or $NR^gR^h$. In certain embodiments, $R^5$ is $C_3$-$C_6$ alkynyl optionally substituted with OH or $NR^gR^h$. In certain embodiments, $R^g$ and $R^h$ are independently selected from hydrogen or $C_1$-$C_4$ alkyl. In certain embodiments, $R^5$ is $C_3$ alkynyl optionally substituted with OH or $NR^gR^h$. In certain embodiments, $R^5$ is —C≡CCH$_2$OH or —C≡CCH$_2$N(CH$_3$)$_2$.

In certain embodiments, $R^5$ is saturated or partially unsaturated $C_3$-$C_6$ cycloalkyl optionally substituted with halogen or $C_1$-$C_4$ alkyl.

In certain embodiments, $R^5$ is a saturated $C_3$-$C_6$ cycloalkyl optionally substituted with halogen or $C_1$-$C_4$ alkyl. In certain embodiments, $R^5$ is saturated $C_3$-$C_6$ cycloalkyl. In certain embodiments, $R^5$ is cyclopropyl.

In certain embodiments, $R^5$ is a saturated or partially unsaturated 4-6 membered heterocyclyl optionally substituted with $C_1$-$C_4$ alkyl.

In certain embodiments, $R^5$ is a saturated or partially unsaturated 4-6 membered heterocyclyl optionally substituted with $C_1$-$C_4$ alkyl. In certain embodiments, $R^5$ is a saturated or partially unsaturated 4-6 membered heterocyclyl optionally substituted with $C_1$-$C_4$ alkyl, wherein the heterocyclyl contains one or two heteroatoms selected from oxygen, nitrogen and sulfur. In certain embodiments, $R^5$ is a saturated or partially unsaturated 4-6 membered heterocyclyl optionally substituted with $C_1$-$C_4$ alkyl, wherein the heterocyclyl contains a nitrogen heteroatom. In certain embodiments, $R^5$ is a saturated or partially unsaturated 4-6 membered heterocyclyl optionally substituted with $C_1$-$C_4$ alkyl, wherein the heterocyclyl is selected from tetrahyrdopyridine and piperidine. In certain embodiments, $R^5$ is 1-methyl-1,2,3,6-tetrahydropyridin-4-yl or 1-methylpiperidin-4-yl.

In certain embodiments, $R^5$ is a partially unsaturated 4-6 membered heterocyclyl optionally substituted with $C_1$-$C_4$ alkyl. In certain embodiments, $R^5$ is a partially unsaturated 4-6 membered heterocyclyl optionally substituted with $C_1$-$C_4$ alkyl, wherein the heterocyclyl is 1,2,3,6-tetrahydropyridinyl. In certain embodiments, $R^5$ is 1-methyl-1,2,3,6-tetrahydropyridin-4-yl.

In certain embodiments, $R^5$ is a saturated 4-6 membered heterocyclyl optionally substituted with $C_1$-$C_4$ alkyl. In certain embodiments, $R^5$ is a saturated 4-6 membered heterocyclyl optionally substituted with $C_1$-$C_4$ alkyl, wherein the heterocyclyl contains one or two heteroatoms selected from oxygen, nitrogen and sulfur. In certain embodiments, $R^5$ is a saturated 4-6 membered heterocyclyl optionally substituted with $C_1$-$C_4$ alkyl, wherein the heterocyclyl contains one nitrogen heteroatom. In certain embodiments, $R^5$ is a saturated 4-6 membered heterocyclyl optionally substituted with $C_1$-$C_4$ alkyl, wherein the heterocyclyl is piperidine. In certain embodiments, $R^5$ is 1-methylpiperidin-4-yl.

In certain embodiments, $R^5$ is a 5-6 membered heteroaryl optionally substituted with $R^c$. In certain embodiments, $R^5$ is a 5-6 membered heteroaryl optionally substituted with $R^c$, wherein the heteroaryl contains one or two heteroatoms selected from oxygen, nitrogen and sulfur. In certain embodiments, $R^5$ is a 5-6 membered heteroaryl optionally substituted with $R^c$, wherein the heteroaryl contains one or two nitrogen heteroatoms. In certain embodiments, $R^5$ is a 5-6 membered heteroaryl optionally substituted with $R^c$, wherein the heteroaryl is selected from pyridinyl, pyrazolyl and imidazolyl. In certain embodiments, $R^5$ is selected from 1-methyl-1H-imidazol-5-yl, pyridin-2-yl, pyridin-3-yl, 6-(dimethylamino) pyridin-3-yl, 6-(piperazin-1-yl)pyridin-3-yl, 6-(4-methylpiperazin-1-yl)pyridin-3-yl, 2-(4-methylpiperazin-1-yl)pyridin-4-yl, 6-aminopyridin-3-yl, 6-(2-morpholinoethylamino) pyridin-3-yl, 6-(4-isopropylpiperazin-1-yl)pyridin-3-yl, 6-(4-(cyclopropylmethyl)piperazin-1-yl)pyridin-3-yl, 1H-pyrazol-4-yl, 1-methyl-1H-pyrazol-4-yl or 6-morpholinopyridin-3-yl.

In certain embodiments, $R^5$ is a 5-6 membered heteroaryl optionally substituted with $R^c$. In certain embodiments, $R^5$ is a 5-6 membered heteroaryl optionally substituted with $R^c$, wherein the heteroaryl is selected from imidazolyl, pyridinyl and pyrazolyl. In certain embodiments, $R^c$ is —$NR^hR^j$, $C_1$-$C_4$ alkyl or a 5-6 membered heterocyclyl optionally substituted by $C_1$-$C_4$ alkyl or —(CH$_2$)$_p$C$_3$-$C_6$ cycloalkyl. In certain embodiments, p is 0 or 1. In certain embodiments, $R^h$ is independently selected from hydrogen and $C_1$-$C_4$ alkyl. In certain embodiments, $R^j$ is hydrogen or $C_1$-$C_4$ alkyl optionally substituted with a 5-6 membered heterocyclyl. In certain embodiments, $R^j$ is hydrogen or $C_1$-$C_4$ alkyl. In certain embodiments, $R^1$ is $C_1$-$C_4$ alkyl optionally substituted with a 5-6 membered heterocyclyl. In certain embodiments, $R^1$ is $C_1$-$C_4$ alkyl optionally substituted with a 5-6 membered heterocyclyl, wherein the heterocyclyl is morpholinyl. In certain embodiments, $R^c$ is a 5-6 membered heterocyclyl optionally substituted by $C_1$-$C_4$ alkyl or —$(CH_2)_pC_3$-$C_6$ cycloalkyl. In certain embodiments, $R^c$ is a 5-6 membered heterocyclyl optionally substituted by $C_1$-$C_4$ alkyl or —$(CH_2)_pC_3$-$C_6$ cycloalkyl, wherein the heterocyclyl is piperazinyl. In certain embodiments, p is 0 or 1. In certain embodiments, $R^5$ is selected from 1-methyl-1H-imidazol-5-yl, pyridin-2-yl, pyridin-3-yl, 6-(dimethylamino)pyridin-3-yl, 6-(piperazin-1-yl)pyridin-3-yl, 6-(4-methylpiperazin-1-yl)pyridin-3-yl, 2-(4-methylpiperazin-1-yl)pyridin-4-yl, 6-aminopyridin-3-yl, 6-(2-morpholinoethylamino)pyridin-3-yl, 6-(4-isopropylpiperazin-1-yl)pyridin-3-yl, 6-(4-(cyclopropylmethyl)piperazin-1-yl)pyridin-3-yl, 1H-pyrazol-4-yl or 1-methyl-1H-pyrazol-4-yl.

In certain embodiments, $R^5$ is a 5-6 membered heteroaryl selected from pyridyl, pyrazolyl and imidazolyl, wherein the heteroaryl is optionally substituted by —$NR^hR^j$, $C_1$-$C_4$ alkyl or a 5-6 membered heterocyclyl optionally substituted by $C_1$-$C_4$ alkyl.

In certain embodiments, $R^5$ is a 5 membered heteroaryl optionally substituted with $R^c$. In certain embodiments, $R^5$ is imidazolyl or pyrazolyl optionally substituted with $R^c$. In certain embodiments, $R^c$ is $C_1$-$C_4$ alkyl. In certain embodiments, $R^c$ is methyl. In certain embodiments, $R^5$ is 1-methyl-1H-imidazol-5-yl or 1-methyl-1H-pyrazol-4-yl.

In certain embodiments, $R^5$ is a 6 membered heteroaryl. In certain embodiments, $R^5$ is pyridinyl. In certain embodiments, $R^5$ is pyridin-2-yl or pyridin-3-yl.

In certain embodiments, $R^5$ is a 6 membered heteroaryl optionally substituted with $R^c$. In certain embodiments, $R^c$ is —$NR^hR^j$, $C_1$-$C_4$ alkyl, or a 5-6 membered heterocyclyl optionally substituted by $C_1$-$C_4$ alkyl or —$(CH_2)_pC_3$-$C_6$ cycloalkyl. In certain embodiments, p is 0 or 1. In certain embodiments, $R^c$ is —$NR^hR^j$. In certain embodiments $R^h$ and $R^j$ are methyl. In certain embodiments, $R^c$ is a 5-6 membered heterocyclyl optionally substituted by $C_1$-$C_4$ alkyl or —$(CH_2)_pC_3$-$C_6$ cycloalkyl, wherein the heterocyclyl is piperazinyl optionally substituted with $C_1$-$C_4$ alkyl or —$(CH_2)_pC_3$-$C_6$ cycloalkyl. In certain embodiments, $R^5$ is pyridinyl optionally substituted with $R^c$. In certain embodiments, $R^5$ is 6-(dimethylamino)pyridin-3-yl, 6-(4-methylpiperazin-1-yl)pyridin-3-yl, 2-(4-methylpiperazin-1-yl)pyridin-4-yl, 6-(4-isopropylpiperazin-1-yl)pyridin-3-yl or 6-(4-(cyclopropylmethyl)piperazin-1-yl)pyridin-3-yl.

In certain embodiments, $R^5$ is a 9-10 membered bicyclic heterocyclyl optionally substituted with $C_1$-$C_4$ alkyl. In certain embodiments, $R^5$ is a 9-10 membered bicyclic heterocyclyl, wherein the heterocyclyl contains one or two heteroatoms selected from oxygen, nitrogen and sulfur. In certain embodiments, $R^5$ is a 9-10 membered bicyclic heterocyclyl, wherein the heterocyclyl contains one oxygen heteroatom. In certain embodiments, $R^5$ is a 9-10 membered bicyclic heterocyclyl, wherein the heterocyclyl is dihydrobenzofuran. In certain embodiments, $R^5$ is 2,3-dihydrobenzofuran-5-yl.

In certain embodiments, $R^5$ is a 9-10 membered bicyclic heterocyclyl optionally substituted with $C_1$-$C_4$ alkyl. In certain embodiments, $R^5$ is a 9-10 membered bicyclic heterocyclyl. In certain embodiments, $R^5$ is a 9-10 membered bicyclic heterocyclyl, wherein the heterocyclyl is selected from 2,3-dihydrobenzofuranyl, 1,3-dihydroisobenzofuranyl, 1,3-dihydrobenzo[c]thiophenyl, 1,3-dihydrobenzo[c]thiophenyl, indolinyl and isoindolinyl, wherein the heterocyclyl is optionally substituted with $C_1$-$C_4$ alkyl. In certain embodiments, $R^5$ is a 9 membered bicyclic heterocyclyl, wherein the heterocyclyl is 2,3-dihydrobenzofuran. In certain embodiments, $R^5$ is 2,3-dihydrobenzofuran-5-yl.

In certain embodiments, $R^5$ is a 9-10 membered bicyclic heteroaryl optionally substituted with $C_1$-$C_4$ alkyl. In certain embodiments, $R^5$ is a 9-10 membered bicyclic heteroaryl optionally substituted with $C_1$-$C_4$ alkyl, wherein the heteroaryl contains one or two heteroatoms selected from oxygen, nitrogen and sulfur. In certain embodiments, $R^5$ is a 9-10 membered bicyclic heteroaryl optionally substituted with $C_1$-$C_4$ alkyl, wherein the heteroaryl contains one nitrogen heteroatom. In certain embodiments, $R^5$ is a 9-10 membered bicyclic heteroaryl optionally substituted with $C_1$-$C_4$ alkyl, wherein the heteroaryl is indole. In certain embodiments, $R^5$ is 1H-indol-5-yl or 1-methyl-1H-indol-5-yl.

In certain embodiments, $R^5$ is a 9-10 membered bicyclic heteroaryl optionally substituted with $C_1$-$C_4$ alkyl. In certain embodiments, $R^5$ is a 9-10 membered bicyclic heteroaryl selected from indolyl, benzofuranyl and benzo[b]thiophenyl, wherein the heteroaryl is optionally substituted with $C_1$-$C_4$ alkyl. In certain embodiments, $R^5$ is a 9-10 membered bicyclic heteroaryl optionally substituted with $C_1$-$C_4$ alkyl, wherein the heteroaryl is indolyl. In certain embodiments, $R^5$ is indolyl optionally substituted with $C_1$-$C_4$ alkyl. In certain embodiments, $R^5$ is indolyl optionally substituted with methyl. In certain embodiments, $R^5$ is 1H-indol-5-yl or 1-methyl-1H-indol-5-yl.

In certain embodiments, $R^5$ is phenyl.

In certain embodiments, $R^5$ is phenyl optionally substituted with $R^d$. In certain embodiments, $R^d$ is halogen, CN, $NR^gR^h$, phenyl, a 5-6 membered heterocyclyl, —$O(C_1$-$C_4$ alkyl) or $C_1$-$C_4$ alkyl, wherein the alkyl or alkoxy are optionally substituted with halogen, OH, oxo, —$O(C_1$-$C_3$ alkyl), $NR^gR^h$ or a 5-6 membered heterocyclyl optionally substituted with $C_1$-$C_3$ alkyl. In certain embodiments, $R^d$ is F or Cl. In certain embodiments, $R^d$ is a 5-6 membered heterocyclyl, wherein the heterocyclyl contains one or two heteroatoms selected from oxygen, nitrogen and sulfur. In certain embodiments, $R^d$ is a 5-6 membered heterocyclyl, wherein the heterocyclyl contains one or two heteroatoms selected from oxygen and nitrogen. In certain embodiments, $R^d$ is a 5-6 membered heterocyclyl, wherein the heterocyclyl is morpholinyl. In certain embodiments, $R^d$ is —$O(C_1$-$C_4$ alkyl), wherein the alkoxy is optionally substituted with OH, —$O(C_1$-$C_3$ alkyl), $NR^gR^h$ or a 5-6 membered heterocyclyl optionally substituted with $C_1$-$C_3$ alkyl. In certain embodiments, $R^d$ is —$O(C_1$-$C_4$ alkyl), wherein the alkoxy is optionally substituted with a 5-6 membered heterocyclyl optionally substituted with $C_1$-$C_3$ alkyl, wherein the heterocyclyl contains one or two heteroatoms selected from oxygen, nitrogen and sulfur. In certain embodiments, $R^d$ is —$O(C_1$-$C_4$ alkyl), wherein the alkoxy is optionally substituted with a 5-6 membered heterocyclyl optionally substituted with $C_1$-$C_3$ alkyl, wherein the heterocyclyl contains two oxygen heteroatoms. In certain embodiments, $R^d$ is —$O(C_1$-$C_4$ alkyl), wherein the alkoxy is optionally substituted with a 5-6 membered heterocyclyl optionally substituted with $C_1$-$C_3$ alkyl, wherein the heterocyclyl is 1,3-dioxolane. In certain embodiments, $R^g$ and $R^h$ are methyl. In certain embodiments, $R^d$ is —$OCH_2CH_2OCH_2CH_3$, —$OCH_2CH(OH)CH_2OH$, (2,2-dimethyl-1,3-dioxolan-4-yl)methoxy or —$OCH_2CH_2N(CH_3)_2$. In certain embodiments, $R^d$ is $C_1$-$C_4$ alkyl substituted with oxo and a 5-6 membered heterocyclyl optionally substituted with $C_1$-$C_3$ alkyl. In certain embodiments, $R^d$ is $C_1$-$C_4$ alkyl substituted with oxo and a 5-6 membered heterocyclyl optionally substituted with $C_1$-$C_3$ alkyl, wherein the heterocyclyl contains one or two heteroatoms selected from oxygen, nitrogen and sulfur. In certain embodiments, $R^d$ is $C_1$-$C_4$ alkyl substituted with oxo and a 5-6 membered heterocyclyl optionally substituted with $C_1$-$C_3$ alkyl, wherein the heterocyclyl contains two nitrogen heteroatoms. In certain embodiments, $R^d$ is $C_1$-$C_4$ alkyl substituted with oxo and a 5-6 membered heterocyclyl optionally substituted with $C_1$-$C_3$ alkyl, wherein the heterocyclyl is piperazinyl. In certain embodiments, $R^d$ is —C(=O)-4-methylpiperazinyl. In certain embodiments, $R^5$ is 2-fluorophenyl, 3-fluorophenyl, 4-fluorophenyl, 2-chlorophenyl, 3-chlorophenyl, 4-chlorophenyl, 3-(dimethylamino)phenyl, 3-($OCH_2CH_2OCH_2CH_3$)phenyl, 3-($OCH_2CH(OH)CH_2OH$)phenyl, 3-((2,2-dimethyl-1,3-dioxolan-4-yl)methoxy)phenyl, 3-($OCH_2CH_2N(CH_3)_2$)phenyl, 4-($OCH_2CH_2N(CH_3)_2$)phenyl, 4-morpholinophenyl, 3-((dimethylamino)methyl)phenyl, 3-cyanophenyl, 4-acetylphenyl, biphenyl-4-yl, 4-(4-methylpiperazine-1-carbonyl)phenyl or 4-(dimethylamino)phenyl.

In certain embodiments, $R^5$ is phenyl optionally substituted with $R^d$. In certain embodiments, $R^d$ is halogen, CN, $NR^gR^h$, phenyl, a 5-6 membered heterocyclyl, —O($C_1$-$C_4$ alkyl) or $C_1$-$C_4$ alkyl, wherein the alkyl or alkoxy are optionally substituted with halogen, OH, oxo, —O($C_1$-$C_3$ alkyl), $NR^gR^h$ or a 5-6 membered heterocyclyl optionally substituted with $C_1$-$C_3$ alkyl. In certain embodiments, $R^d$ is F or Cl. In certain embodiments, $R^d$ is a 5-6 membered heterocyclyl, wherein the heterocyclyl is morpholinyl. In certain embodiments, $R^d$ is —O($C_1$-$C_4$ alkyl), wherein the alkyl is optionally substituted with OH, —O($C_1$-$C_3$ alkyl) or $NR^gR^h$. In certain embodiments, $R^d$ is —$OCH_2CH_2OCH_2CH_3$ or —$OCH_2CH(OH)CH_2OH$. In certain embodiments, $R^g$ and $R^h$ are methyl. In certain embodiments, $R^d$ is —$OCH_2CH_2N(CH_3)_2$. In certain embodiments, $R^d$ is $C_1$-$C_4$ alkyl substituted with oxo and a 5-6 membered heterocyclyl optionally substituted with $C_1$-$C_3$ alkyl. In certain embodiments, $R^d$ is $C_1$-$C_4$ alkyl substituted with oxo and a 5-6 membered heterocyclyl optionally substituted with $C_1$-$C_3$ alkyl, wherein the heterocyclyl is piperazinyl. In certain embodiments, $R^d$ is —C(=O)-4-methylpiperazinyl. In certain embodiments, $R^5$ is 2-fluorophenyl, 3-fluorophenyl, 4-fluorophenyl, 2-chlorophenyl, 3-chlorophenyl, 4-chlorophenyl, 3-(dimethylamino)phenyl, 3-($OCH_2CH_2OCH_2CH_3$)phenyl, 3-($OCH_2CH(OH)CH_2OH$)phenyl, 3-($OCH_2CH_2N(CH_3)_2$)phenyl, 4-($OCH_2CH_2N(CH_3)_2$)phenyl, 4-morpholinophenyl, 3-((dimethylamino)methyl)phenyl, 3-cyanophenyl, 4-acetylphenyl, biphenyl-4-yl or 4-(4-methylpiperazine-1-carbonyl)phenyl.

In certain embodiments, $R^5$ is phenyl optionally substituted with halogen, $NR^gR^h$, phenyl, a 5-6 membered heterocyclyl, —O($C_1$-$C_4$ alkyl) or $C_1$-$C_4$ alkyl, wherein the alkyl or alkoxy are optionally substituted with halogen, OH, oxo, —O($C_1$-$C_3$ alkyl), $NR^gR^h$, or a 5-6 membered heterocyclyl optionally substituted with $C_1$-$C_3$ alkyl.

In certain embodiments of Formula I, $R^5$ is hydrogen, such that compounds have the structure of Formula Ib:

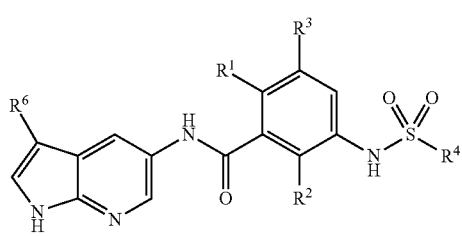

Ib wherein $R^1$, $R^2$, $R^3$, $R^4$ and $R^6$ are as defined herein.

In a further embodiment of the present invention, $R^1$ and $R^2$ are F, $R^3$ is hydrogen, and $R^4$ is propyl, such that compound have the structure of Formula Ib1:

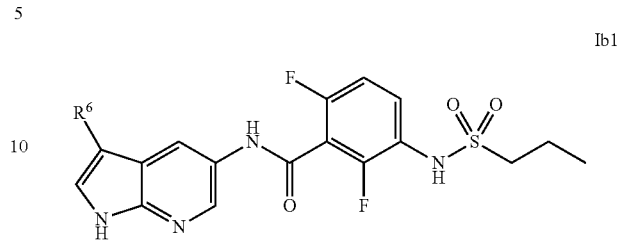

Ib1 wherein $R^6$ is as defined herein.

In certain embodiments of Formula I, $R^6$ is hydrogen, such that compounds have the structure of Formula Ic:

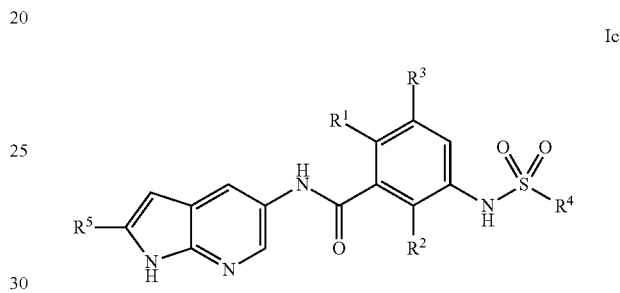

Ic wherein $R^1$, $R^2$, $R^3$, $R^4$ and $R^5$ are as defined herein.

In a further embodiment of the present invention, $R^1$ and $R^2$ are F, $R^3$ is hydrogen, and $R^4$ is propyl, such that compound have the structure of Formula Ic1:

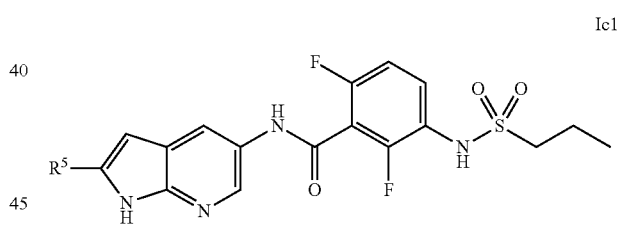

Ic1 wherein $R^5$ is as defined herein.

It will be appreciated that certain compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

It will also be appreciated that compounds of Formula I include tautomeric forms. Tautomers are compounds that are interconvertible by tautomerization. This commonly occurs due to the migration of a hydrogen atom or proton, accompanied by the switch of a single bond and adjacent double bond. For instance, 1H-pyrrolo[2,3-b]pyridine is one of the tautomeric forms of 7-azaindole. Another tautomeric form of 7-azaindole is 7H-pyrrolo[2,3-b]pyridine. Other tautomers of Formula I may also form at other positions, including, but not limited to, the sulfonamide or $R^5/R^6$ position depending on the substitution. The compounds of Formula I are intended to include all tautomeric forms.

The compounds of Formula I include the tautomer 7H-pyrrolo[2,3-b]pyridine, shown as Formula II:

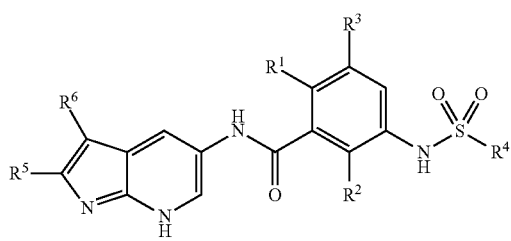

wherein $R^1$, $R^2$, $R^3$, $R^4$, $R^5$ and $R^6$ are as defined herein.

In another embodiment of the present invention, intermediates of Formula III are provided:

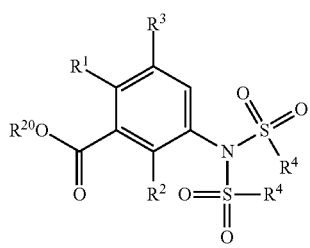

wherein $R^{20}$ is hydrogen, $C_1$-$C_6$ alkyl, benzyl or phenyl and $R^1$, $R^2$, $R^3$ and $R^4$ are as defined herein.

In another embodiment of the present invention, intermediates of Formula IV:

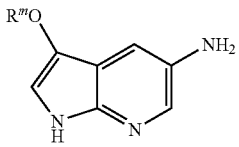

wherein $R^m$ is selected from hydrogen and $C_1$-$C_4$ alkyl. In certain embodiments, $R^m$ is $C_1$-$C_4$ alkyl. Compounds of Formula IV include 3-methoxy-1H-pyrrolo[2,3-b]pyridin-5-amine and 3-ethoxy-1H-pyrrolo[2,3-b]pyridin-5-amine.

It will also be appreciated that certain compounds of Formula I may be used as intermediates for further compounds of Formula I.

It will be further appreciated that the compounds of the present invention may exist in unsolvated, as well as solvated forms with pharmaceutically acceptable solvents, such as water, ethanol, and the like, and it is intended that the invention embrace both solvated and unsolvated forms.

The term "prodrug" as used in this application refers to a precursor or derivative form of a compound of the invention that is less active or inactive compared to the parent compound or drug and is capable of being metabolized in vivo into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug.

Prodrugs of compounds of Formula I may not be as active as the compounds of Formula I in the assay as described in Example A. However, the prodrugs are capable of being converted in vivo into more active metabolites of compounds of Formula I.

Synthesis of Compounds

Compounds of the present invention may be synthesized by synthetic routes that include processes analogous to those well-known in the chemical arts, particularly in light of the description contained herein. The starting materials are generally available from commercial sources such as Sigma-Aldrich (St. Louis, Mo.), Alfa Aesar (Ward Hill, Mass.), or TCI (Portland, Oreg.), or are readily prepared using methods well known to those skilled in the art (e.g., prepared by methods generally described in Louis F. Fieser and Mary Fieser, *Reagents for Organic Synthesis*. v. 1-23, New York: Wiley 1967-2006 ed. (also available via the Wiley InterScience® website), or *Beilsteins Handbuch der organischen Chemie*, 4, Aufl. ed. Springer-Verlag, Berlin, including supplements (also available via the Beilstein online database)).

For illustrative purposes, Schemes 1-16 show a general method for preparing the compounds of the present invention, as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

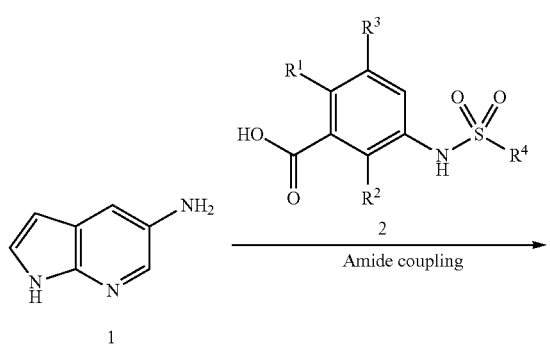

Scheme 1

Scheme 1 shows a general method for preparing compound 4, wherein X is halogen and R¹, R², R³ and R⁴ are as defined herein. Pyrrolopyridine 1 may be coupled with compound 2 in the presence of a coupling reagent (such as 2-(1H-benzotriazole-1-yl)-1,1,3,3-tetramethyluronium hexafluorophosphate, "HBTU") to provide compound 3. Compound 3 is then halogenated, for example, by n-chlorosuccinimide ("NCS") or bromine to provide compound 4.

Scheme 2 shows a general method for preparing compound 2, wherein R¹, R², R³ and R⁴ are as defined herein. Benzoic acid 5 is nitrated in the presence of nitric acid, and the following reduction to aniline 6 can be accomplished in a number of ways, for example, by SnCl₂ dihydrate, Zn/acid, or by hydrogenation. Sulfonylation of aniline 6 with a substituted sulphonyl chloride (e.g., propyl sulphonyl chloride) under aqueous basic conditions (e.g., Na₂CO₃) provides compound 2.

Scheme 3 illustrates another method for preparing compound 3 (a subset of Formula I), wherein R¹, R², R³ and R⁴ are as defined herein. Pyrrolopyridine 1 may be coupled with bis-sulfonylated benzoic acid 7 providing compound 8. Basic hydrolysis with aqueous NaOH provides compound 3.

Scheme 4 shows a general method for preparing compound 7, wherein $R^1$, $R^2$, $R^3$ and $R^4$ are as defined herein. Aniline 6 is sulfonylated in an organic solvent, such as dichloromethane ("DCM"), in the presence of a base, such as triethylamine, to provide compound 7.

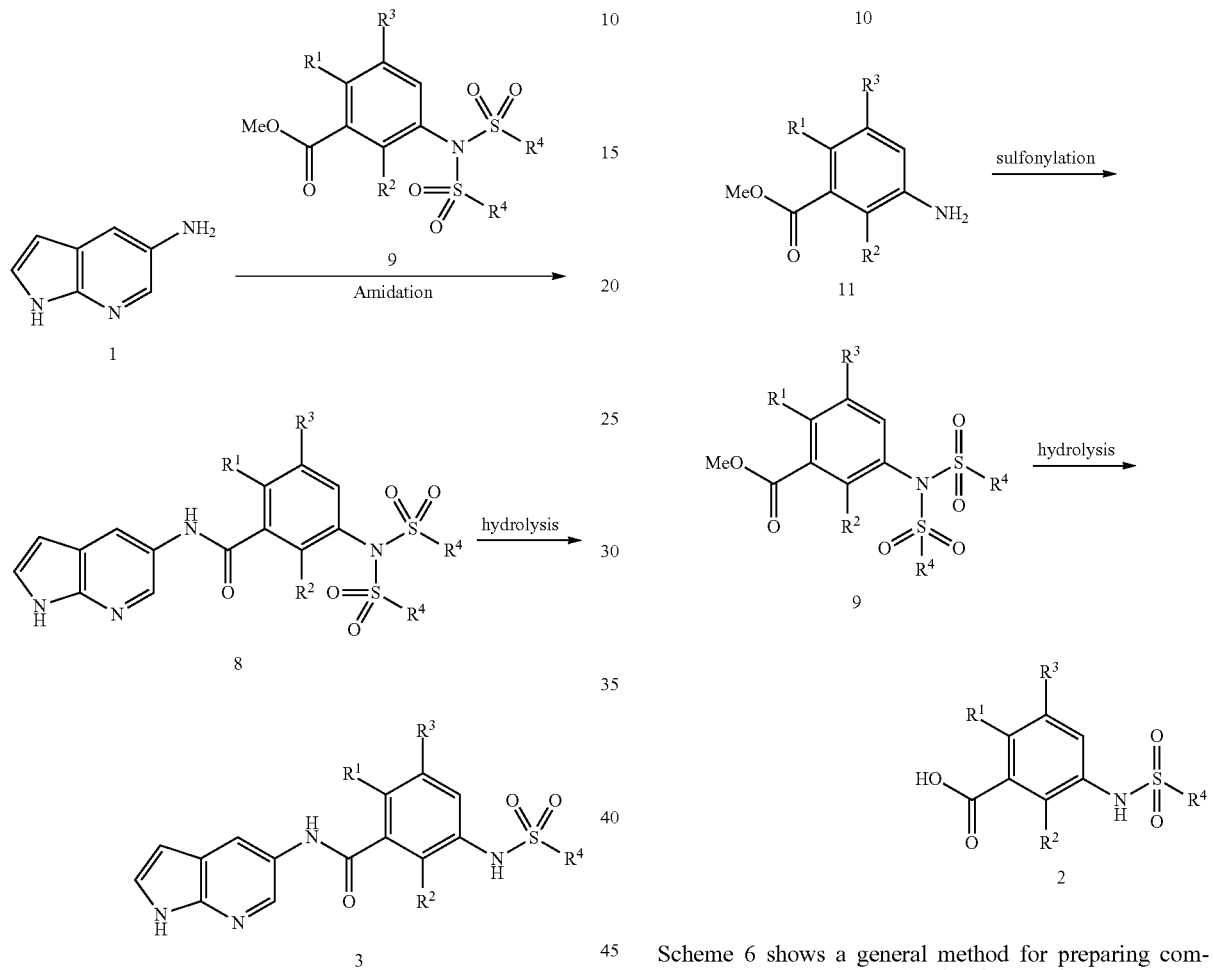

Scheme 5 illustrates another method for preparing compound 3, wherein $R^1$, $R^2$, $R^3$ and $R^4$ are as defined herein. Pyrrolopyridine 1 may be coupled with bis-sulfonylated benzoic ester 9 in the presence of trimethyl aluminum providing compound 8. Basic hydrolysis with aqueous NaOH provides compound 3.

Scheme 6 shows a general method for preparing compounds 2 and 9, wherein $R^1$, $R^2$, $R^3$ and $R^4$ are as defined herein. Benzoic acid 5 is nitrated in the presence of nitric acid, and the following esterification to compound 10 can be accomplished in a number of ways, for example, by treatment with trimethylsilyl diazomethane in MeOH or via Fischer esterification conditions, such as treatment with trimethylsilyl chloride ("TMSCl") in MeOH. Reduction of the nitro group and sulfonylation under standard conditions provides compound 9. Basic hydrolysis with aqueous NaOH provides an alternative synthesis to compound 2.

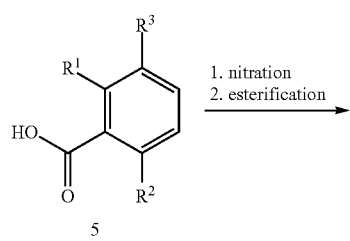

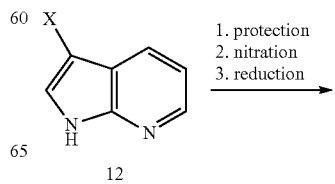

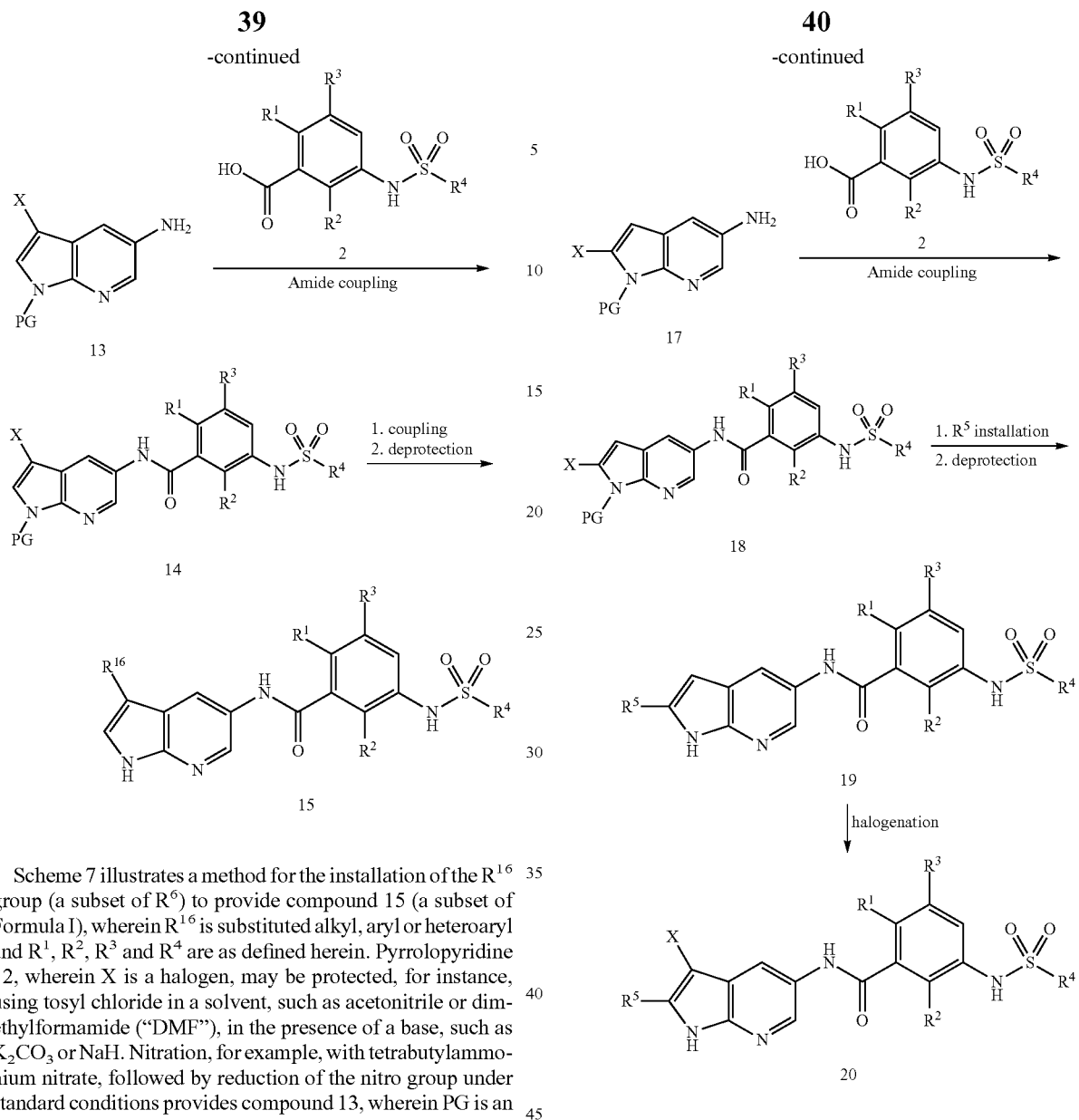

Scheme 7 illustrates a method for the installation of the $R^{16}$ group (a subset of $R^6$) to provide compound 15 (a subset of Formula I), wherein $R^{16}$ is substituted alkyl, aryl or heteroaryl and $R^1$, $R^2$, $R^3$ and $R^4$ are as defined herein. Pyrrolopyridine 12, wherein X is a halogen, may be protected, for instance, using tosyl chloride in a solvent, such as acetonitrile or dimethylformamide ("DMF"), in the presence of a base, such as $K_2CO_3$ or NaH. Nitration, for example, with tetrabutylammonium nitrate, followed by reduction of the nitro group under standard conditions provides compound 13, wherein PG is an amine protecting group, such as a tosyl group. Aniline 13 and benzoic acid 2 are coupled under standard conditions to provide amide 14. A cross-coupling reaction with compound 14, for example, Suzuki, Stille or Negishi reactions, in the presence of a catalyst, such as tetrakis(triphenylphosphine)palladium, can be used to install a variety of alkyl, aryl and heteroaryl groups at the $R^6$ position of Formula I. Removal of the protecting group under basic conditions, for example, with $K_2CO_3$, at an appropriate temperature, for example 0° C. to reflux, provides compound 15.

Additionally in Scheme 7, $R^{16}$ may be CN.

Scheme 8

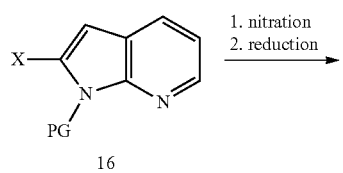

Scheme 8 shows a method of preparing compounds 19 and 20 (both a subset of Formula I), wherein X is a halogen and $R^1$, $R^2$, $R^3$, $R^4$ and $R^5$ are as defined herein. Preparation of compound 16, wherein PG is a protecting group (preferably —$SO_2Ph$) and X is a halogen (preferably iodine), can be carried out as described in the literature (Benoit, Joseph et al., "Synthesis of Pyrido[2,3-b]indole Derivatives via Diels-Alder Reactions of 2- and 3-Vinylpyrrolo[2,3-b]pyridines." Tetrahedron 56(20), pp. 3189-3196 (2000)). Compound 16 may be functionalized to install the 5-amino group via nitration (preferably tetrabutylammonium nitrate/trifluoroacetic acid anhydride) followed by reduction (preferably employing either $SnCl_2$ or $H_2$ on Pd/C) to give compound 17. Standard amide coupling (preferably using 1-ethyl-3-(3-dimethylaminopropyl)carbodiimide ("EDCI")/1-hydroxybenzotriazole ("HOBt")) with aryl amine 2 affords compound 18. Installation of the $R^5$ group can be accomplished via Pd-catalyzed coupling reaction (e.g., Sonogashira coupling, Suzuki coupling, etc.), and removal of the protecting group affords compound 19. If desired, halogenation of compound 19 can be affected under standard halogenation (N-bromosuccinimide ("NBS") or NCS) conditions.

Scheme 9

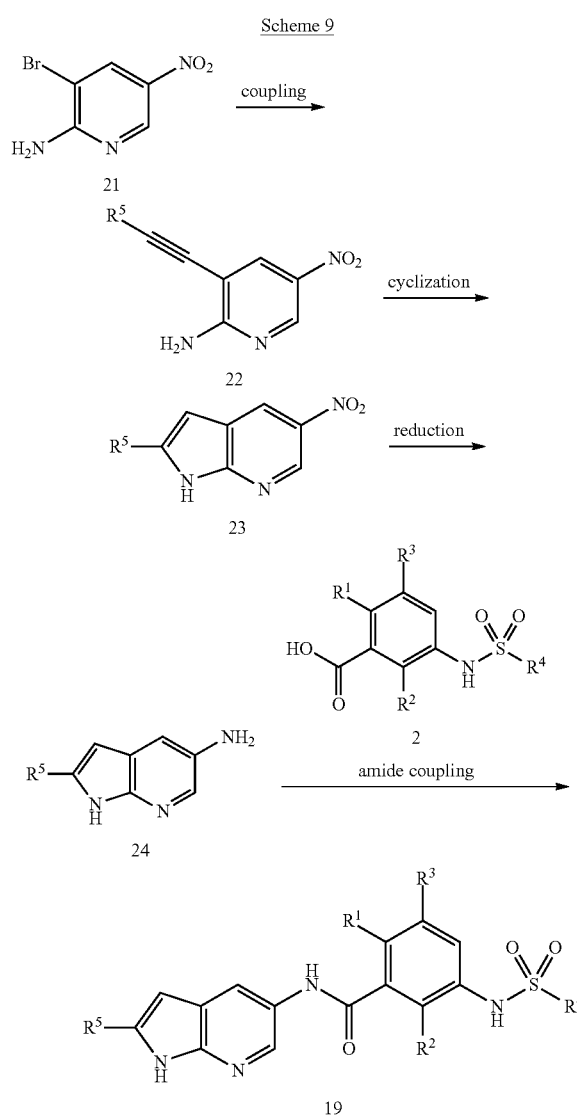

Scheme 9 illustrates another method for preparing compound 19, wherein $R^1$, $R^2$, $R^3$, $R^4$ and $R^5$ are as defined herein. Starting from compound 21, a Sonogashira coupling reaction is used to produce alkyne 22. Cyclization of pyridine 22 under various conditions (e.g., KOt-Bu or CuI/N-methylpyrrolidone ("NMP")) affords pyrrolopyridine compound 23. Reduction of the nitro group (SnCl$_2$ or hydrogenation) affords compound 24, which provides compound 19 after amide coupling under standard conditions.

Scheme 10

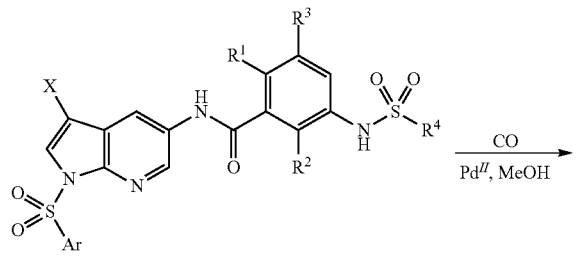

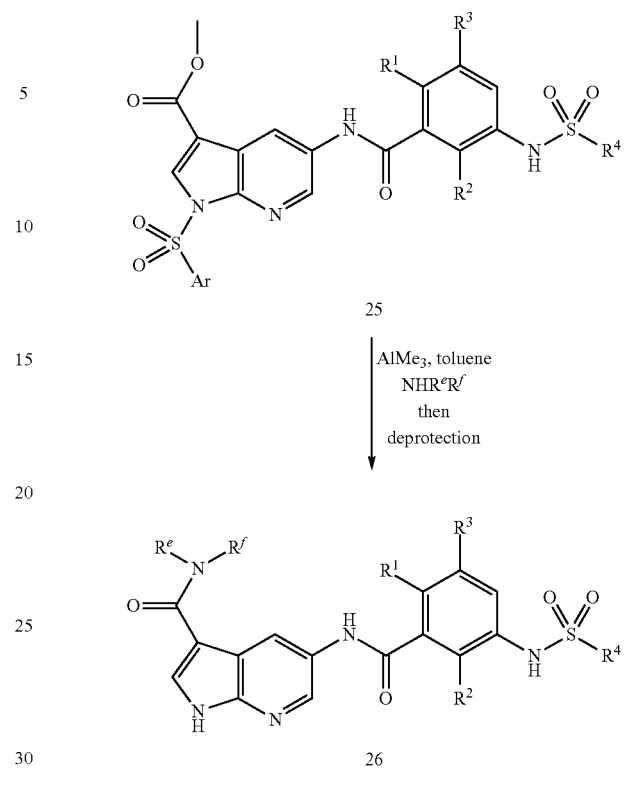

Scheme 10 illustrates a general method for the preparation of compound 26 (a subset of Formula I), wherein $R^1$, $R^2$, $R^3$, $R^4$, $R^e$ and $R^f$ are defined herein. Compound 14, wherein X is Br or I and Ar is aryl, can be treated with an alcoholic solvent, such as methanol, under an atmosphere (or several atmospheres) of carbon monoxide with an appropriate palladium catalyst (such as PdCl$_2$(PPh$_3$)$_2$) to give the compound 25. Amide formation is then carried out by subjecting compound 25 to an amine in the presence of trimethyl aluminum followed by basic hydrolysis to give compound 26.

Scheme 11

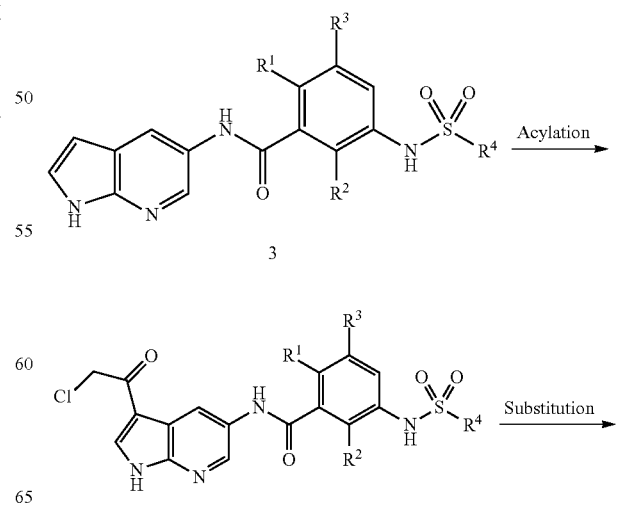

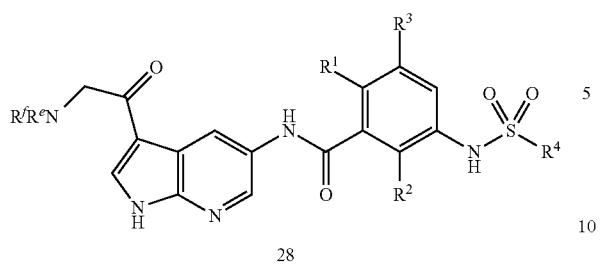

28

Scheme 11 illustrates a general method for the preparation of compound 28 (a subset of Formula I), wherein $R^1$, $R^2$, $R^3$, $R^4$, $R^e$ and $R^f$ are defined herein. Compound 3 can be treated with a Lewis acid, such as $AlCl_3$, and an acid chloride in a solvent or a mixture of solvents, such as DCM and $CH_3NO_2$, to produce ketone 27 (a subset of Formula I). Nucleophilic substitution with an amine of Formula $R^fR^eNH$ can be carried out on compound 27 in a suitable solvent, such as EtOH, to provide compound 28.

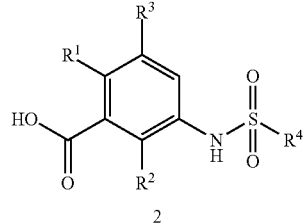

2

Scheme 12 shows a general method for preparing compound 2, wherein $R^1$, $R^2$, $R^3$ and $R^4$ are as defined herein. Benzoic acid 29 is esterified to methyl benzoate 10 by treatment with trimethylsilyl diazomethane in MeOH or via Fischer esterification conditions, such as treatment with TMSCl in MeOH. Reduction of ester 10 is performed using a standard condition, such as treatment with Pd/C and $H_2$. Sulfonamide 30 is obtained by treatment of aniline 11 with a sulfonyl chloride in the presence of a base, such as pyridine, in an organic solvent, such as DCM. Hydrolysis of compound 30 is accomplished under basic conditions, such as aqueous LiOH in the appropriate solvent system such as tetrahydrofuran ("THF") and/or MeOH, to provide compound 2.

Scheme 12

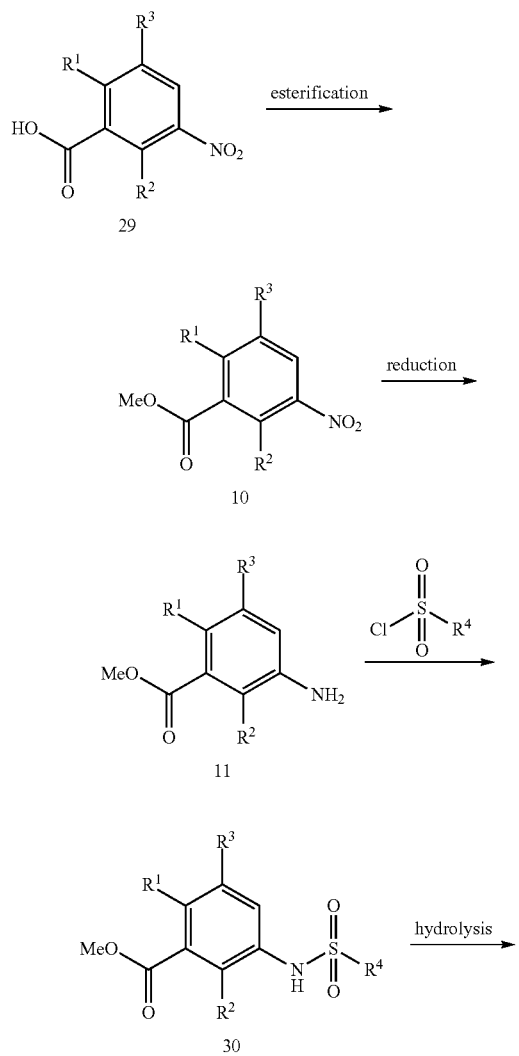

Scheme 13

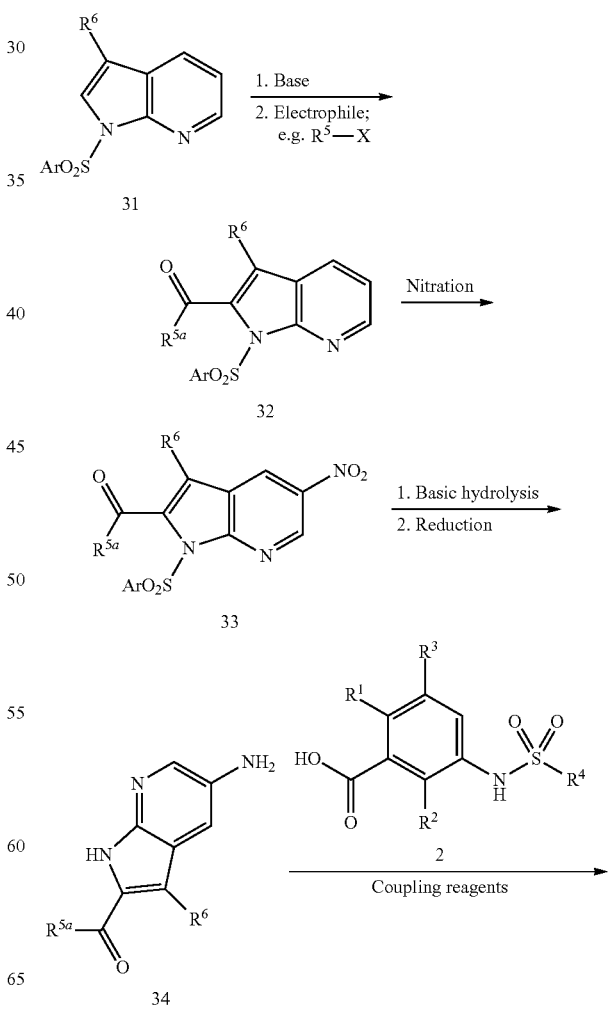

-continued

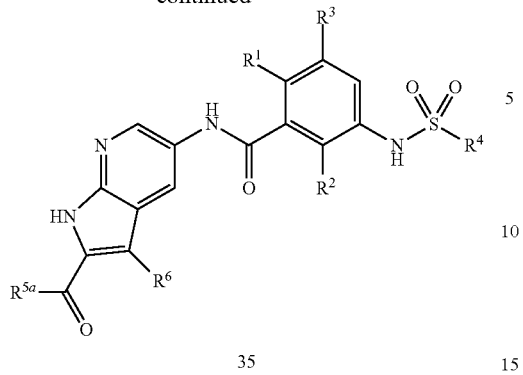

35

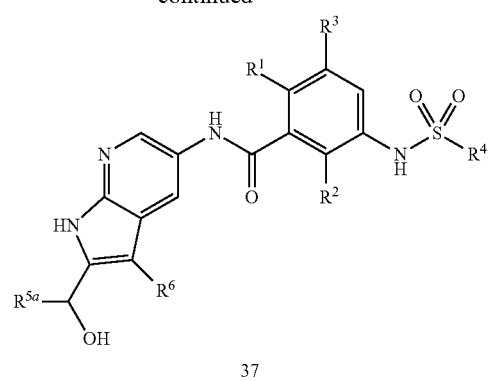

37

Scheme 13 shows a general method for preparing compound 35 (a subset of Formula I), wherein $R^{5a}$ is $C_1$-$C_5$ alkyl optionally substituted with halogen, $OR^g$ or $NR^gR^h$, and $R^1$, $R^2$, $R^3$, $R^4$, $R^6$, $R^g$ and $R^h$ are as defined herein. The N-sulfonylated pyrrolopyridine 31, wherein Ar is, for example, phenyl or 4-methylphenyl, is deprotonated with a base, such as n-BuLi or lithium diisopropylamide ("LDA"), and subsequently treated with an electrophile such as $R^{5a}C(=O)$—X, wherein X is iodo, bromo, chloro, $OSO_2$—R, wherein R is methyl, trifluoromethyl, phenyl or p-toluene, or an anhydride, such as $R^{5a}C(O)$—O—$C(O)R^{5a}$, or similar electrophiles. The substituted N-sulfonylated pyrrolopyridine 32 is then treated with a nitration reagent, for example tetrabutylammonium nitrate. Basic hydrolysis of the nitro intermediate 33 through addition of an inorganic base, such as potassium carbonate, in the presence of water and solvent, such as methanol, is followed by reduction of the nitro group through reduction with iron or palladium catalyzed hydrogenation to yield the amine 34. Standard amide bond coupling with an acid 2 provides pyrrolopyridine 35.

Scheme 14 shows a general method for preparing Compound 37, wherein $R^1$, $R^2$, $R^3$, $R^4$, and $R^6$ are as defined herein, and $R^{5a}$ is defined above. The carbonyl function of compound 33, wherein Ar is defined above, can be converted to an alcohol function using reducing agents, such as $NaBH_4$, to provide compound 33a. Compound 33a may then be further reacted according to Scheme 13 to provide compound 37.

Scheme 15

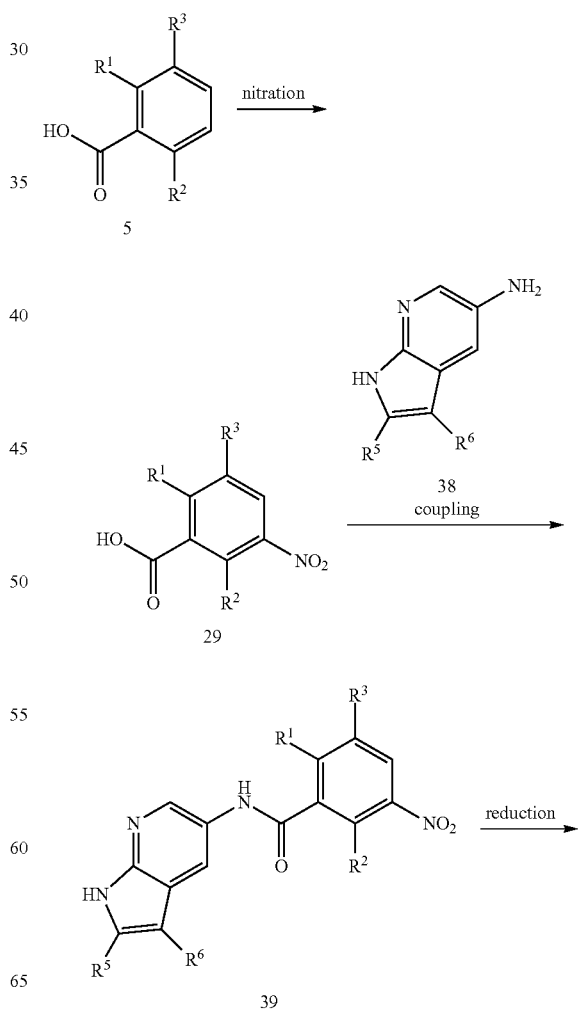

Scheme 14

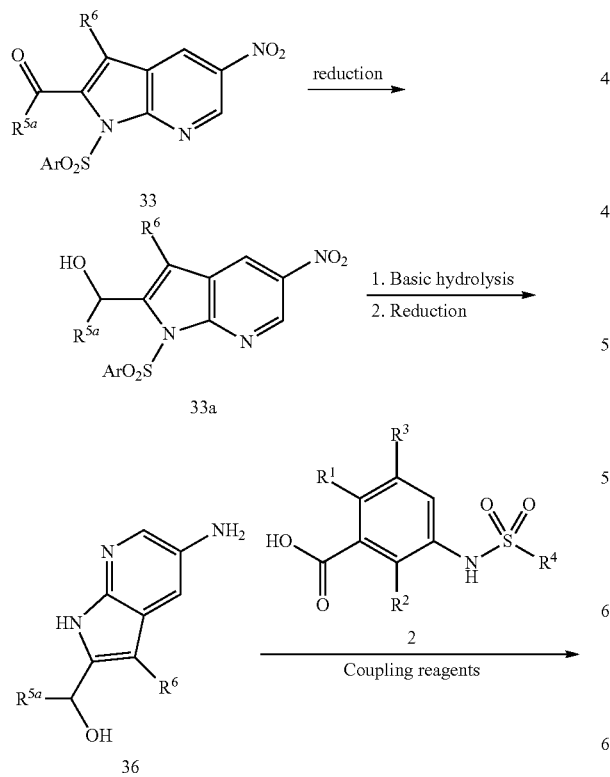

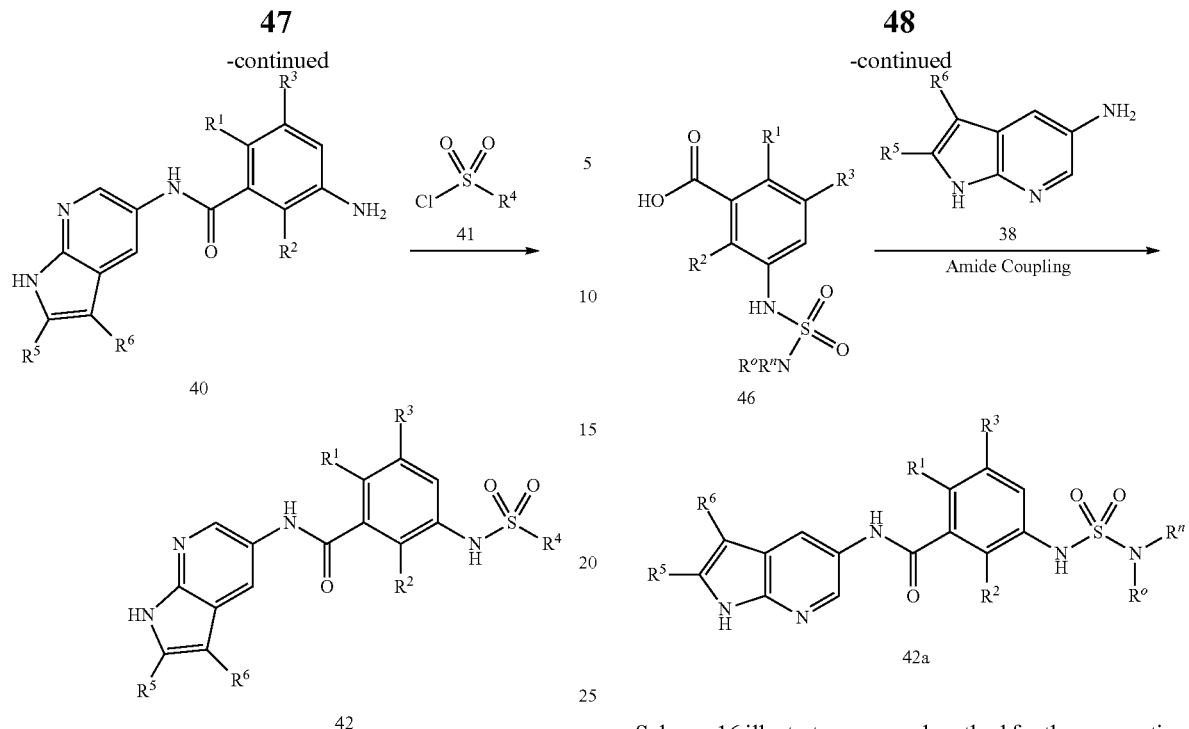

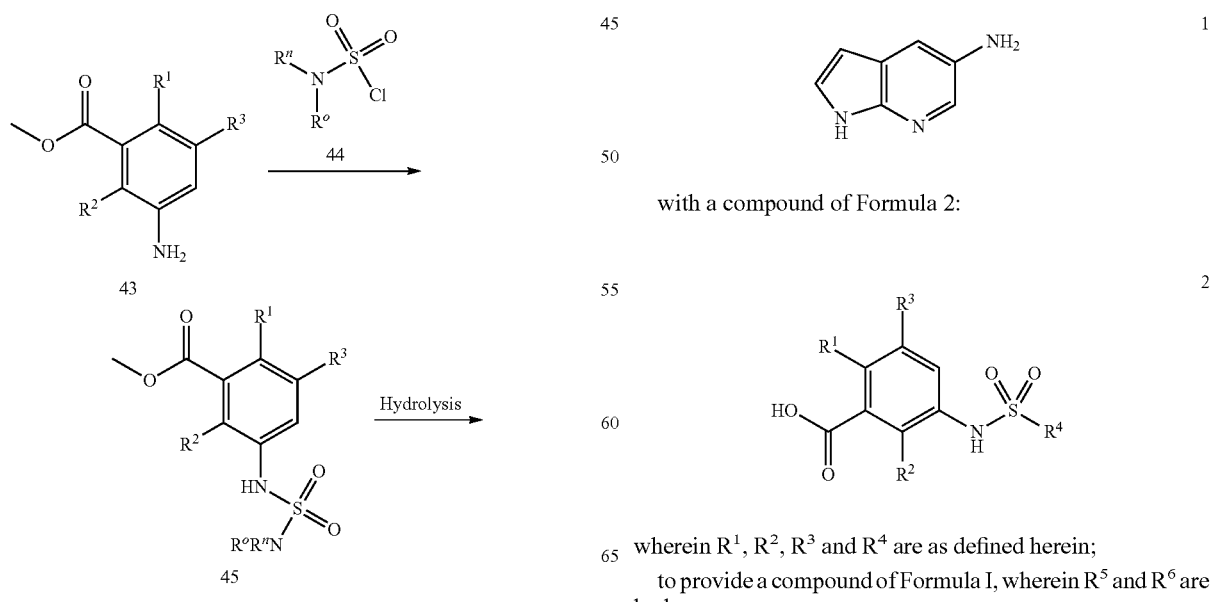

Scheme 15 shows a general method for preparing compound 42, wherein $R^1$, $R^2$, $R^3$, $R^4$, $R^5$ and $R^6$ are as defined herein. Benzoic acid 5 is nitrated in the presence of nitric acid, either neat or in the presence of another acid, such as sulfuric acid or trifluoroacetic acid, to provide nitrated benzoic acid 29. Compound 29 may be coupled with compound 38 with an activating reagent, such as EDCI, in the presence of an additive, such as HOBt, in a suitable solvent, such as DMF or DCM, to provide compound 39. Compound 39 may be reduced to aniline 40 in a number of ways, for example, by $SnCl_2$ dihydrate, Zn/acid, or by hydrogenation. Sulfonamide 42 is obtained by treatment of aniline 40 with a sulfonyl chloride 41 in the presence of a base, such as pyridine, in an organic solvent, such as DCM.

Scheme 16 illustrates a general method for the preparation of compound 42a (a subset of Formula I and Compound 42), wherein $R^1$, $R^2$, $R^3$, $R^5$, $R^6$, $R^n$ and $R^o$ are defined herein. Compound 43 can be treated with a base, such as triethylamine, and sulfamyl chloride 44 in a solvent, such as DCM, to produce the sulfamide 45. Hydrolysis can be carried out on compound 45 with a base, such as sodium hydroxide, in a suitable solvent or mixture of solvents, such as THF and MeOH, to provide the acid 46. Amide bond coupling of 46 and 38 can be carried out with a coupling agent, such as EDCI, in a solvent, such as DMF, to provide compound 42a.

Accordingly, another embodiment of the present invention provides a process for preparing compounds of Formula I (or a subset thereof, including Formula 15, Formula 19, Formula 20, Formula 26, Formula 27 and Formula 28), comprising:

(a) coupling a compound of Formula 1:

with a compound of Formula 2:

wherein $R^1$, $R^2$, $R^3$ and $R^4$ are as defined herein;

to provide a compound of Formula I, wherein $R^5$ and $R^6$ are hydrogen;

(b) halogenating a compound of Formula I, wherein $R^5$ and $R^6$ are hydrogen to provide another compound of Formula I, wherein $R^5$ is hydrogen and $R^6$ is halogen;

(c) coupling a compound of Formula 1:

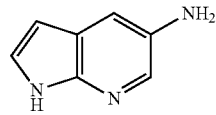

1 with a compound of Formula III:

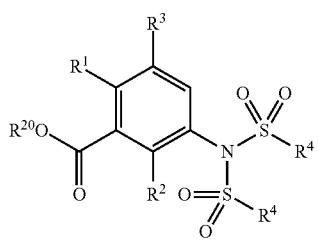

III wherein $R^{20}$ is hydrogen, $C_1$-$C_6$ alkyl, benzyl or phenyl and $R^1$, $R^2$, $R^3$ and $R^4$ are as defined herein;

to provide a compound of Formula 8:

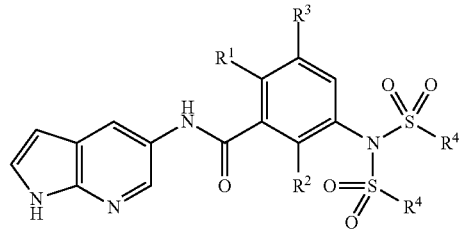

8 followed by hydrolysis to provide a compound of Formula I, wherein $R^5$ and $R^6$ are hydrogen;

(d) coupling a compound of Formula 13:

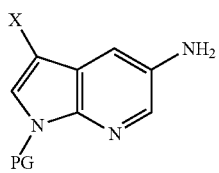

13 wherein X is halogen and PG is an amine protecting group;
with a compound of Formula 2:

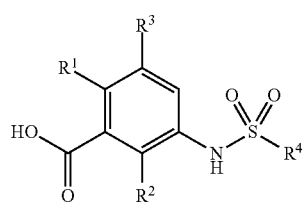

2 wherein $R^1$, $R^2$, $R^3$ and $R^4$ are as defined herein;

to provide a compound of Formula 14:

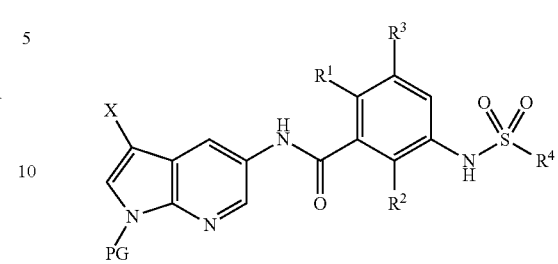

14 followed by a cross-coupling reaction and deprotection to provide a compound of Formula 15:

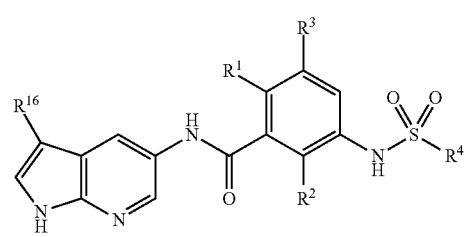

15 wherein $R^{16}$ is phenyl optionally substituted with one to three $R^a$ groups, 5 or 6 membered heteroaryl optionally substituted with $C_1$-$C_4$ alkyl or benzyl or $C_1$-$C_4$ alkyl optionally substituted with one to three $R^b$ groups; each $R^a$ is independently selected from halogen, CN, $CF_3$, —O($C_1$-$C_4$ alkyl), $C_1$-$C_4$ alkyl or 5 or 6 membered heterocyclyl; each $R^b$ is independently selected from halogen, OH, $OCH_3$, oxo, —$NR^eR^f$, phenyl optionally substituted with a halogen, or a 5 or 6 membered heterocyclyl optionally substituted with halogen; and $R^e$ and $R^f$ are independently selected from hydrogen, $C_1$-$C_4$ alkyl or phenyl;

(e) coupling a compound of Formula 17:

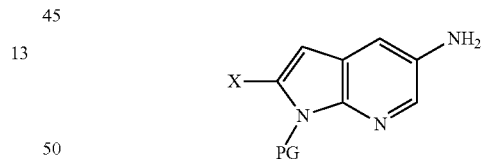

17 wherein X is halogen and PG is an amine protecting group;
with a compound of Formula 2:

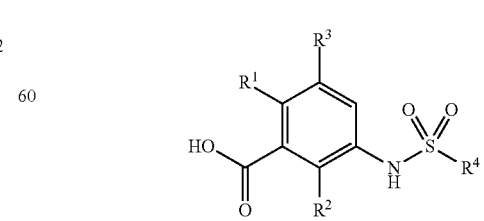

2 wherein $R^1$, $R^2$, $R^3$ and $R^4$ are as defined herein;

to provide a compound of Formula 18:

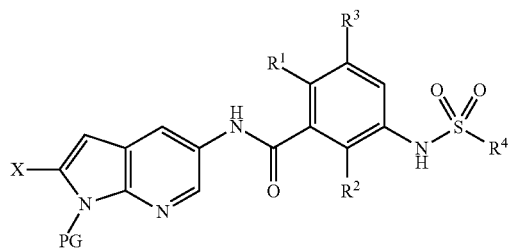

followed by installation of the R⁵ group and deprotection to provide a compound of Formula 19:

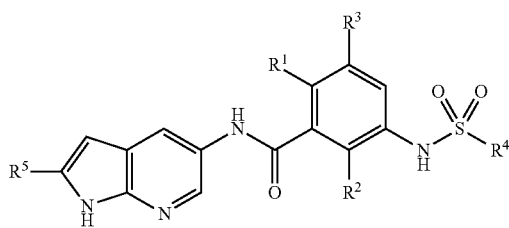

wherein R⁵ is as defined herein;
(f) halogenating a compound of Formula 19:

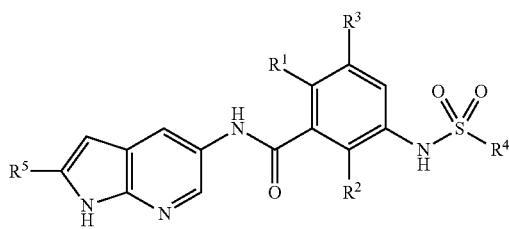

wherein $R^1$, $R^2$, $R^3$, $R^4$ and $R^5$ are as defined herein;
to provide a compound of Formula 20:

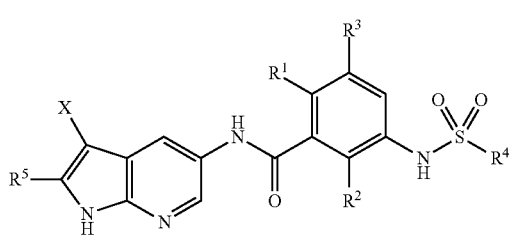

wherein X is halogen;

(g) coupling a compound of Formula 24:

with a compound of Formula 2:

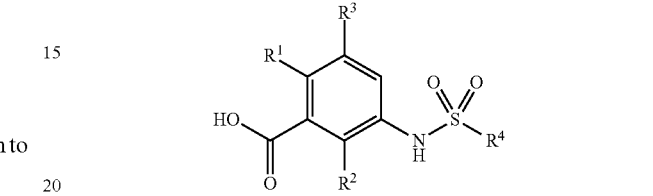

wherein $R^1$, $R^2$, $R^3$ and $R^4$ are as defined herein;
to provide a compound of Formula 19:

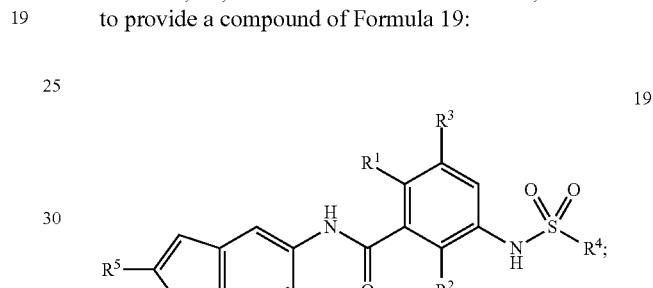

(h) subjecting compound 25:

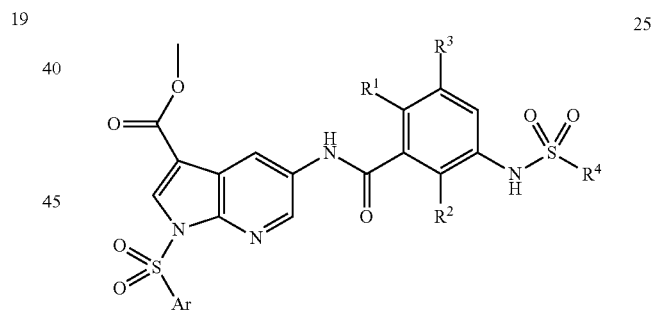

wherein Ar is a 5 or 6 membered aryl and $R^1$, $R^2$, $R^3$ and $R^4$ are as defined herein;
to an amine in the presence of trimethyl aluminum to provide compound 26:

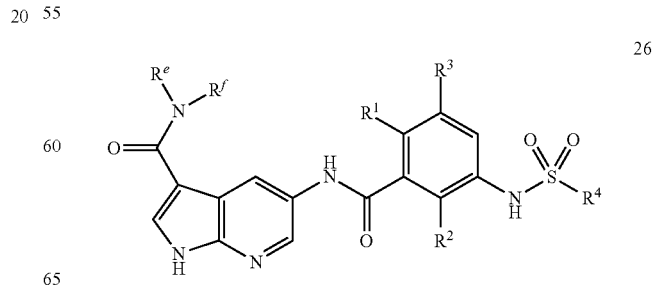

wherein $R^e$ and $R^f$ are as defined herein;

(i) treating compound 3:

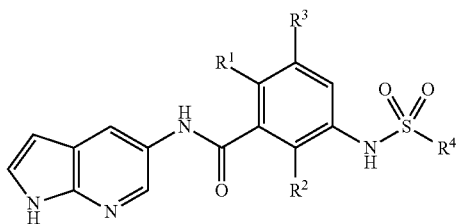

wherein $R^1$, $R^2$, $R^3$ and $R^4$ are as defined herein;
with a Lewis acid and an acid chloride in a solvent to provide compound 27:

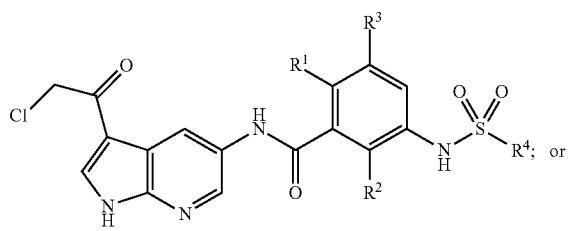

(j) performing a nucleophilic substitution in a suitable solvent on compound 27:

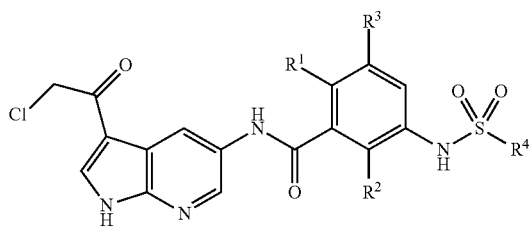

wherein $R^1$, $R^2$, $R^3$ and $R^4$ are as defined herein;
to provide a compound of Formula 28:

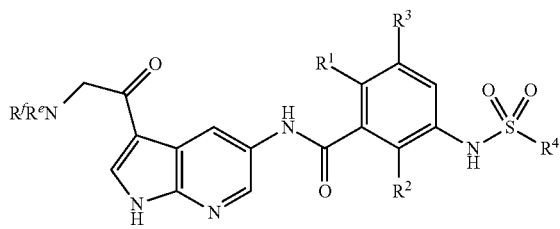

wherein $R^e$ and $R^f$ are as defined herein.

Another embodiment of the present invention provides a process for preparing compounds of Formulas 35 or 37 (subsets of Formula I), comprising:

(a) coupling a compound of Formula 34:

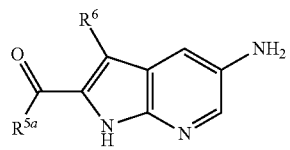

wherein $R^{5a}$ is $C_1$-$C_5$ alkyl optionally substituted with halogen, $OR^g$ or $NR^gR^h$, and $R^6$, $R^g$ and $R^h$ are as defined herein; with a compound of Formula 2:

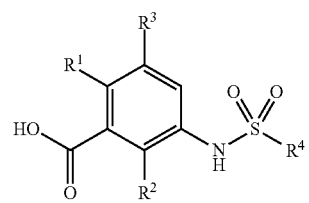

wherein $R^1$, $R^2$, $R^3$ and $R^4$ are as defined herein; to provide a compound of Formula 35:

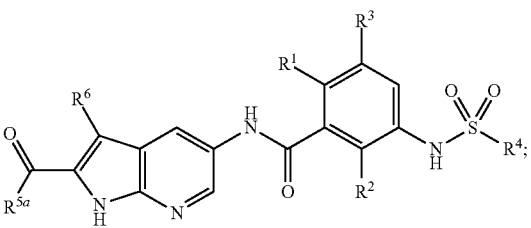

(b) coupling a compound of Formula 36:

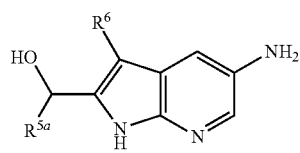

wherein $R^{5a}$ is $C_1$-$C_5$ alkyl optionally substituted with halogen, $OR^g$ or $NR^gR^h$, and $R^6$, $R^g$ and $R^h$ are as defined herein; with a compound of Formula 2:

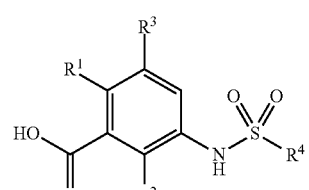

wherein $R^1$, $R^2$, $R^3$ and $R^4$ are as defined herein; to provide a compound of Formula 37:

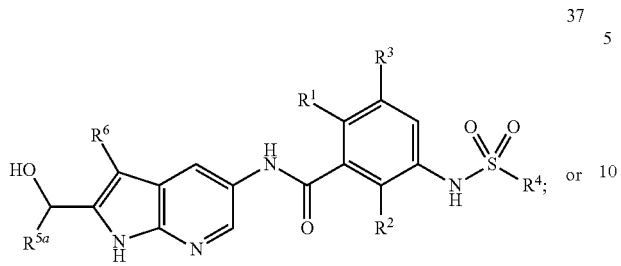

(c) treating a compound of Formula 40:

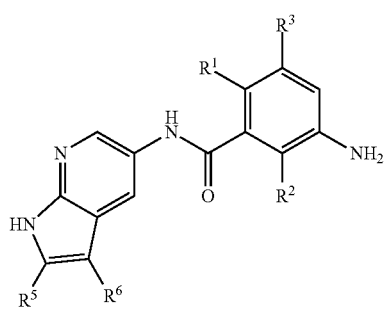

wherein $R^1$, $R^2$, $R^3$, $R^5$ and $R^6$ are as defined herein; with a sulfonyl chloride of Formula 41:

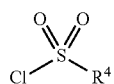

wherein $R^4$ is as defined herein; in the presence of a base and in an organic solvent to provide a compound of Formula 42:

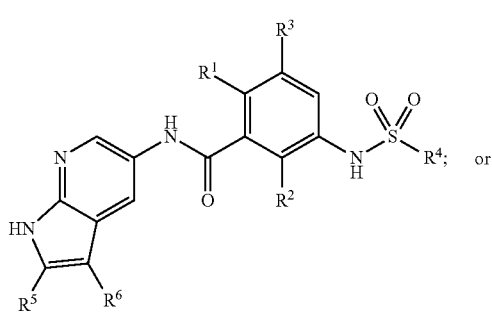

(d) coupling a compound of Formula 46:

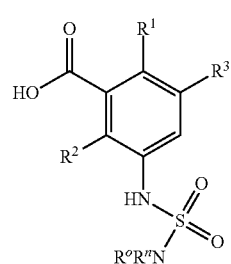

wherein $R^1$, $R^2$, $R^3$, $R''$ and $R^o$ are as defined herein; with a compound of Formula 38:

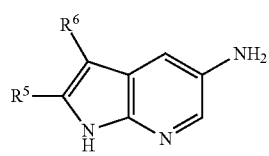

wherein $R^5$ and $R^6$ are as defined herein; with a coupling agent and in a solvent to provide a compound of Formula 42a:

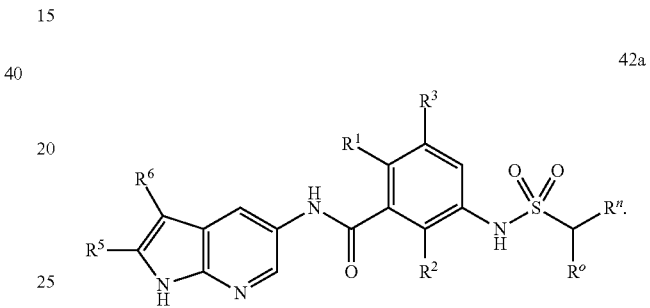

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butyloxycarbonyl ("Boc"), benzyloxycarbonyl ("CBz") and 9-fluorenylmethyleneoxycarbonyl ("Fmoc"). The need for such protection is readily determined by one skilled in the art. For a general description of protecting groups and their use, see T. W. Greene, et al. *Greene's Protective Groups in Organic Synthesis*. New York: Wiley Interscience, 2006.

Methods of Separation

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H., et al. "Chromatographic resolution of enantiomers: Selective review." *J. Chromatogr.*, 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. *Stereochemistry of Organic Compounds*. New York: John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III, Peyton. "Resolution of (±)-5-Bromonornicotine. Synthesis of (R)- and (S)-Nornicotine of High Enantiomeric Purity." *J. Org. Chem. Vol.* 47, No. 21 (1982): pp. 4165-4167), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111).

By method (3), a racemic mixture of two enantiomers can be separated by chromatography using a chiral stationary phase (Lough, W. J., Ed. *Chiral Liquid Chromatography*. New York: Chapman and Hall, 1989; Okamoto, Yoshio, et al. "Optical resolution of dihydropyridine enantiomers by high-performance liquid chromatography using phenylcarbamates of polysaccharides as a chiral stationary phase." *J. of Chromatogr.* Vol. 513 (1990): pp. 375-378). Enriched or purified enantiomers can be distinguished by methods used to distinguish other chiral molecules with asymmetric carbon atoms, such as optical rotation and circular dichroism.

Biological Evaluation

B-Raf mutant protein 447-717 (V600E) was co-expressed with the chaperone protein Cdc37, complexed with Hsp90 (Roe, S. Mark, et al. "The Mechanism of Hsp90 Regulation by the Protein Kinase-Specific Cochaperone p50$^{cdc37}$." *Cell.* Vol. 116 (2004): pp. 87-98; Stancato, L F, et al. "Raf exists in a native heterocomplex with Hsp90 and p50 that can be reconstituted in a cell free system." *J. Biol. Chem.* 268(29) (1993): pp. 21711-21716).

Determining the activity of Raf in the sample is possible by a number of direct and indirect detection methods (US 2004/0082014). Activity of human recombinant B-Raf protein may be assessed in vitro by assay of the incorporation of radio labeled phosphate to recombinant MAP kinase (MEK), a known physiologic substrate of B-Raf, according to US 2004/0127496 and WO 03/022840. The activity/inhibition of V600E full-length B-Raf was estimated by measuring the incorporation of radio labeled phosphate from [γ-$^{33}$P]ATP into FSBA-modified wild-type MEK (see Example A).

Administration and Pharmaceutical Formulations

The compounds of the invention may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compounds may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

One embodiment of the present invention includes a pharmaceutical composition comprising a compound of Formula I, or a stereoisomer or pharmaceutically acceptable salt thereof. In a further embodiment, the present invention provides a pharmaceutical composition comprising a compound of Formula I, or a stereoisomer or pharmaceutically acceptable salt thereof, together with a pharmaceutically acceptable carrier or excipient.

Another embodiment of the present invention provides a pharmaceutical composition comprising a compound of Formula I for use in the treatment of a hyperproliferative disease.

Another embodiment of the present invention provides a pharmaceutical composition comprising a compound of Formula I for use in the treatment of cancer.

Methods of Treatment with Compounds of the Invention

The invention includes methods of treating or preventing disease or condition by administering one or more compounds of this invention, or a stereoisomer or pharmaceutically acceptable salt thereof. In one embodiment, a human patient is treated with a compound of Formula I, or a stereoisomer or pharmaceutically acceptable salt thereof, and a pharmaceutically acceptable carrier, adjuvant, or vehicle in an amount to detectably inhibit B-Raf activity.

In another embodiment, a human patient is treated with a compound of Formula I, or a stereoisomer, tautomer, prodrug or pharmaceutically acceptable salt thereof, and a pharmaceutically acceptable carrier, adjuvant, or vehicle in an amount to detectably inhibit B-Raf activity.

In another embodiment of the present invention, a method of treating a hyperproliferative disease in a mammal comprising administering a therapeutically effective amount of the compound of Formula I, or a stereoisomer, tautomer, prodrug or pharmaceutically acceptable salt thereof, to the mammal is provided.

In another embodiment of the present invention, a method of treating a hyperproliferative disease in a mammal comprising administering a therapeutically effective amount of the compound of Formula I, or a stereoisomer or pharmaceutically acceptable salt thereof, to the mammal is provided.

In another embodiment of the present invention, a method of treating kidney disease in a mammal comprising administering a therapeutically effective amount of the compound of Formula I, or a stereoisomer, tautomer, prodrug or pharmaceutically acceptable salt thereof, to the mammal is provided. In a further embodiment, the kidney disease is polycystic kidney disease.

In another embodiment, a method of treating or preventing cancer in a mammal in need of such treatment, wherein the method comprises administering to said mammal a therapeutically effective amount of a compound of Formula I, or a stereoisomer or pharmaceutically acceptable salt thereof. The cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, NSCLC, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia. Another embodiment of the present invention provides the use of a compound of Formula I, or a stereoisomer or pharmaceutically acceptable salt thereof, in the manufacture of a medicament for the treatment of cancer.

In another embodiment, a method of treating or preventing cancer in a mammal in need of such treatment, wherein the method comprises administering to said mammal a therapeutically effective amount of a compound of Formula I, or a stereoisomer, tautomer, prodrug or pharmaceutically acceptable salt thereof.

Another embodiment of the present invention provides the use of a compound of Formula I, or a stereoisomer, tautomer, prodrug or pharmaceutically acceptable salt thereof, in the manufacture of a medicament for the treatment of cancer.

Another embodiment of the present invention provides the use of a compound of Formula I, or a stereoisomer, tautomer, prodrug or pharmaceutically acceptable salt thereof, in the manufacture of a medicament for the treatment of kidney disease. In a further embodiment, the kidney disease is polycystic kidney disease.

In another embodiment, a method of preventing or treating cancer, comprising administering to a mammal in need of such treatment an effective amount of a compound of Formula I, or a stereoisomer, tautomer, prodrug or pharmaceutically acceptable salt thereof, alone or in combination with one or more additional compounds having anti-cancer properties.

In another embodiment, a method of preventing or treating cancer, comprising administering to a mammal in need of such treatment an effective amount of a compound of Formula I, or a stereoisomer or pharmaceutically acceptable salt thereof, alone or in combination with one or more additional compounds having anti-cancer properties.

In one further embodiment, the cancer is a sarcoma.

In another further embodiment, the cancer is a carcinoma. In one further embodiment, the carcinoma is squamous cell carcinoma. In another further embodiment, the carcinoma is an adenoma or adenocarcinoma.

In another embodiment, a method of treating or preventing a disease or disorder modulated by B-Raf, comprising administering to a mammal in need of such treatment an effective amount of a compound of Formula I, or a stereoisomer or pharmaceutically acceptable salt thereof. Examples of such diseases and disorders include, but are not limited to, cancer. The cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, NSCLC, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

In another embodiment, a method of treating or preventing a disease or disorder modulated by B-Raf, comprising administering to a mammal in need of such treatment an effective amount of a compound of Formula I, or a stereoisomer, tautomer, prodrug or pharmaceutically acceptable salt thereof.

In another embodiment of the present invention, a method of preventing or treating kidney disease, comprising administering to a mammal in need of such treatment an effective amount of a compound of Formula I, or a stereoisomer, prodrug or pharmaceutically acceptable salt thereof, alone or in combination with one or more additional compounds. In another embodiment of the present invention, a method of preventing or treating polycystic kidney disease, comprising administering to a mammal in need of such treatment an effective amount of a compound of Formula I, or a stereoisomer, prodrug or pharmaceutically acceptable salt thereof, alone or in combination with one or more additional compounds.

Another embodiment of the present invention provides the use of a compound of Formula I, or a stereoisomer or pharmaceutically acceptable salt thereof, in the manufacture of a medicament for the treatment of cancer. The cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, NSCLC, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia. In a further embodiment, the use of a compound of Formula I in the manufacture of a medicament, for use as a b-Raf inhibitor in the treatment of a patient undergoing cancer therapy.

Another embodiment of the present invention provides the use of a compound of Formula I, or a stereoisomer, tautomer, prodrug or pharmaceutically acceptable salt thereof, in the manufacture of a medicament for the treatment of cancer.

Another embodiment of the present invention provides the use of a compound of Formula I, or a stereoisomer, tautomer, prodrug or pharmaceutically acceptable salt thereof, in the manufacture of a medicament for the treatment of polycystic kidney disease. In a further embodiment, the kidney disease is polycystic kidney disease.

Another embodiment of the present invention provides the compounds of Formula I for use in therapy.

Another embodiment of the present invention provides the compounds of Formula I for use in the treatment of a hyperproliferative disease. In a further embodiment, the hyperproliferative disease is cancer (as further defined and may be individually selected from those above).

Another embodiment of the present invention provides the compounds of Formula I for use in the treatment of kidney disease. In a further embodiment, the kidney disease is polycystic kidney disease.

Combination Therapy

The compounds of this invention and stereoisomers and pharmaceutically acceptable salts thereof may be employed alone or in combination with other therapeutic agents for treatment. The compounds of the present invention can be used in combination with one or more additional drugs, for example an anti-hyperproliferative, anti-cancer, or chemotherapeutic agent. The second compound of the pharmaceutical combination formulation or dosing regimen preferably has complementary activities to the compound of this invention such that they do not adversely affect each other. Such agents are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

A "chemotherapeutic agent" is a chemical compound useful in the treatment of cancer, regardless of mechanism of action. Chemotherapeutic agents include compounds used in "targeted therapy" and conventional chemotherapy. A number of suitable chemotherapeutic agents to be used as combination therapeutics are contemplated for use in the methods of the present invention. The present invention contemplates, but is not limited to, administration of numerous anticancer agents, such as: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons [e.g., IFN-a, etc.] and interleukins [e.g., IL-2, etc.], etc.); adoptive immunotherapy agents; hematopoietic growth factors; agents that induce tumor cell differentiation (e.g., all-trans-retinoic acid, etc.); gene therapy reagents; antisense therapy reagents and nucleotides; tumor vaccines; inhibitors of angiogenesis, and the like.

Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sunitinib (SUTENT®, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (NEXAVAR®, Bayer), Irinotecan (CAMPTOSAR®, Pfizer) and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid;

gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotiethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the Raf inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

EXAMPLES

In order to illustrate the invention, the following Examples are included. However, it is to be understood that these Examples do not limit the invention and are only meant to suggest a method of practicing the invention. Persons skilled in the art will recognize that the chemical reactions described may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Sigma-Aldrich, Alfa Aesar, or TCI, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography purification was done on a Biotage system (Manufacturer: Dyax Corporation) having a silica gel column or on a silica SepPak cartridge (Waters) or on a Teledyne Isco Combiflash purification system using prepacked silica gel cartridges. $^1$H NMR spectra were recorded on a Varian instrument operating at 400 MHz. $^1$H-NMR spectra were obtained as $CDCl_3$, $CD_2Cl_2$, $CD_3OD$, $D_2O$, $d_6$-DMSO, $d_6$-acetone or $CD_3CN$ solutions (reported in ppm), using tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05 ppm; $CD_3CN$: 1.94 ppm) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz).

Example A

B-Raf $IC_{50}$ Assay Protocol

Activity of human recombinant B-Raf protein may be assessed in vitro by assay of the incorporation of radio labeled phosphate to recombinant MAP kinase (MEK), a known physiologic substrate of B-Raf, according to US 2004/0127496 and WO 03/022840. Catalytically active human recombinant B-Raf protein is obtained by purification from sf9 insect cells infected with a human B-Raf recombinant baculovirus expression vector.

The activity/inhibition of V600E full-length B-Raf was estimated by measuring the incorporation of radio labeled phosphate from [γ-$^{33}$P]ATP into FSBA-modified wild-type MEK. The 30-μL assay mixtures contained 25 mM Na Pipes, pH 7.2, 100 mM KCl, 10 mM $MgCl_2$, 5 mM β-glycerophosphate, 100 μM Na Vanadate, 4 μM ATP, 500 nCi [γ-$^{33}$P]ATP, 1 μM FSBA-MEK and 20 nM V600E full-length B-Raf. Incubations were carried out at 22° C. in a Costar 3365 plate (Corning). Prior to the assay, the B-Raf and FSBA-MEK were preincubated together in assay buffer at 1.5× (20 μl, of 30 nM and 1.5 μM, respectively) for 15 minutes, and the assay was initiated by the addition of 10 μL of 10 μM ATP. Following the 60-minute incubation, the assay mixtures were quenched by the addition of 100 μL of 25% TCA, the plate was mixed on a rotary shaker for 1 minute, and the product was captured on a Perkin-Elmer GF/B filter plate using a Tomtec Mach III Harvester. After sealing the bottom of the plate, 35 μl, of Bio-Safe II (Research Products International) scintillation cocktail were added to each well and the plate was top-sealed and counted in a Topcount NXT (Packard).

The compounds of Examples 1-173 were tested in the above assay and found to have an $IC_{50}$ of less than 1 μM.

Example B

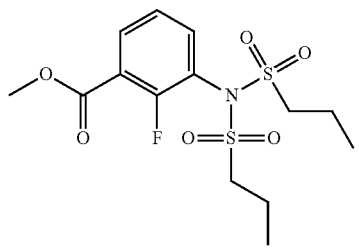

methyl 2,6-difluoro-3-(N-(propylsulfonyl)propylsulfonamido)benzoate

Step A: A 1 L flask was charged with 2,6-difluoro-3-nitrobenzoic acid (17.0 g, 83.7 mmol) and MeOH (170 mL, 0.5M). The flask was placed in a cold water bath, and an addition funnel charged with a 2M solution of trimethylsilyl ("TMS") diazomethane in hexanes (209 mL, 419 mmol) was attached to the flask. The TMS diazomethane solution was added slowly to the reaction flask over the course of 2 hours. A large excess of reagent was required in order for the reaction to reach completion as determined by the ceased evolution of $N_2$ upon further addition of reagent. The volatiles were removed in vacuo to afford methyl 2,6-difluoro-3-nitrobenzoate as a solid (18.2 g, 99%). The material was taken directly onto Step B.

Step B: 10% (wt.) Pd on activated carbon (4.46 g, 4.19 mmol) was added to a 1 L flask charged with methyl 2,6-difluoro-3-nitrobenzoate (18.2 g, 83.8 mmol) under an atmosphere of $N_2$. Ethanol (350 mL, 0.25M) was added, and then $H_2$ was passed through the reaction mixture for 15 minutes. The reaction mixture was then left to stir under two $H_2$ balloons overnight. The following day, the reaction mixture was re-flushed with fresh $H_2$ balloons and stirred an additional 4 hours. Upon consumption of the starting material and intermediate hydroxylamine as determined by TLC, $N_2$ gas was flushed through the reaction mixture. The mixture was then filtered through glass microfibre filter ("GF/F") paper twice. The volatiles were removed to afford methyl 3-amino-2,6-difluorobenzoate as an oil (15.66 g, 99%). The material was taken directly onto the next step.

Step C: Propane-1-sulfonyl chloride (23.46 mL, 209.3 mmol) was slowly added to a solution of methyl 3-amino-2,6-difluorobenzoate (15.66 g, 83.7 mmol) and triethylamine (35.00 mL, 251.1 mmol) in $CH_2Cl_2$ (175 mL, 0.5M) maintained in a cool water bath. The reaction mixture was stirred for 1 hour at room temperature. Water (300 mL) was added, and the organic layer was separated, washed with water (2×300 mL), brine (200 mL), dried ($Na_2SO_4$), filtered and concentrated to an oil. The crude material was subjected to silica gel chromatography by loading onto a Biotage 75M column with dichloromethane then eluting with 15% ethyl acetate ("EtOAc")/hexane. The isolated fractions were triturated with hexanes to afford methyl 2,6-difluoro-3-(N-(propylsulfonyl)propylsulfonamido)benzoate (24.4 g, 73% yield for 3 steps) as a solid. $^1$H NMR (400 MHz, $CDCl_3$) δ 7.52-7.45 (m, 1H), 7.08-7.02 (m, 1H), 3.97 (s, 3H), 3.68-3.59 (m, 2H), 3.53-3.45 (m, 2H), 2.02-1.89 (m, 4H), 1.10 (t, J=7.4 Hz, 6H). m/z (APCI-neg) M-($SO_2$Pr)=292.2.

Example C

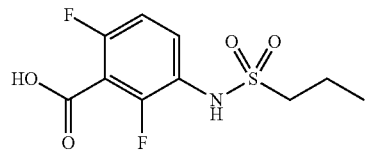

2,6-difluoro-3-(propylsulfonamido)benzoic acid

A 1N aqueous NaOH solution (150 mL, 150 mmol) was added to a solution of methyl 2,6-difluoro-3-(N-(propylsulfonyl)propylsulfonamido)benzoate (20.0 g, 50.1 mmol) in 4:1 THF/MeOH (250 mL, 0.2M). The reaction mixture was stirred at room temperature overnight. The majority of the organic solvents were then removed in vacuo (water bath temperature 35° C.). 1N HCl (150 mL) was slowly added to the mixture, and the resulting solid was filtered and rinsed with water (4×50 mL). The material was then washed with $Et_2O$ (4×15 mL) to give 2,6-difluoro-3-(propylsulfonamido) benzoic acid as a solid (10.7 g, 77% yield). $^1$H NMR (400 MHz, $d_6$-DMSO) δ 9.74 (s, 1H), 7.57-7.50 (m, 1H), 7.23-7.17 (m, 1H), 3.11-3.06 (m, 2H), 1.79-1.69 (m, 2H), 0.98 (t, J=7.4 Hz, 3H). m/z (APCI-neg) M−1=278.0.

Example D

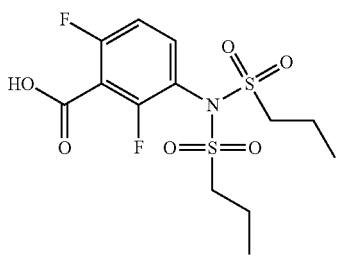

2,6-difluoro-3-(N-(propylsulfonyl)propylsulfonamido)benzoic acid

Propane-1-sulfonyl chloride (1.225 mL, 10.92 mmol) was added to a mixture of 3-amino-2,6-difluorobenzoic acid (0.573 g, 3.310 mmol), triethylamine (2.030 mL, 14.56 mmol) and $CH_2Cl_2$ (17 mL, 0.2M) cooled to 0° C. The reaction mixture was allowed to warm to room temperature and stirred for 1 hour. The mixture was then partitioned between saturated $NaHCO_3$ (100 mL) and ethyl acetate (75 mL). The aqueous layer was washed with ethyl acetate (50 mL) and then acidified with concentrated HCl to a pH of about 1. The acidified aqueous layer was extracted with ethyl acetate (2×50 mL), and the combined ethyl acetate extracts were dried ($Na_2SO_4$), filtered and concentrated. The resulting residue was triturated with hexanes to afford 2,6-difluoro-3-(N-(propylsulfonyl)propyl-sulfonamido)benzoic acid as a solid (0.948 g, 74% yield). $^1$H NMR (400 MHz, $d_6$-DMSO) δ 7.90-7.84 (m, 1H), 7.39-7.34 (m, 1H), 3.73-3.58 (m, 4H), 1.88-1.74 (m, 4H), 1.01 (t, J=7.5 Hz, 6H). m/z (APCI-neg) M-($SO_2Pr$)=278.1.

Example E

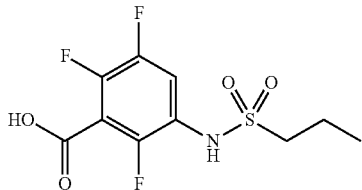

2,3,6-trifluoro-5-(propylsulfonamido)benzoic acid 2,3,6-Trifluoro-5-(propylsulfonamido)benzoic acid (8.5%) was prepared according to the general procedure of Example D, substituting 3-amino-2,5,6-trifluorobenzoic acid for 3-amino-2,6-difluorobenzoic acid.

Example F

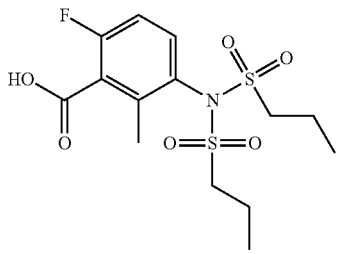

6-fluoro-2-methyl-3-(N-(propylsulfonyl)propylsulfonamido)benzoic acid

6-Fluoro-2-methyl-3-(N-(propylsulfonyl)propylsulfonamido)benzoic acid (11%) was prepared according to the general procedure of Example D, substituting 3-amino-6-fluoro-2-methylbenzoic acid for 3-amino-2,6-difluorobenzoic acid.

Example G

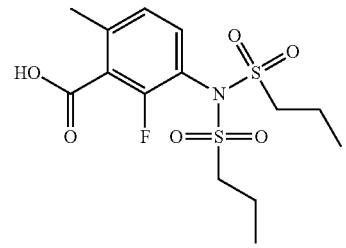

2-fluoro-6-methyl-3-(N-(propylsulfonyl)propylsulfonamido)benzoic acid

2-Fluoro-6-methyl-3-(N-(propylsulfonyl)propylsulfonamido)benzoic acid (3%) was prepared according to the general procedure of Example D, substituting 3-amino-2-fluoro-6-methylbenzoic acid for 3-amino-2,6-difluorobenzoic acid.

Example H

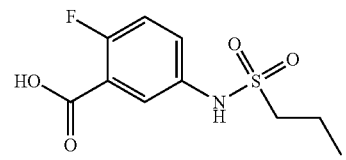

2-fluoro-5-(propylsulfonamido)benzoic acid

Propane-1-sulfonyl chloride (0.0871 mL, 0.774 mmol) was dissolved in 10% $Na_2CO_3$ (1.65 mL, 1.55 mmol) at room temperature. 5-Amino-2-fluorobenzoic acid (0.100 g, 0.645 mmol) was added and heated to 60° C. overnight. Propane-1-sulfonyl chloride (0.0871 mL, 0.774 mmol) was added again, and the reaction mixture was heated at 60° C. for another hour. The reaction mixture was cooled to room temperature, diluted with water, taken to a pH of 10 with 10% $Na_2CO_3$ and extracted with DCM (2×). The reaction mixture was then taken to a pH of 2 with 1N HCl, extracted with DCM (3×) and concentrated to a solid, 2-fluoro-5-(propylsulfonamido)benzoic acid (29%).

Example I

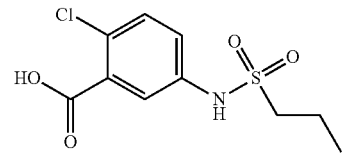

2-chloro-5-(propylsulfonamido)benzoic acid

2-Chloro-5-(propylsulfonamido)benzoic acid (14%) was prepared according to the general procedure for Example H, substituting 5-amino-2-chlorobenzoic acid for 5-amino-2-fluorobenzoic acid.

Example J

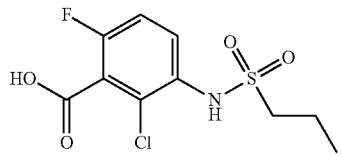

2-chloro-6-fluoro-3-(propylsulfonamido)benzoic acid

Step A: 2-Chloro-6-fluorobenzoic acid (2.00 g, 11.5 mmol) was dissolved in sulfuric acid (20 mL) and cooled to 0° C. Nitric acid (0.529 mL, 12.6 mmol) was added, and the reaction mixture was warmed to room temperature for one hour. The reaction mixture was diluted with water, and the aqueous portion was extracted with DCM (3×), dried over $Na_2SO_4$, concentrated to a solid, 2-chloro-6-fluoro-3-nitrobenzoic acid (97%), which was used directly in the next step without further purification.

Step B: 2-Chloro-6-fluoro-3-nitrobenzoic acid (0.100 g, 0.455 mmol) and Zn dust (0.298 g, 4.55 mmol) were taken up in THF (4 mL) and saturated aqueous $NH_4Cl$ (2 mL) and stirred at room temperature overnight. The reaction mixture was filtered through Celite, concentrated to a solid, and dissolved in water. The pH was adjusted to 2 with 1N HCl, and the aqueous portion was extracted with DCM (3×). The organic portion was dried over $Na_2SO_4$ and concentrated to a solid, 3-amino-2-chloro-6-fluorobenzoic acid (49%), which was used directly in the next step without further purification.

Step C: 2-Chloro-6-fluoro-3-(propylsulfonamido)benzoic acid (13%) was prepared according to the general procedure for Example H, substituting 3-amino-2-chloro-6-fluorobenzoic acid for 5-amino-2-fluorobenzoic acid.

Example K

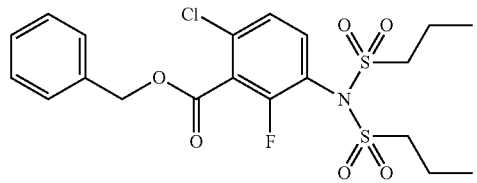

benzyl 6-chloro-2-fluoro-3-(N-(propylsulfonyl)propylsulfonamido)benzoate

Step A: A flame dried flask equipped with a stir bar and rubber septum was charged with 4-chloro-2-fluoroaniline (5.00 g, 34.35 mmol) and dry THF (170 mL). This solution was chilled to −78° C., and n-BuLi (14.7 mL, 1.07 eq. of 2.5M solution in hexanes) was then added over a 15 minute period. This mixture was stirred at −78° C. for 20 minutes, and then a THF solution (25 mL) of 1,2-bis(chlorodimethylsilyl)ethane (7.76 g, 1.05 eq.) was added slowly (over a 10 minute period) to the reaction mixture. This was stirred for 1 hour, and then 2.5M n-BuLi in hexanes (15.11 mL, 1.1 eq.) was added slowly. After allowing the mixture to warm to room temperature for one hour, the mixture was chilled back to −78° C. A third allotment of n-BuLi (15.66 mL, 1.14 eq.) was added slowly, and the mixture was stirred at −78° C. for 75 minutes. Benzyl chloroformate (7.40 g, 1.2 eq.) was then added slowly, and the mixture was stirred at −78° C. for one hour. The cooling bath was then removed. The mixture was allowed to warm for 30 minutes and then quenched with water (70 mL) and concentrated HCl (25 mL). The mixture was allowed to continue to warm to room temperature. The mixture was then extracted with EtOAc. The extracts were washed twice with a saturated $Na_2HCO_3$ solution, once with water, dried over sodium sulfate and concentrated. The resulting residue was flashed on a 65 Biotage (30% ethyl acetate/hexane) to produce benzyl 3-amino-6-chloro-2-fluorobenzoate (4.3 g, 45%) as an oil. $^1$H NMR (DMSO-$d_6$, 400 MHz) δ 7.37-7.48 (m, 5H), 7.07 (dd, 1H, J=8, 2), 6.87 (t, 1H, J=8), 5.61 (br s, 2H), 5.40 (s, 2H).

Step B: Benzyl 3-amino-6-chloro-2-fluorobenzoate (4.3 g, 15.37 mmol) was dissolved in dry dichloromethane (270 mL). Triethylamine (5.36 mL, 2.5 eq.) was added, and the mixture was chilled to 0° C. Propane-1-sulfonyl chloride (3.63 mL, 32.3 mmol, 2.1 eq.) was then added via syringe, and a precipitate resulted. Once the addition was complete, the mixture was allowed to warm to room temperature, and the starting material was consumed as determined by TLC (3:1 hexane:ethyl acetate). The mixture was then diluted with dichloromethane (200 mL), washed with 2M aqueous HCl (2×100 mL), saturated $Na_2HCO_3$ solution, dried over sodium sulfate and concentrated. The resulting residue was purified on a 65 Biotage chromatography system (40% ethyl acetate/hexane) to produce benzyl 6-chloro-2-fluoro-3-(N-(propylsulfonyl)propylsulfonamido)benzoate (5.5 g, 72%) as an oil that slowly solidified upon standing. NMR (CDCl$_3$, 400 MHz) δ 7.28-7.45 (m, 7H), 5.42 (s, 2H), 3.58-3.66 (m, 2H), 3.43-3.52 (m, 2H), 1.08 (t, 6H, J=8).

Example L

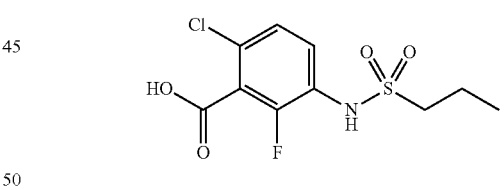

6-chloro-2-fluoro-3-(propylsulfonamido)benzoic acid

Benzyl 6-chloro-2-fluoro-3-(N-(propylsulfonyl)propylsulfonamido)benzoate (5.4 g, 10.98 mmol) was dissolved in THF (100 mL) and 1M aqueous KOH (100 mL). This mixture was refluxed for 16 hours and then allowed to cool to room temperature. The mixture was then acidified to a pH of 2 with 2M aqueous HCl and extracted with EtOAc (2 X). The extracts were washed with water, dried over sodium sulfate and concentrated to a solid that was triturated with hexanes/ether to give 6-chloro-2-fluoro-3-(propylsulfonamido)benzoic acid (2.2 g, 68%) as a solid. NMR (DMSO-$d_6$, 400 MHz) δ 9.93 (s, 1H), 7.49 (t, 1H, J=8), 7.38 (dd, 1H, J=8, 2), 3.11-3.16 (m, 2H), 1.68-1.78 (m, 2H), 0.97 (t, 3H, J=8).

Example M

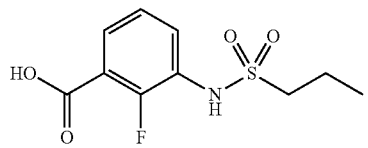

2-fluoro-3-(propylsulfonamido)benzoic acid

6-Chloro-2-fluoro-3-(propylsulfonamido)benzoic acid (0.5 g, 1.69 mmol) was dissolved in methanol (15 mL), and Pearlman's catalyst (one weight equivalent, 0.5 g, 20% Pd(OH)$_2$ on carbon, 50% by weight water) was added. This mixture was subjected to a balloon of hydrogen for 3 hours and then filtered through GF/F filter paper. The filtrate was concentrated to 2-fluoro-3-(propylsulfonamido)benzoic acid (396 mg, 90%) as a solid. MS (M-H+) 262. NMR (DMSO-d$_6$, 400 MHz) δ 13.36 (s, 1H), 9.76 (s, 1H), 7.58-7.70 (m, 2H), 7.26 (t, 1H, J=8), 3.10 (t, 2H, J=8), 1.69-1.80 (m, 2H), 0.98 (t, 3H, J=8).

Example N

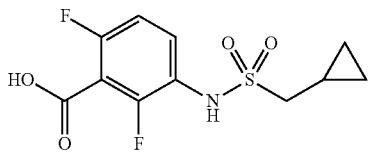

3-(cyclopropylmethylsulfonamido)-2,6-difluorobenzoic acid

Step A: Cyclopropylmethanesulfonyl chloride (1.27 g, 8.20 mmol) was added to a mixture of 3-amino-2,6-difluorobenzoic acid (0.430 g, 2.48 mmol), triethylamine (1.52 mL, 10.9 mmol) and CH$_2$Cl$_2$ (12 mL, 0.2M) cooled to 0° C. The reaction mixture was allowed to warm to room temperature and stirred for 1 hour. The mixture was then partitioned between saturated NaHCO$_3$ (75 mL) and ethyl acetate (50 mL). The aqueous layer was washed with ethyl acetate (50 mL) and then acidified to a pH of 1 with concentrated HCl. The acidified aqueous layer was extracted twice with ethyl acetate (2×50 mL), and the combined ethyl acetate extracts were dried (Na$_2$SO$_4$), filtered and concentrated to provide crude 3-(1-cyclopropyl-N-(cyclopropylmethylsulfonyl)methylsulfonamido)-2,6-difluorobenzoic acid (380 mg, 37%).

Step B: A solution of 1N NaOH (2.78 mL, 2.78 mmol) was added to a solution of crude 3-(1-cyclopropyl-N-(cyclopropylmethylsulfonyl)methylsulfonamido)-2,6-difluorobenzoic acid (380 mg, 0.928 mmol) in 4:1 THF/MeOH (5 mL, 0.2M). The reaction mixture was stirred at room temperature for 1 hour, after which most of the organic solvents were removed. 1N HCl (3 mL) was slowly added to the mixture to acidify to a pH of 1. The acidified aqueous layer was extracted with ethyl acetate (75 mL). The ethyl acetate extract was washed with water (2×20 mL), brine (20 mL), dried (Na$_2$SO$_4$), filtered and concentrated. Trituration of the residue with Et$_2$O afforded 3-(cyclopropylmethylsulfonamido)-2,6-difluorobenzoic acid as a solid (139 mg, 51%). $^1$H NMR (400 MHz, d$_6$-DMSO) δ 9.76 (s, 1H), 7.60-7.54 (m, 1H), 7.22-7.16 (m, 1H), 3.10 (d, J=7.0 Hz, 2H), 1.10-0.99 (m, 1H), 0.58-0.53 (m, 2H), 0.36-0.31 (m, 2H); m/z (APCI-neg) M−1=289.9.

Example O

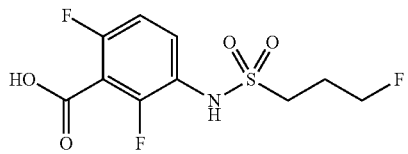

2,6-difluoro-3-(3-fluoropropylsulfonamido)benzoic acid

Methyl 2,6-difluoro-3-(N-(3-fluoropropylsulfonyl)-3-fluoropropylsulfonamido)benzoate was made according to the general procedure for Example B, substituting 3-fluoropropyl sulfonyl chloride for propane-1-sulfonyl chloride. $^1$H NMR (400 MHz, DMSO-d$_6$) δ 8.05-7.99 (m, 1H), 7.44 (t, 1H), 4.62 (t, 2H), 4.50 (t, 2H), 3.93 (s, 3H), 3.89-3.74 (m, 4H), 2.26-2.11 (m, 4H).

2,6-Difluoro-3-(3-fluoropropylsulfonamido)benzoic acid was prepared according to the general procedure for Example C, substituting methyl 2,6-difluoro-3-(N-(3-fluoropropylsulfonyl)-3-fluoropropylsulfonamido)benzoate for methyl 2,6-difluoro-3-(N-(propylsulfonyl)-propylsulfonamido)benzoate. $^1$H NMR (500 MHz, DMSO-d$_6$) δ 14.05 (br s, 1H), 9.71 (s, 1H), 7.56-7.50 (m, 1H), 7.20 (t, 1H), 3.12-3.08 (m, 2H), 1.73-1.66 (m, 2H), 1.39 (sx, 2H), 0.87 (t, 3H).

Example P

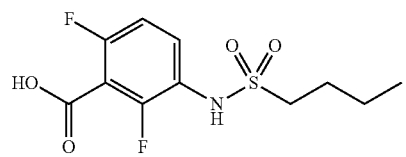

3-(butylsulfonamido)-2,6-difluorobenzoic acid

Methyl 2,6-difluoro-3-(N-(butylsulfonyl)-butylsulfonamido)benzoate was made according to the general procedure for Example B, substituting butane-1-sulfonyl chloride for propane-1-sulfonyl chloride. $^1$H NMR (500 MHz, DMSO-d$_6$) δ 7.99-7.94 (m, 1H), 7.42 (t, 1H), 3.92 (s, 3H), 3.74-3.62 (m, 4H), 1.81-1.68 (m, 4H), 1.42 (sx, 4H), 0.89 (t, 6H).

3-(Butylsulfonamido)-2,6-difluorobenzoic acid was prepared according to the general procedure for Example C, substituting methyl 2,6-difluoro-3-(N-(butylsulfonyl)-butylsulfonamido)benzoate for methyl 2,6-difluoro-3-(N-(propylsulfonyl)-propylsulfonamido)benzoate. $^1$H NMR (400 MHz, DMSO-d$_6$) δ 14.05 (br s, 1H), 9.71 (s, 1H), 7.56-7.50 (m, 1H), 7.20 (t, 1H), 3.12-3.08 (m, 2H), 1.73-1.66 (m, 2H), 1.39 (sx, 2H), 0.87 (t, 3H).

Example Q

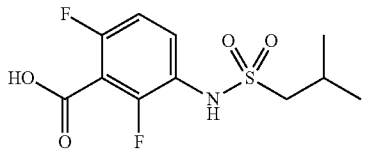

2,6-difluoro-3-(2-methylpropylsulfonamido)benzoic acid

Methyl-2,6-difluoro-3-(N-(2-methylpropylsulfonyl)-2-methylpropyl-sulfonamido)benzoate was made according to the general procedure for Example B, substituting 2-methylpropyl sulfonyl chloride for propane-1-sulfonyl chloride. m/z (LC-MS) M+1=428.4.

2,6-Difluoro-3-(2-methylpropylsulfonamido)benzoic acid was prepared according to the general procedure for Example C, substituting methyl-2,6-difluoro-3-(N-(2-methylpropyl-sulfonyl)-2-methylpropylsulfonamido)benzoate for methyl 2,6-difluoro-3-(N-(propylsulfonyl)-propylsulfonamido)benzoate. $^1$H NMR (400 MHz, DMSO-$d_6$) δ 14.01 (s, 1H), 9.71 (s, 1H), 7.56 (dd, 1H), 7.22 (dd, 1H), 3.02 (d, 2H), 2.18-2.15 (m, 1H), 1.03 (d, 6H); m/z (LC-MS) M+1=294.3.

Example R

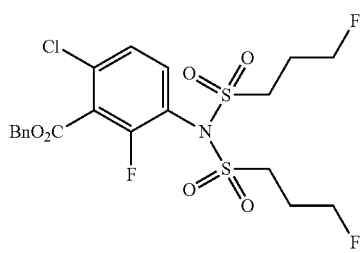

benzyl 6-chloro-2-fluoro-3-(3-fluoro-N-(3-fluoropropylsulfonyl)propylsulfonamido)benzoate Benzyl 6-chloro-2-fluoro-3-(3-fluoro-N-(3-fluoropropylsulfonyl)propylsulfonamido)benzoate (92%) was prepared according to the general procedure for Example K, Step B substituting 3-fluoropropane-1-sulfonyl chloride for propane-1-sulfonyl chloride.

Example S

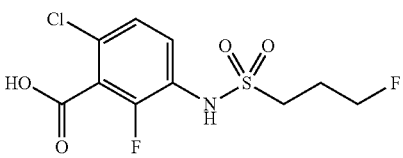

6-chloro-2-fluoro-3-(3-fluoropropylsulfonamido) benzoic acid

6-Chloro-2-fluoro-3-(3-fluoropropylsulfonamido)benzoic acid (71%) was prepared according to the general procedure for Example L substituting benzyl 6-chloro-2-fluoro-3-(3-fluoro-N-(3-fluoropropylsulfonyl)propylsulfonamido)benzoate for benzyl 6-chloro-2-fluoro-3-(N-(propylsulfonyl) propylsulfonamido)benzoate.

Example T

2-fluoro-3-(3-fluoropropylsulfonamido)benzoic acid

2-Fluoro-3-(3-fluoropropylsulfonamido)benzoic acid (81%) was prepared according to the general procedure for Example M substituting 6-chloro-2-fluoro-3-(3-fluoropropylsulfonamido)benzoic acid for 6-chloro-2-fluoro-3-(propylsulfonamido)benzoic acid.

Example U

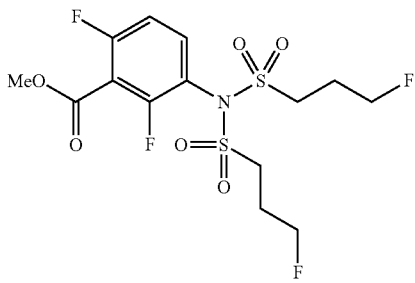

methyl 2,6-difluoro-3-(3-fluoro-N-(3-fluoropropylsulfonyl)propyl sulfonamido)benzoate 3-Fluoropropane-1-sulfonyl chloride (14.3 mL, 129 mmol) was slowly added to a solution of methyl 3-amino-2, 6-difluorobenzoate (24.1 g, 129 mmol) and pyridine (31.2 mL, 386 mmol) in $CH_2Cl_2$ (360 mL). The reaction mixture was stirred for over two days at room temperature. The reaction mixture was diluted with methylene chloride. The reaction mixture was then washed with an aqueous solution of saturated sodium bicarbonate, 1N HCl, and brine, then dried ($Na_2SO_4$), filtered and concentrated to an oil to give methyl 2,6-difluoro-3-(3-fluoro-N-(3-fluoropropylsulfonyl)propyl-sulfonamido)benzoate (38.1 g). $^1$H NMR (400 MHz, $CDCl_3$, ppm) 7.69 (dt, 1H), 7.00 (dt, 1H), 6.55 (s, 1H), 4.56 (dd, 2H), 3.28-3.17 (m, 2H), 2.32-2.15 (m, 2H).

Example V

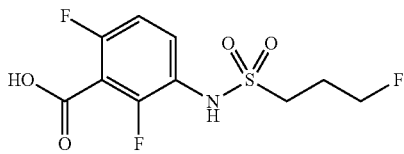

2,6-difluoro-3-(3-fluoropropylsulfonamido)benzoic acid 2,6-Difluoro-3-(N-(3-fluoropropylsulfonyl)propylsulfonamido)benzoate (38 g, 120 mmol) was dissolved in 5:2 THF/MeOH (250 mL), and a solution of lithium hydroxide (8.77 g, 366 mmol) in water (50 mL) was added. The reaction mixture was stirred at room temperature for four hours. The majority of the organic solvents were then removed in vacuo. 2.5N HCl (500 mL) was slowly added to the mixture, and the resulting solid was filtered and rinsed with cold ether to give 2,6-difluoro-3-(3-fluoropropylsulfonamido)benzoic acid as a solid (29.3 g, 81% yield). $^1$H NMR (400 MHz, CDCl$_3$ ppm) 9.85 (s, 1H), 7.54 (dt, 1H), 7.21 (dt, 1H), 4.54 (td, 2H), 2.20-2.00 (m, 2H), 3.24-3.18 (m, 2H).

Example W

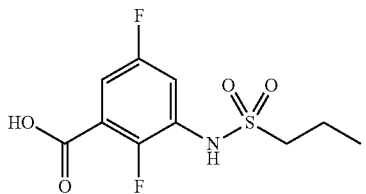

2,5-difluoro-3-(propylsulfonamido)benzoic acid

Step A: 2,5-Difluoro-3-nitrobenzoic acid (2.01 g, 9.90 mmol, 31.3% yield) was dissolved in concentrated sulfuric acid (25 mL) and cooled to 0° C. Nitric Acid (1.46 mL, 34.8 mmol) was added, and the reaction mixture was stirred at room temperature for one hour. The solution was extracted with DCM (3×), and the combined organic layers were dried over sodium sulfate and concentrated. The residue was purified by column chromatography (1:1 hexanes:1% HCOOH/EtOAc) giving 2,5-difluoro-3-nitrobenzoic acid (2.01 g, 31.3%) as a solid.

Step B: 2,5-Difluoro-3-nitrobenzoic acid (2.00 g, 9.847 mmol) was dissolved in MeOH (60 mL). TMSCl (6.220 mL, 49.24 mmol) was added, and the reaction mixture was stirred at reflux for 4 hours. The reaction mixture was concentrated to about 20 mL, and the crystals produced were filtered and dried under high vacuum providing methyl 2,5-difluoro-3-nitrobenzoate (1.55 g, 72.4%) as a crystalline solid.

Step C: Methyl 3-amino-2,5-difluorobenzoate (96.5%) was prepared according to the general procedure for Example B, Step B, substituting methyl 2,5-difluoro-3-nitrobenzoate for methyl 2,6-difluoro-3-nitrobenzoate.

Step D: Methyl 2,5-difluoro-3-(N-(propylsulfonyl)propylsulfonamido)-benzoate was prepared according to the general procedure for Example B, Step C, substituting methyl 3-amino-2,5-difluorobenzoate for methyl 3-amino-2,6-difluorobenzoate.

Step E: 2,5-Difluoro-3-(propylsulfonamido)benzoic acid (83.8%, two steps) was prepared according to the general procedure for Example C, substituting methyl 2,5-difluoro-3-(N-(propylsulfonyl)propylsulfonamido)benzoate for methyl 2,6-difluoro-3-(N-(propylsulfonyl)propylsulfonamido)benzoate. $^1$H NMR (400 MHz, d$_6$-DMSO) δ 13.67 (br s, 1H), 10.07 (s, 1H), 7.46-7.50 (m, 1H), 7.38-7.42 (m, 1H), 3.17-3.21 (m, 2H), 1.70-1.76 (m, 2H), 0.95-0.99 (m, 3H); m/z (APCI-neg) M−1=278.1.

Example X

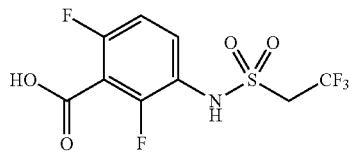

2,6-difluoro-3-(2,2,2-trifluoroethylsulfonamido)benzoic acid

Step A: 2,2,2-Trifluoroethyl-sulfonyl chloride (459 mL, 4.15 mmol) was slowly added to a solution of methyl 3-amino-2,6-difluorobenzoate (311 g, 1.66 mmol) and pyridine (0.806 mL, 9.97 mmol) in dichloromethane (8.92 mL, 139 mmol), while applying external cooling using an acetone dry ice bath. The reaction mixture was stirred for 45 minutes, and the dry ice bath was removed. The reaction mixture was kept stirring for another hour. The mixture was diluted with EtOAc (100 mL), washed with water (2×25 mL) and brine (25 mL), dried (Na$_2$SO$_4$), filtered, and then concentrated to an oil. The crude product was purified by column chromatography, eluting with 15% EtOAc/hexane to afford methyl 2,6-difluoro-3-(2-trifluoroethylsulfonamido)benzoate as a solid (513 mg, 92.6% yield). $^1$H NMR (400 MHz, d$_6$-DMSO) δ 8.10-8.01 (m, 1H), 7.48 (t, 1H), 4.68 (s, 2H), 4.58 (s, 2H), 3.98 (s, 3H).

Step B: 2,6-Difluoro-3-(2-trifluoroethylsulfonamido)benzoic acid was prepared according to the general procedure for Example C, substituting methyl 2,6-difluoro-3-(2-trifluoroethylsulfonamido)benzoate for methyl 2,6-difluoro-3-(N-(propylsulfonyl)-propylsulfonamido)benzoate. $^1$H NMR (500 MHz, d$_6$-DMSO) δ 14.08 (br s, 1H), 9.75 (s, 1H), 7.58-7.52 (m, 1H), 7.25 (t, 1H), 3.15-3.11 (s, 2H).

Example Y

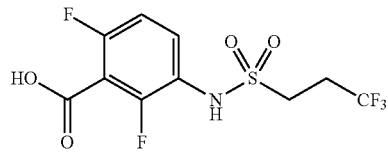

2,6-difluoro-3-(3,3,3-trifluoropropylsulfonamido) benzoic acid

Step A: Methyl 2,6-difluoro-3-(N-(3,3,3-trifluoropropylsulfonyl)-3,3,3-trifluoropropyl-sulfonamido)benzoate was made according to the general procedure for Example B, substituting 3,3,3-trifluoropropyl sulfonyl chloride for propane-1-sulfonyl chloride. $^1$H NMR (400 MHz, d$_6$-DMSO) δ 8.05-7.99 (m, 1H), 7.44 (t, 1H), 4.62 (t, 2H), 4.50 (t, 2H), 3.93 (s, 3H), 3.89-3.74 (m, 4H), 2.26-2.11 (m, 4H).

Step B: 2,6-Difluoro-3-(3,3,3-trifluoropropylsulfonamido)benzoic acid was prepared according to the general procedure for Example C, substituting methyl 2,6-difluoro-3-(N-(3,3,3-trifluoropropylsulfonyl)-3,3,3-trifluoropropylsulfonamido)benzoate for methyl 2,6-difluoro-3-(N-(propylsulfonyl)-propylsulfonamido)benzoate. $^1$H NMR (500 MHz, d$_6$-DMSO) δ 14.05 (br s, 1H), 9.71 (s, 1H), 7.56-7.50 (m, 1H), 7.20 (t, 1H), 3.12-3.08 (m, 2H), 1.73-1.66 (m, 2H).

Example Z

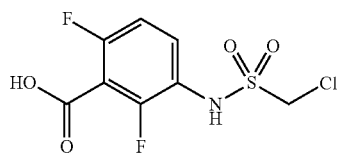

2,6-difluoro-3-(2-chloromethylsulfonamido)benzoic acid

Step A: Methyl 2,6-difluoro-3-(N-(2-chloromethylsulfonyl)-2-chloromethylsulfonamido) benzoate was made according to the general procedure for Example B, substituting 2-chloromethyl sulfonyl chloride for propane-1-sulfonyl chloride. $^1$H NMR (400 MHz, d$_6$-DMSO) δ 8.08-7.97 (m, 1H), 7.45 (t, 1H), 4.65 (s, 2H), 4.55 (s, 2H), 4.02 (s, 3H).

Step B: 2,6-Difluoro-3-(2-chloromethylsulfonamido)benzoic acid was prepared according to the general procedure for Example C, substituting methyl 2,6-difluoro-3-(N-(2-chloromethylsulfonyl)-2-chloromethylsulfonamido)benzoate for methyl 2,6-difluoro-3-(N-(propylsulfonyl)-propylsulfonamido)benzoate. $^1$H NMR (500 MHz, d$_6$-DMSO) δ 14.10 (br s, 1H), 9.78 (s, 1H), 7.62-7.56 (m, 1H), 7.28 (t, 1H), 3.19-3.15 (s, 2H).

Example AB

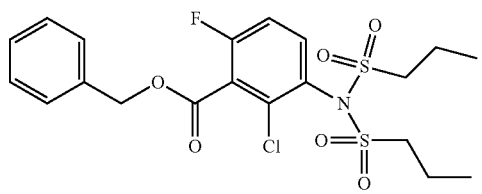

benzyl 2-chloro-6-fluoro-3-(N-(propyl sulfonyl)propylsulfonamido)benzoate

Step A: Benzyl 3-amino-2-chloro-6-fluorobenzoate (56%) was prepared according to the general procedure for Example K, substituting 2-chloro-4-fluoroaniline for 4-chloro-2-fluoroaniline. $^1$H NMR (400 MHz, DMSO-d$_6$) δ 7.48-7.32 (m, 5H), 7.11-7.05 (t, 1H), 6.94-6.89 (q, 1H), 5.53-5.49 (s, 2H), 5.41-5.39 (s, 2H).

Step B: Benzyl 3-amino-2-chloro-6-fluorobenzoate (330 mg, 1.2 mmol) was dissolved in dry dichloromethane (11.8 mL). Triethylamine (0.494 mL, 3.54 mmol) was added, and the mixture was chilled to 0° C. Propane-1-sulfonyl chloride (0.332 mL, 2.95 mmol) was then added via syringe. Once the addition was complete, the mixture was allowed to warm to ambient temperature and stir for 16 hours. The mixture was diluted with dichloromethane (11 mL) and washed with water (2×50 mL) and brine (25 mL), dried over sodium sulfate, and concentrated. The resulting residue was applied directly to a silica gel column and eluted with a gradient (5% to 40%) of ethyl acetate-hexanes to provide benzyl 2-chloro-6-fluoro-3-(N-(propylsulfonyl)propylsulfonamido)benzoate (413 mg, 0.840 mmol, 71.1% yield). $^1$H NMR (400 MHz, d$_6$-DMSO) δ 8.00-7.94 (q, 1H), 7.59-7.52 (t, 1H), 7.50-7.35 (m, 5H), 5.48-5.44 (s, 2H), 3.80-3.60 (m, 4H), 1.89-1.75 (m, 4H), 1.05-0.98 (t, 6H).

Example AC

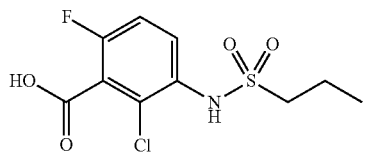

2-chloro-6-fluoro-3-(propylsulfonamido)benzoic acid

Step A: Benzyl 2-chloro-6-fluoro-3-(N-(propylsulfonyl)propylsulfonamido)benzoate (413.2 mg, 0.840 mmol) was dissolved in THF (8.4 mL) and 2.0M aqueous LiOH (1.26 mL). The mixture was refluxed for 16 hours and then allowed to cool to ambient temperature. The mixture was acidified to a pH of 0 with 1.0M HCl (5.0 mL) and then adjusted to a pH of 4 using saturated sodium bicarbonate. The mixture was extracted with EtOAc (2×). The extracts were washed with water (2×) and brine (1×), dried over sodium sulfate and concentrated to afford benzyl 2-chloro-6-fluoro-3-(propylsulfonamido)benzoate (174.5 mg, 0.4523 mmol, 53.9% yield). MS (APCI-neg) m/z=384.1 (M-H).

Step B: Benzyl 2-chloro-6-fluoro-3-(propylsulfonamido)benzoate (174.5 mg, 0.4523 mmol) was dissolved in 3:1 dioxane:water (7.5 mL) and treated with barium hydroxide (100.7 mg, 0.5879 mmol). The reaction mixture was heated to 80° C. for 16 hours and then allowed to cool to ambient temperature. The mixture was acidified to a pH of 0 with concentrated HCl. The reaction mixture was allowed to stir for 10 minutes, after which the pH was adjusted to a pH of 4 using saturated sodium bicarbonate. The mixture was extracted with EtOAc (2×). The extracts were washed with water (2×) and brine (1×), dried over sodium sulfate, and concentrated to afford 2-chloro-6-fluoro-3-(propylsulfonamido)benzoic acid (75.7 mg, 0.2560 mmol, 56.6% yield). MS (APCI-neg) m/z=293.9 (M-H).

Example AD

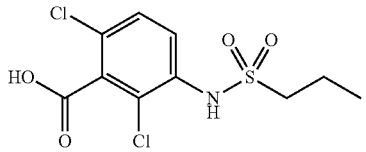

2,6-dichloro-3-(propylsulfonamido)benzoic acid

Step A: 2,6-Dichloro-3-nitrobenzoic acid (2.13 g, 9.03 mmol) was dissolved in 2:1 THF:saturated aqueous $NH_4Cl$ and cooled to 0° C. The mixture was treated with zinc (11.8 g, 181 mmol). The reaction mixture was allowed to warm to ambient temperature and stir for 24 hours. The reaction mixture was filtered through GF/F paper while rinsing with THF. The mixture was acidified to a pH of 1 using 1.0M HCl and extracted with 15% 2-propanol:DCM (3×). The extracts were washed with water and brine, dried over sodium sulfate and concentrated to afford 3-amino-2,6-dichlorobenzoic acid (1.40 g, 6.82 mmol, 75.5% yield). MS (APCI-neg) m/z=203.6 (M-H).

Step B: 3-Amino-2,6-dichlorobenzoic acid (1.40 g, 6.82 mmol) was dissolved in dry dichloromethane (66.7 mL). Triethylamine (4.09 mL, 29.4 mmol) was added, and the mixture was chilled to 0° C. Propane-1-sulfonyl chloride (2.48 mL, 22 mmol) was then added via syringe. Once the addition was complete, the mixture was allowed to warm to ambient temperature and stir for 1 hour. The mixture was concentrated in vacuo and diluted with diethyl ether. The mixture was washed with 0.25M NaOH (80 mL), and the aqueous layer was acidified to a pH of 1 using 1.0M HCl. The aqueous layer was extracted with 15% 2-propanol:DCM (2×300 mL). The organic layer was collected, dried over sodium sulfate, and concentrated to afford 2,6-dichloro-3-(propylsulfonamido)benzoic acid (1.55 g, 4.96 mmol, 74.4% yield). $^1$H NMR (400 MHz, $d_6$-DMSO) δ 9.77-9.75 (s, 1H), 7.84-7.80 (d, 1H), 7.71-7.68 (d, 1H), 3.82-3.72 (m, 2H), 1.89-1.70 (m, 2H), 1.05-1.03 (m, 3H).

Example 1

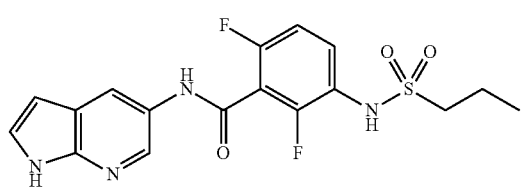

2,6-difluoro-3-(propylsulfonamido)-N-(1H-pyrrolo[2,3-b]pyridin-5-yl)benzamide

1H-Pyrrolo[2,3-b]pyridin-5-amine (9.97 g, 74.88 mmol), 2,6-difluoro-3-(propylsulfonamido)benzoic acid (23.00 g, 82.37 mmol), EDCI (15.79 g, 82.37 mmol), and HOBt (11.13 g, 82.37 mmol) were charged to a 2 L round-bottomed flask. DMF was added to give a homogeneous solution, and the reaction mixture was stirred at room temperature overnight. The solution was partitioned between water and EtOAc. The aqueous layer was extracted with EtOAc (3×), and the combined organics were washed with water (3×), brine, dried over $Na_2SO_4$ and concentrated to a slurry. DCM (500 mL) was added to this slurry, and the mixture was reconcentrated. Additional DCM (500 mL) was added, and the slurry was filtered, washed with DCM and dried under vacuum providing 2,6-difluoro-3-(propylsulfonamido)-N-(1H-pyrrolo[2,3-b]pyridin-5-yl)benzamide (15.49 g, 52.5%) as a solid. $^1$H NMR (400 MHz, DMSO-$d_6$) δ 11.65 (br s, 1H), 10.85 (s, 1H), 9.79 (br s, 1H), 8.34-8.37 (m, 2H), 7.51-7.57 (m, 1H), 7.48-7.50 (m, 1H), 6.46-6.48 (m, 1H), 3.11-3.15 (m, 2H), 1.75-1.80 (m, 2H), 0.98-1.02 (m, 3H); m/z (APCI-pos) M+1=395.1.

Example 2

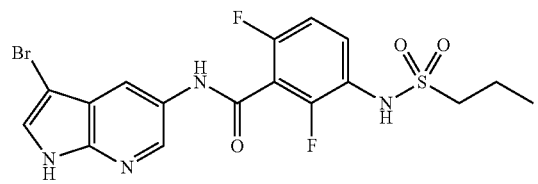

N-(3-bromo-1H-pyrrolo[2,3-b]pyridin-5-yl)-2,6-difluoro-3-(propylsulfonamido)benzamide 2,6-Difluoro-3-(propylsulfonamido)-N-(1H-pyrrolo[2,3-b]pyridin-5-yl)benzamide (0.500 g, 1.268 mmol) was charged to a 100 mL round-bottom flask. $CHCl_3$ (25 mL) was added to form a slurry. N-Bromosuccinimide (0.271 g, 1.52 mmol) was added and stirred for 20 minutes. The reaction mixture was filtered, washed with DCM, and dried under vacuum providing N-(3-bromo-1H-pyrrolo[2,3-b]pyridin-5-yl)-2,6-difluoro-3-(propylsulfonamido)benzamide (0.427 g, 71.2%) as a solid. $^1$H NMR (400 MHz, DMSO-$d_6$) δ 12.12 (br s, 1H), 11.04 (s, 1H), 9.81 (br s, 1H), 8.41-8.43 (m, 1H), 8.34-8.35 (m, 1H), 7.74-7.76 (m, 1H), 7.53-7.59 (m, 1H), 7.25-7.30 (m, 1H), 3.11-3.15 (m, 2H), 1.75-1.80 (m, 2H), 0.98-1.02 (m, 3H); m/z (APCI-pos) M+1=473.0, 475.0.

Example 3

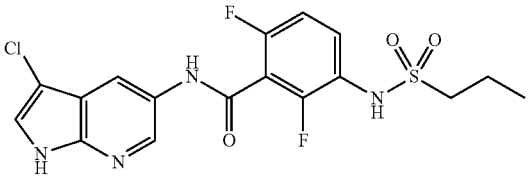

N-(3-chloro-1H-pyrrolo[2,3-b]pyridin-5-yl)-2,6-difluoro-3-(propylsulfonamido)benzamide 2,6-Difluoro-3-(propylsulfonamido)-N-(1H-pyrrolo[2,3-b]pyridin-5-yl)benzamide (0.300 g, 0.7607 mmol) was dissolved in DMF (10 mL), and N-chlorosuccinimide (0.122 g, 0.913 mmol) was added and stirred overnight. The solution was partitioned between water and EtOAc. The organic portion was washed with water (3×), brine, dried over $Na_2SO_4$ and concentrated to an oil. DCM was added to the oil, and a solid, N-(3-chloro-1H-pyrrolo[2,3-b]pyridin-5-yl)-2,6-difluoro-3-(propylsulfonamido)benzamide (217.4 mg, 66.7%), precipitated out, which was collected by filtration. $^1$H NMR (400 MHz, DMSO-d6) δ 12.03 (br s, 1H), 11.04 (s, 1H), 9.81 (br s, 1H), 8.40-8.43 (m, 2H), 7.72-7.74 (m, 1H), 7.53-7.59 (m, 1H), 7.26-7.30 (m, 1H), 3.11-3.15 (m, 2H), 1.75-1.80 (m, 2H), 0.98-1.02 (m, 3H); m/z (APCI-neg) M-1=427.1, 429.2.

Example 4

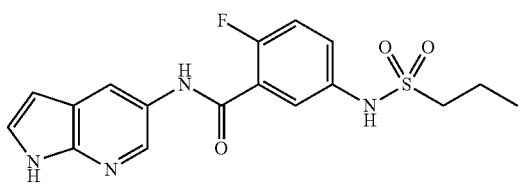

2-fluoro-5-(propylsulfonamido)-N-(1H-pyrrolo[2,3-b]pyridin-5-yl)benzamide

2-Fluoro-5-(propylsulfonamido)-N-(1H-pyrrolo[2,3-b]pyridin-5-yl)benzamide (11%) was prepared according to the general procedure for Example 1, substituting 2-fluoro-5-(propylsulfonamido)benzoic acid for 2,6-difluoro-3-(propylsulfonamido)benzoic acid. $^1$H NMR (400 MHz, DMSO-$d_6$) δ 11.61 (br s, 1H), 10.41 (s, 1H), 9.95 (br s, 1H), 8.40-8.41 (m, 1H), 8.33-8.34 (m, 1H), 7.47-7.48 (m, 2H), 7.33-7.38 (m, 2H), 6.48 (s, 1H), 3.09-3.12 (m, 2H), 1.68-1.73 (m, 2H), 0.94-0.97 (m, 3H); m/z (APCI-neg) M−1=375.3.

Example 5

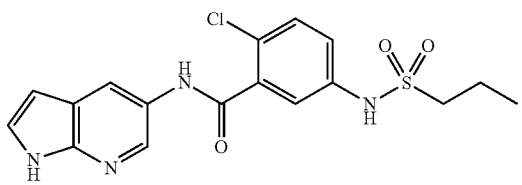

2-chloro-5-(propylsulfonamido)-N-(1H-pyrrolo[2,3-b]pyridin-5-yl)benzamide

2-Chloro-5-(propylsulfonamido)-N-(1H-pyrrolo[2,3-b]pyridin-5-yl)benzamide (56%) was prepared according to the general procedure for Example 1, substituting 2-chloro-5-(propylsulfonamido)benzoic acid for 2,6-difluoro-3-(propylsulfonamido)benzoic acid. $^1$H NMR (400 MHz, DMSO-$d_6$) δ 11.62 (br s, 1H), 10.53 (s, 1H), 10.14 (br s, 1H), 8.39-8.40 (m, 1H), 8.34-8.35 (m, 1H), 7.52-7.54 (m, 1H), 7.47-7.49 (m, 1H), 7.34 (s, 1H), 7.31-7.32 (m, 1H), 6.46-6.47 (m, 1H), 3.14-3.18 (m, 2H), 1.68-1.74 (m, 2H), 0.95-0.98 (m, 3H); m/z (APCI-neg) M−1=391.7, 393.6.

Example 6

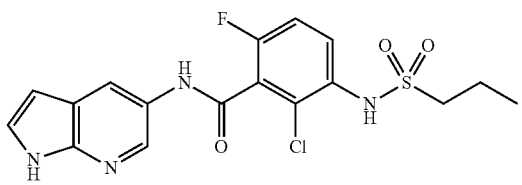

2-chloro-6-fluoro-3-(propylsulfonamido)-N-(1H-pyrrolo[2,3-b]pyridin-5-yl)benzamide 2-Chloro-6-fluoro-3-(propylsulfonamido)-N-(1H-pyrrolo[2,3-b]pyridin-5-yl)benzamide (19%) was prepared according to the general procedure for Example 1, substituting 2-chloro-6-fluoro-3-(propylsulfonamido)benzoic acid for 2,6-difluoro-3-(propylsulfonamido)benzoic acid. $^1$H NMR (400 MHz, DMSO-$d_6$) δ 11.65 (br s, 1H), 10.81 (s, 1H), 9.69 (br s, 1H), 8.35-8.36 (m, 2H), 7.56-7.60 (m, 1H), 7.48-7.50 (m, 1H), 7.39-7.43 (m, 1H), 6.47 (s, 1H), 3.11-3.15 (m, 2H), 1.76-1.82 (m, 2H), 0.98-1.02 (m, 3H); m/z (APCI-neg) M−1=409.2, 411.1.

Example 7

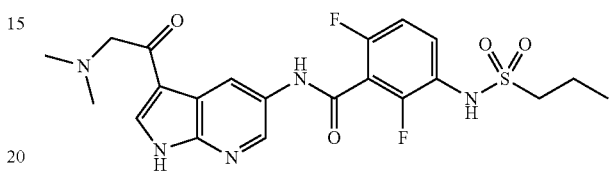

N-(3-(2-(dimethylamino)acetyl)-1H-pyrrolo[2,3-b]pyridin-5-yl)-2,6-difluoro-3-(propylsulfonamido)benzamide Step A: A solution of aluminum trichloride (0.266 g, 2.00 mmol) in 1:1 DCM:CH$_3$NO$_2$ (5 mL) was added slowly to a slurry of 2,6-difluoro-3-(propylsulfonamido)-N-(1H-pyrrolo[2,3-b]pyridin-5-yl)benzamide (0.100 g, 0.254 mmol) in 1:1 DCM:CH$_3$NO$_2$ (2 mL) at 0° C. The solution was stirred at 0° C. for 40 minutes. A solution of 2-chloroacetyl chloride (0.0307 mL, 0.380 mmol) in DCM (1 mL) was added, and the reaction mixture was allowed to warm to room temperature overnight. Additional 2-chloroacetyl chloride (5 eq.) was added, and the reaction mixture was warmed to 50° C. for 20 hours. The solution was cooled and diluted with saturated aqueous ammonium chloride and extracted with EtOAc (3 X). The organic layers were dried over Na$_2$SO$_4$, filtered and concentrated under reduced pressure. They were then purified via column chromatography (5% MeOH/DCM) to afford N-(3-(2-chloroacetyl)-1H-pyrrolo[2,3-b]pyridin-5-yl)-2,6-difluoro-3-(propylsulfonamido)benzamide (59 mg, 50%) as a solid.

Step B: N-(3-(2-Chloroacetyl)-1H-pyrrolo[2,3-b]pyridin-5-yl)-2,6-difluoro-3-(propylsulfonamido)benzamide (0.181 mL, 0.0361 mmol), EtOH (0.2 mL), and dimethylamine as a solution in MeOH (0.181 mL, 0.361 mmol) was charged to a 2 dram vial. The vial was capped and stirred at 60° C. for 4 hours. The mixture was concentrated under reduced pressure. The residue was taken up in 1M HCL (1 mL) and washed with EtOAc (2×1 mL). The aqueous portion was neutralized and extracted with 25% isopropyl alcohol ("IPA")-DCM (3×2 mL), which was concentrated to provide N-(3-(2-(dimethylamino)acetyl)-1H-pyrrolo[2,3-b]pyridin-5-yl)-2,6-difluoro-3-(propylsulfonamido)benzamide (7 mg, 40.4%) as a solid. $^1$H NMR (400 MHz, CD$_3$OD) δ 9.03-9.06 (m, 1H), 8.56-8.58 (m, 1H), 8.46 (s, 1H), 7.63-7.69 (m, 1H), 7.12-7.16 (m, 1H), 3.11-3.14 (m, 2H), 3.03 (s, 6H), 2.90 (s, 2H), 1.85-1.90 (m, 2H), 1.05-1.08 (m, 3H); m/z (APCI-pos) M+1=480.1.

Example 8

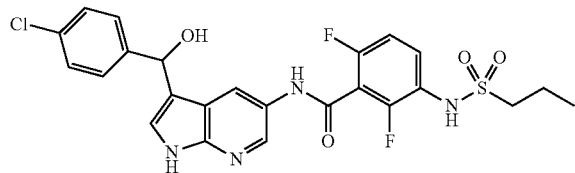

N-(3-((4-chlorophenyl)(hydroxy)methyl)-1H-pyrrolo[2,3-b]pyridin-5-yl)-2,6-difluoro-3-(propylsulfonamido)benzamide KOH (0.012 g, 0.22 mmol) was added to 2,6-difluoro-3-(propylsulfonamido)-N-(1H-pyrrolo[2,3-b]pyridin-5-yl)benzamide (0.37 mL, 0.074 mmol) in MeOH (0.4 mL), followed by the addition of 4-chlorobenzaldehyde (0.013 g, 0.096 mmol). The reaction mixture was stirred at room temperature overnight. The contents were then diluted with EtOAc and NH₄Cl (aq.) and extracted with EtOAc (3×). The organic layers were dried over Na₂SO₄ and concentrated under reduced pressure. The resulting residue was purified via column chromatography (5% MeOH/DCM) to afford N-(3-((4-chlorophenyl)(hydroxy)methyl)-1H-pyrrolo[2,3-b]pyridin-5-yl)-2,6-difluoro-3-(propylsulfonamido)benzamide (23 mg, 58%). $^1$H NMR (400 MHz, CD₃OD) δ 8.41-8.42 (m, 1H), 8.28-8.29 (m, 1H), 7.60-7.67 (m, 1H), 7.46-7.49 (m, 2H), 7.34-7.36 (m, 2H), 7.09-7.14 (m, 1H), 6.06 (s, 1H), 3.09-3.13 (m, 2H), 1.82-1.91 (m, 2H), 1.03-1.07 (m, 3H); m/z (APCI-pos) M+1=535.1.

Example 9

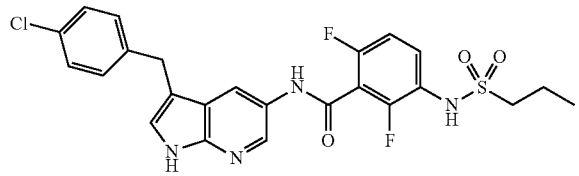

N-(3-(4-chlorobenzyl)-1H-pyrrolo[2,3-b]pyridin-5-yl)-2,6-difluoro-3-(propylsulfonamido)benzamide Triethylsilane (0.0590 mL, 0.355 mmol) and trifluoroacetic acid ("TFA"; 0.0180 mL, 0.234 mmol) were added to N-(3-((4-chlorophenyl)(hydroxy)methyl)-1H-pyrrolo[2,3-b]pyridin-5-yl)-2,6-difluoro-3-(propylsulfonamido)benzamide (0.005 g, 0.009 mmol) in CH₃CN (1 mL). The solution was warmed to 80° C. for 10 minutes. The solution was cooled and concentrated under reduced pressure to provide N-(3-(4-chlorobenzyl)-1H-pyrrolo[2,3-b]pyridin-5-yl)-2,6-difluoro-3-(propylsulfonamido)benzamide (4 mg, 82.5%). $^1$H NMR (400 MHz, CD₃OD) δ 8.63-8.44 (m, 1H), 8.30-8.32 (m, 1H), 7.62-7.68 (m, 1H), 7.35 (s, 1H), 7.27 (s, 4H), 7.10-7.15 (m, 1H), 4.11 (s, 2H), 3.09-3.13 (m, 2H), 1.84-1.89 (m, 2H), 1.03-1.07 (m, 3H); m/z (APCI-pos) M+1=519.1.

Example 10

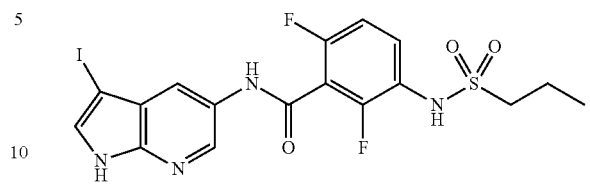

2,6-difluoro-N-(3-iodo-1H-pyrrolo[2,3-b]pyridin-5-yl)-3-(propylsulfonamido)benzamide 2,6-Difluoro-N-(3-iodo-1H-pyrrolo[2,3-b]pyridin-5-yl)-3-(propylsulfonamido)benzamide (100%) was prepared according to the general procedure for Example 2 substituting N-iodosuccinimide for N-chlorosuccinimide. $^1$H NMR (400 MHz, DMSO-d₆) δ 12.15 (br s, 1H), 11.01 (s, 1H), 9.81 (br s, 1H), 8.37 (s, 2H), 8.21 (s, 1H), 7.75 (br s, 1H), 7.53-7.59 (m, 1H), 7.26-7.30 (m, 1H), 3.11-3.15 (m, 2H), 1.75-1.80 (m, 2H), 0.98-1.02 (m, 3H); m/z (APCI-pos) M+1=520.9.

Example 11

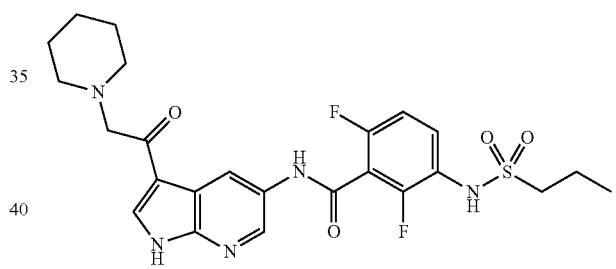

2,6-difluoro-N-(3-(2-(piperidin-1-yl)acetyl)-1H-pyrrolo[2,3-b]pyridin-5-yl)-3-(propylsulfonamido)benzamide Piperidine (0.0105 mL, 0.106 mmol) was added to N-(3-(2-chloroacetyl)-1H-pyrrolo[2,3-b]pyridin-5-yl)-2,6-difluoro-3-(propylsulfonamido)benzamide (0.005 g, 0.0106 mmol) in EtOH (0.2 mL), which was stirred at 60° C. for 1 hour. The reaction mixture was cooled and concentrated under reduced pressure. The residue was purified via column chromatography (10% MeOH/EtOAc, to 30% MeOH (7N NH₃/EtOAc). The pooled fractions were taken up in 10% MeOH/DCM and filtered to provide 2,6-difluoro-N-(3-(2-(piperidin-1-yl)acetyl)-1H-pyrrolo[2,3-b]pyridin-5-yl)-3-(propylsulfonamido)benzamide (3 mg, 54.4%). $^1$H NMR (400 MHz, CD₃OD) δ 9.05-9.07 (m, 1H), 8.54-8.57 (m, 1H), 8.44 (s, 1H), 7.63-7.69 (m, 1H), 7.12-7.17 (m, 1H), 4.71 (s, 2H), 3.59 (s, 2H), 3.10-3.14 (m, 2H), 1.92-1.99 (m, 6H), 1.84-1.90 (m, 2H), 1.04-1.08 (m, 3H); m/z (APCI-pos) M+1=520.2.

Example 12

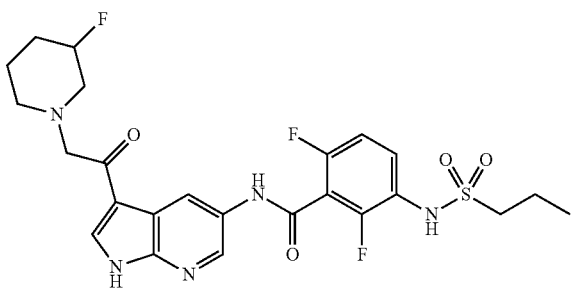

2,6-difluoro-N-(3-(2-(3-fluoropiperidin-1-yl)acetyl)-1H-pyrrolo[2,3-b]pyridin-5-yl)-3-(propylsulfonamido)benzamide Hunig's base (0.0196 mL, 0.106 mmol) and 3-fluoropiperidine (0.0148 g, 0.106 mmol) were added to N-(3-(2-chloroacetyl)-1H-pyrrolo[2,3-b]pyridin-5-yl)-2,6-difluoro-3-(propylsulfonamido)benzamide (0.005 g, 0.0106 mmol) in EtOH (0.2 mL), which was stirred at 60° C. for 3 hours. The reaction mixture was concentrated under reduced pressure, and the residue was purified via column chromatography (5% to 10% MeOH/DCM) to provide 2,6-difluoro-N-(3-(2-(3-fluoropiperidin-1-yl)acetyl)-1H-pyrrolo[2,3-b]pyridin-5-yl)-3-(propylsulfonamido)benzamide (3 mg, 52.6%). $^1$H NMR (400 MHz, CD$_3$OD) δ 8.90-8.92 (m, 1H), 8.62-8.63 (m, 1H), 8.60 (s, 1H), 7.63-7.69 (m, 1H), 7.13-7.16 (m, 1H), 4.60-4.80 (m, 1H), 3.76 (s, 2H), 3.08-3.15 (m, 2H), 2.86-2.94 (m, 1H), 2.59-2.79 (m, 4H), 2.50-2.55 (m, 1H), 1.80-1.93 (m, 4H), 1.57-1.71 (m, 2H), 1.04-1.08 (m, 3H); m/z (APCI-pos) M+1=538.1.

Example 13

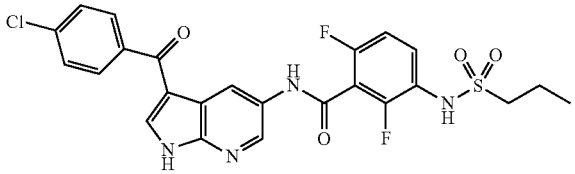

N-(3-(4-chlorobenzoyl)-1H-pyrrolo[2,3-b]pyridin-5-yl)-2,6-difluoro-3-(propylsulfonamido)benzamide MnO$_2$ (0.016 g, 0.19 mmol) was added to N-(3-((4-chlorophenyl)(hydroxy)methyl)-1H-pyrrolo[2,3-b]pyridin-5-yl)-2,6-difluoro-3-(propylsulfonamido)benzamide (0.004 g, 0.0075 mmol) in CHCl$_3$ (0.2 mL). The reaction mixture was stirred at room temperature for 60 hours. The contents were filtered through a plug of silica to afford N-(3-(4-chlorobenzoyl)-1H-pyrrolo[2,3-b]pyridin-5-yl)-2,6-difluoro-3-(propylsulfonamido)benzamide (1 mg, 25%) as a solid. $^1$H NMR (400 MHz, CD$_3$OD) δ 8.94-8.94 (m, 1H), 8.68-8.60 (m, 1H), 8.04 (s, 1H), 7.83-7.86 (m, 2H), 7.63-7.69 (m, 1H), 7.56-7.58 (m, 2H), 7.11-7.17 (m, 1H), 3.10-3.14 (m, 2H), 1.85-1.90 (m, 2H), 1.04-1.08 (m, 3H); m/z (APCI-neg) M−1=531.2.

Example 14

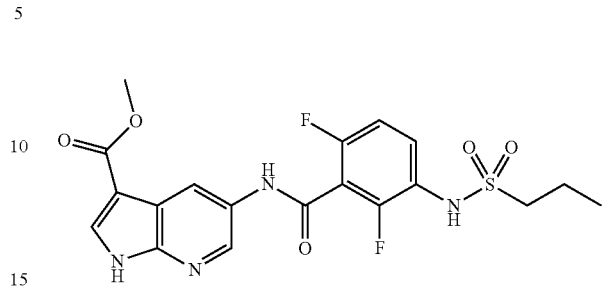

methyl 5-(2,6-difluoro-3-(propylsulfonamido)benzamido)-1H-pyrrolo[2,3-b]pyridine-3-carboxylate 2,6-Difluoro-N-(3-iodo-1H-pyrrolo[2,3-b]pyridin-5-yl)-3-(propylsulfonamido)benzamide (62.0 mg, 0.094 mmol) was dissolved in methanol (1 mL). Triethylamine ("TEA"; 39 µL, 0.281 mmol) and PdCl$_2$(PPh$_3$)$_2$ (6.6 mg, 0.10 mmol) were added, and the mixture was warmed to 70° C. under a balloon of carbon monoxide for 3 hours. The reaction mixture was then stirred at room temperature for 12 hours. The mixture was then concentrated under reduced pressure and purified by flash chromatography using a Waters Sep Pak cartridge (10 g, 1:1 EtOAc/hexane as the eluant) to give methyl 5-(2,6-difluoro-3-(propylsulfonamido)benzamido)-1H-pyrrolo[2,3-b]pyridine-3-carboxylate (41 mg, 73%). $^1$H NMR (400 MHz, DMSO-d$_6$) δ 11.25 (s, 1H), 9.81 (s, 1H), 8.82-8.84 (m, 1H), 8.64-8.66 (m, 1H), 7.53-7.81 (m, 4H), 7.25-7.32 (m, 1H), 3.89 (s, 3H), 3.08-3.16 (m, 2H), 1.71-1.82 (m, 2H), 0.95-1.03 (m, 3H); m/z (APCI-neg) M−1=591.1; (APCI-pos) M+1=593.1.

Example 15

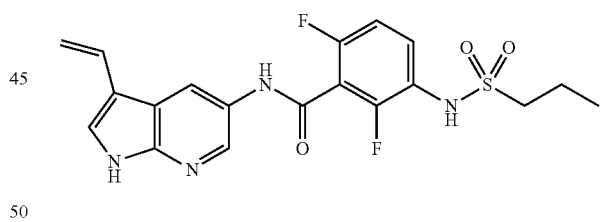

2,6-difluoro-3-(propylsulfonamido)-N-(3-vinyl-1H-pyrrolo[2,3-b]pyridin-5-yl)benzamide Step A: 2,6-Difluoro-N-(3-iodo-1-(phenylsulfonyl)-1H-pyrrolo[2,3-b]pyridin-5-yl)-3-(propylsulfonamido)benzamide (0.050 g, 0.076 mmol), potassium vinyltrifluoroborate (0.012 g, 0.091 mmol), triethylamine (d. 0.726; 0.011 mL, 0.076 mmol) and PdCl$_2$(dppf)*DCM (0.0031 g, 0.0038 mmol) were dissolved in 3:1 IPA/THF (1.0 mL), degassed with argon for 10 minutes and heated to 70° C. overnight. The solution was partitioned between water and EtOAc. The organic portion was washed with water (3×), brine, dried over Na$_2$SO$_4$ and concentrated. The resulting residue was purified by column chromatography (2:1 hexane/EtOAc) giving 2,6-difluoro-N-(1-(phenylsulfonyl)-3-vinyl-1H-pyrrolo[2,3-b]pyridin-5-yl)-3-(propylsulfonamido)benzamide (57%).

Step B: 2,6-Difluoro-N-(1-(phenylsulfonyl)-3-vinyl-1H-pyrrolo[2,3-b]pyridin-5-yl)-3-(propylsulfonamido)benzamide (0.0061 g, 0.0109 mmol) was dissolved in MeOH (1.0 mL) and water (0.3 mL). K$_2$CO$_3$ (0.0150 g, 0.109 mmol) was added, and the reaction mixture was stirred at room temperature overnight. The solution was partitioned between water and EtOAc. The organic portion was washed with water (3×), brine, dried over Na$_2$SO$_4$ and concentrated. The resulting residue was purified by column chromatography (1:1 hexane/EtOAc/1% HCO$_2$H) to give 2,6-difluoro-3-(propylsulfonamido)-N-(3-vinyl-1H-pyrrolo[2,3-b]pyridin-5-yl)benzamide (2.8 mg, 61.2%). $^1$H NMR (400 MHz, DMSO-d$_6$) δ 11.81 (br s, 1H), 10.92 (s, 1H), 9.80 (br s, 1H), 8.61-8.62 (m, 1H), 8.44-8.45 (m, 1H), 7.65-7.67 (m, 1H), 7.52-7.58 (m, 1H), 7.24-7.29 (m, 1H), 6.81-6.88 (m, 1H), 5.56-5.61 (m, 1H), 5.11-5.14 (m, 1H), 3.10-3.14 (m, 2H), 1.74-1.80 (m, 2H), 0.98-1.02 (m, 3H); m/z (APCI-neg) M−1=419.3.

EtOAc. The organic portion was washed with water (3×), brine, dried over Na$_2$SO$_4$ and concentrated to an oil, N-(3-cyano-1-(phenylsulfonyl)-1H-pyrrolo[2,3-b]pyridin-5-yl)-2,6-difluoro-3-(propylsulfonamido)benzamide. The oil (0.021 g, 0.038 mmol) was dissolved in MeOH (1.0 mL) and water (0.3 mL). K$_2$CO$_3$ (0.053 g, 0.38 mmol) was added, and the mixture stirred for 1 hour at room temperature. The solution was partitioned between water and EtOAc. The organic layer was washed with water (3×), brine, dried over Na$_2$SO$_4$ and concentrated. The residue was purified by column chromatography (5% MeOH/DCM) giving N-(3-cyano-1H-pyrrolo[2,3-b]pyridin-5-yl)-2,6-difluoro-3-(propylsulfonamido)benzamide (2.9 mg, 18%) as a solid. $^1$H NMR (400 MHz, DMSO-d$_6$) δ 11.16 (s, 1H), 8.57-8.58 (m, 1H), 8.52-8.53 (m, 1H), 8.47 (s, 1H), 7.53-7.59 (m, 1H), 7.25-7.29 (m, 1H), 3.09-3.13 (m, 2H), 1.74-1.80 (m, 2H), 0.98-1.01 (m, 3H); m/z (APCI-neg) M−1=418.2.

Example 16

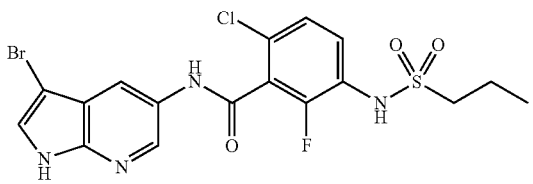

N-(3-bromo-1H-pyrrolo[2,3-b]pyridin-5-yl)-6-chloro-2-fluoro-3-(propylsulfonamido)benzamide N-(3-bromo-1H-pyrrolo[2,3-b]pyridin-5-yl)-6-chloro-2-fluoro-3-(propylsulfonamido)benzamide (62%) was prepared according to the general procedure for Example 2, substituting 6-chloro-2-fluoro-3-(propylsulfonamido)-N-(1H-pyrrolo[2,3-b]pyridin-5-yl)benzamide for 2,6-difluoro-3-(propylsulfonamido)-N-(1H-pyrrolo[2,3-b]pyridin-5-yl)benzamide. $^1$H NMR (400 MHz, DMSO-d$_6$) δ 12.13 (br s, 1H), 11.02 (s, 1H), 9.99 (br s, 1H), 8.39 (br s, 1H), 8.35 (br s, 1H), 7.52-7.56 (m, 1H), 7.44-7.46 (m, 1H), 3.15-3.19 (m, 2H), 1.74-1.79 (m, 2H), 0.98-1.01 (m, 3H); m/z (APCI-pos) M+1=473.0, 475.0.

Example 17

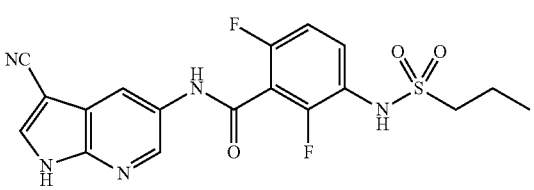

N-(3-cyano-1H-pyrrolo[2,3-b]pyridin-5-yl)-2,6-difluoro-3-(propylsulfonamido)benzamide 2,6-Difluoro-N-(3-iodo-1-(phenylsulfonyl)-1H-pyrrolo[2,3-b]pyridin-5-yl)-3-(propylsulfonamido)benzamide (0.025 g, 0.0379 mmol) and Cu(I)CN (0.0678 g, 0.758 mmol) were taken up in DMF (0.5 mL) and heated to 100° C. overnight. The solution was partitioned between water and Example 18

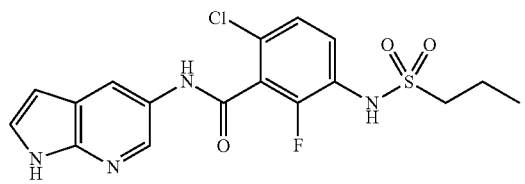

6-chloro-2-fluoro-3-(propylsulfonamido)-N-(1H-pyrrolo[2,3-b]pyridin-5-yl)benzamide 6-Chloro-2-fluoro-3-(propylsulfonamido)-N-(1H-pyrrolo[2,3-b]pyridin-5-yl)benzamide (62%) was prepared according to the general procedure for Example 1, substituting 6-chloro-2-fluoro-3-(propylsulfonamido)benzoic acid for 2,6-difluoro-3-(propylsulfonamido)benzoic acid. $^1$H NMR (400 MHz, DMSO-d$_6$) δ 11.75 (br s, 1H), 10.82 (s, 1H), 9.97 (br s, 1H), 8.35-8.36 (m, 2H), 7.42-7.55 (m, 3H), 6.47-6.48 (m, 1H), 3.14-3.18 (m, 2H), 1.73-1.79 (m, 2H), 0.98-1.01 (m, 3H); m/z (APCI-neg) M−1=409.1, 411.2.

Example 19

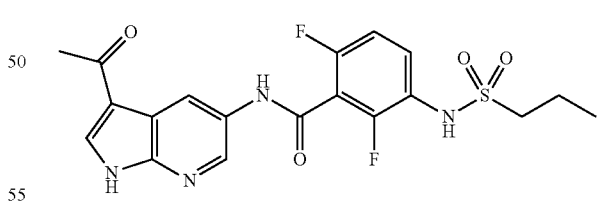

N-(3-acetyl-1H-pyrrolo[2,3-b]pyridin-5-yl)-2,6-difluoro-3-(propylsulfonamido)benzamide A slurry of aluminum trichloride (0.270 g, 2.03 mmol) was added to a slurry of 2,6-difluoro-3-(propylsulfonamido)-N-(1H-pyrrolo[2,3-b]pyridin-5-yl)benzamide (0.100 g, 0.254 mmol) in DCM (0.7 mL) at 0° C., and the reaction mixture was allowed to stir at 0° C. for 40 minutes. Acetyl chloride (0.0271 mL, 0.380 mmol) was added, and the mixture was allowed warm to room temperature overnight. CH$_3$NO$_2$ (200

μL) was added, and the reaction mixture was sonicated for 2 minutes, and allowed to stir at room temperature overnight. The reaction mixture was quenched with ice and then partitioned between aqueous sodium bicarbonate and EtOAc. The organic layer was dried over $Na_2SO_4$ and concentrated under reduced pressure. The resulting residue was purified via column chromatography (5% MeOH/EtOAc) to yield N-(3-acetyl-1H-pyrrolo[2,3-b]pyridin-5-yl)-2,6-difluoro-3-(propylsulfonamido)benzamide (71 mg, 64%) as a solid. $^1$H NMR (400 MHz, $CDCl_3$) δ 8.98-8.99 (m, 1H), 8.63-8.64 (m, 1H), 8.04 (s, 1H), 7.49-7.54 (m, 1H), 7.15-7.18 (m, 1H), 3.10-3.30 (m, 2H), 2.55 (s, 3H), 1.93-2.00 (m, 2H), 1.09-1.13 (m, 3H); m/z (APCI-pos) M+1=437.1.

Example 20

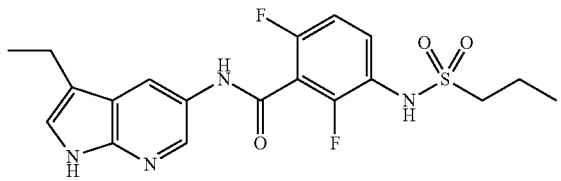

N-(3-ethyl-1H-pyrrolo[2,3-b]pyridin-5-yl)-2,6-difluoro-3-(propylsulfonamido)benzamide 2,6-Difluoro-N-(1-(phenylsulfonyl)-3-vinyl-1H-pyrrolo[2,3-b]pyridin-5-yl)-3-(propylsulfonamido)benzamide (0.0093 g, 0.017 mmol) was dissolved in MeOH (1.0 mL). 10% Pd/C (2.0 mg) was added and followed by stirring under a balloon of $H_2$ for 1 hour. Water (0.3 mL) and $K_2CO_3$ (0.0235 g, 0.170 mmol) were added, and the reaction mixture was stirred at 50° C. for 18 hours. The organic portion was washed with water (3×), brine, dried over $Na_2SO_4$ and concentrated. The resulting residue was purified by column chromatography (1:2 hexane/EtOAc) giving N-(3-ethyl-1H-pyrrolo[2,3-b]pyridin-5-yl)-2,6-difluoro-3-(propylsulfonamido)benzamide (2.7 mg, 37.6%). $^1$H NMR (400 MHz, DMSO-$d_6$) δ 11.33 (br s, 1H), 10.84 (s, 1H), 9.79 (br s, 1H), 8.32-8.34 (m, 2H), 7.51-7.57 (m, 1H), 7.24-7.27 (m, 2H), 3.10-3.14 (m, 2H), 2.67-2.73 (m, 2H), 1.74-1.80 (m, 2H), 1.25-1.28 (m, 2H), 0.98-1.01 (m, 3H); m/z (APCI-neg) M−1=421.2.

Example 21

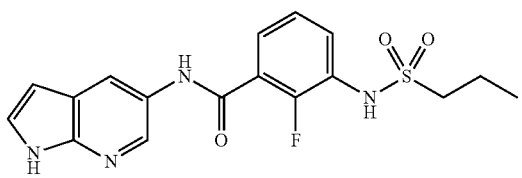

2-fluoro-3-(propylsulfonamido)-N-(1H-pyrrolo[2,3-b]pyridin-5-yl)benzamide

2-Fluoro-3-(propylsulfonamido)-N-(1H-pyrrolo[2,3-b]pyridin-5-yl)benzamide (49%) was prepared according to the general procedure for Example 1, substituting 2-fluoro-3-(propylsulfonamido)benzoic acid for 2,6-difluoro-3-(propylsulfonamido)benzoic acid. $^1$H NMR (400 MHz, DMSO-$d_6$) δ 11.61 (br s, 1H), 10.48 (s, 1H), 9.81 (br s, 1H), 8.40 (br s, 1H), 8.35 (br s, 1H), 7.53-7.57 (m, 1H), 7.48-7.52 (m, 2H), 7.28-7.32 (m, 1H), 6.46 (m, 1H), 3.14-3.18 (m, 2H), 1.75-1.80 (m, 2H), 0.98-1.02 (m, 3H); m/z (APCI-neg) M−1=375.2.

Example 22

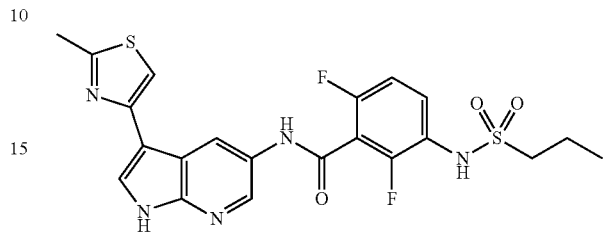

2,6-difluoro-N-(3-(2-methylthiazol-4-yl)-1H-pyrrolo[2,3-b]pyridin-5-yl)-3-(propylsulfonamido)benzamide $NaHCO_3$ (0.00098 g, 0.012 mmol) and ethanethioamide (0.00096 g, 0.013 mmol) were added to N-(3-(2-chloroacetyl)-1H-pyrrolo[2,3-b]pyridin-5-yl)-2,6-difluoro-3-(propylsulfonamido)benzamide (0.005 g, 0.011 mmol) in THF (0.1 mL), and the reaction mixture was warmed to 70° C. for 4 hours. MeOH (0.2 mL) was added, along with another equivalent of ethanethioamide (0.00096 g, 0.013 mmol) and $NaHCO_3$ (0.00098 g, 0.012 mmol). After 9 hours at 70° C., the reaction mixture was cooled and partitioned between EtOAc and aqueous sodium bicarbonate. The organic layers were dried over $Na_2SO_4$ and concentrated under reduced pressure. The resulting residue was purified via column chromatography (10% MeOH-DCM) to provide 2,6-difluoro-N-(3-(2-methylthiazol-4-yl)-1H-pyrrolo[2,3-b]pyridin-5-yl)-3-(propylsulfonamido)benzamide (1 mg, 19%). $^1$H NMR (400 MHz, $CHCl_3$-d1) δ 8.84-8.85 (m, 1H), 7.86 (s, 1H), 7.60-7.66 (m, 1H), 7.32 (s, 1H), 7.02-7.06 (m, 1H), 3.06-3.12 (m, 2H), 2.80 (s, 3H), 1.85-1.93 (m, 2H), 1.04-1.08 (m, 3H); m/z (APCI-pos) M+1=492.1.

Example 23

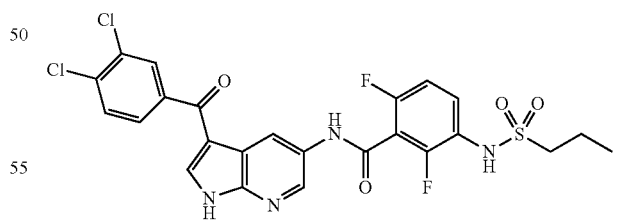

N-(3-(3,4-dichlorobenzoyl)-1H-pyrrolo[2,3-b]pyridin-5-yl)-2,6-difluoro-3-(propylsulfonamido)benzamide A slurry of aluminum trichloride (0.078 g, 0.59 mmol) was added to a slurry of 2,6-difluoro-3-(propylsulfonamido)-N-(1H-pyrrolo[2,3-b]pyridin-5-yl)benzamide (0.029 g, 0.074 mmol) in DCM (1.2 mL) at 0° C., and the reaction mixture was allowed to stir at 0° C. for 40 minutes. 3,4-Dichlorobenzoyl chloride (0.023 g, 0.11 mmol) was added, and the mixture was allowed to slowly warm to room temperature overnight. $CH_3NO_2$ (300 μL) was added, and the reaction mixture was sonicated for 2 minutes. The reaction mixture was then stirred at room temperature overnight. The reaction mixture was quenched with ice and then partitioned between aqueous sodium bicarbonate and EtOAc. The organic layers were dried over $Na_2SO_4$ and concentrated under reduced pressure. The residual solids were triturated with 5% MeOH/EtOAc to provide N-(3-(3,4-dichlorobenzoyl)-1H-pyrrolo[2,3-b]pyridin-5-yl)-2,6-difluoro-3-(propylsulfonamido)benzamide (9 mg, 22%). $^1$H NMR (400 MHz, $CD_3OD$) δ 8.98-8.99 (m, 1H), 8.66-8.68 (m, 1H), 8.09 (s, 1H), 7.63-7.79 (m, 3H), 7.13-7.17 (m, 1H), 3.11-3.15 (m, 2H), 1.85-1.91 (m, 2H), 1.05-1.09 (m, 3H); m/z (APCI-pos) M+1=567.0.

Example 24

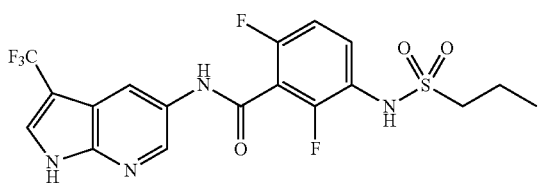

2,6-difluoro-3-(propylsulfonamido)-N-(3-(trifluoromethyl)-1H-pyrrolo[2,3-b]pyridin-5-yl)benzamide Step A: Trifluoroacetic anhydride ("TFAA"; 3.3 mL) was added to a solution of tetrabutylammonium nitrate (7.3 g) in dichloromethane (70 mL) cooled to 0° C. After 5 minutes, 3-(trifluoromethyl)-1H-pyrrolo[2,3-b]pyridine (0.64 g; prepared as described in Schirok, Hartmut, et al. "Synthesis and Derivatization of 3-Perfluoroalkyl-Substituted 7-Azaindoles." *Synthesis*, No. 2 (2007): pp. 251-258) was added portionwise. The resulting solution was stirred at room temperature overnight. The reaction mixture was diluted with dilute aqueous sodium bicarbonate and extracted with dichloromethane (2×). The organic layer was dried over magnesium sulfate, filtered, and evaporated to yield crude solid, which was subjected to chromatography on a silica gel plug with ethyl acetate to provide 5-nitro-3-(trifluoromethyl)-1H-pyrrolo[2,3-b]pyridine (0.58 g, 73%) as a solid.

Step B: Tin chloride dihydrate (4.0 g) was added to 5-nitro-3-(trifluoromethyl)-1H-pyrrolo[2,3-b]pyridine (0.58 g) in ethyl acetate (50 mL). The resulting solution was refluxed for 3 hours. The cooled solution was treated with dilute aqueous sodium bicarbonate. The resulting slurry was filtered through celite, and the filter cake was washed with ethyl acetate. The layers were separated. The organic layer was washed with brine, dried over magnesium sulfate, filtered, and evaporated to provide 5-amino-3-(trifluoromethyl)-1H-pyrrolo[2,3-b]pyridine (320 mg, 63%) as a solid.

Step C: Diisopropylethylamine (127 μL), 5-amino-3-(trifluoromethyl)-1H-pyrrolo[2,3-b]pyridine (67.8 mg), hydroxybenzotriazole monohydrate (41 mg) and 1-ethyl-(3-dimethylaminopropyl)carbodiimide hydrochloride (56 mg) was added to 5-amino-3-(trifluoromethyl)-1H-pyrrolo[2,3-b]pyridine (48.8 mg) in dichloromethane (1 mL) and N,N-dimethylformamide (1 mL). The reaction mixture was stirred at ambient temperature overnight and evaporated under vacuum. The resulting residue was partitioned between ethyl acetate and dilute aqueous ammonium chloride. The ethyl acetate layer was washed with brine, dried over magnesium sulfate, filtered, and concentrated to a glass. The crude product was purified by chromatography (10:1 ethyl acetate/methanol) to provide 2,6-difluoro-3-(propylsulfonamido)-N-(3-(trifluoromethyl)-1H-pyrrolo[2,3-b]pyridin-5-yl)benzamide (20 mg, 18%) as a glass. $^1$H NMR (400 MHz, $CD_3CN$) δ 10.31 (br s, 1H), 9.13 (s, 1H), 8.53 (s, 1H), 8.51 (s, 1H), 7.89 (s, 1H), 7.67-7.60 (m, 1H), 7.16-7.11 (m, 1H), 3.16-3.12 (m, 2H), 2.22 (br s, 1H), 1.90-1.80 (m, 2H), 1.04 (t, 3H); m/z (ESI pos) 463.1 (100%) [M+1].

Example 25

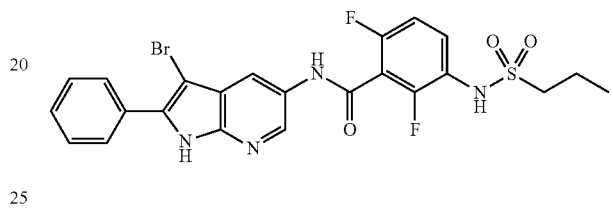

N-(3-bromo-2-phenyl-1H-pyrrolo[2,3-b]pyridin-5-yl)-2,6-difluoro-3-(propylsulfonamido)benzamide N-Bromosuccinimide (1.1 eq.) was added to a slurry of 2,6-difluoro-N-(2-phenyl-1H-pyrrolo[2,3-b]pyridin-5-yl)-3-(propylsulfonamido)benzamide (11 mg, 1.0 eq.) in $CHCl_3$ (1.0 mL), and the reaction mixture stirred at ambient temperature for 16 hours. The reaction mixture was filtered, and the solids were washed with $CH_2Cl_2$. The resulting solids were then purified by silica gel chromatography (eluting with 5% MeOH/$CH_2Cl_2$) to afford N-(3-bromo-2-phenyl-1H-pyrrolo[2,3-b]pyridin-5-yl)-2,6-difluoro-3-(propylsulfonamido)benzamide as a solid (9 mg, 69%). $^1$H NMR (400 MHz, DMSO-$d_6$) δ 12.53 (s, 1H), 11.08 (s, 1H), 9.82 (s, 1H), 8.47-8.44 (m, 1H), 8.39-8.37 (m, 1H), 7.95-7.91 (m, 2H), 7.61-7.53 (m, 3H), 7.51-7.45 (m, 1H), 7.32-7.26 (m, 1H), 3.16-3.11 (m, 2H), 1.83-1.74 (m, 2H), 1.03-0.98 (m, 3H); m/z (APCI-neg) M−1=549.1.

Example 26

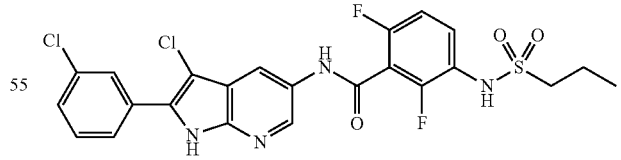

N-(3-chloro-2-(3-chlorophenyl)-1H-pyrrolo[2,3-b]pyridin-5-yl)-2,6-difluoro-3-(propylsulfonamido)benzamide N-(3-chloro-2-(3-chlorophenyl)-1H-pyrrolo[2,3-b]pyridin-5-yl)-2,6-difluoro-3-(propylsulfonamido)benzamide (38%) was prepared according to Example 25, substituting N-chlorosuccinimide for N-bromosuccinimide, DMF for CHCl₃, and N-(2-(3-chlorophenyl)-1H-pyrrolo[2,3-b]pyridin-5-yl)-2,6-difluoro-3-(propylsulfonamido)benzamide for 2,6-difluoro-N-(2-phenyl-1H-pyrrolo[2,3-b]pyridin-5-yl)-3-(propylsulfonamido)benzamide. ¹H NMR (400 MHz, DMSO-d₆) δ 12.55 (s, 1H), 11.11 (s, 1H), 9.82 (s, 1H), 8.49-8.46 (m, 2H), 8.01-7.99 (m, 1H), 7.96-7.93 (m, 1H), 7.63-7.52 (m, 3H), 7.32-7.26 (m, 1H), 3.16-3.11 (m, 2H), 1.82-1.74 (m, 2H), 1.03-0.98 (m, 3H); m/z (APCI-pos) M+1=539.0.

Example 27

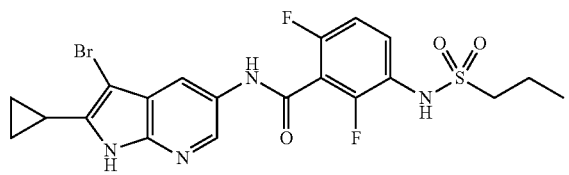

N-(3-bromo-2-cyclopropyl-1H-pyrrolo[2,3-b]pyridin-5-yl)-2,6-difluoro-3-(propylsulfonamido benzamide N-(3-Bromo-2-cyclopropyl-1H-pyrrolo[2,3-b]pyridin-5-yl)-2,6-difluoro-3-(propylsulfonamido)benzamide was prepared according to the general procedure of Example 25 substituting N-(2-cyclopropyl-1H-pyrrolo[2,3-b]pyridin-5-yl)-2,6-difluoro-3-(propylsulfonamido)benzamide for 2,6-difluoro-N-(2-phenyl-1H-pyrrolo[2,3-b]pyridin-5-yl)-3-(propylsulfonamido)benzamide. ¹H NMR (400 MHz, DMSO-d₆) δ 11.66 (s, 1H), 10.96 (s, 1H), 9.80 (s, 1H), 8.31-8.29 (m, 1H), 8.18-8.16 (m, 1H), 7.58-7.52 (m, 1H), 7.30-7.24 (m, 1H), 3.15-3.10 (m, 2H), 2.16-2.10 (m, 1H), 1.82-1.73 (m, 2H), 1.10-1.03 (m, 4H), 1.02-0.97 (m, 3H); m/z (APCI-neg) M−1=513.2.

Example 28

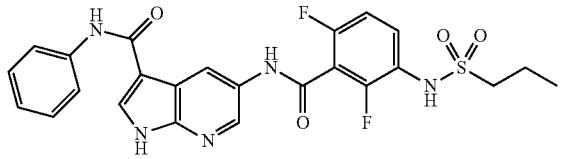

5-(2,6-difluoro-3-(propylsulfonamido)benzamido)-N-phenyl-1H-pyrrolo[2,3-b]pyridine-3-carboxamide A round bottom flask equipped with a stir bar and nitrogen inlet was charged with aniline (4.2 mg, 0.046 mmol) and dry toluene (0.5 mL) under a nitrogen atmosphere. Trimethyl aluminum (8.0 μL, 0.160 mmol, 7 eq.) was added to this solution, and this mixture was stirred at room temperature for 20 minutes. Methyl 5-(2,6-difluoro-3-(propylsulfonamido)benzamido)-1H-pyrrolo[2,3-b]pyridine-3-carboxylate (13.5 mg, 0.023 mmol, see Example 14) was added in one portion, and the reaction mixture warmed to 90° C. for 30 minutes. The reaction mixture was then allowed to cool to room temperature. The mixture was then quenched carefully with 30% aqueous sodium potassium tartrate and extracted with ethyl acetate (2×). The extracts were dried over sodium sulfate and concentrated under reduced pressure. The resulting residue was dissolved in THF (1 mL), and a 1M aqueous LiOH solution (1 mL) was then added. The mixture was stirred at room temperature for 16 hours, diluted with AcOH/water and extracted with EtOAc (2×). The extracts were washed with saturated sodium bicarbonate solution, dried over sodium sulfate and concentrated. The resulting residue was subjected to preparative TLC purification (2×0.5 mm plates, 10% MeOH/DCM) to afford 5-(2,6-difluoro-3-(propylsulfonamido)benzamido)-N-phenyl-1H-pyrrolo[2,3-b]pyridine-3-carboxamide (4.2 mg, 36%). ¹H NMR (400 MHz, DMSO-d₆) δ 12.31 (s, 1H), 10.97 (s, 1H), 9.76-9.87 (m 2H), 8.89-8.96 (m, 1H), 8.42-8.55 (m 2H), 7.73-7.80 (m, 2H), 7.51-7.59 (m, 1H), 7.20-7.38 (m, 3H), 7.03-7.11 (m, 1H), 3.06-3.14 (m, 2H), 1.71-1.82 (m, 2H), 0.94-1.04 (m, 3H); m/z (APCI-neg) M−1=512.1; (APCI-pos) M+1=514.0.

The following compounds in Table 1 were prepared following the above procedures.

TABLE 1

| Ex. # | Structure | Name | MS/NMR |
|---|---|---|---|
| 29 | 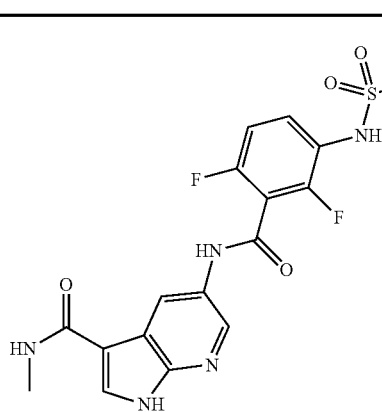 | 5-(2,6-difluoro-3-(propylsulfonamido)-benzamido)-N-methyl-1H-pyrrolo[2,3-b]pyridine-3-carboxamide | ¹H NMR (400 MHz, CD₃OD) δ 8.76-8.80 (m, 1H), 8.56-8.61 (m, 1H), 8.01 (s, 1H), 7.61-7.69 (m, 1H), 7.09-7.17 (m, 1H), 3.07-3.14 (m, 2H), 2.92 (s, 3H), 1.82-1.93 (m, 2H), 1.03-1.09 (m, 3H); m/z (APCI-neg) M − 1 = 450.2; (APCI-pos) M + 1 = 452.1 |

TABLE 1-continued

| Ex. # | Structure | Name | MS/NMR |
|---|---|---|---|
| 30 | 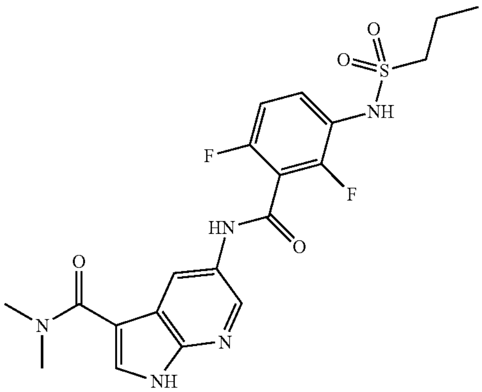 | 5-(2,6-difluoro-3-(propylsulfonamido)-benzamido)-N,N-dimethyl-1H-pyrrolo[2,3-b]pyridine-3-carboxamide | $^1$H NMR (400 MHz, CD$_3$OD) δ 8.53-8.60 (m, 2H), 7.85 (s, 1H), 7.61-7.69 (m, 1H), 7.10-7.16 (m, 1H), 3.22 (s, 3H), 3.08-3.14 (m 2H), 1.83-1.92 (m, 2H), 1.03-1.09 (m, 3H); m/z (APCI-neg) M − 1 = 464.2; (APCI-pos) M + 1 = 466.1 |
| 31 | 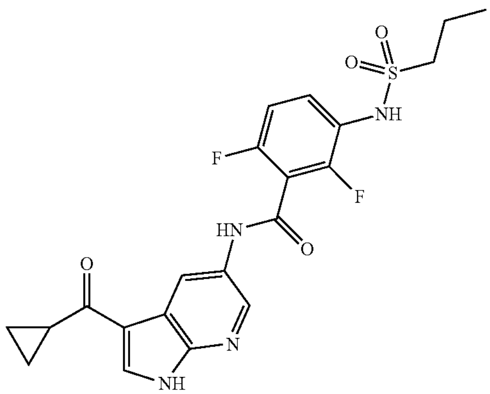 | N-(3-(cyclopropanecarbonyl)-1H-pyrrolo[2,3-b]pyridin-5-yl)-2,6-difluoro-3-(propylsulfonamido)-benzamide | $^1$H NMR (400 MHz, CD$_3$OD) δ 8.87-8.89 (m, 1H), 8.63-8.65 (m, 1H), 8.49 s, 1H), 7.61-7.69 (m, 1H), 7.10-7.16 (m, 1H), 3.09-3.15 (m, 2H), 2.65-2.74 (m, 1H), 1.81-1.92 (m, 2H), 1.11-1.16 (m, 2H), 1.04-1.09 (m, 3H), 0.97-1.04 (m, 2H); m/z (APCI-pos) M + 1 = 463.1 |

Example 32

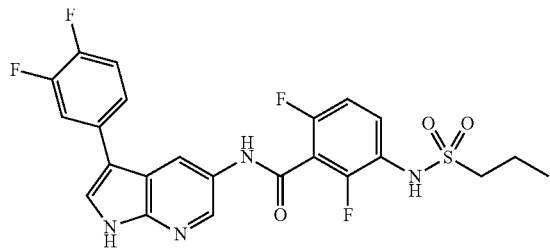

N-(3-(3,4-difluorophenyl)-1H-pyrrolo[2,3-b]pyridin-5-yl)-2,6-difluoro-3-(propylsulfonamido)benzamide Step A: 3-Iodo-1H-pyrrolo[2,3-b]pyridine (4.55 g, 18.7 mmol) and K$_2$CO$_3$ (7.73 g, 55.9 mmol) were dissolved in acetonitrile (200 mL). Benzenesulfonyl chloride (4.76 mL, 37.3 mmol) was added, and the reaction mixture was heated to reflux for 10 hours. The reaction mixture was cooled and partitioned between EtOAc and water. The organic layer was washed with water (2×), brine, and dried over Na$_2$SO$_4$ and concentrated. The resulting residue was purified by column chromatography (4:1 to 0:1 hexane/DCM) giving 3-iodo-1-(phenylsulfonyl)-1H-pyrrolo[2,3-b]pyridine (5.31 g, 74.1%).

Step B: Tetrabutylammonium nitrate (6.31 g, 20.7 mmol) was dissolved in DCM (50 mL) and cooled to 0° C. TFAA (2.93 mL, 20.7 mmol) was added and stirred for 10 minutes. This solution was transferred via syringe to a precooled solution of 3-iodo-1-(phenylsulfonyl)-1H-pyrrolo[2,3-b]pyridine (5.31 g, 13.8 mmol) in DCM (50 mL) at 0° C. and was stirred at 0° C. overnight. Water (100 mL) was added, and the layers were separated. The aqueous portion was extracted with DCM (1×). The organic layers were combined, dried over Na$_2$SO$_4$ and concentrated to a solid. This solid was sonicated for 10 minutes in 9:1 Et$_2$O/DCM and filtered to give 3-iodo-5-nitro-1-(phenylsulfonyl)-1H-pyrrolo[2,3-b]pyridine (3.46 g, 58.3%) as a solid.

Step C: 3-Iodo-5-nitro-1-(phenylsulfonyl)-1H-pyrrolo[2,3-b]pyridine (1.00 g, 2.33 mmol) and SnCl$_2$ dihydrate (2.63 g, 11.7 mmol) in EtOAc (25 mL) were heated to 75° C. for 4 hours. The reaction mixture was cooled to room temperature, and saturated aqueous NaHCO$_3$ (25 mL) was added. The resulting precipitate was filtered through celite. The layers were separated. The organic portion was washed with water, brine, dried over Na$_2$SO$_4$ and concentrated to give 3-iodo-1-(phenylsulfonyl)-1H-pyrrolo[2,3-b]pyridin-5-amine (0.933 g, 100%) as a powder, which was used directly in the next step without further purification.

Step D: 3-Iodo-1-(phenylsulfonyl)-1H-pyrrolo[2,3-b]pyridin-5-amine (0.506 g, 1.27 mmol), 2,6-difluoro-3-(propylsulfonamido)benzoic acid (0.389 g, 1.39 mmol), EDCI (0.267 g, 1.39 mmol) and HOBt (0.188 g, 1.39 mmol) were dissolved in DMF (10 mL) and stirred at room temperature overnight. The organic portion was washed with water (3×), brine, dried over Na$_2$SO$_4$ and concentrated. The resulting residue was purified by column chromatography (1:1:1 hexane/Et$_2$O/DCM) giving 2,6-difluoro-N-(3-iodo-1-(phenylsulfonyl)-1H-pyrrolo[2,3-b]pyridin-5-yl)-3-(propylsulfonamido)benzamide (0.738 g, 88.2%).

Step E: 2,6-Difluoro-N-(3-iodo-1-(phenylsulfonyl)-1H-pyrrolo[2,3-b]pyridin-5-yl)-3-(propylsulfonamido)benzamide (0.025 g, 0.038 mmol), 3,4-difluorophenylboronic acid (0.0090 g, 0.057 mmol), $K_2CO_3$ (0.026 g, 0.19 mmol), and $Pd(PPh_3)_4$ (0.0022 g, 0.0019 mmol) were taken up in 4:1 acetonitrile ("ACN")/water (1.5 mL) and degassed with argon for 10 minutes. The reaction mixture was heated to 160° C. for 10 minutes under microwave irradiation. The solution was partitioned between water and EtOAc. The organic portion was washed with water (3x), brine, dried over $Na_2SO_4$ and concentrated to an oil. DCM was added to the oil, and a solid precipitated out, which was collected by filtration giving N-(3-(3,4-difluorophenyl)-1H-pyrrolo[2,3-b]pyridin-5-yl)-2,6-difluoro-3-(propylsulfonamido)benzamide (8.5 mg, 44%). $^1$H NMR (400 MHz, DMSO-$d_6$) δ 12.08 (br s, 1H), 10.97 (s, 1H), 9.80 (br s, 1H), 8.66 (br s, 1H), 8.52 (br s, 1H), 7.99 (br s, 1H), 7.69-7.75 (m, 1H), 7.51-7.59 (m, 3H), 7.25-7.30 (m, 1H), 3.11-3.15 (m, 2H), 1.74-1.80 (m, 2H), 0.98-1.02 (m, 3H); m/z (APCI-pos) M+1=505.2.

The following compounds in Table 2 were prepared following the above procedures.

TABLE 2

| Ex. # | Structure | Name | MS/NMR |
|---|---|---|---|
| 33 | 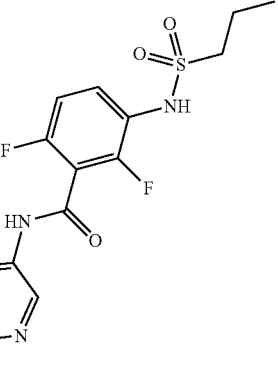 | 2,6-difluoro-N-(3-phenyl-1H-pyrrolo[2,3-b]pyridin-5-yl)-3-(propylsulfonamido)-benzamide | $^1$H NMR (400 MHz, DMSO-$d_6$) δ 11.98 (br s, 1H), 10.95 (s, 1H), 9.80 (br s, 1H), 8.69 (br s, 1H), 8.49 (br s, 1H), 7.90 (br s, 1H), 7.68-7.69 (m, 2H), 7.52-7.58 (m, 1H), 7.45-7.49 (m, 2H), 7.25-7.29 (m, 2H), 3.07-3.11 (m, 2H), 1.75-1.80 1.80 (m, 2H), 0.98-1.02 (m, 3H); m/z (APCI-pos) M + 1 = 471.1 |
| 34 | 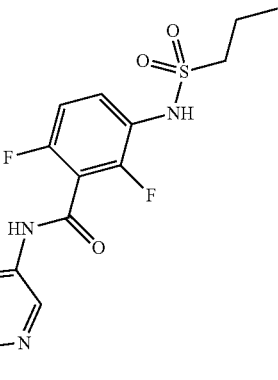 | 2,6-difluoro-3-(propylsulfonamido)-N-(3-(pyridin-3-yl)-1H-pyrrolo[2,3-b]pyridin-5-yl)benzamide | $^1$H NMR (400 MHz, DMSO-$d_6$) δ 12.14 (br s, 1H), 10.98 (s, 1H), 9.81 (br s, 1H), 8.94 (br s, 1H), 8.71 (br s, 1H), 8.51 (br s, 1H), 8.46-8.49 (m, 1H), 8.05-8.09 (m, 2H), 7.53-7.59 (m, 1H), 7.47-7.51 (m, 1H), 7.25-7.30 (m, 1H), 3.11-3.15 (m, 2H), 1.75-1.80 (m, 2H), 0.98-1.02 (m, 3H); m/z (APCI-pos) M + 1 = 472.2 |
| 35 | 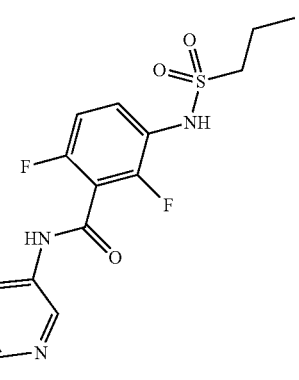 | 2,6-difluoro-N-(3-(4-fluorophenyl)-1H-pyrrolo[2,3-b]pyridin-5-yl)-3-(propylsulfonamido)-benzamide | $^1$H NMR (400 MHz, DMSO-$d_6$) δ 11.96 (br s, 1H), 10.91 (s, 1H), 9.78 (br s, 1H), 8.68 (br s, 1H), 8.48 (br s, 1H), 7.88 (br s, 1H), 7.68-7.72 (m, 2H), 7.49-7.54 (m, 1H), 7.28-7.33 (m, 2H), 7.16-7.20 (m, 1H), 3.03-3.06 (m, 2H), 1.72-1.78 (m, 2H), 0.96-1.00 (m, 3H); m/z (APCI-pos) M + 1 = 489.1 |

TABLE 2-continued

| Ex. # | Structure | Name | MS/NMR |
|---|---|---|---|
| 36 | 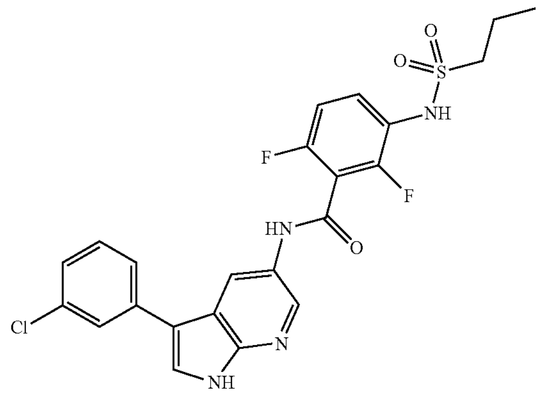 | N-(3-(3-chlorophenyl)-1H-pyrrolo[2,3-b]pyridin-5-yl)-2,6-difluoro-3-(propylsulfonamido)-benzamide | $^1$H NMR (400 MHz, DMSO-d$_6$) δ 12.10 (br s, 1H), 10.98 (s, 1H), 9.81 (br s, 1H), 8.66 (br s, 1H), 8.56 (br s, 1H), 8.04 (br s, 1H), 7.73 (br s, 1H), 7.66-7.68 (m, 1H), 7.53-7.59 (m, 1H), 7.47-7.52 (m, 1H), 7.25-7.33 (m, 2H), 3.11-3.15 (m, 2H), 1.75-1.80 (m, 2H), 0.98-1.02 (m, 3H); m/z (APCI-neg) M − 1 = 503.2, 505.2 |
| 37 | 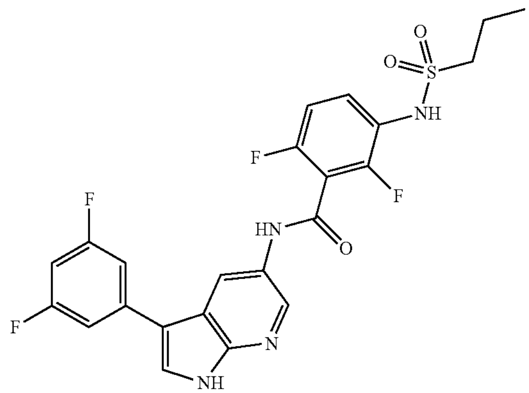 | N-(3-(3,5-difluorophenyl)-1H-pyrrolo[2,3-b]pyridin-5-yl)-2,6-difluoro-3-(propylsulfonamido)-benzamide | $^1$H NMR (400 MHz, DMSO-d$_6$) δ 12.19 (br s, 1H), 10.99 (s, 1H), 9.81 (br s, 1H), 8.67 (br s, 1H), 8.59 (br s, 1H), 8.12 (br s, 1H), 7.53-7.59 (m, 1H), 7.40-7.41 (m, 2H), 7.26-7.30 (m, 1H), 7.07-7.12 (m, 1H), 3.11-3.15 (m, 2H), 1.75-1.80 (m, 2H), 0.98-1.02 (m, 3H); m/z (APCI-neg) M − 1 = 505.2 |
| 38 | 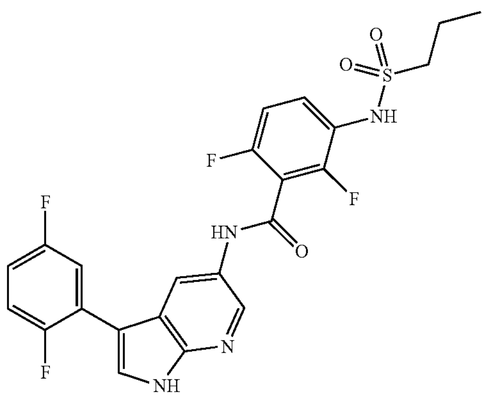 | N-(3-(2,5-difluorophenyl)-1H-pyrrolo[2,3-b]pyridin-5-yl)-2,6-difluoro-3-(propylsulfonamido)-benzamide | $^1$H NMR (400 MHz, DMSO-d$_6$) δ 12.20 (br s, 1H), 10.97 (s, 1H), 9.80 (br s, 1H), 8.54 (br s, 1H), 8.50 (br s, 1H), 7.90 (br s, 1H), 7.49-7.58 (m, 2H), 7.38-7.43 (m, 1H), 7.25-7.29 (m, 1H), 7.16-7.21 (m, 1H), 3.11-3.15 (m, 2H), 1.72-1.82 (m, 2H), 0.98-1.01 (m, 3H); m/z (APCI-neg) M − 1 = 505.2 |
| 39 | 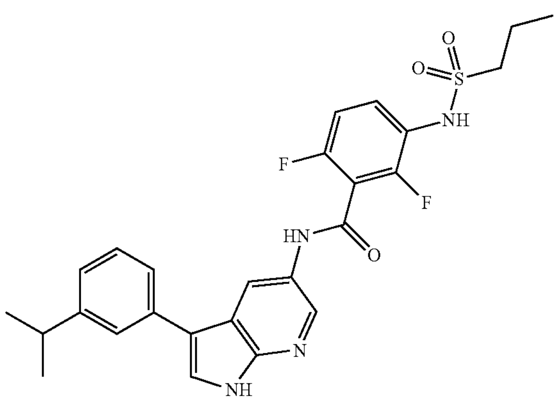 | 2,6-difluoro-N-(3-(3-isopropylphenyl)-1H-pyrrolo[2,3-b]pyridin-5-yl)-3-(propylsulfonamido)-benzamide | $^1$H NMR (400 MHz, DMSO-d$_6$) δ 11.94 (br s, 1H), 10.95 (s, 1H), 9.80 (br s, 1H), 8.70 (br s, 1H), 8.51 (br s, 1H), 7.88 (br s, 1H), 7.52-7.58 (m, 2H), 7.47-7.49 (m, 1H), 7.35-7.39 (m, 1H), 7.25-7.30 (m, 1H), 7.14-7.16 (m, 1H), 3.11-3.15 (m, 2H), 2.97-2.94 (m, 1H), 1.74-1.80 (m, 2H), 1.27-1.29 (m, 6H), 0.98-1.01 (m, 3H); m/z (APCI-neg) M − 1 = 511.3 |

TABLE 2-continued

| Ex. # | Structure | Name | MS/NMR |
|---|---|---|---|
| 40 | 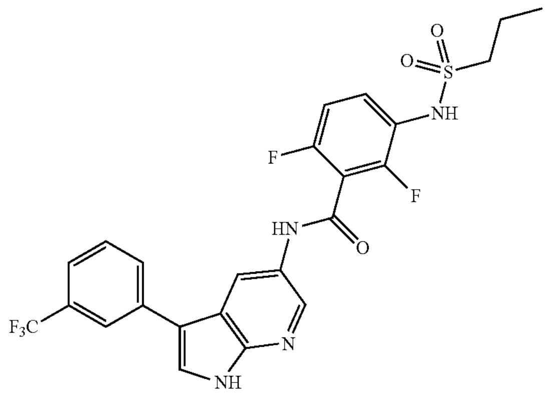 | 2,6-difluoro-3-(propylsulfonamido)-N-(3-(3-(trifluoromethyl)phenyl)-1H-pyrrolo[2,3-b]pyridin-5-yl)benzamide | $^1$H NMR (400 MHz, DMSO-d$_6$) δ 12.15 (br s, 1H), 11.00 (s, 1H), 9.81 (br s, 1H), 8.68 (br s, 1H), 8.57 (br s, 1H), 8.12 (br s, 1H), 7.98-8.01 (m, 2H), 7.69-7.73 (m, 1H), 7.60-7.62 (m, 1H), 7.53-7.59 (m, 1H), 7.26-7.30 (m, 1H), 3.11-3.15 (m, 2H), 1.75-1.80 (m, 2H), 0.98-1.02 (m, 3H); m/z (APCI-neg) M − 1 = 537.2 |
| 41 | 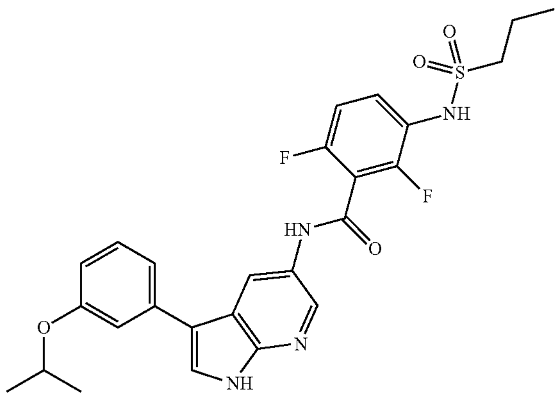 | 2,6-difluoro-N-(3-(3-isopropoxyphenyl)-1H-pyrrolo[2,3-b]pyridin-5-yl)-3-(propylsulfonamido)-benzamide | $^1$H NMR (400 MHz, DMSO-d$_6$) δ 11.97 (br s, 1H), 10.96 (s, 1H), 9.80 (br s, 1H), 8.67 (br s, 1H), 8.51 (br s, 1H), 7.92 (br s, 1H), 7.52-7.58 (m, 1H), 7.33-7.37 (m, 1H), 7.22-7.29 (m, 2H), 7.18 (br s, 1H), 6.82-6.84 (m, 1H), 4.67-4.73 (m, 1H), 3.11-3.15 (m, 2H), 1.75-1.80 (m, 2H), 1.30-1.32 (m, 6H), 0.98-1.02 (m, 3H); m/z (APCI-neg) M − 1 = 527.3 |
| 42 | 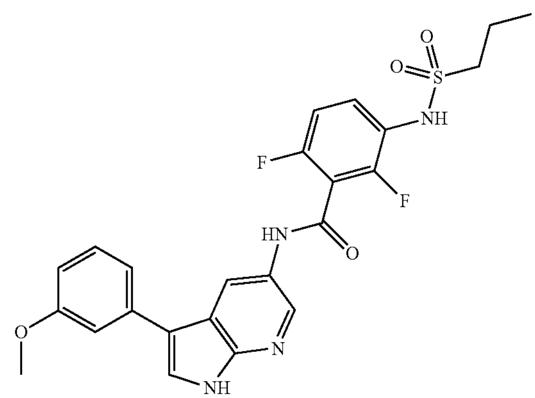 | 2,6-difluoro-N-(3-(3-methoxyphenyl)-1H-pyrrolo[2,3-b]pyridin-5-yl)-3-(propylsulfonamido)-benzamide | $^1$H NMR (400 MHz, DMSO-d$_6$) δ 11.98 (br s, 1H), 10.95 (s, 1H), 9.80 (br s, 1H), 8.70 (br s, 1H), 8.51 (br s, 1H), 7.93 (br s, 1H), 7.52-7.58 (m, 2H), 7.36-7.40 (m, 1H), 7.23-7.30 (m, 3H), 6.84-6.86 (m, 1H), 3.83 (s, 3H), 3.11-3.15 (m, 2H), 1.74-1.80 (m, 2H), 0.98-1.02 (m, 3H); m/z (APCI-neg) M − 1 = 499.2 |
| 43 | 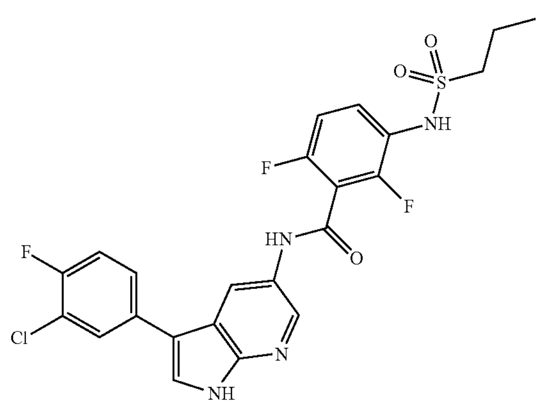 | N-(3-(3-chloro-4-fluorophenyl)-1H-pyrrolo[2,3-b]pyridin-5-yl)-2,6-difluoro-3-(propylsulfonamido)-benzamide | $^1$H NMR (400 MHz, DMSO-d$_6$) δ 12.08 (br s, 1H), 10.98 (s, 1H), 9.80 (br s, 1H), 8.63 (br s, 1H), 8.55 (br s, 1H), 8.00 (br s, 1H), 7.85-7.86 (m, 1H), 7.66-7.70 (m, 1H), 7.50-7.58 (m, 2H), 7.25-7.29 (m, 1H), 3.11-3.14 (m, 2H), 1.74-1.80 (m, 2H), 0.98-1.01 (m, 3H); m/z (APCI-neg) M − 1 = 521.2 |

TABLE 2-continued

| Ex. # | Structure | Name | MS/NMR |
|---|---|---|---|
| 44 | 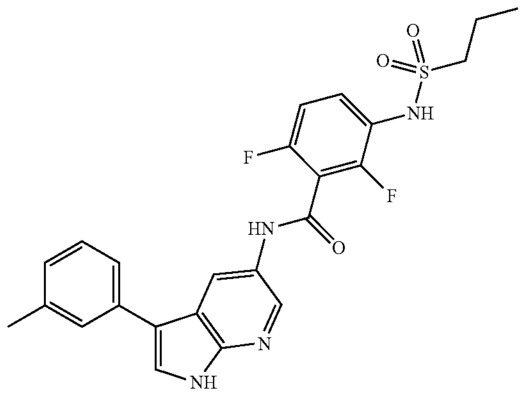 | 2,6-difluoro-3-(propylsulfonamido)-N-(3-m-tolyl-1H-pyrrolo[2,3-b]pyridin-5-yl)benzamide | $^1$H NMR (400 MHz, DMSO-d$_6$) δ 11.94 (br s, 1H), 10.94 (s, 1H), 9.80 (br s, 1H), 8.65 (br s, 1H), 8.53 (br s, 1H), 7.87 (br s, 1H), 7.52-7.58 (m, 1H), 7.46-7.50 (m, 2H), 7.33-7.37 (m, 3H), 7.25-7.29 (m, 1H), 3.11-3.15 (m, 2H), 2.50 (s, 3H), 1.75-1.80 (m, 2H), 0.98-1.01 (m, 3H); m/z (APCI-neg) M − 1 = 483.3 |
| 45 | 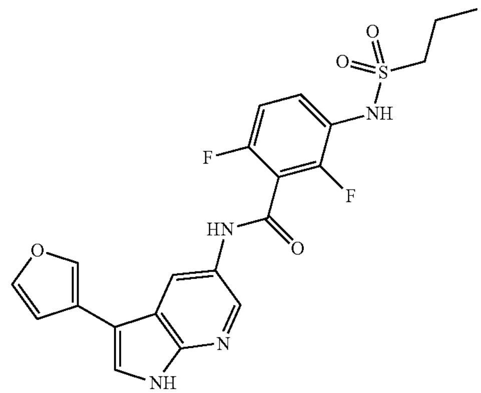 | 2,6-difluoro-N-(3-(furan-3-yl)-1H-pyrrolo[2,3-b]pyridin-5-yl)-3-(propylsulfonamido)-benzamide | $^1$H NMR (400 MHz, DMSO-d$_6$) δ 11.81 (br s, 1H), 10.89 (s, 1H), 9.78 (br s, 1H), 8.48 (br s, 1H), 8.44 (br s, 1H), 7.98 (br s, 1H), 7.79 (br s, 1H), 7.74 (br s, 1H), 7.50-7.56 (m, 1H), 7.23-7.27 (m, 1H), 6.90 (s, 1H), 3.09-3.13 (m, 2H), 1.72-1.78 (m, 2H), 0.96-1.00 (m, 3H); m/z (APCI-neg) M − 1 = 459.3 |
| 46 | 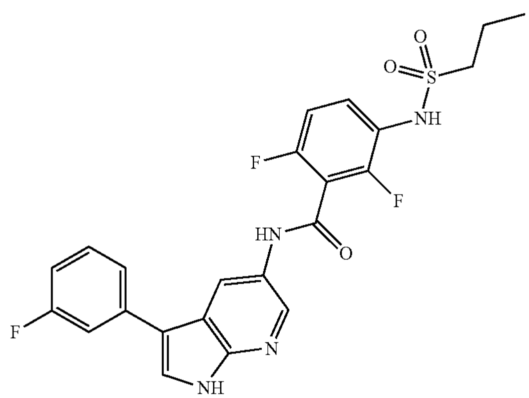 | 2,6-difluoro-N-(3-(3-fluorophenyl)-1H-pyrrolo[2,3-b]pyridin-5-yl)-3-(propylsulfonamido)-benzamide | $^1$H NMR (400 MHz, DMSO-d$_6$) δ 12.09 (br s, 1H), 10.97 (s, 1H), 9.80 (br s, 1H), 8.69 (br s, 1H), 8.54 (br s, 1H), 8.02-8.03 (m, 1H), 7.48-7.59 (m, 4H), 7.25-7.29 (m, 1H), 7.06-7.11 (m, 1H), 3.11-3.15 (m, 2H), 1.75-1.80 (m, 2H), 0.98-1.01 (m, 3H); m/z (APCI-neg) M − 1 = 487.5 |
| 47 | 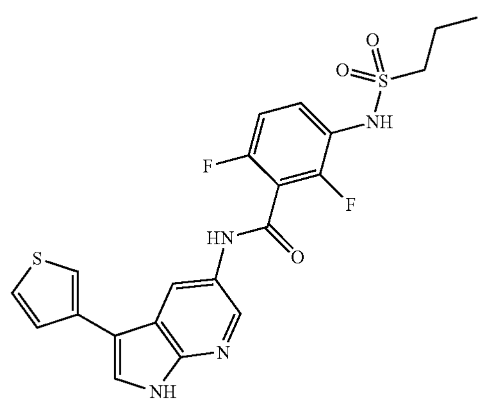 | 2,6-difluoro-3-(propylsulfonamido)-N-(3-(thiophen-3-yl)-1H-pyrrolo[2,3-b]pyridin-5-yl)benzamide | $^1$H NMR (400 MHz, DMSO-d$_6$) δ 11.88 (br s, 1H), 10.93 (s, 1H), 9.81 (br s, 1H), 8.67 (br s, 1H), 8.46 (br s, 1H), 7.90 (br s, 1H), 7.60-7.62 (m, 1H), 7.53-7.58 (m, 2H), 7.25-7.29 (m, 1H), 3.11-3.14 (m, 2H), 1.75-1.80 (m, 2H), 0.98-1.02 (m, 3H); m/z (APCI-neg) M − 1 = 475.4 |

TABLE 2-continued

| Ex. # | Structure | Name | MS/NMR |
|---|---|---|---|
| 48 | 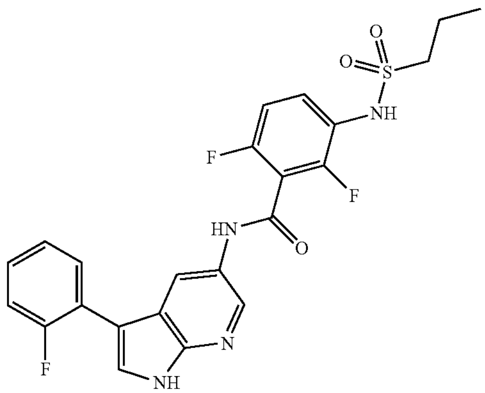 | 2,6-difluoro-N-(3-(2-fluorophenyl)-1H-pyrrolo[2,3-b]pyridin-5-yl)-3-(propylsulfonamido)-benzamide | $^1$H NMR (400 MHz, DMSO-d$_6$) δ 12.15 (br s, 1H), 11.00 (s, 1H), 9.81 (br s, 1H), 8.68 (br s, 1H), 8.57 (br s, 1H), 8.12 (br s, 1H), 7.98-8.01 (m, 2H), 7.69-7.73 (m, 1H), 7.60-7.62 (m, 1H), 7.53-7.59 (m, 1H), 7.26-7.30 (m, 1H), 3.11-3.15 (m, 2H), 1.75-1.80 (m, 2H), 0.98-1.02 (m, 3H); m/z (APCI-neg) M − 1 = 537.2 |
| 49 | 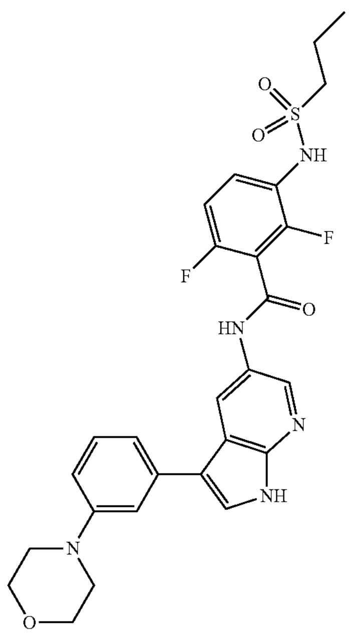 | 2,6-difluoro-N-(3-(3-morpholinophenyl)-1H-pyrrolo[2,3-b]pyridin-5-yl)-3-(propylsulfonamido)-benzamide | $^1$H NMR (400 MHz, DMSO-d$_6$) δ 11.92 (br s, 1H), 10.93 (s, 1H), 8.68 (br s, 1H), 8.50 (br s, 1H), 7.79 (br s, 1H), 7.52-7.56 (m, 1H), 7.30-7.34 (m, 1H), 7.24-7.29 (m, 1H), 7.20 (br s, 1H), 7.11-7.13 (m, 1H), 6.86-6.88 (m, 1H), 3.76-3.78 (m, 2H), 3.18-3.20 (m, 2H), 3.10-3.14 (m, 2H), 1.74-1.80 (m, 2H), 0.98-1.01 (m, 3H); m/z (APCI-neg) M − 1 = 554.3 |
| 50 | 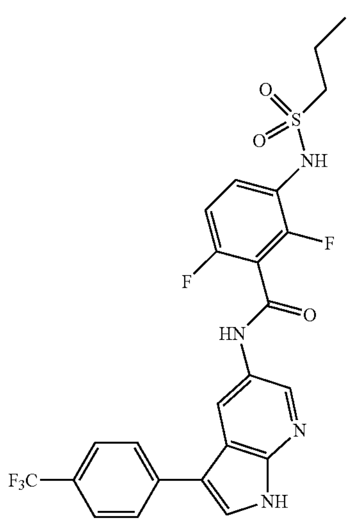 | 2,6-difluoro-3-(propylsulfonamido)-N-(3-(4-(trifluoromethyl)phenyl)-1H-pyrrolo[2,3-b]pyridin-5-yl)benzamide | $^1$H NMR (400 MHz, DMSO-d$_6$) δ 12.20 (br s, 1H), 11.65 (s, 1H), 9.80 (br s, 1H), 8.74 (br s, 1H), 8.51 (br s, 1H), 8.36-8.37 (m, 1H), 8.11 (br s, 1H), 7.90-7.93 (m, 2H), 7.80-7.82 (m, 2H), 7.51-7.59 (m, 2H), 7.24-7.30 (m, 1H), 3.11-3.15 (m, 2H), 1.75-1.80 (m, 2H), 0.98-1.02 (m, 3H); m/z (APCI-neg) M − 1 = 537.3 |

TABLE 2-continued

| Ex. # | Structure | Name | MS/NMR |
|---|---|---|---|
| 51 | 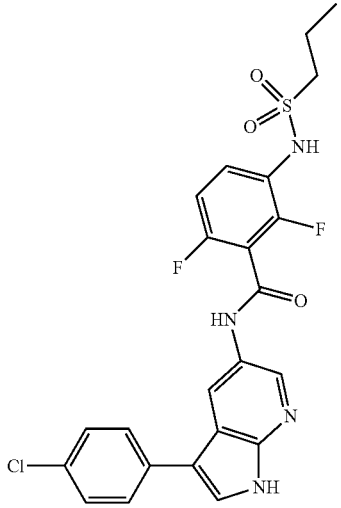 | N-(3-(4-chlorophenyl)-1H-pyrrolo[2,3-b]pyridin-5-yl)-2,6-difluoro-3-(propylsulfonamido)-benzamide | $^1$H NMR (400 MHz, DMSO-$d_6$) δ 12.06 (br s, 1H), 10.97 (s, 1H), 9.80 (br s, 1H), 8.68 (br s, 1H), 8.49 (br s, 1H), 7.96 (br s, 1H), 7.70-7.72 (m, 1H), 7.49-7.69 (m, 3H), 7.25-7.29 (m, 1H), 3.11-3.15 (m, 2H), 1.75-1.80 (m, 2H), 0.98-1.02 1.02 (m, 3H); m/z (APCI-neg) M − 1 = 504.0 |
| 52 | 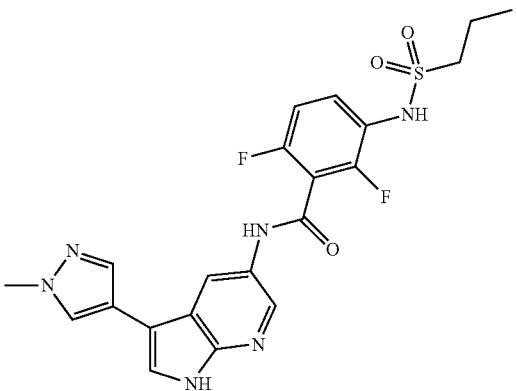 | 2,6-difluoro-N-(3-(1-methyl-1H-pyrazol-4-yl)-1H-pyrrolo[2,3-b]pyridin-5-yl)-3-(propylsulfonamido)-benzamide | $^1$H NMR (400 MHz, DMSO-$d_6$) δ 11.72 (br s, 1H), 10.90 (s, 1H), 9.80 (br s, 1H), 8.50 (br s, 1H), 8.41 (br s, 1H), 7.99 (s, 1H), 7.75 (s, 1H), 7.70 (s, 1H), 7.52-7.58 (m, 1H), 7.25-7.29 (m, 1H), 3.90 (s, 3H), 3.11-3.15 (m, 2H), 1.73-1.82 (m, 2H), 0.98-1.02 (m, 3H); m/z (APCI-neg) M − 1 = 473.2 |
| 53 | 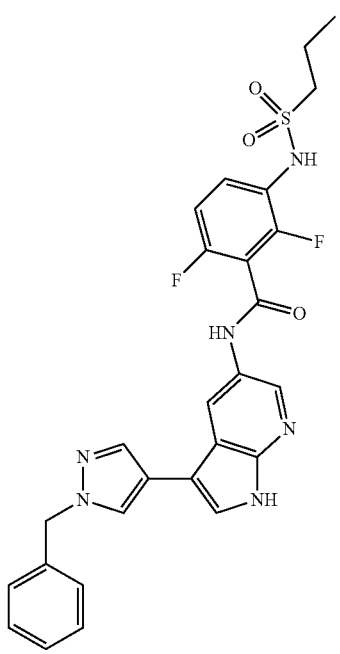 | N-(3-(1-benzyl-1H-pyrazol-4-yl)-1H-pyrrolo[2,3-b]pyridin-5-yl)-2,6-difluoro-3-(propylsulfonamido)-benzamide | $^1$H NMR (400 MHz, DMSO-$d_6$) δ 11.73 (br s, 1H), 10.89 (s, 1H), 9.80 (br s, 1H), 8.49 (br s, 1H), 8.44 (br s, 1H), 8.15 (s, 1H), 7.82 (s, 1H), 7.72 (br s, 1H), 7.52-7.58 (m, 1H), 7.34-7.37 (m, 2H), 7.25-7.30 (m, 3H), 5.40 (s, 2H), 3.11-3.15 (m, 2H), 1.74-1.80 (m, 2H), 0.98-1.02 (m, 3H); m/z (APCI-neg) M − 1 = 549.2 |

TABLE 2-continued

| Ex. # | Structure | Name | MS/NMR |
|---|---|---|---|
| 54 | 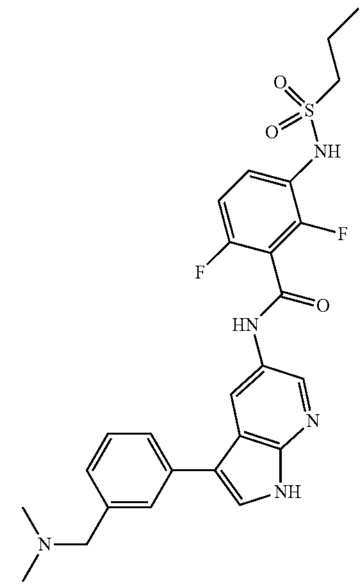 | N-(3-(3-((dimethylamino)methyl)phenyl)-1H-pyrrolo[2,3-b]pyridin-5-yl)-2,6-difluoro-3-(propylsulfonamido)benzamide | $^1$H NMR (400 MHz, DMSO-d$_6$) δ 11.96 (br s, 1H), 10.95 (s, 1H), 9.82 (br s, 1H), 8.67 (br s, 1H), 8.50 (br s, 1H), 7.88 (br s, 1H), 7.53-7.59 (m, 3H), 7.40-7.43 (m, 1H), 7.24-7.28 (m, 1H), 3.48 (s, 2H), 3.10-3.14 (m, 2H), 2.21 (s, 6H), 1.74-1.80 (m, 2H), 0.98-1.01 (m, 3H); m/z (APCI-pos) M + 1 = 528.1 |
| 55 | 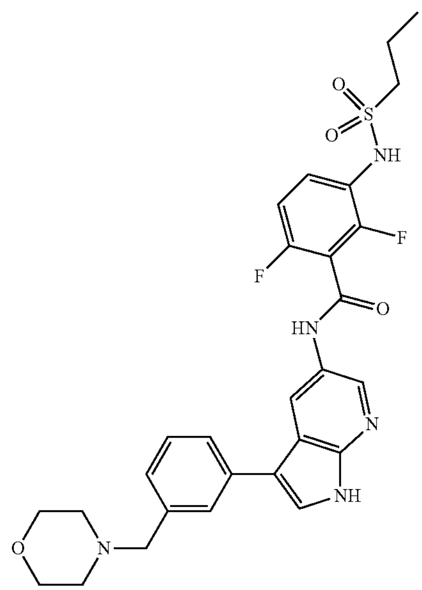 | 2,6-difluoro-N-(3-(3-(morpholinomethyl)phenyl)-1H-pyrrolo[2,3-b]pyridin-5-yl)-3-(propylsulfonamido)benzamide | $^1$H NMR (400 MHz, DMSO-d$_6$) δ 11.96 (br s, 1H), 10.94 (s, 1H), 9.80 (br s, 1H), 8.70 (br s, 1H), 8.45 (br s, 1H), 7.89 (br s, 1H), 7.62 (br s, 1H), 7.55-7.57 (m, 2H), 7.40-7.43 (m, 1H), 7.25-7.29 (m, 1H), 7.20-7.22 (m, 1H), 3.60 (br s, 4H), 3.54 (s, 2H), 3.11-3.14 (m, 2H), 2.41 (br s, 4H), 1.74-1.80 (m, 2H), 0.98-1.01 (m, 3H); m/z (APCI-pos) M + 1 = 570.1 |

Example 56

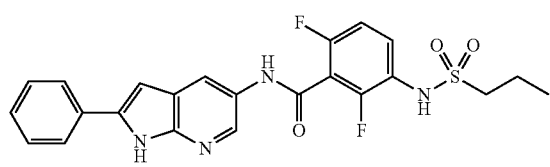

2,6-difluoro-N-(2-phenyl-1H-pyrrolo[2,3-b]pyridin-5-yl)-3-(propylsulfonamido)benzamide Step A: A solution of 3-bromo-5-nitropyridin-2-amine (655 mg, 3.0 mmol, 1.0 eq.) in 1:1 TEA/DMF (40 mL) was degassed with argon for 10 minutes, and ethynylbenzene (1.5 eq.), CuI (0.04 eq.), and PdCl$_2$(PPh$_3$)$_2$ (0.04 eq.) were sequentially added. The mixture was degassed with argon for 10 minutes, and then stirred at room temperature for 16 hours. The volatiles were removed under reduced pressure, and CH$_2$Cl$_2$ (25 mL) was added. The mixture was sonicated for 15 minutes, cooled to 0° C., and collected by vacuum filtration to afford 5-nitro-3-(phenylethynyl)pyridin-2-amine (356 mg, 50%).

Step B: A solution of 5-nitro-3-(phenylethynyl)pyridin-2-amine (356 mg, 1.0 eq.) in NMP (6 mL) was treated with KOt-Bu (2.2 eq.), and the solution was heated to 90° C. for 48 hours. The reaction mixture was purified directly by silica gel chromatography (eluting with a gradient of 100% hexanes to 40% EtOAc/hexanes) to afford 5-nitro-2-phenyl-1H-pyrrolo[2,3-b]pyridine (161 mg, 45%).

Step C: 2-Phenyl-1H-pyrrolo[2,3-b]pyridin-5-amine (57%) was prepared following Example 32, Step C, substituting 5-nitro-2-phenyl-1H-pyrrolo[2,3-b]pyridine for 3-iodo-5-nitro-1-(phenylsulfonyl)-1H-pyrrolo[2,3-b]pyridine.

Step D: 2,6-Difluoro-N-(2-phenyl-1H-pyrrolo[2,3-b]pyridin-5-yl)-3-(propylsulfonamido)benzamide (23%) was prepared following Example 32, step D, substituting 2-phenyl-1H-pyrrolo[2,3-b]pyridin-5-amine for 3-iodo-1-(phenylsulfonyl)-1H-pyrrolo[2,3-b]pyridin-5-amine. $^1$H NMR (400 MHz, MeOD-d$_4$) δ 8.36 (s, 2H), 7.87-7.85 (m, 2H), 7.68-7.62 (m, 1H), 7.49-7.45 (m, 2H), 7.38-7.35 (m, 1H), 7.16-7.11 (m, 1H), 6.87 (s, 1H), 3.14-3.10 (m, 2H), 1.91-1.83 (m, 2H), 1.06 (t, J=7.4 Hz, 3H); m/z (APCI-pos) M+1=471.1.

The following compounds in Table 3 were prepared following the above procedures.

TABLE 3

| Ex. # | Structure | Name | MS/NMR |
| --- | --- | --- | --- |
| 57 | 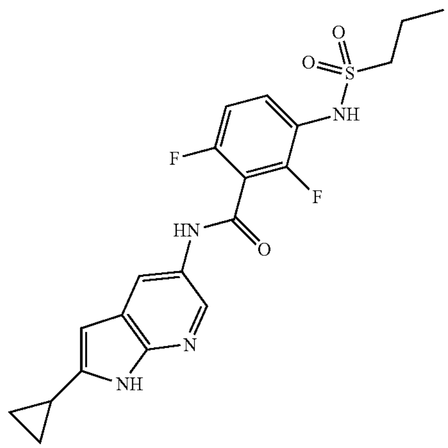 | N-(2-cyclopropyl-1H-pyrrolo[2,3-b]pyridin-5-yl)-2,6-difluoro-3-(propylsulfonamido)benzamide | $^1$H NMR (400 MHz, DMSO-d$_6$) δ 11.45 (s, 1H), 10.76 (s, 1H), 9.78 (s, 1H), 8.24 (s, 1H), 8.14 (s, 1H), 7.54-7.50 (m, 1H), 7.28-7.23 (m, 1H), 6.12 (s, 1H), 3.14-3.10 (m, 2H), 2.05-2.01 (m, 1H), 1.80-1.74 (m, 2H), 1.02-0.97 (m, 5H), 0.87-0.83 (m, 2H); m/z (APCI-pos) M + 1 = 435.1 |
| 58 | 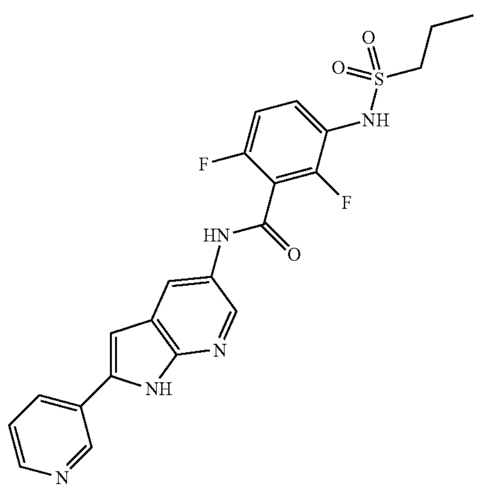 | 2,6-difluoro-3-(propylsulfonamido)-N-(2-(pyridin-3-yl)-1H-pyrrolo[2,3-b]pyridin-5-yl)benzamide | $^1$H NMR (400 MHz, DMSO-d$_6$) δ 12.33 (s, 1H), 10.92 (s, 1H), 9.18-9.16 (m, 1H), 8.56-8.54 (m, 1H), 8.43-8.39 (m, 1H), 8.32-8.29 (m, 1H), 7.55-7.49 (m, 2H), 7.30-7.25 (m, 1H), 7.13-7.10 (m, 1H), 3.16-3.10 (m, 2H), 1.81-1.74 (m, 2H), 1.02-0.98 (m, 3H); m/z (APCI-pos) M + 1 = 472.1 |
| 59 | 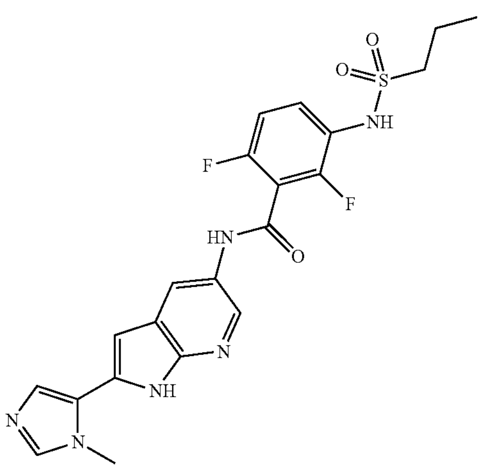 | 2,6-difluoro-N-(2-(1-methyl-1H-imidazol-5-yl)-1H-pyrrolo[2,3-b]pyridin-5-yl)-3-(propylsulfonamido)benzamide | $^1$H NMR (400 MHz, DMSO-d$_6$) δ 12.35 (s, 1H), 10.99 (s, 1H), 9.81 (s, 1H), 9.08 (s, 1H), 8.51-8.46 (m, 2H), 8.01-7.97 (m, 1H), 7.60-7.52 (m, 1H), 7.32-7.24 (m, 1H), 7.04-7.00 (m, 1H), 4.04 (s, 3H), 3.17-3.11 (m, 2H), 1.82-1.74 (m, 2H), 1.03-0.98 (m, 3H); m/z (APCI-neg) M − 1 = 473.2 |

TABLE 3-continued

| Ex. # | Structure | Name | MS/NMR |
|---|---|---|---|
| 60 | 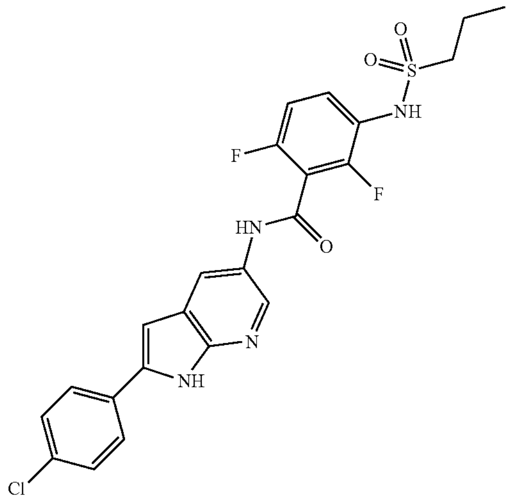 | N-(2-(4-chlorophenyl)-1H-pyrrolo[2,3-b]pyridin-5-yl)-2,6-difluoro-3-(propylsulfonamido)benzamide | $^1$H NMR (400 MHz, DMSO-d$_6$) δ 12.23 (s, 1H), 10.90 (s, 1H), 9.80 (s, 1H), 8.41-8.35 (m, 2H), 8.00-7.94 (m, 2H), 7.58-7.52 (m, 3H), 7.31-7.24 (m, 1H), 7.01 (s, 1H), 3.16-3.10 (m, 2H), 1.82-1.73 (m, 2H), 1.04-0.97 (m, 3H); m/z (APCI-neg) M − 1 = 503.2 |
| 61 | 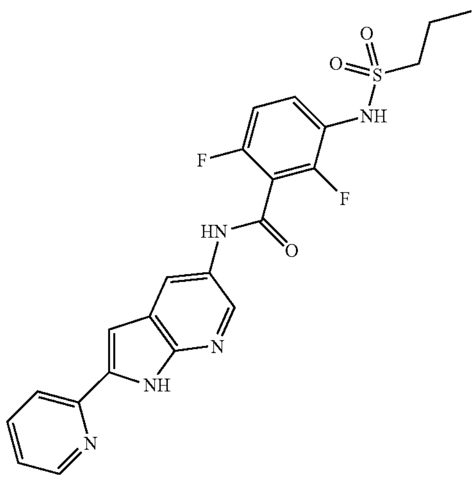 | 2,6-difluoro-3-(propylsulfonamido)-N-(2-(pyridin-2-yl)-1H-pyrrolo[2,3-b]pyridin-5-yl)benzamide | $^1$H NMR (400 MHz, d$_6$-DMSO) δ 12.25 (s, 1H), 10.92 (s, 1H), 9.80 (s, 1H), 8.68-8.65 (m, 1H), 8.43-8.40 (m, 2H), 8.07-8.04 (m, 1H), 7.93-7.88 (m, 1H), 7.59-7.52 (m, 1H), 7.37-7.19 (m, 3H), 3.16-3.11 (m, 2H), 1.81-1.75 (m, 2H), 1.02-0.98 (m, 3H); m/z (APCI-pos) M + 1 = 472.1 |

Example 62

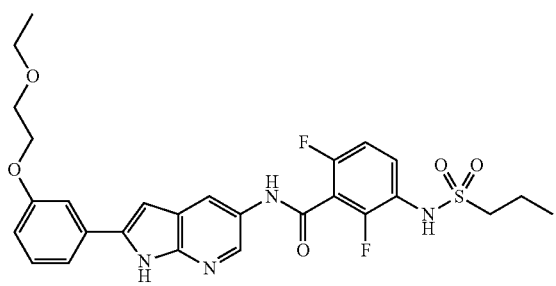

N-(2-(3-(2-ethoxyethoxy)phenyl)-1H-pyrrolo[2,3-b]pyridin-5-yl)-2,6-difluoro-3-(propylsulfonamido)benzamide Step A: 3-Ethynylphenol (1.707 g, 12.45 mmol, 1.0 eq.) and 1-bromo-2-ethoxyethane (1.1 eq.) were taken up in DMF (20 mL), and Cs$_2$CO$_3$ (2.2 eq.) was added. The mixture was heated to 90° C. for 16 hours, and then cooled to room temperature. The mixture was diluted with water (50 mL) and EtOAc (30 mL), and the layers were separated. The organic layers were washed with water (2×50 mL) and brine (3×50 mL), and dried (MgSO$_4$). The resulting residue was purified by chromatography (10% EtOAc/hexanes) to yield 1-(2-ethoxyethoxy)-3-ethynylbenzene as an oil (2.63 g, 96%).

Step B: N-(2-(3-(2-Ethoxyethoxy)phenyl)-1H-pyrrolo[2,3-b]pyridin-5-yl)-2,6-difluoro-3-(propylsulfonamido)benzamide was prepared following Example 56, substituting 1-(2-ethoxyethoxy)-3-ethynylbenzene for ethynylbenzene. $^1$H NMR (400 MHz, MeOD-d$_4$) δ 8.36 (s, 2H), 7.68-7.63 (m, 1H), 7.47-7.45 (m, 2H), 7.40-7.36 (m, 1H), 7.16-7.12 (m, 1H), 6.98-6.95 (m, 1H), 6.87 (s, 1H), 4.24-4.20 (m, 2H), 3.85-3.84 (m, 2H), 3.66-3.61 (m, 2H), 3.14-3.10 (m, 2H), 1.92-1.83 (m, 2H), 1.26-1.22 (m, 3H), 1.08-1.04 (m, 3H); m/z (APCI-pos) M+1=559.1.

Example 63

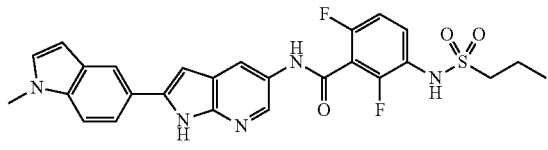

2,6-difluoro-N-(2-(1-methyl-1H-indol-5-yl)-1H-pyrrolo[2,3-b]pyridin-5-yl)-3-(propylsulfonamido)benzamide Step A: 2-Iodo-5-nitro-1-(phenylsulfonyl)-1H-pyrrolo[2,3-b]pyridine (76%) was prepared following Example 32, Step B, substituting 2-iodo-1-(phenylsulfonyl)-1H-pyrrolo[2,3-b]pyridine for 3-iodo-1-(phenylsulfonyl)-1H-pyrrolo[2,3-b]pyridine.

Step B: 2-Iodo-1-(phenylsulfonyl)-1H-pyrrolo[2,3-b]pyridin-5-amine (46%) was prepared following Example 32, Step C, substituting 2-iodo-5-nitro-1-(phenylsulfonyl)-1H-pyrrolo[2,3-b]pyridine for 3-iodo-5-nitro-1-(phenylsulfonyl)-1H-pyrrolo[2,3-b]pyridine.

Step C: 2,6-Difluoro-N-(2-iodo-1-(phenylsulfonyl)-1H-pyrrolo[2,3-b]pyridin-5-yl)-3-(propylsulfonamido)benzamide (87%) was prepared following Example 32, Step D, substituting 2-iodo-1-(phenylsulfonyl)-1H-pyrrolo[2,3-b]pyridin-5-amine for 3-iodo-1-(phenylsulfonyl)-1H-pyrrolo[2,3-b]pyridin-5-amine.

Step D: A mixture of 2,6-difluoro-N-(2-iodo-1-(phenylsulfonyl)-1H-pyrrolo[2,3-b]pyridin-5-yl)-3-(propylsulfonamido)benzamide (27 mg, 40 mmol, 1.0 eq.), 1-methyl-1H-indol-5-ylboronic acid (1.5 eq.), $K_2CO_3$ (20 eq.) and $Pd(PPh_3)_4$ (0.05 eq.) were taken up in 4:1 MeCN/water (0.7 mL) and heated to 160° C. for 15 minutes under microwave irradiation. The mixture was diluted with 1:1 EtOAc/water (6 mL), filtered through GF/F paper, and the layers were separated. The organic layer was dried over $MgSO_4$, filtered, and concentrated to afford 2,6-difluoro-N-(2-(1-methyl-1H-indol-5-yl)-1-(phenylsulfonyl)-1H-pyrrolo[2,3-b]pyridin-5-yl)-3-(propylsulfonamido)benzamide (19 mg, 70%).

Step E: 2N $K_2CO_3$ (1 mL) was added to a solution of 2,6-difluoro-N-(2-(1-methyl-1H-indol-5-yl)-1-(phenylsulfonyl)-1H-pyrrolo[2,3-b]pyridin-5-yl)-3-(propylsulfonamido)benzamide (19 mg, 29 mmol) in MeOH (3 mL), and the mixture was heated to 60° C. for 16 hours. The volatiles were removed under reduced pressure, and the resulting residue was partitioned between EtOAc and water. The layers were separated, and the organic layers were dried ($MgSO_4$), filtered and concentrated. Dichloromethane was added to the residue, and the resulting solid was collected by vacuum filtration giving 2,6-difluoro-N-(2-(1-methyl-1H-indol-5-yl)-1H-pyrrolo[2,3-b]pyridin-5-yl)-3-(propylsulfonamido)benzamide (10 mg, 66%). $^1$H NMR (400 MHz, DMSO-$d_6$) δ 12.04 (s, 1H), 10.84 (s, 1H), 9.80 (s, 1H), 8.33-8.28 (m, 2H), 8.15 (s, 1H), 7.77-7.73 (m, 1H), 7.57-7.52 (m, 2H), 7.39-7.38 (m, 1H), 7.29-7.25 (m, 1H), 6.86 (s, 1H), 6.50-6.49 (m, 1H), 3.83 (s, 3H), 3.15-3.11 (m, 2H), 1.83-1.73 (m, 2H), 1.03-0.98 (m, 3H); m/z (APCI-neg) M−1=522.2.

Example 64

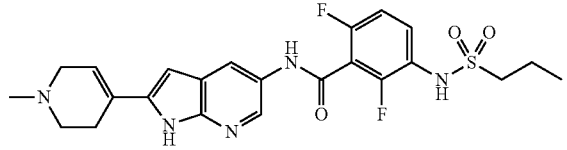

2,6-difluoro-N-(2-(1-methyl-1,2,3,6-tetrahydropyridin-4-yl)-1H-pyrrolo[2,3-b]pyridin-5-yl)-3-(propylsulfonamido)benzamide Step A: tert-Butyl 4-(5-(2,6-difluoro-3-(propylsulfonamido)benzamido)-1-(phenylsulfonyl)-1H-pyrrolo[2,3-b]pyridin-2-yl)-5,6-dihydropyridine-1(2H)-carboxylate (90% yield) was prepared following Example 63, Step D, substituting tert-butyl 4-(4,4,5,5-tetramethyl-1,3,2-dioxaborolan-2-yl)-5,6-dihydropyridine-1(2H)-carboxylate (Eastwood, Paul R., "A versatile synthesis of 4-aryl tetrahydropyridines via palladium mediated Suzuki cross-coupling with cyclic vinyl boronates." *Tetrahedron Lett.* 41(19) (2000): pp. 3705-3708) for 1-methyl-1H-indol-5-ylboronic acid.

Step B: A solution of tert-butyl 4-(5-(2,6-difluoro-3-(propylsulfonamido)benzamido)-1-(phenylsulfonyl)-1H-pyrrolo[2,3-b]pyridin-2-yl)-5,6-dihydropyridine-1(2H)-carboxylate (50 mg, 0.07 mmol) in $CH_2Cl_2$ (5 mL) was treated with trifluoroacetic acid (3 mL). After 2 hours, the volatiles were removed under reduced pressure, and the residue was partitioned between EtOAc and saturated $NaHCO_3$. The organic layer was dried ($MgSO_4$), filtered, concentrated, and purified by silica gel chromatography (eluting with 90:10:1 $CH_2Cl_2$/MeOH/$NH_4OH$) to afford 2,6-difluoro-N-(1-(phenylsulfonyl)-2-(1,2,3,6-tetrahydropyridin-4-yl)-1H-pyrrolo[2,3-b]pyridin-5-yl)-3-(propylsulfonamido)benzamide (29 mg, 67%) as a solid.

Step C: A solution of 2,6-difluoro-N-(1-(phenylsulfonyl)-2-(1,2,3,6-tetrahydropyridin-4-yl)-1H-pyrrolo[2,3-b]pyridin-5-yl)-3-(propylsulfonamido)benzamide (15 mg, 0.024 mmol) in 5:1 $CH_2Cl_2$/MeOH (6 mL) was treated with 37% aqueous formaldehyde (100 μL) and a drop of AcOH. After 5 minutes, the mixture was treated with sodium triacetoxyborohydride (26 mg, 5 eq.), and the reaction mixture was stirred for 16 hours at ambient temperature. The mixture was treated with MeOH (1 mL), concentrated under reduced pressure, and purified by silica gel chromatography (eluting with 10% MeOH/$CH_2Cl_2$) to afford 2,6-difluoro-N-(2-(1-methyl-1,2,3,6-tetrahydropyridin-4-yl)-1-(phenylsulfonyl)-1H-pyrrolo[2,3-b]pyridin-5-yl)-3-(propylsulfonamido)benzamide.

Step D: 2,6-Difluoro-N-(2-(1-methyl-1,2,3,6-tetrahydropyridin-4-yl)-1H-pyrrolo[2,3-b]pyridin-5-yl)-3-(propylsulfonamido)benzamide was prepared in 54% yield following Example 63, Step E, substituting 2,6-difluoro-N-(2-(1-methyl-1,2,3,6-tetrahydropyridin-4-yl)-1-(phenylsulfonyl)-1H-pyrrolo[2,3-b]pyridin-5-yl)-3-(propylsulfonamido)benzamide for 2,6-difluoro-N-(2-(1-methyl-1H-indol-5-yl)-1-(phenylsulfonyl)-1H-pyrrolo[2,3-b]pyridin-5-yl)-3-(propylsulfonamido)benzamide. $^1$H NMR (400 MHz, MeOD-$d_4$) δ 8.35-8.28 (m, 2H), 7.69-7.60 (m, 1H), 7.17-7.09 (m, 1H), 6.49 (s, 1H), 6.39 (s, 1H). 3.24 (s, 2H), 3.14-3.08 (m, 2H), 2.81-2.75 (m, 2H), 2.72-2.67 (m, 2H), 2.45 (s, 3H), 1.91-1.83 (m, 2H), 1.09-1.03 (m, 3H); m/z (APCIZ-pos) M+1=489.9.

The following compounds in Table 4 were prepared following the above procedures.

TABLE 4

| Ex. # | Structure | Name | MS/NMR |
|---|---|---|---|
| 65 | 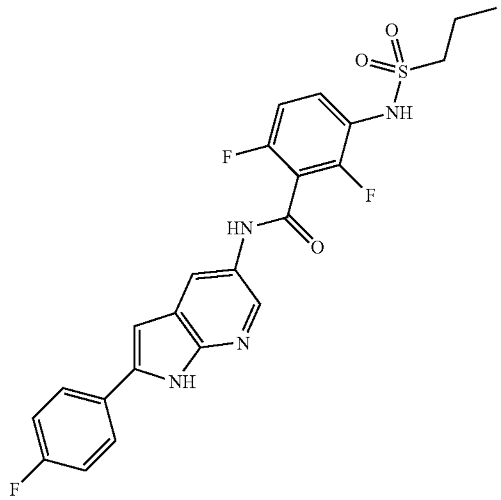 | 2,6-difluoro-N-(2-(4-fluorophenyl)-1H-pyrrolo[2,3-b]pyridin-5-yl)-3-(propylsulfonamido)-benzamide | ¹H NMR (400 MHz, DMSO-d₆) δ 12.17 (s, 1H), 10.89 (s, 1H), 9.80 (s, 1H), 8.37-8.35 (m, 2H), 8.00-7.97 (m, 2H), 7.58-7.52 (m, 1H), 7.35-7.25 (m, 3H), 6.95 (s, 1H), 3.15-3.11 (m, 2H), 1.81-1.75 (m, 2H), 1.02-0.98 (m, 3H); m/z (APCI-neg) M − 1 = 487.2 |
| 66 | 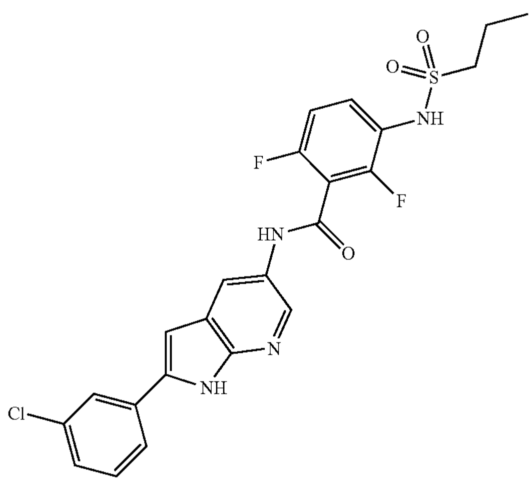 | N-(2-(3-chlorophenyl)-1H-pyrrolo[2,3-b]pyridin-5-yl)-2,6-difluoro-3-(propylsulfonamido)-benzamide | ¹H NMR (400 MHz, DMSO-d₆) δ 12.24 (s, 1H), 10.92 (s, 1H), 9.80 (s, 1H), 8.41-8.38 (m, 2H), 8.06-8.04 (m, 1H), 7.93-7.90 (m, 1H), 7.59-7.48 (m, 2H), 7.43-7.39 (m, 1H), 7.30-7.25 (m, 1H), 7.09-7.08 (m, 1H), 3.16-3.11 (m, 2H), 1.83-1.73 (m, 2H), 1.03-0.98 (m, 3H); m/z (APCI-pos) M + 1 = 505.0 |
| 67 | 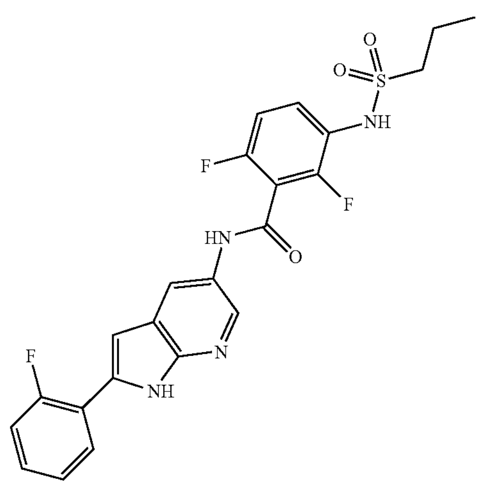 | 2,6-difluoro-N-(2-(2-fluorophenyl)-1H-pyrrolo[2,3-b]pyridin-5-yl)-3-(propylsulfonamido)-benzamide | ¹H NMR (400 MHz, DMSO-d₆) δ 12.16 (s, 1H), 10.92 (s, 1H), 9.81 (s, 1H), 8.45-8.37 (m, 2H), 8.03-7.97 (m, 1H), 7.59-7.51 (m, 1H), 7.46-7.24 (m, 4H), 6.97-6.94 (m, 1H), 3.16-3.11 (m, 2H), 1.83-1.73 (m, 2H), 1.03-0.98 (m, 3H); m/z (APCI-neg) M − 1 = 487.2 |

TABLE 4-continued

| Ex. # | Structure | Name | MS/NMR |
|---|---|---|---|
| 68 | 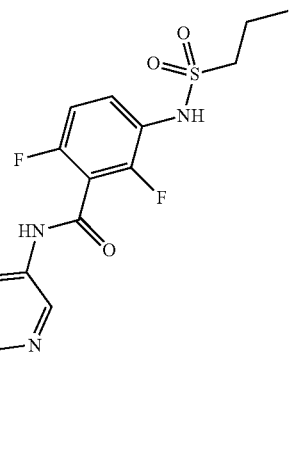 | 2,6-difluoro-N-(2-(3-fluorophenyl)-1H-pyrrolo[2,3-b]pyridin-5-yl)-3-(propylsulfonamido)-benzamide | $^1$H NMR (400 MHz, DMSO-$d_6$) δ 12.23 (s, 1H), 10.91 (s, 1H), 9.80 (br s, 1H), 8.41-8.37 (m, 2H), 7.83-7.78 (m, 2H), 7.58-7.49 (m, 2H), 7.29-7.15 (m, 2H), 7.08-7.06 (m, 1H), 3.15-3.09 (m, 2H), 1.83-1.73 (m, 2H), 1.02-0.98 (m, 3H); m/z (APCI-pos) M + 1 = 489.1 |
| 69 | 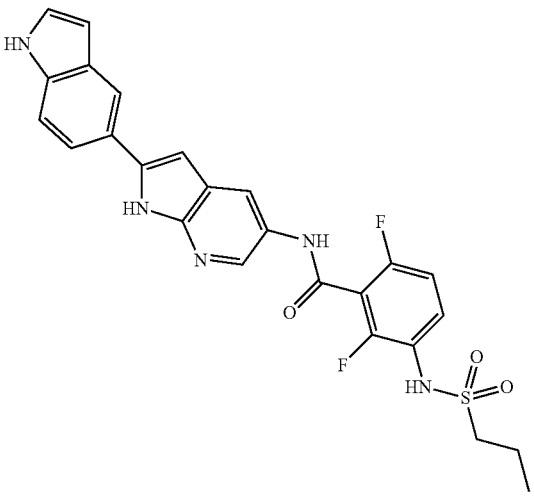 | N-(2-(1H-indol-5-yl)-1H-pyrrolo[2,3-b]pyridin-5-yl)-2,6-difluoro-3-(propylsulfonamido)-benzamide | $^1$H NMR (400 MHz, DMSO-$d_6$) δ 12.02 (s, 1H), 11.23 (s, 1H), 10.83 (s, 1 H), 9.80 (br s, 1H), 8.33-8.28 (m, 2H), 8.15 (s, 1H), 7.70-7.66 (m, 1H), 7.57-7.45 (m, 2H), 7.41-7.38 (m, 1H), 7.29-7.22 (m, 1H), 6.84-6.82 (m, 1H), 6.51-6.49 (m, 1H), 3.14-3.09 (m, 2H), 1.82-1.74 (m, 2H), 1.02-0.98 (m, 3H); m/z (APCI-neg) M − 1 = 508.2 |
| 70 | 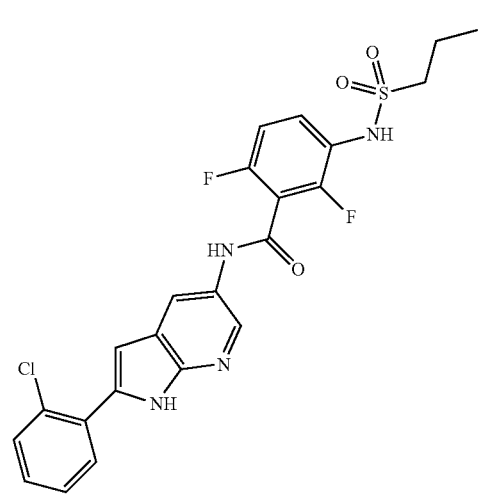 | N-(2-(2-chlorophenyl)-1H-pyrrolo[2,3-b]pyridin-5-yl)-2,6-difluoro-3-(propylsulfonamido)-benzamide | $^1$H NMR (400 MHz, DMSO-$d_6$) δ 12.06 (s, 1H), 10.90 (s, 1H), 9.80 (br s, 1H), 8.44-8.39 (m, 2H), 7.78-7.74 (m, 1H), 7.64-7.61 (m, 1H), 7.58-7.41 (m, 1H), 7.29-7.23 (m, 1H), 6.91-6.89 (m, 1H), 3.14-3.09 (m, 2H), 1.81-1.73 (m, 2H), 1.02-0.98 (m, 3H); m/z (APCI-pos) M + 1 = 505.1 |

TABLE 4-continued

| Ex. # | Structure | Name | MS/NMR |
|---|---|---|---|
| 71 | 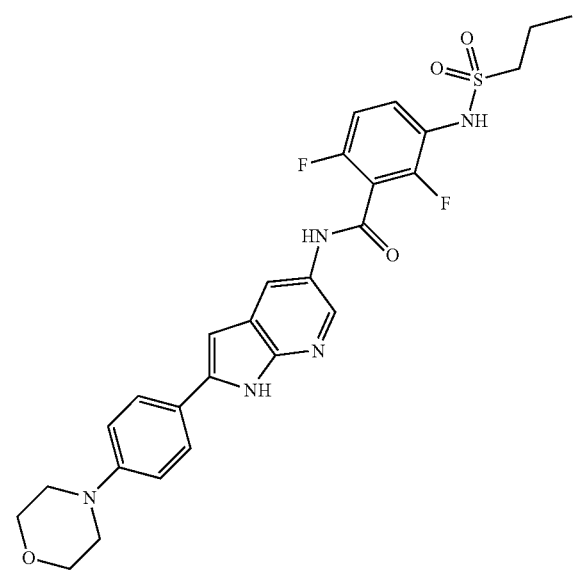 | 2,6-difluoro-N-(2-(4-morpholinophenyl)-1H-pyrrolo[2,3-b]pyridin-5-yl)-3-(propylsulfonamido)-benzamide | $^1$H NMR (400 MHz, DMSO-$d_6$) δ 11.98 (br s, 1H), 10.84 (br s, 1H), 9.80 (br s, 1H), 8.31-8.31 (m, 1H), 8.25-8.27 (m, 1H), 7.79-7.83 (m, 2H), 7.51-7.58 (m, 1H), 7.24-7.30 (m, 1H), 7.01-7.06 (m, 2H), 3.74-3.78 (m, 4H), 3.17-3.22 (m, 4H), 3.10-3.16 (m, 2H), 1.73-1.83 (m, 2H), 0.97-1.03 (m, 3H); m/z (APCI-pos) M + 1 = 556.1 |
| 72 | 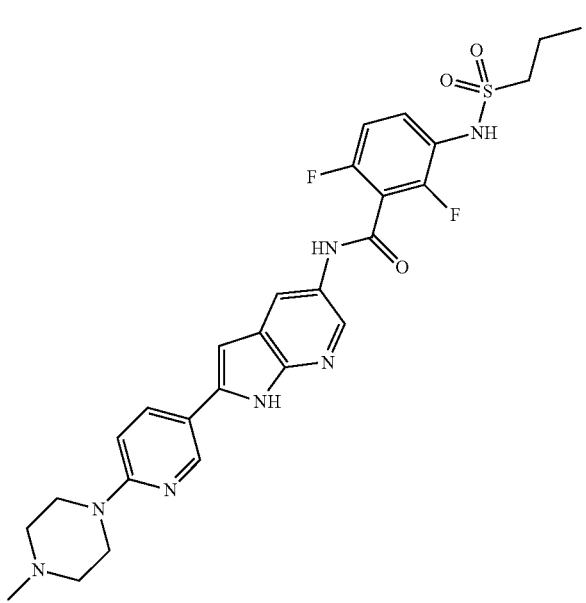 | 2,6-difluoro-N-(2-(6-(4-methylpiperazin-1-yl)pyridin-3-yl)-1H-pyrrolo[2,3-b]pyridin-5-yl)-3-(propylsulfonamido)-benzamide | $^1$H NMR (400 MHz, DMSO-$d_6$) δ 8.75-8.79 (m, 1H), 8.43-46 (m, 2H), 8.05-8.09 (m, 1H), 7.58-7.65 (m, 1H), 7.02-7.08 (m, 1H), 6.90-6.93 (m, 1H), 6.79 (s, 1H), 3.61-3.65 (m, 4H), 3.05-3.10 (m, 2H), 2.43-2.48 (m, 4H), 2.27 (s, 3H), 1.79-1.89 (m, 2H), 1.00-1.05 (m, 3H); m/z (APCI-pos) M + 1 = 570.1 |

TABLE 4-continued
| Ex. # | Structure | Name | MS/NMR |
|---|---|---|---|
| 73 | 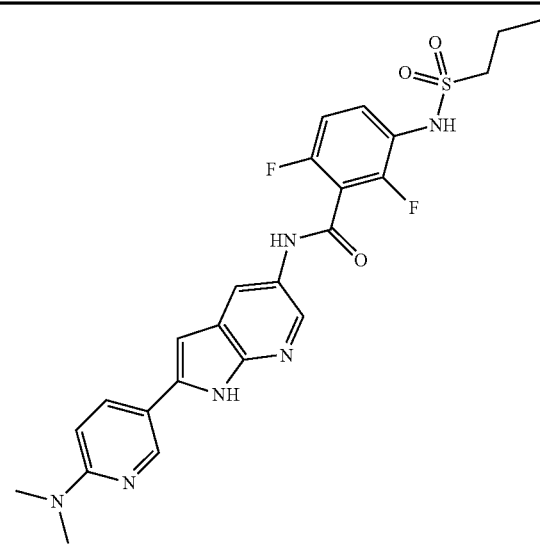 | N-(2-(6-(dimethylamino)pyridin-3-yl)-1H-pyrrolo[2,3-b]pyridin-5-yl)-2,6-difluoro-3-(propylsulfonamido)-benzamide | $^1$H NMR (400 MHz, CD$_3$OD) δ 8.74-8.75 (m, 1H), 8.43-46 (m, 2H), 8.02-8.06 (m, 1H), 7.52-7.60 (m, 1H), 6.91-6.97 (m, 1H), 6.73-6.77 (m, 2H), 2.95-3.01 (m, 2H), 1.85 (s, 6H), 1.76-1.84 (m, 2H), 0.97-1.03 (m, 3H); m/z (APCI-pos) M + 1 = 515.1 |
| 74 | 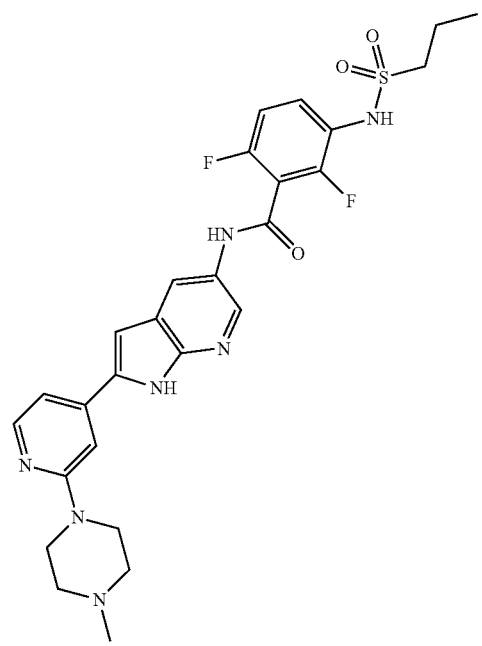 | 2,6-difluoro-N-(2-(2-(4-methylpiperazin-1-yl)pyridin-4-yl)-1H-pyrrolo[2,3-b]pyridin-5-yl)-3-(propylsulfonamido)-benzamide | $^1$H NMR (400 MHz, CD$_3$OD) δ 8.22-8.25 (m, 1H), 8.15-8.18 (m, 1H), 7.78-7.82 (m, 1H), 7.44-7.51 (m, 1H), 7.32 (s, 1H), 7.22-7.26 (m, 1H), 7.08 (s, 1H), 6.98-7.04 (m, 1H), 4.12-4.25 (m, 2H), 3.58-3.67 (m, 2H), 3.43-3.55 (m, 2H), 3.09-3.26 (m, 4H), 2.86 (s, 3H), 1.64-1.74 (m, 2H), 0.83-0.89 (m, 3H); m/z (APCI-pos) M + 1 = 570.1 |

TABLE 4-continued

| Ex. # | Structure | Name | MS/NMR |
|---|---|---|---|
| 75 | 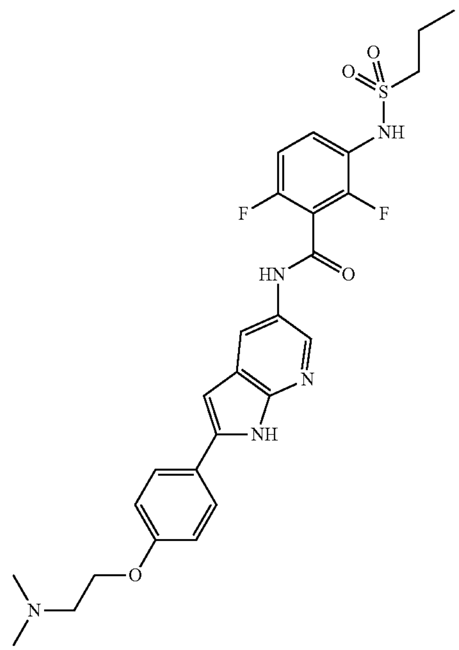 | N-(2-(4-(2-(dimethylamino)ethoxy)-phenyl)-1H-pyrrolo[2,3-b]pyridin-5-yl)-2,6-difluoro-3-(propylsulfonamido)-benzamide | $^1$H NMR (400 MHz, d$_6$-DMSO) δ 12.04 (s, 1H), 10.84 (s, 1H), 9.78 (br s, 1H), 8.35-8.28 (m, 2H), 7.88-7.84 (m, 2H), 7.57-7.50 (m, 1H), 7.27-7.21 (m, 1H), 7.07-7.03 (m, 2H), 6.83-6.82 (m, 1H), 4.14-4.09 (m, 2H), 3.13-3.07 (m, 2H), 2.68-2.63 (m, 2H), 2.23 (s, 6H), 1.81-1.73 (m, 2H), 1.02-0.97 (m, 3H); m/z (APCI-pos) m/z M + 1 = 558.1 |
| 76 | 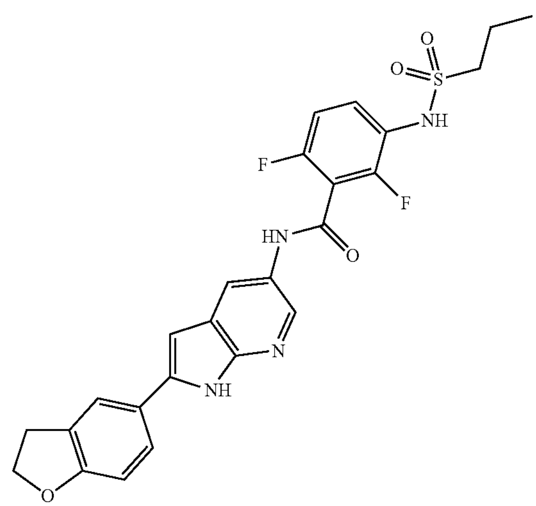 | N-(2-(2,3-dihydrobenzofuran-5-yl)-1H-pyrrolo[2,3-b]pyridin-5-yl)-2,6-difluoro-3-(propylsulfonamido)-benzamide | $^1$H NMR (400 MHz, d$_6$-DMSO) δ 12.03 (s, 1H), 10.83 (s, 1H), 9.80 (br s, 1H), 8.32-8.27 (m, 2H), 7.82 (s, 1H), 7.71-7.67 (m, 1H), 7.57-7.50 (m, 1H), 7.27-7.20 (m, 1H), 6.88-6.84 (m, 1H), 6.79-6.77 (m, 1H), 4.62-4.56 (m, 2H), 3.28-3.22 (m, 2H), 3.12-3.07 (m, 2H), 1.80-1.72 (m, 2H), 1.02-0.97 (m, 3H); m/z (APCI-pos) M + 1 = 513.1 |
| 77 | 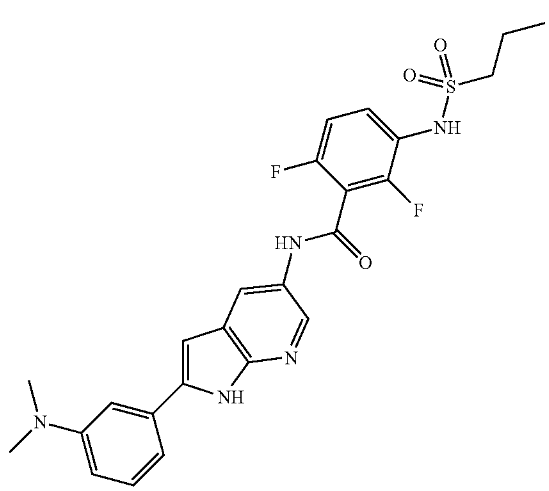 | N-(2-(3-(dimethylamino)-phenyl)-1H-pyrrolo[2,3-b]pyridin-5-yl)-2,6-difluoro-3-(propylsulfonamido)-benzamide | $^1$H NMR (400 MHz, d$_6$-DMSO) δ 12.13 (s, 1H), 10.87 (s, 1H), 9.80 (s, 1H), 8.38-8.30 (m, 2H), 7.58-7.51 (m, 1H), 7.30-7.20 (m, 4H), 6.93-6.91 (m, 1H), 6.74-6.70 (m, 1H), 3.16-3.10 (m, 2H), 1.81-1.75 (m, 2H), 1.03-0.98 (m, 3H); m/z (APCI-pos) M + 1 = 514.1 |

TABLE 4-continued

| Ex. # | Structure | Name | MS/NMR |
|---|---|---|---|
| 78 | 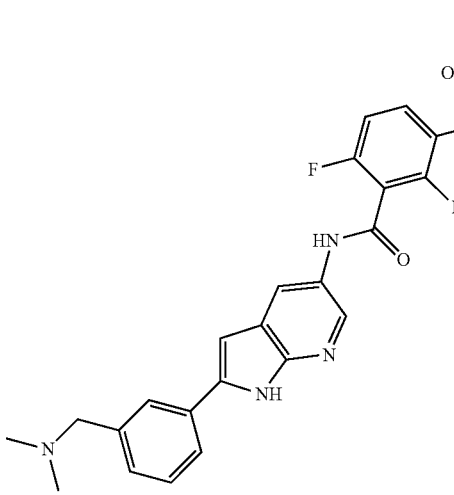 | N-(2-(3-((dimethylamino)-methyl)phenyl)-1H-pyrrolo[2,3-b]pyridin-5-yl)-2,6-difluoro-3-(propylsulfonamido)-benzamide | $^1$H NMR (400 MHz, d$_6$-DMSO) δ 12.16 (s, 1H), 10.88 (s, 1H), 9.80 (br s, 1H), 8.37-8.34 (m, 2H), 7.87-7.81 (m, 2H), 7.58-7.52 (m, 1H), 7.45-7.40 (m, 1H), 7.30-7.25 (m, 2H), 6.96-6.94 (m, 1H), 3.47 (s, 2H), 3.16-3.10 (m, 2H), 2.20 (s, 6H), 1.81-1.74 (m, 2H), 1.02-0.98 (m, 3H); m/z (APCI-pos) M + 1 = 528.1 |
| 79 | 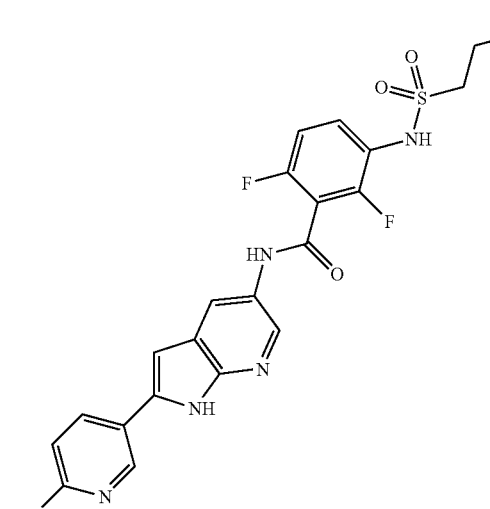 | N-(2-(6-aminopyridin-3-yl)-1H-pyrrolo[2,3-b]pyridin-5-yl)-2,6-difluoro-3-(propylsulfonamido)-benzamide | $^1$H NMR (400 MHz, d$_6$-DMSO) δ 11.93 (s, 1H), 10.83 (s, 1H), 9.80 (br s, 1H), 8.52 (s, 1H), 8.31-8.23 (m, 2H), 7.91-7.87 (m, 1H), 7.58-7.51 (m, 1H), 7.29-7.24 (m, 1H), 6.72-6.70 (m, 1H), 6.55-6.51 (m, 1H), 6.23 (br s, 2H), 3.15-3.10 (m, 2H), 1.81-1.74 (m, 2H), 1.02-0.98 (m, 3H); m/z (APCI-pos) M + 1 = 487.1 |
| 80 | 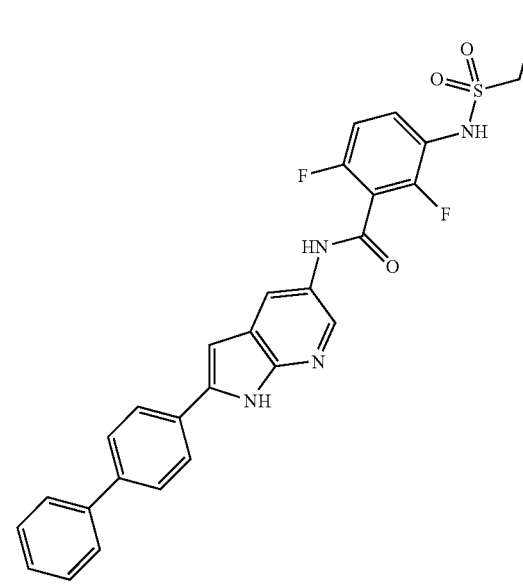 | N-(2-(biphenyl-4-yl)-1H-pyrrolo[2,3-b]pyridin-5-yl)-2,6-difluoro-3-(propylsulfonamido)-benzamide | $^1$H NMR (400 MHz, DMSO-d$_6$) δ 12.21-12.25 (br s, 1H), 10.85-10.88 (br s, 1H), 8.36-8.41 (m, 2H), 8.02-8.07 (m, 2H), 7.74-7.82 (m, 4H), 7.46-7.57 (m, 3H), 7.36-7.42 (m, 1H), 7.16-7.23 (m, 1H), 7.02-7.04 (m, 1H), 3.02-3.09 (m, 2H), 1.70-1.80 (m, 2H), 0.95-1.02 (m, 3H); m/z (APCI-pos) M + 1 = 547.1 |

TABLE 4-continued
| Ex. # | Structure | Name | MS/NMR |
|---|---|---|---|
| 81 | 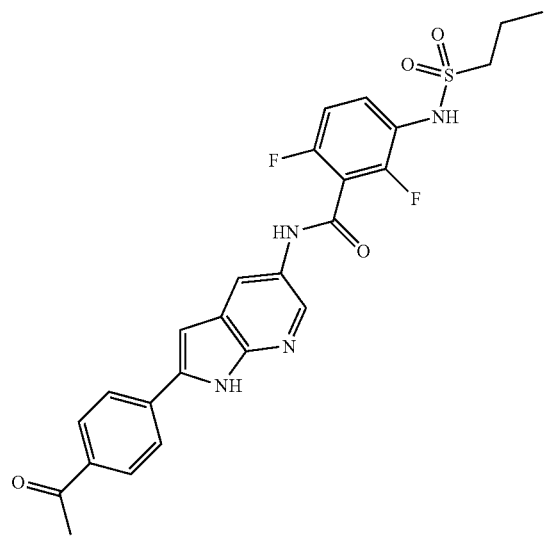 | N-(2-(4-acetylphenyl)-1H-pyrrolo[2,3-b]pyridin-5-yl)-2,6-difluoro-3-(propylsulfonamido)-benzamide | $^1$H NMR (400 MHz, DMSO-d$_6$) δ 12.32-12.37 (br s, 1H), 10.87-10.91 (br s, 1H), 8.40-8.45 (m, 2H), 8.0-8.12 (m, 4H), 7.46-7.57 (m, 2H), 7.14-7.25 (m, 2H), 3.02-3.10 (m, 2H), 2.62 (s, 3H), 1.70-1.80 (m, 2H), 0.95-1.02 (m, 3H); m/z (APCI-pos) M + 1 = 513.1 |
| 82 | 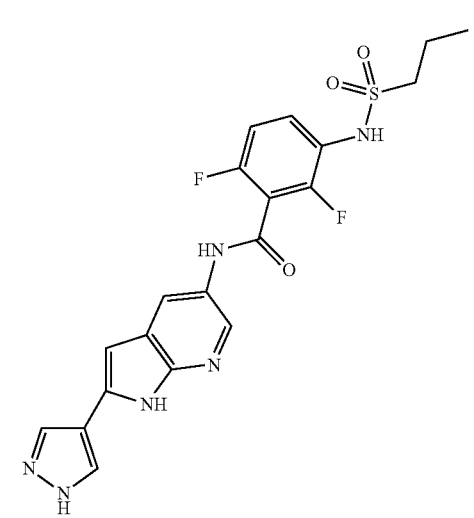 | N-(2-(1H-pyrazol-4-yl)-1H-pyrrolo[2,3-b]pyridin-5-yl)-2,6-difluoro-3-(propylsulfonamido)-benzamide | $^1$H NMR (400 MHz, CD$_3$OD) δ 8.90 (s, 1H), 8.59-8.62 (m, 1H), 8.25-8.31 (m, 2H), 7.62-7.72 (m, 1H), 7.13-7.20 (m, 1H), 7.00 (s, 1H), 3.10-3.15 (m, 2H), 1.82-1.93 (m, 2H), 1.02-1.09 (m, 3H); m/z (APCI-pos) M + 1 = 461.1 |

| Ex. # | Structure | Name | MS/NMR |
|---|---|---|---|
| 83 | 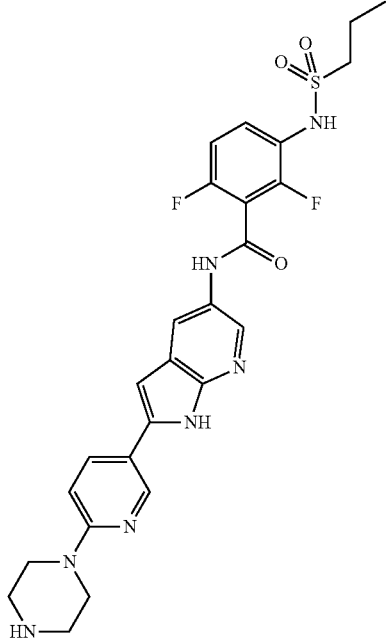 | 2,6-difluoro-N-(2-(6-(piperazin-1-yl)pyridin-3-yl)-1H-pyrrolo[2,3-b]pyridin-5-yl)-3-(propylsulfonamido)-benzamide | $^1$H NMR (400 MHz, CD$_3$OD) δ 8.94-8.96 (m, 1H), 8.73-8.74 (m, 1H), 8.69-8.71 (m, 1H), 8.54-8.58 (m, 1H), 7.61-7.71 (m, 1H), 7.55-7.59 (m, 1H), 7.29 (s, 1H), 7.14-7.20 (m, 1H), 4.10-4.15 (m, 4H), 3.48-3.53 (m, 4H), 3.11-3.15 (m, 2H), 1.82-1.93 (m, 2H), 1.04-1.09 (m, 3H); m/z (APCI-pos) M + 1 = 556.1 |
| 84 | 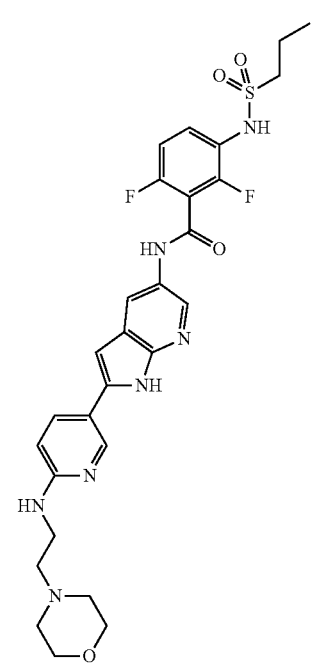 | 2,6-difluoro-N-(2-(6-(2-morpholinoethylamino)-pyridin-3-yl)-1H-pyrrolo[2,3-b]pyridin-5-yl)-3-(propylsulfonamido)-benzamide | $^1$H NMR (400 MHz, CD$_3$OD) δ 8.46-8.48 (m, 1H), 8.31-8.33 (m, 1H), 8.28-8.30 (m, 1H), 7.88-7.93 (m, 1H), 7.51-7.58 (m, 1H), 6.95-7.02 (m, 1H), 6.68 (s, 1H), 6.63-6.67 (m, 1H), 3.69-3.75 (m, 4H), 3.48-3.52 (m, 2H), 2.98-3.04 (m, 2H), 2.61-2.67 (m, 2H), 2.50-2.57 (m, 4H), 1.80-1.90 (m, 2H), 1.00-1.06 (m, 3H); m/z (APCI-pos) M + 1 = 600.1 |

TABLE 4-continued

| Ex. # | Structure | Name | MS/NMR |
|---|---|---|---|
| 85 | 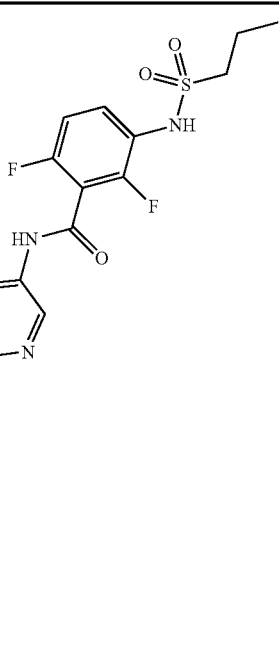 | 2,6-difluoro-N-(2-(4-(4-methylpiperazine-1-carbonyl)phenyl)-1H-pyrrolo[2,3-b]pyridin-5-yl)-3-(propylsulfonamido)-benzamide | $^1$H NMR (400 MHz, CD$_3$OD) δ 8.39-8.41 (m, 1H), 7.94-7.98 (m, 1H), 7.51-7.64 (m, 4H), 7.37-7.42 (m, 1H), 7.97-7.04 (m, 1H), 6.96 (s, 1H), 6.63-6.67 (m, 1H), 3.70-3.85 (m, 4H), 3.00-3.06 (m, 2H), 2.38-2.60 (m, 4H), 2.34 (s, 3H), 1.81-1.91 (m, 2H), 1.01-1.06 (m, 3H); m/z (APCI-pos) M + 1 = 597.1 |
| 86 | 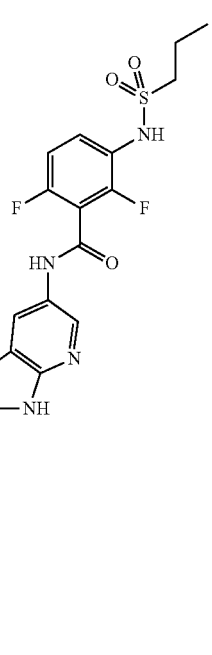 | 2,6-difluoro-N-(2-(6-(4-isopropylpiperazin-1-yl)pyridin-3-yl)-1H-pyrrolo[2,3-b]pyridin-5-yl)-3-(propylsulfonamido)-benzamide | $^1$H NMR (400 MHz, DMSO-d$_6$) δ 12.02-12.06 (br s, 1H), 10.84-10.86 (br s, 1H), 9.65-9.80 (br s, 1H), 8.69-8.72 (m, 1H), 8.32-8.35 (m, 1H), 8.25-8.28 (m, 1H), 8.02-8.08 (m, 1H), 7.51-7.59 (m, 1H), 7.24-7.30 (m, 1H), 6.92-6.97 (m, 1H), 6.79-6.82 (m, 1H), 3.51-3.64 (m, 3H), 3.10-3.17 (m, 2H), 2.68-2.82 (m, 2H), 2.53-2.68 (m, 3H), 1.74-1.82 (m, 2H), 1.22-1.25 (m, 1H), 0.96-1.06 (m, 9H); m/z (APCI-pos) M + 1 = 598.1 |

TABLE 4-continued

| Ex. # | Structure | Name | MS/NMR |
|---|---|---|---|
| 87 | 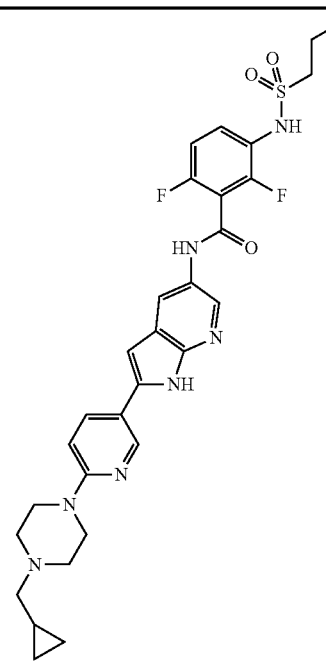 | N-(2-(6-(4-(cyclopropylmethyl)piperazin-1-yl)pyridin-3-yl)-1H-pyrrolo[2,3-b]pyridin-5-yl)-2,6-difluoro-3-(propylsulfonamido)-benzamide | $^1$H NMR (400 MHz, CD$_3$OD) δ 8.62-8.64 (m, 1H), 8.31-8.34 (m, 2H), 8.01-8.06 (m, 1H), 7.61-7.68 (m, 1H), 7.10-7.16 (m, 1H), 6.93-6.97 (m, 1H), 6.75 (s, 1H); 3.67-3.74 (m, 4H), 3.09-3.15 (m, 2H), 2.76-2.84 (m, 4H), 2.41-2.46 (m, 2H), 1.84-1.91 (m, 2H), 1.04-1.09 (m, 1H), 0.83-0.93 (m, 3H), 0.58-0.64 (m, 2H), 0.20-0.24 (m, 2H); m/z (APCI-pos) M + 1 = 610.1 |
| 88 | 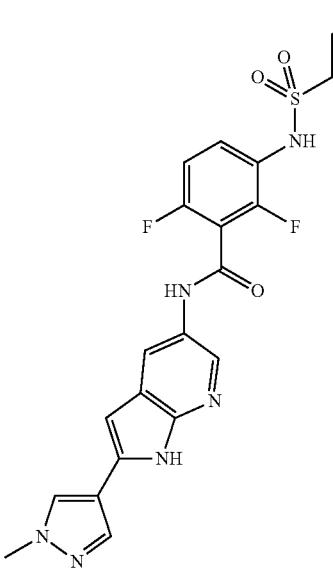 | 2,6-difluoro-N-(2-(1-methyl-1H-pyrazol-4-yl)-1H-pyrrolo[2,3-b]pyridin-5-yl)-3-(propylsulfonamido)-benzamide | $^1$H NMR (400 MHz, CD$_3$OD) δ 8.21-8.31 (m, 1H), 8.06 (s, 1H), 7.93 (s, 1H), 7.61-7.69 (m, 1H), 7.10-7.16 (m, 1H), 6.60 (s, 1H), 3.96 (s, 3H), 3.09-3.15 (m, 2H), 1.84-1.93 (m, 2H), 1.04-1.09 (m, 3H); m/z (APCI-pos) M + 1 = 475.1 |

TABLE 4-continued
| Ex. # | Structure | Name | MS/NMR |
|---|---|---|---|
| 89 | 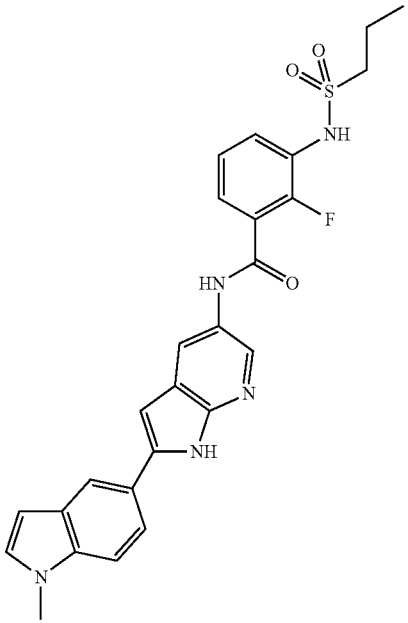 | 2-fluoro-N-(2-(1-methyl-1H-indol-5-yl)-1H-pyrrolo[2,3-b]pyridin-5-yl)-3-(propylsulfonamido)-benzamide | $^1$H NMR (400 MHz, DMSO-$d_6$) δ 12.00 (s, 1H), 10.48 (s, 1H), 9.83 (s, 1H), 8.37-8.35 (m, 1H), 8.30-8.28 (m, 1H), 8.16-8.14 (m, 1H), 7.77-7.73 (m, 1H), 7.59-7.48 (m, 3H), 7.39-7.37 (m, 1H), 7.34-7.29 (m, 1H), 6.86-6.84 (m, 1H), 6.51-6.49 (m, 1H), 3.83 (s, 3H), 3.20-3.14 (m, 2H), 1.84-1.74 (m, 2H), 1.03-0.98 (m, 3H); m/z (APCI-pos) M + 1 = 506.1 |
| 90 | 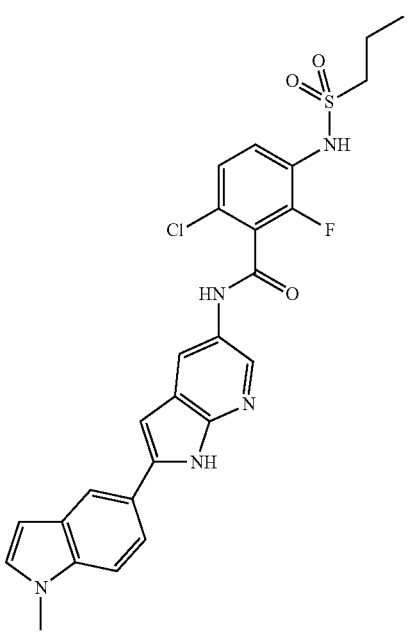 | 6-chloro-2-fluoro-N-(2-(1-methyl-1H-indol-5-yl)-1H-pyrrolo[2,3-b]pyridin-5-yl)-3-(propylsulfonamido)-benzamide | $^1$H NMR (400 MHz, DMSO-$d_6$) δ 12.04 (s, 1H), 10.79 (s, 1H), 9.98 (br s, 1H), 8.33-8.27 (m, 2H), 8.15 (s, 1H), 7.77-7.73 (m, 1H), 7.55-7.49 (m, 2H), 7.43-7.37 (m, 2H), 6.87-6.85 (m, 1H), 6.51-6.49 (m, 1H), 3.83 (s, 3H), 3.17-3.10 (m, 2H), 1.81-1.73 (m, 2H), 1.02-0.97 (m, 3H); m/z (APCI-pos) M + 1 = 540.1 |

Example 91

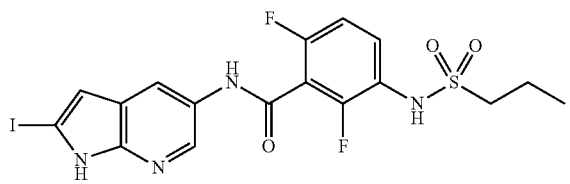

2,6-difluoro-N-(2-iodo-1H-pyrrolo[2,3-b]pyridin-5-yl)-3-(propylsulfonamido)benzamide Following Example 63, Step E, 2,6-difluoro-N-(2-iodo-1H-pyrrolo[2,3-b]pyridin-5-yl)-3-(propylsulfonamido)benzamide was prepared from 2,6-difluoro-N-(2-iodo-1-(phenylsulfonyl)-1H-pyrrolo[2,3-b]pyridin-5-yl)-3-(propylsulfonamido)benzamide in quantitative yield. $^1$H NMR (400 MHz, DMSO-d$_6$) δ 12.24 (s, 1H), 10.87 (s, 1H), 9.78 (br s, 1H), 8.32-8.28 (m, 2H), 7.55-7.48 (m, 1H), 7.24-7.18 (m, 1H), 6.74 (s, 1H), 3.11-3.04 (m, 2H), 1.80-1.70 (m, 2H), 1.01-0.96 (m, 3H); m/z (APCI-pos) M+1=521.0.

Example 92

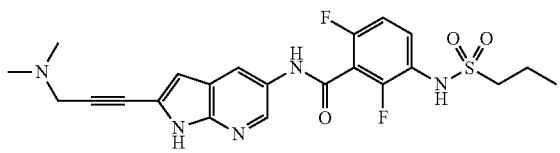

N-(2-(3-(dimethylamino)prop-1-ynyl)-1H-pyrrolo[2,3-b]pyridin-5-yl)-2,6-difluoro-3-(propylsulfonamido)benzamide Step A: A solution of 2,6-difluoro-N-(2-iodo-1-(phenylsulfonyl)-1H-pyrrolo[2,3-b]pyridin-5-yl)-3-(propylsulfonamido)benzamide (91 mg, 0.14 mmol, 1.0 eq.), N,N-dimethylprop-2-yn-1-amine (2.7 eq.), CuI (0.2 eq.) and PdCl$_2$(PPh$_3$)$_2$ (0.2 eq.) in 1:1 TEA/THF (8 mL) was degassed under argon for 10 minutes. The mixture was heated to 60° C. for 16 hours, and the volatiles were removed under reduced pressure. The resulting residue was diluted with EtOAc and water and filtered through GF/F paper. The layers were separated. The organic layer was dried (MgSO$_4$) and purified by silica gel chromatography (eluting with 100% EtOAc) to afford N-(2-(3-(dimethylamino)prop-1-ynyl)-1-(phenylsulfonyl)-1H-pyrrolo[2,3-b]pyridin-5-yl)-2,6-difluoro-3-(propylsulfonamido)benzamide as an oil (54 mg, 64%).

Step B: N-(2-(3-(Dimethylamino)prop-1-ynyl)-1H-pyrrolo[2,3-b]pyridin-5-yl)-2,6-difluoro-3-(propylsulfonamido)benzamide was prepared according to Example 63, Step E, substituting N-(2-(3-(dimethylamino)prop-1-ynyl)-1-(phenylsulfonyl)-1H-pyrrolo[2,3-b]pyridin-5-yl)-2,6-difluoro-3-(propylsulfonamido)benzamide for 2,6-difluoro-N-(2-(1-methyl-1H-indol-5-yl)-1-(phenylsulfonyl)-1H-pyrrolo[2,3-b]pyridin-5-yl)-3-(propylsulfonamido)benzamide. $^1$H NMR (400 MHz, d$_6$-DMSO) δ 12.14 (s, 1H), 10.91 (s, 1H), 9.79 (br s, 1H), 8.40-8.35 (m, 2H), 7.58-7.50 (m, 1H), 7.29-7.22 (m, 1H), 6.73-6.71 (m, 1H), 3.53 (s, 2H), 3.14-3.09 (m, 2H), 2.27 (s, 6H), 1.80-1.73 (m, 2H), 1.02-0.97 (m, 3H); m/z (APCI-pos) M+1=475.9.

Example 93

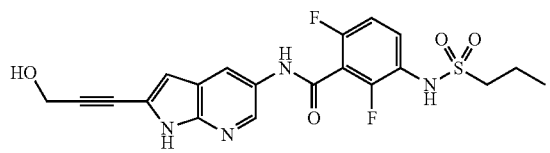

2,6-difluoro-N-(2-(3-hydroxyprop-1-ynyl)-1H-pyrrolo[2,3-b]pyridin-5-yl)-3-(propylsulfonamido)benzamide Step A: 2,6-Difluoro-N-(2-(3-hydroxyprop-1-ynyl)-1-(phenylsulfonyl)-1H-pyrrolo[2,3-b]pyridin-5-yl)-3-(propylsulfonamido)benzamide was prepared according to the general procedure of Example 92, Step A, substituting prop-2-yn-1-ol for N,N-dimethylprop-2-yn-1-amine.

Step B: 2,6-Difluoro-N-(2-(3-hydroxyprop-1-ynyl)-1H-pyrrolo[2,3-b]pyridin-5-yl)-3-(propylsulfonamido)benzamide was prepared according to the general procedure of Example 92, Step B, substituting 2,6-difluoro-N-(2-(3-hydroxyprop-1-ynyl)-1-(phenylsulfonyl)-1H-pyrrolo[2,3-b]pyridin-5-yl)-3-(propylsulfonamido)benzamide for N-(2-(3-(dimethylamino)prop-1-ynyl)-1-(phenylsulfonyl)-1H-pyrrolo[2,3-b]pyridin-5-yl)-2,6-difluoro-3-(propylsulfonamido)benzamide. $^1$H NMR (400 MHz, CD$_3$OD) δ 8.41-8.35 (m, 2H), 7.68-7.61 (m, 1H), 7.15-7.10 (m, 1H), 6.69 (s, 1H), 4.46 (s, 2H), 3.13-3.09 (m, 2H), 1.90-1.82 (m, 2H), 1.08-1.03 (m, 3H); m/z (APCI-neg) M−1=447.2.

Example 94

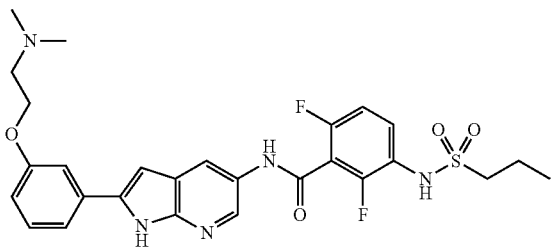

N-(2-(3-(2-(dimethylamino)ethoxy)phenyl)-1H-pyrrolo[2,3-b]pyridin-5-yl)-2,6-difluoro-3-(propylsulfonamido)benzamide Step A: Diisopropyl diazene-1,2-dicarboxylate (1.1 eq.) was added dropwise to a 0° C. solution of 3-bromophenol (1.155 g, 6.68 mmol, 1.0 eq.), 2-(dimethylamino)ethanol (1.1 eq.) and triphenylphosphine (1.1 eq.) in THF (20 mL). The mixture was allowed to warm to room temperature over 16 hours, and then the volatiles were removed under reduced pressure. The resulting residue was partitioned between EtOAc (20 mL) and 1N HCl (20 mL), and the aqueous layer was collected and washed with EtOAc. The aqueous layer was neutralized with saturated NaHCO₃ (50 mL), extracted with EtOAc, and dried (MgSO₄). Purification via silica chromatography (eluting with 4% MeOH/DCM) afforded 2-(3-bromophenoxy)-N,N-dimethylethanamine (1.032 g, 63%) as an oil.

Step B: A mixture of 2-(3-bromophenoxy)-N,N-dimethylethanamine (500 mg, 2.05 mmol, 1.0 eq.), 4,4,4',4',5,5,5',5'-octamethyl-2,2'-bi(1,3,2-dioxaborolane) (1.2 eq.), KOAc (3.0 eq.), and PdCl₂(dppf).DCM (0.03 eq.) were slurried in dioxane (6 mL) and degassed with argon for 10 minutes. The mixture was heated to 90° C. for 16 hours, cooled to room temperature and filtered through GF/F paper. The filtrate was washed with 5% aqueous NaCl (2×50 mL), dried (MgSO₄), and purified via silica gel chromatography (eluting with 8% MeOH/DCM) to afford N,N-dimethyl-2-(3-(4,4,5,5-tetramethyl-1,3,2-dioxaborolan-2-yl)phenoxy)ethanamine (111 mg, 19%) as an oil. ¹H NMR (400 MHz, CDCl₃) δ 7.41-7.28 (m, 3H), 7.05-7.01 (m, 1H), 4.14-4.10 (m, 2H), 2.78-2.74 (m, 2H), 2.37 (s, 6H), 1.34 (s, 12H).

Step C: Following Example 63 (Steps D and E), N-(2-(3-(2-(dimethylamino)ethoxy)phenyl)-1H-pyrrolo[2,3-b]pyridin-5-yl)-2,6-difluoro-3-(propylsulfonamido)benzamide was prepared from 2,6-difluoro-N-(2-iodo-1-(phenylsulfonyl)-1H-pyrrolo[2,3-b]pyridin-5-yl)-3-(propylsulfonamido)benzamide substituting N,N-dimethyl-2-(3-(4,4,5,5-tetramethyl-1,3,2-dioxaborolan-2-yl)phenoxy)ethanamine for 1-methyl-1H-indol-5-ylboronic acid. ¹H NMR (400 MHz, d₆-DMSO) δ 12.14 (s, 1H), 10.88 (s, 1H), 9.78 (br s, 1H), 8.39-8.33 (m, 2H), 7.58-7.50 (m, 3H), 7.39-7.34 (m, 1H), 7.29-7.22 (m, 1H), 7.00-6.98 (m, 1H), 6.95-6.91 (m, 1H), 4.17-4.13 (m, 2H), 3.14-3.09 (m, 2H), 2.71-2.66 (m, 2H), 2.26 (s, 6H), 1.82-1.73 (m, 2H), 1.02-0.98 (m, 3H); m/z (APCI-pos) M+1=558.1.

Example 95

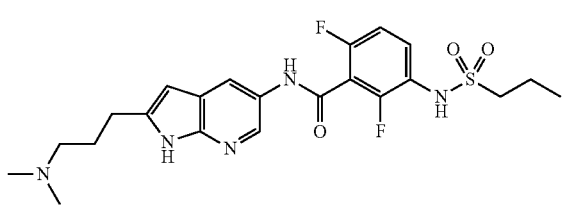

N-(2-(3-(dimethylamino)propyl)-1H-pyrrolo[2,3-b]pyridin-5-yl)-2,6-difluoro-3-(propylsulfonamido)benzamide A solution of N-(2-(3-(dimethylamino)prop-1-ynyl)-1H-pyrrolo[2,3-b]pyridin-5-yl)-2,6-difluoro-3-(propylsulfonamido)benzamide (30 mg, 63 mmol) in MeOH (10 mL) was treated with 10% Pd/C and allowed to stir under a balloon atmosphere of hydrogen for 4 hours. The mixture was filtered through GF/F paper, rinsing with MeOH. The filtrate was purified by silica gel chromatography (eluting with 10% MeOH/DCM containing 1% NH₄OH) to afford N-(2-(3-(dimethylamino)propyl)-1H-pyrrolo[2,3-b]pyridin-5-yl)-2,6-difluoro-3-(propylsulfonamido)benzamide (13 mg, 27 mmol, 43%) as a solid. ¹H NMR (400 MHz, d₆-DMSO) δ 11.50 (s, 1H), 10.77 (s, 1H), 9.80 (br s, 1H), 8.27-8.18 (m, 2H), 7.56-7.49 (m, 1H), 7.26-7.20 (m, 1H), 6.19-6.17 (m, 1H), 3.12-3.08 (m, 2H), 2.76-2.71 (m, 2H), 2.32-2.27 (m, 2H), 2.17 (s, 6H), 1.87-1.72 (m, 2H), 1.01-0.97 (m, 3H); m/z (APCI-pos) M+1=480.1.

Example 96

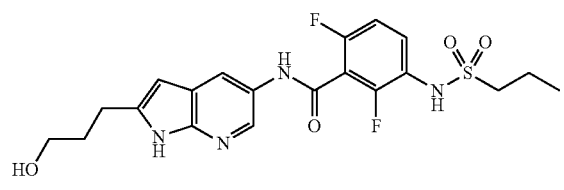

2,6-difluoro-N-(2-(3-hydroxypropyl)-1H-pyrrolo[2,3-b]pyridin-5-yl)-3-(propylsulfonamido)benzamide 2,6-Difluoro-N-(2-(3-hydroxypropyl)-1H-pyrrolo[2,3-b]pyridin-5-yl)-3-(propylsulfonamido)benzamide was prepared according to the general procedure of Example 95 substituting 2,6-difluoro-N-(2-(3-hydroxyprop-1-ynyl)-1H-pyrrolo[2,3-b]pyridin-5-yl)-3-(propylsulfonamido)benzamide for N-(2-(3-(dimethylamino)prop-1-ynyl)-1H-pyrrolo[2,3-b]pyridin-5-yl)-2,6-difluoro-3-(propylsulfonamido)benzamide. ¹H NMR (400 MHz, CD₃OD) δ 8.28-8.21 (m, 2H), 7.67-7.61 (m, 1H), 7.15-7.09 (m, 1H), 6.24 (s, 1H), 3.66-3.62 (m, 2H), 3.13-3.09 (m, 2H), 2.90-2.85 (m, 2H), 2.01-1.84 (m, 2H), 1.08-1.03 (m, 3H); m/z (APCI-pos) M+1=453.1.

Example 97

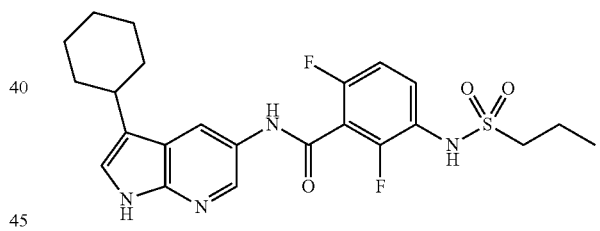

N-(3-cyclohexyl-1H-pyrrolo[2,3-b]pyridin-5-yl)-2,6-difluoro-3-(propylsulfonamido)benzamide Step A: N-(3-cyclohexenyl-1-(phenylsulfonyl)-1H-pyrrolo[2,3-b]pyridin-5-yl)-2,6-difluoro-3-(propylsulfonamido)benzamide was prepared according to the general procedure for Example 32, Step E, substituting cyclohexenylboronic acid for 3,4-difluorophenylboronic acid. The product was taken directly onto Step B.

Step B: N-(3-cyclohexenyl-1-(phenylsulfonyl)-1H-pyrrolo[2,3-b]pyridin-5-yl)-2,6-difluoro-3-(propylsulfonamido)benzamide was subjected to methanol/2M aqueous potassium carbonate (1 mg/1 mL) at 60° C. for 1 hour to give N-(3-cyclohexenyl-1H-pyrrolo[2,3-b]pyridin-5-yl)-2,6-difluoro-3-(propylsulfonamido)benzamide (100%). m/z (APCI-neg) M−1=473.2, (APCI-pos) M+1=475.1.

Step C: N-(3-cyclohexenyl-1H-pyrrolo[2,3-b]pyridin-5-yl)-2,6-difluoro-3-(propylsulfonamido)benzamide (40 mg, 0.084 mmol) was dissolved in methanol (1 mL), and 10% Pd/C (40 mg, 1 eq.) was then added. This mixture was subjected to 45 psi of hydrogen for 16 hours and filtered through GF/F filter paper. The filtrate was then concentrated. The resulting solids were purified by preparative TLC (2×0.5 mm plates, 10% MeOH/DCM as the eluent) to give N-(3-cyclohexyl-1H-pyrrolo[2,3-b]pyridin-5-yl)-2,6-difluoro-3-(propylsulfonamido)benzamide (10 mg, 25%). $^1$H NMR (400 MHz, DMSO-d$_6$) δ 11.34 (s, 1H), 10.82 (s, 1H), 9.79 (br s, 1H), 8.32-8.39 (m, 2H), 7.50-7.56 (m, 1H), 7.19-7.28 (m, 2H), 3.07-3.15 (m, 2H), 2.68-2.78 (m, 1H), 1.96-2.02 (m, 2H), 1.70-1.84 (m, 5H), 1.38-1.49 (m, 4H), 1.21-1.31 (m, 1H), 0.95-1.03 (m, 3H); m/z (APCI-neg) M−1=475.3, (APCI-pos) M+1=477.2.

Example 98

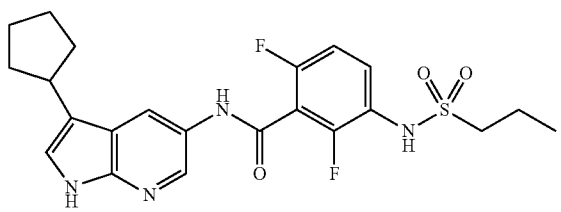

N-(3-cyclopentyl-1H-pyrrolo[2,3-b]pyridin-5-yl)-2, 6-difluoro-3-(propylsulfonamido)benzamide N-(3-Cyclopentyl-1H-pyrrolo[2,3-b]pyridin-5-yl)-2,6-difluoro-3-(propylsulfonamido)benzamide (12%) was prepared according to the general procedure for Example 97, Step B, substituting N-(3-cyclopentenyl-1H-pyrrolo[2,3-b]pyridin-5-yl)-2,6-difluoro-3-(propylsulfonamido)benzamide for N-(3-cyclohexenyl-1H-pyrrolo[2,3-b]pyridin-5-yl)-2,6-difluoro-3-(propylsulfonamido)benzamide. $^1$H NMR (400 MHz, CD$_3$OD) δ 8.42-8.45 (m, 1H), 8.33-8.35 (m, 1H), 7.60-7.67 (m, 1H), 7.20 (s, 1H), 7.08-7.15 (m, 1H), 3.23-3.33 (m, 1H), 3.06-3.15 (m, 2H), 2.12-2.23 (m, 2H), 1.67-1.91 (m, 8H), 1.02-1.09 (m, 3H); m/z (APCI-neg) M−1=461.3, (APCI-pos) M+1=463.2.

Example 99

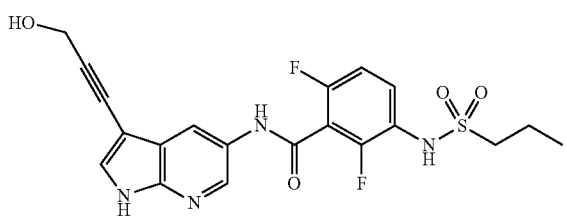

2,6-difluoro-N-(3-(3-hydroxyprop-1-ynyl)-1H-pyrrolo[2,3-b]pyridin-5-yl)-3-(propylsulfonamido)benzamide Step A: 2,6-Difluoro-N-(3-(3-hydroxyprop-1-ynyl)-1-(phenylsulfonyl)-1H-pyrrolo[2,3-b]pyridin-5-yl)-3-(propylsulfonamido)benzamide was prepared according to the general procedure for Example 92, Step A, substituting prop-2-yn-1-ol for N,N-dimethylprop-2-yn-1-amine.

Step B: 2,6-Difluoro-N-(3-(3-hydroxyprop-1-ynyl)-1H-pyrrolo[2,3-b]pyridin-5-yl)-3-(propylsulfonamido)benzamide (54%) was prepared according to the general procedure for Example 15, Step B, substituting 2,6-difluoro-N-(3-(3-hydroxyprop-1-ynyl)-1-(phenylsulfonyl)-1H-pyrrolo[2,3-b]pyridin-5-yl)-3-(propylsulfonamido)benzamide for 2,6-difluoro-N-(1-(phenylsulfonyl)-3-vinyl-1H-pyrrolo[2,3-b]pyridin-5-yl)-3-(propylsulfonamido)benzamide. $^1$H NMR (400 MHz, DMSO-d$_6$) δ 12.07 (br s, 1H), 11.00 (s, 1H), 9.80 (br s, 1H), 8.47 (s, 1H), 8.38 (s, 1H), 7.82 (br s, 1H), 7.53-7.59 (m, 1H), 7.25-7.30 (m, 1H), 5.31-5.28 (m, 1H), 4.36-4.35 (m, 2H), 3.11-3.15 (m, 2H), 1.75-1.80 (m, 2H), 0.98-1.02 (m, 3H); m/z (APCI-pos) M+1=447.5.

Example 100

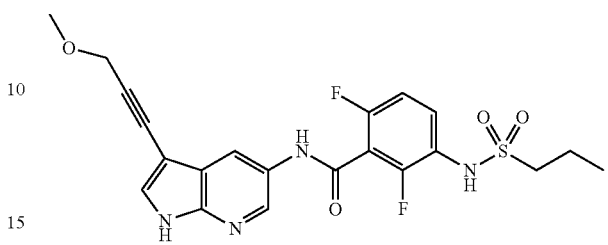

2,6-difluoro-N-(3-(3-methoxyprop-1-ynyl)-1H-pyrrolo pyridin-5-yl)-3-(propylsulfonamido)benzamide Step A: 2,6-Difluoro-N-(3-(3-methoxyprop-1-ynyl)-1-(phenylsulfonyl)-1H-pyrrolo[2,3-b]pyridin-5-yl)-3-(propylsulfonamido)benzamide was prepared according to the general procedure for Example 92, Step A, substituting 3-methoxyprop-1-yn-1-ol for N,N-dimethylprop-2-yn-1-amine.

Step B: 2,6-Difluoro-N-(3-(3-hydroxyprop-1-ynyl)-1H-pyrrolo[2,3-b]pyridin-5-yl)-3-(propylsulfonamido)benzamide (55%) was prepared according to the general procedure for Example 15, Step B, substituting 2,6-difluoro-N-(3-(3-methoxyprop-1-ynyl)-1-(phenylsulfonyl)-1H-pyrrolo[2,3-b]pyridin-5-yl)-3-(propylsulfonamido)benzamide for 2,6-difluoro-N-(1-(phenylsulfonyl)-3-vinyl-1H-pyrrolo[2,3-b]pyridin-5-yl)-3-(propylsulfonamido)benzamide. $^1$H NMR (400 MHz, DMSO-d$_6$) δ 12.13 (br s, 1H), 11.01 (s, 1H), 9.80 (br s, 1H), 8.45 (s, 1H), 8.43 (s, 1H), 7.88 (br s, 1H), 7.53-7.59 (m, 1H), 7.25-7.30 (m, 1H), 4.38 (s, 1H), 4.36-3.36 (s, 1H), 3.11-3.15 (m, 2H), 1.75-1.80 (m, 2H), 0.98-1.02 (m, 3H); m/z (APCI-pos) M+1=461.2.

Example 101

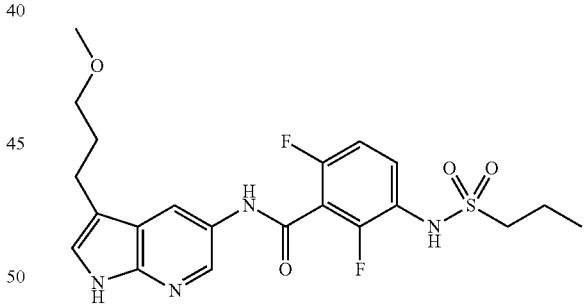

2,6-difluoro-N-(3-(3-methoxypropyl)-1H-pyrrolo[2,3-b]pyridin-5-yl)-3-(propylsulfonamido)benzamide 2,6-Difluoro-N-(3-(3-methoxypropyl)-1H-pyrrolo[2,3-b]pyridin-5-yl)-3-(propylsulfonamido)benzamide (90%) was prepared according to the general procedure for Example 95 substituting 2,6-difluoro-N-(3-(3-methoxyprop-1-ynyl)-1-(phenylsulfonyl)-1H-pyrrolo[2,3-b]pyridin-5-yl)-3-(propylsulfonamido)benzamide for N-(2-(3-(dimethylamino)prop-1-ynyl)-1H-pyrrolo[2,3-b]pyridin-5-yl)-2,6-difluoro-3-(propylsulfonamido)benzamide. $^1$H NMR (400 MHz, DMSO-d$_6$) δ 11.33 (br s, 1H), 10.83 (s, 1H), 9.79 (br s, 1H), 8.47-8.38 (m, 2H), 7.51-7.57 (m, 1H), 7.24-7.28 (m, 2H), 4.45-4.48 (m, 1H), 3.44-3.49 (m, 2H), 3.11-3.15 (m, 2H), 2.68-2.72 (m, 2H), 1.75-1.81 (m, 4H), 0.98-1.02 (m, 3H); m/z (APCI-pos) M+1=451.2.

Example 102

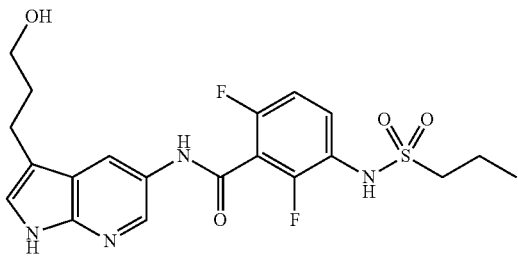

2,6-difluoro-N-(3-(3-hydroxypropyl)-1H-pyrrolo[2,3-b]pyridin-5-yl)-3-(propylsulfonamido)benzamide

2,6-Difluoro-N-(3-(3-hydroxypropyl)-1H-pyrrolo[2,3-b]pyridin-5-yl)-3-(propylsulfonamido)benzamide (77%) was prepared according to the general procedure for Example 95 substituting 2,6-difluoro-N-(3-(3-hydroxyprop-1-ynyl)-1H-pyrrolo[2,3-b]pyridin-5-yl)-3-(propylsulfonamido)benzamide for N-(2-(3-(dimethylamino)prop-1-ynyl)-1H-pyrrolo[2,3-b]pyridin-5-yl)-2,6-difluoro-3-(propylsulfonamido)benzamide. $^1$H NMR (400 MHz, DMSO-$d_6$) δ 11.33 (br s, 1H), 10.83 (s, 1H), 9.79 (br s, 1H), 8.47-8.38 (m, 2H), 7.51-7.57 (m, 1H), 7.24-7.28 (m, 2H), 4.45-4.48 (m, 1H), 3.44-3.49 (m, 2H), 3.11-3.15 (m, 2H), 2.68-2.72 (m, 2H), 1.75-1.81 (m, 4H), 0.98-1.02 (m, 3H); m/z (APCI-pos) M+1=451.2.

Example 103

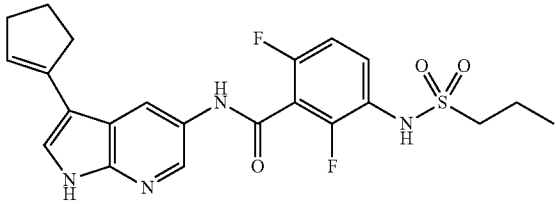

N-(3-cyclopentenyl-1H-pyrrolo[2,3-b]pyridin-5-yl)-2,6-difluoro-3-(propylsulfonamido)benzamide

Step A: N-(3-Cyclopentenyl-1-(phenylsulfonyl)-1H-pyrrolo[2,3-b]pyridin-5-yl)-2,6-difluoro-3-(propylsulfonamido)benzamide was prepared according to the general procedure for Example 32, Step E, substituting cyclopentenylboronic acid for 3,4-difluorophenylboronic acid. The product was taken directly onto Step B.

Step B: N-(3-Cyclopentenyl-1H-pyrrolo[2,3-b]pyridin-5-yl)-2,6-difluoro-3-(propylsulfonamido)benzamide (25%) was prepared according to the general procedure for Example 97, Step B, substituting N-(3-cyclopentenyl-1-(phenylsulfonyl)-1H-pyrrolo[2,3-b]pyridin-5-yl)-2,6-difluoro-3-(propylsulfonamido)benzamide for N-(3-cyclohexenyl-1-(phenylsulfonyl)-1H-pyrrolo[2,3-b]pyridin-5-yl)-2,6-difluoro-3-(propylsulfonamido)benzamide. $^1$H NMR (400 MHz, CD$_3$OD) δ 8.67-8.69 (m, 1H), 8.41-8.42 (m, 1H), 7.61-7.69 (m, 1H), 7.38 (s, 1H), 7.10-7.17 (m, 1H), 6.13-6.16 (m, 1H), 3.08-3.15 (m, 2H), 2.73-2.81 (m, 2H), 2.55-2.63 (m, 2H), 1.97-2.05 (m, 2H), 1.82-1.92 (m, 2H), 1.02-1.08 (m, 3H); m/z (APCI-neg) M−1=459.2, (APCI-pos) M+1=461.1.

Example 104

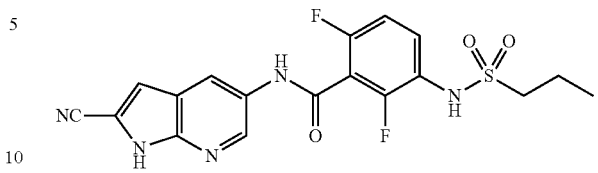

N-(2-cyano-1H-pyrrolo[2,3-b]pyridin-5-yl)-2,6-difluoro-3-(propylsulfonamido)benzamide

N-(2-Cyano-1H-pyrrolo[2,3-b]pyridin-5-yl)-2,6-difluoro-3-(propylsulfonamido)benzamide was prepared following Example 17 substituting 2,6-difluoro-N-(2-iodo-1-(phenylsulfonyl)-1H-pyrrolo[2,3-b]pyridin-5-yl)-3-(propylsulfonamido)benzamide for 2,6-difluoro-N-(3-iodo-1-(phenylsulfonyl)-1H-pyrrolo[2,3-b]pyridin-5-yl)-3-(propylsulfonamido)benzamide. $^1$H NMR (400 MHz, $d_6$-DMSO) δ 12.98 (br s, 1H), 11.08 (s, 1H), 9.80 (br s, 1H), 8.60 (s, 2H), 7.59-7.52 (m, 1H), 7.43 (s, 1H), 7.30-7.24 (m, 1H), 3.15-3.09 (m, 2H), 1.80-1.73 (m, 2H), 1.02-0.97 (m, 3H); m/z (APCI-neg) M−1=418.1.

Example 105

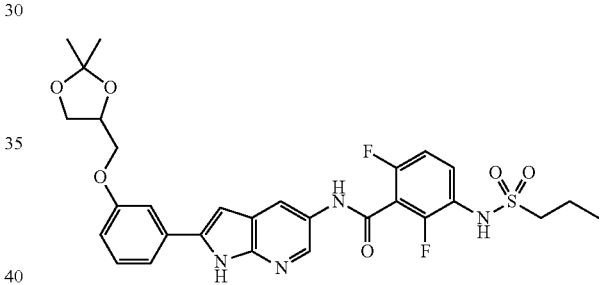

N-(2-(3-((2,2-dimethyl-1,3-dioxolan-4-yl)methoxy)phenyl)-1H-pyrrolo[2,3-b]pyridin-5-yl)-2,6-difluoro-3-(propyl sulfonamido)benzamide

Step A: 4-((3-Bromophenoxy)methyl)-2,2-dimethyl-1,3-dioxolane (81% yield) was prepared following Example 94, Step A, substituting (2,2-dimethyl-1,3-dioxolan-4-yl)methanol for 2-(dimethylamino)ethanol.

Step B: 2-(3-((2,2-Dimethyl-1,3-dioxolan-4-yl)methoxy)phenyl)-4,4,5,5-tetramethyl-1,3,2-dioxaborolane (77% yield) was prepared following Example 94, Step B, substituting 4-((3-bromophenoxy)methyl)-2,2-dimethyl-1,3-dioxolane for 2-(3-bromophenoxy)-N,N-dimethylethanamine. $^1$H NMR (400 MHz, CDCl$_3$) δ 7.43-7.39 (m, 1H), 7.34-7.27 (m, 2H), 7.05-7.01 (m, 1H), 4.51-4.44 (m, 1H), 4.19-4.08 (m, 2H), 3.99-3.95 (m, 1H), 3.92-3.88 (m, 1H), 1.47 (s, 3H), 1.41 (s, 3H), 1.34 (s, 12H).

Step C: Following Example 63 (Steps D and E), N-(2-(3-((2,2-dimethyl-1,3-dioxolan-4-yl)methoxy)phenyl)-1H-pyrrolo[2,3-b]pyridin-5-yl)-2,6-difluoro-3-(propylsulfonamido)benzamide was prepared from 2,6-difluoro-N-(2-iodo-1-(phenylsulfonyl)-1H-pyrrolo[2,3-b]pyridin-5-yl)-3-(propylsulfonamido)benzamide substituting 2-(3-((2,2-dimethyl-1,3-dioxolan-4-yl)methoxy)phenyl)-4,4,5,5-tetramethyl-1,3,2-dioxaborolane for 1-methyl-1H-indol-5-ylboronic acid. $^1$H NMR (400 MHz, $d_6$-DMSO) δ 12.15 (s, 1H), 10.89 (s, 1H), 9.78 (s, 1H), 8.39-8.34 (m, 2H), 7.58-7.52 (m, 3H), 7.40-7.35 (m, 1H), 7.30-7.24 (m, 1H), 7.01-6.99 (m, 1H), 6.96-6.92 (m, 1H), 4.49-4.43 (m, 1H), 4.16-4.09 (m, 3H), 3.82-3.77 (m, 1H), 3.15-3.11 (m, 2H), 1.81-1.75 (m, 2H), 1.39 (s, 3H), 1.33 (s, 3H), 1.02-0.98 (m, 3H); m/z (APCI-pos) M+1=601.1.

Example 106

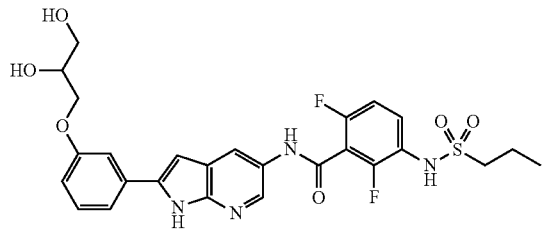

N-(2-(3-(2,3-dihydroxypropoxy)phenyl)-1H-pyrrolo[2,3-b]pyridin-5-yl)-2,6-difluoro-3-(propylsulfonamido)benzamide A solution of N-(2-(3-((2,2-dimethyl-1,3-dioxolan-4-yl)methoxy)phenyl)-1H-pyrrolo[2,3-b]pyridin-5-yl)-2,6-difluoro-3-(propylsulfonamido)benzamide (22 mg, 36 mmol) in 2:1 THF/MeOH (3 mL) was treated with 1N HCl (1 mL) and the mixture stirred at room temperature for 16 hours. The volatiles were removed via rotary evaporation, and the resulting residue was partitioned between EtOAc and aqueous NaHCO$_3$. The layers were separated, and the organic layer was dried (MgSO$_4$), filtered and concentrated to a solid. The solid was triturated with DCM and collected via vacuum filtration to afford N-(2-(3-(2,3-dihydroxypropoxy)phenyl)-1H-pyrrolo[2,3-b]pyridin-5-yl)-2,6-difluoro-3-(propylsulfonamido)benzamide (13 mg, 64%) as a solid. $^1$H NMR (400 MHz, d$_6$-DMSO) δ 12.16 (s, 1H), 10.89 (s, 1H), 9.80 (s, 1H), 8.40-8.33 (m, 2H), 7.58-7.49 (m, 3H), 7.40-7.34 (m, 1H), 7.31-7.24 (m, 1H), 7.00-6.90 (m, 2H), 5.00-4.96 (m, 1H), 4.72-4.67 (m, 1H), 4.12-4.07 (m, 1H), 4.01-3.99 (m, 1H), 3.88-3.81 (m, 1H), 3.52-3.47 (m, 1H), 3.16-3.10 (m, 2H), 1.82-1.74 (m, 2H), 1.04-0.97 (m, 3H); m/z (APCI-pos) M+1=561.2.

Example 107

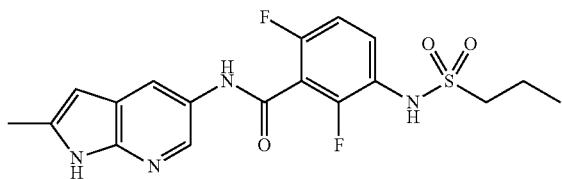

2,6-difluoro-N-(2-methyl-1H-pyrrolo[2,3-b]pyridin-5-yl)-3-(propylsulfonamido)benzamide Step A: 2-Methyl-5-nitro-1-(phenylsulfonyl)-1H-pyrrolo[2,3-b]pyridine (75%) was prepared according to the general procedure for Example 32, Step B, substituting 2-methyl-1-(phenylsulfonyl)-1H-pyrrolo[2,3-b]pyridine (prepared as described in Mendiola, Javier, et al. "Reaction of Bromomethylazoles and Tosylmethyl Isocyanide. A Novel Heterocyclization Method for the Synthesis of the Core of Marine Alkaloids Variolins and Related Azolopyrimidines." J. Org. Chem. 69(15) (2004): pp. 4974-4983) for 3-iodo-1-(phenylsulfonyl)-1H-pyrrolo[2,3-b]pyridine.

Step B: 2-Methyl-1-(phenylsulfonyl)-1H-pyrrolo[2,3-b]pyridin-5-amine was prepared according to the general procedure for Example 32, Step C, substituting 2-methyl-5-nitro-1-(phenylsulfonyl)-1H-pyrrolo[2,3-b]pyridine for 3-iodo-5-nitro-1-(phenylsulfonyl)-1H-pyrrolo[2,3-b]pyridine. The material was used directly in the next step.

Step C: 2,6-Difluoro-N-(2-methyl-1-(phenylsulfonyl)-1H-pyrrolo[2,3-b]pyridin-5-yl)-3-(propylsulfonamido)benzamide was prepared according to the general procedure for Example 32, Step D, substituting 2-methyl-1-(phenylsulfonyl)-1H-pyrrolo[2,3-b]pyridin-5-amine for 3-iodo-1-(phenylsulfonyl)-1H-pyrrolo[2,3-b]pyridin-5-amine. The material was used directly in the next step.

Step D: 2,6-Difluoro-N-(2-methyl-1-(phenylsulfonyl)-1H-pyrrolo[2,3-b]pyridin-5-yl)-3-(propylsulfonamido)benzamide (0.379 g, 0.691 mmol) was dissolved in MeOH (6 mL) and water (2 mL). K$_2$CO$_3$ (1.91 g, 13.8 mmol) was added, and the reaction mixture was stirred at reflux overnight. The solution was partitioned between water and EtOAc. The organic layer was washed with water (3×), brine, dried over Na$_2$SO$_4$ and concentrated to a solid. The solid was triturated with DCM to provide 2,6-difluoro-N-(2-methyl-1H-pyrrolo[2,3-b]pyridin-5-yl)-3-(propylsulfonamido)benzamide as a solid (150 mg, 53% for three steps). $^1$H NMR (400 MHz, DMSO-d$_6$) δ 11.48 (br s, 1H), 10.80 (s, 1H), 9.80 (br s, 1H), 8.26 (br s, 1H), 8.20 (br s, 1H), 7.53-7.59 (m, 1H), 7.25-7.30 (m, 1H), 6.17 (br s, 1H), 3.10-3.14 (m, 2H), 2.40 (br s, 3H), 1.74-1.82 (m, 2H), 0.98-1.03 (m, 3H); m/z (APCI-neg) M−1=407.2.

Example 108

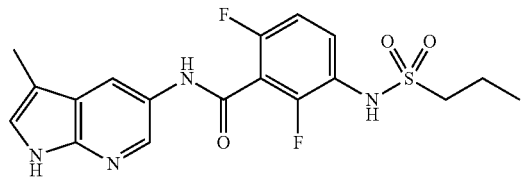

2,6-difluoro-N-(3-methyl-1H-pyrrolo[2,3-b]pyridin-5-yl)-3-(propylsulfonamido)benzamide Step A: 3-Methyl-1-(phenylsulfonyl)-1H-pyrrolo[2,3-b]pyridine (99%) was prepared according to the general procedure for Example 32, Step A, substituting 3-methyl-1H-pyrrolo[2,3-b]pyridine for 3-iodo-1H-pyrrolo[2,3-b]pyridine.

Step B: 3-Methyl-5-nitro-1-(phenylsulfonyl)-1H-pyrrolo[2,3-b]pyridine (65%) was prepared according to the general procedure for Example 32, Step B, substituting 3-methyl-1-(phenylsulfonyl)-1H-pyrrolo[2,3-b]pyridine for 3-iodo-1-(phenylsulfonyl)-1H-pyrrolo[2,3-b]pyridine.

Step C: 3-Methyl-1-(phenylsulfonyl)-1H-pyrrolo[2,3-b]pyridin-5-amine was prepared according to the general procedure for Example 32, Step C, substituting 2-methyl-5-nitro-1-(phenylsulfonyl)-1H-pyrrolo[2,3-b]pyridine for 3-iodo-5-nitro-1-(phenylsulfonyl)-1H-pyrrolo[2,3-b]pyridine. The material was used directly in the next step.

Step D: 2,6-Difluoro-N-(3-methyl-1-(phenylsulfonyl)-1H-pyrrolo[2,3-b]pyridin-5-yl)-3-(propylsulfonamido)benzamide was prepared according to the general procedure for Example 32, Step D, substituting 2-methyl-1-(phenylsulfonyl)-1H-pyrrolo[2,3-b]pyridin-5-amine for 3-iodo-1-(phenylsulfonyl)-1H-pyrrolo[2,3-b]pyridin-5-amine. The material was used directly in the next step.

Step E: 2,6-Difluoro-N-(3-methyl-1-(phenylsulfonyl)-1H-pyrrolo[2,3-b]pyridin-5-yl)-3-(propylsulfonamido)benzamide (0.654 g, 1.19 mmol) was dissolved in MeOH (9 mL) and water (3 mL). K$_2$CO$_3$ (3.295 g, 23.84 mmol) was added, and the reaction mixture was stirred at reflux overnight. The solution was partitioned between water and EtOAc. The organic layer was washed with water (3×), brine, dried over Na$_2$SO$_4$ and concentrated to a solid. The solid was triturated with DCM to provide 2,6-difluoro-N-(2-methyl-1H-pyrrolo[2,3-b]pyridin-5-yl)-3-(propylsulfonamido)benzamide as a solid (148 mg, 30% for three steps). $^1$H NMR (400 MHz, DMSO-d$_6$) δ 11.31 (br s, 1H), 10.85 (s, 1H), 9.79 (br s, 1H), 8.31 (br s, 2H), 7.51-7.57 (m, 1H), 7.24-7.29 (m, 2H), 3.11-3.15 (m, 2H), 2.26 (br s, 3H), 1.75-1.80 (m, 2H), 0.98-1.02 (m, 3H); m/z (APCI-neg) M−1=407.2.

Example 109

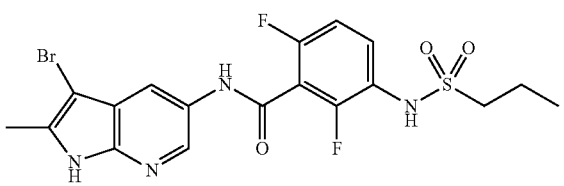

N-(3-bromo-2-methyl-1H-pyrrolo[2,3-b]pyridin-5-yl)-2,6-difluoro-3-(propylsulfonamido)benzamide N-(3-Bromo-2-methyl-1H-pyrrolo[2,3-b]pyridin-5-yl)-2,6-difluoro-3-(propylsulfonamido)benzamide (36%) was prepared according to the general procedure for Example 2, substituting 2,6-difluoro-N-(2-methyl-1H-pyrrolo[2,3-b]pyridin-5-yl)-3-(propylsulfonamido)benzamide for 2,6-difluoro-3-(propylsulfonamido)-N-(1H-pyrrolo[2,3-b]pyridin-5-yl)benzamide. $^1$H NMR (400 MHz, DMSO-d$_6$) δ 12.03 (s, 1H), 10.97 (s, 1H), 9.80 (br s, 1H), 8.31 (br s, 1H), 8.21 (br s, 1H), 7.52-7.58 (m, 1H), 7.25-7.29 (m, 1H), 3.11-3.15 (m, 2H), 2.40 (s, 3H), 1.74-1.80 (m, 2H), 0.98-1.02 (m, 3H); m/z (APCI-neg) M−1=487.1, 487.9.

Example 110

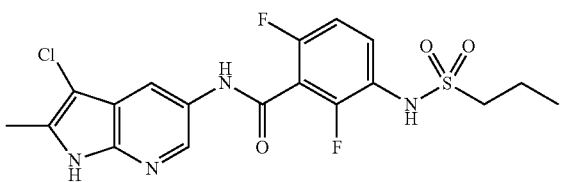

N-(3-chloro-2-methyl-1H-pyrrolo[2,3-b]pyridin-5-yl)-2,6-difluoro-3-(propylsulfonamido)benzamide N-(3-Chloro-2-methyl-1H-pyrrolo[2,3-b]pyridin-5-yl)-2,6-difluoro-3-(propylsulfonamido)benzamide (55%) was prepared according to the general procedure for Example 3, substituting 2,6-difluoro-N-(2-methyl-1H-pyrrolo[2,3-b]pyridin-5-yl)-3-(propylsulfonamido)benzamide for 2,6-difluoro-3-(propylsulfonamido)-N-(1H-pyrrolo[2,3-b]pyridin-5-yl)benzamide. $^1$H NMR (400 MHz, DMSO-d$_6$) δ 11.93 (br s, 1H), 10.97 (s, 1H), 9.79 (br s, 1H), 8.32 (br s, 1H), 8.28 (br s, 1H), 7.52-7.58 (m, 1H), 7.25-7.29 (m, 1H), 3.10-3.14 (m, 2H), 2.40 (s, 3H), 1.74-1.80 (m, 2H), 0.98-1.01 (m, 3H); m/z (APCI-neg) M−1=441.2.

Example 111

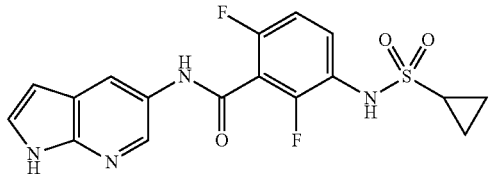

3-(cyclopropanesulfonamido)-2,6-difluoro-N-(1H-pyrrolo[2,3-b]pyridin-5-yl)benzamide Step A: 5-Amino-7-azaindole (820 mg, 6.2 mmol), 2,6-difluoro-3-nitrobenzoic acid (1200 mg, 6.2 mmol), EDCI (1200 mg, 6.2 mmol), and HOBt.H$_2$O (930 mg, 6.2 mmol) were combined in dry DMF (20 mL) and stirred at room temperature for 16 hours. The reaction mixture was then diluted with brine, extracted with EtOAc (2×), extracts washed with water (1×), dried over sodium sulfate and concentrated under reduced pressure. The resulting crude product was purified via silica gel chromatography using an ISCO system (5% MeOH/DCM) to provide 2,6-difluoro-5-nitro-(3H-imidazo[4,5-b]pyridin-6-yl)benzamide (1.76 g, 88%). m/z (LC-MS) M+1=319.

Step B: 2,6-Difluoro-5-nitro-(3H-imidazo[4,5-b]pyridin-6-yl)benzamide (805 mg, 2.5 mmol) in ethanol (20 mL) and water (6 mL), iron powder (565 mg, 10 mmol) and NH$_4$Cl (1350 mg, 25 mmol) were stirred at 80° C. for 4 hours. The mixture was cooled to room temperature and diluted with 20% MeOH in CH$_2$Cl$_2$. The mixture was then filtered through a celite pad, concentrated and used directly in the next step. m/z (LC-MS) M+1=289.

Step C: A 5 mL flask was charged with 5-amino-2,6-difluoro-(3H-imidazo[4,5-b]pyridin-6-yl)benzamide (30 mg, 0.1 mmol), cyclopropyl sulfonyl chloride (10 mg, 0.1 mmol) and diisopropylethylamine (40 μL) in CH$_2$Cl$_2$ (1 mL). This mixture was stirred at room temperature for 16 hours. The reaction mixture was then diluted with brine, extracted with EtOAc (2×), extracts washed with water (1×), dried over sodium sulfate and concentrated under reduced pressure. The resulting crude product was purified via silica gel chromatography using an ISCO system (10% MeOH/DCM) to give the title compound (14 mg, 30%). m/z (LC-MS) M+1=393.

Example 112

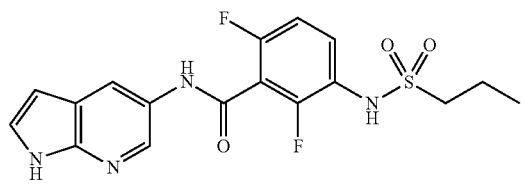

2,6-difluoro-3-(propylsulfonamido)-N-(1H-pyrrolo[2,3-b]pyridin-5-yl)benzamide

Step A: 2,6-Difluoro-3-(N-(propylsulfonyl)propylsulfonamido)-N-(1H-pyrrolo[2,3-b]pyridin-5-yl)benzamide was prepared according to the general procedure for Example 1, substituting 2,6-difluoro-3-(N-(propylsulfonyl)propylsulfonamido)benzoic acid for 2,6-difluoro-3-(propylsulfonamido)benzoic acid.

Step B: A 1M solution of NaOH (809 μL, 0.809 mmol) was added to a solution of 2,6-difluoro-3-(N-(propylsulfonyl)propylsulfonamido)-N-(1H-pyrrolo[2,3-b]pyridin-5-yl)benzamide (135 mg, 0.270 mmol) in 4:1 THF/MeOH (1.4 mL, 0.2M). The reaction mixture was stirred at room temperature for 30 minutes. The majority of the organic solvents were removed in vacuo. The resulting residue was acidified with 1N HCl (0.8 mL) and then partitioned between EtOAc (30 mL) and water (10 mL). The organic layer was washed with water (3×10 mL), brine (10 mL), dried (Na₂SO₄), filtered and concentrated. The resulting residue was triturated with minimal CH₂Cl₂, and the precipitate was filtered and rinsed with Et₂O to afford 2,6-difluoro-3-(propylsulfonamido)-N-(1H-pyrrolo[2,3-b]pyridin-5-yl)benzamide as a solid (48 mg, 45% yield for 2 steps).

Example 113

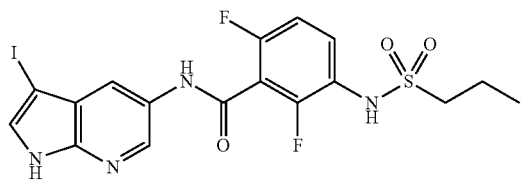

2,6-difluoro-N-(3-iodo-1H-pyrrolo[2,3-b]pyridin-5-yl)-3-(propylsulfonamido)benzamide Step A: Trimethylaluminum (0.51 mL, 1.01 mmol, 2.0M solution in toluene) was added dropwise via a syringe to a cold (0° C.) suspension of 2-iodo-1-(phenylsulfonyl)-1H-pyrrolo[2,3-b]pyridin-5-amine (0.135 g, 0.338 mmol) in toluene (10 mL). The cold bath was removed and the mixture was stirred at room temperature for 20 minutes. Methyl 2,6-difluoro-3-(N-(propylsulfonyl)propylsulfonamido)benzoate (0.149 g, 0.372 mmol) was added, and the reaction mixture was heated to 90° C. under N₂ for 2 hours. The reaction mixture was cooled to room temperature and diluted with ethyl acetate (50 mL) 30% Aqueous potassium sodium tartrate solution (50 mL) was carefully added, and the resulting emulsion was stirred at room temperature for 30 minutes. The aqueous layer was extracted with ethyl acetate (2×50 mL). The combined organic layers were dried, filtered and concentrated. The crude product was purified by column chromatography, eluting with hexanes/ethyl acetate (4:1), hexanes/ethyl acetate (2:1) to give 2,6-difluoro-N-(2-iodo-1-(phenylsulfonyl)-1H-pyrrolo[2,3-b]pyridin-5-yl)-3-(N-(propylsulfonyl)propylsulfonamido)benzamide (0.225 g, 87%) as a foam.

Step B: K₂CO₃ (0.406 g, 2.94 mmol) was added to a solution of 2,6-difluoro-N-(2-iodo-1-(phenylsulfonyl)-1H-pyrrolo[2,3-b]pyridin-5-yl)-3-(N-(propylsulfonyl)propylsulfonamido)benzamide (0.225 g, 0.294 mmol) in MeOH/H₂O (4:1, 10 mL), and the reaction mixture was heated to 60° C. for 1 hour. The reaction mixture was cooled to room temperature and concentrated. The resulting residue was taken up in ethyl acetate (100 mL) and washed with water (50 mL). The crude product was purified by column chromatography, eluting with hexanes/ethyl acetate (2:1), hexanes/ethyl acetate (1:1) to give 2,6-difluoro-N-(2-iodo-1-(phenylsulfonyl)-1H-pyrrolo[2,3-b]pyridin-5-yl)-3-(N-(propylsulfonyl)propylsulfonamido)benzamide (0.120 g, 79%) as a solid. ¹H NMR (400 MHz, CD₃OD) δ 8.3 (br s, 2H), 7.6 (m, 1H), 7.1 (m, 1H), 6.7 (s, 1H), 3.1 (m, 2H), 1.9 (m, 2H), 1.0 (t, J=7.4 Hz, 3H); m/z (APCI-nega) M−1=519.1.

Example 114

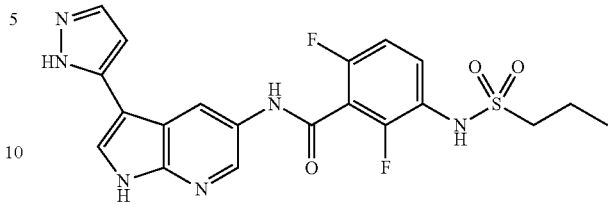

N-(3-(1H-pyrazol-5-yl)-1H-pyrrolo[2,3-b]pyridin-5-yl)-2,6-difluoro-3-(propylsulfonamido)benzamide Step A: TEA (0.0163 mL, 0.117 mmol) and propane-1-sulfonyl chloride (0.00882 mL, 0.0779 mmol) were added to N-(3-acetyl-1H-pyrrolo[2,3-b]pyridin-5-yl)-2,6-difluoro-3-(propylsulfonamido)benzamide (0.195 mL, 0.0390 mmol) in DCM (0.4 mL). The solution was stirred at room temperature for 16 hours before concentration under reduced pressure. The resulting residue was purified via column chromatography (2% MeOH/DCM) to afford impure N-(3-acetyl-1-(propylsulfonyl)-1H-pyrrolo[2,3-b]pyridin-5-yl)-2,6-difluoro-3-(N-(propylsulfonyl)propylsulfonamido)benzamide (0.020 g, 0.0308 mmol, 79.1% yield).

Step B: 1-tert-butoxy-N,N,N',N'-tetramethylmethanediamine (0.0132 mL, 0.0607 mmol) was added to N-(3-acetyl-1-(propylsulfonyl)-1H-pyrrolo[2,3-b]pyridin-5-yl)-2,6-difluoro-3-(N-(propylsulfonyl)propylsulfonamido)benzamide (0.0197 g, 0.0304 mmol) in THF (0.3 mL). The solution was stirred at reflux for 4 hours, cooled to room temperature and concentrated under reduced pressure. The resulting residue was taken up in EtOH (0.3 mL), and hydrazine (0.00973 g, 0.304 mmol) was added. The solution was stirred at reflux for 8 hours. The solution was then cooled to room temperature and concentrated under reduced pressure. The resulting residue was purified by column chromatography (5% to 10% MeOH/DCM), then purified again with reversed phase (C-18) chromatography using gradient elution with 1% to 50% CH₃CN/water to afford N-(3-(1H-pyrazol-3-yl)-1H-pyrrolo[2,3-b]pyridin-5-yl)-2,6-difluoro-3-(propylsulfonamido)benzamide (0.002 g, 0.0043 mmol, 14.3% yield). ¹H NMR (400 MHz, CD₃OD) δ 8.71-8.75 (m, 1H), 8.49-8.51 (m, 1H), 7.78 (s, 1H), 7.66-7.70 (m, 1H), 7.50-7.58 (m, 1H), 6.93-6.99 (m, 1H), 6.12-6.14 (m, 1H), 2.96-3.02 (m, 2H), 1.80-1.89 (m, 2H), 1.00-1.05 (m, 3H); m/z (APCI-pos) M+1=461.1.

Example 115

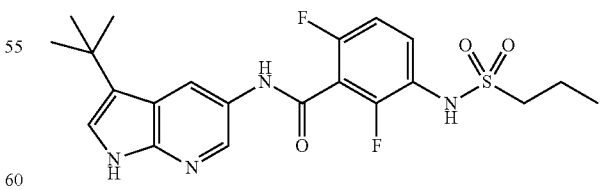

N-(3-tert-butyl-1H-pyrrolo[2,3-h]pyridin-5-yl)-2,6-difluoro-3-(propylsulfonamido)benzamide Step A: 5-Nitro-1H-pyrrolo[2,3-b]pyridine (150 mg, 0.92 mmol) was taken up in dry dichloromethane (9 mL) and was chilled to 0° C. Aluminum chloride (613 mg, 4.60 mmol, 5 eq.) was then added, and the mixture was allowed to stir at 0° C. for 15 minutes. 2-Methyl-2-bromopropane (107 μL, 0.919 mmol) was then added, and the mixture was allowed to gradually warm to room temperature over a 16 hour period. The mixture was then poured into cold saturated bicarbonate solution and extracted with dichloromethane (2×). The extracts were dried over sodium sulfate and concentrated. Prep plate purification (2×1.0 mm plates, 3:1 hexane:ethyl acetate) afforded 3-tert-butyl-5-nitro-1H-pyrrolo[2,3-b]pyridine (8.3 mg, 4%) as a solid. $^1$H NMR (400 MHz, DMSO-d$_6$) δ 12.25 (br s, 1H), 9.07-9.09 (m, 1H), 8.84-8.86 (m, 1H), 7.48 (s, 1H), 1.42 (s, 9H); m/z (APCI-neg) M−1=218.3.

Step B: 3-tert-Butyl-5-nitro-1H-pyrrolo[2,3-b]pyridine (8.3 mg, 0.038 mmol) was taken up in methanol (0.5 mL), and tin (II) chloride dehydrate was then added. The mixture was warmed to 70° C. for 16 hours, diluted with ethyl acetate, washed with aqueous saturated bicarbonate solution, dried over sodium sulfate and concentrated to 3-tert-butyl-1H-pyrrolo[2,3-b]pyridin-5-amine (8 mg, 100%). m/z (APCI-pos) M+1=190.2.

Step C: N-(3-tert-Butyl-1H-pyrrolo[2,3-b]pyridin-5-yl)-2,6-difluoro-3-(propylsulfonamido)benzamide (23%) was prepared according to the general procedure for Example 1, substituting 3-tert-butyl-1H-pyrrolo[2,3-b]pyridin-5-amine for 1H-pyrrolo[2,3-b]pyridin-5-amine. $^1$H NMR (400 MHz, DMSO-d$_6$) δ 11.34 (s, 1H), 10.82 (s, 1H), 9.78 (br s, 1H), 8.51-8.53 (m, 1H), 8.38-8.40 (m, 2H), 7.50-7.57 (m, 1H), 7.21-7.27 (m, 1H), 7.17-7.19 (m, 1H), 3.06-3.14 (m, 2H), 1.72-1.80 (m, 2H), 1.39 (s, 9H), 0.96-1.03 (m, 3H); m/z (APCI-neg) M−1=449.2, (APCI-pos) M+1=451.1.

Example 116

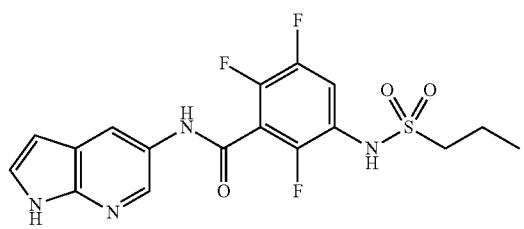

2,3,6-trifluoro-5-(propylsulfonamido)-N-(1H-pyrrolo[2,3-b]pyridin-5-yl)benzamide Step A: 2,6-Difluoro-3-(N-(propylsulfonyl)propylsulfonamido)-N-(1H-pyrrolo[2,3-b]pyridin-5-yl)benzamide was prepared according to the general procedure for Example 1, substituting 2,3,6-trifluoro-5-(N-(propylsulfonyl)propylsulfonamido)benzoic acid for 2,6-difluoro-3-(propylsulfonamido)benzoic acid.

Step B: 2,3,6-Trifluoro-5-(propylsulfonamido)-N-(1H-pyrrolo[2,3-b]pyridin-5-yl)benzamide (47%, 2 steps) was prepared according to the general procedure of Example 112, Step B, substituting 2,3,6-trifluoro-5-(N-(propylsulfonyl)propylsulfonamido)-N-(1H-pyrrolo[2,3-b]pyridin-5-yl)benzamide for 2,6-difluoro-3-(N-(propylsulfonyl)propylsulfonamido)-N-(1H-pyrrolo[2,3-b]pyridin-5-yl)benzamide. $^1$H NMR (400 MHz, DMSO-d$_6$) δ 11.68 (br s, 1H), 10.95 (s, 1H), 10.07 (br s, 1H), 8.35-8.36 (m, 2H), 7.62-7.68 (m, 1H), 7.50-7.51 (m, 1H), 6.47-6.49 (m, 1H), 3.19-3.23 (m, 2H), 1.72-1.79 (m, 2H), 0.98-1.02 (m, 3H); m/z (APCI-pos) M+1=413.1.

Example 117

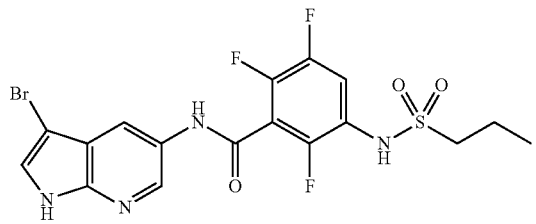

N-(3-bromo-1H-pyrrolo[2,3-b]pyridin-5-yl)-2,3,6-trifluoro-5-(propylsulfonamido)benzamide N-(3-Bromo-1H-pyrrolo[2,3-b]pyridin-5-yl)-2,3,6-trifluoro-5-(propylsulfonamido)benzamide (64%) was prepared according to the general procedure of Example 2, substituting 2,3,6-trifluoro-5-(propylsulfonamido)-N-(1H-pyrrolo[2,3-b]pyridin-5-yl)benzamide for 2,6-difluoro-3-(propylsulfonamido)-N-(1H-pyrrolo[2,3-b]pyridin-5-yl)benzamide. $^1$H NMR (400 MHz, DMSO-d$_6$) δ 12.15 (br s, 1H), 11.13 (s, 1H), 10.08 (br s, 1H), 8.40 (br s, 1H), 8.34 (br s, 1H), 7.76 (br s, 1H), 7.63-7.70 (m, 1H), 3.18-3.22 (m, 2H), 1.74-1.79 (m, 2H), 0.98-1.02 (m, 3H); m/z (APCI-pos) M+1=491.1, 493.0.

Example 118

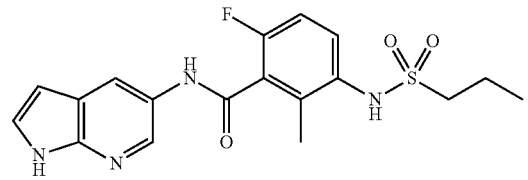

6-fluoro-2-methyl-3-(propylsulfonamido)-N-(1H-pyrrolo[2,3-b]pyridin-5-yl)benzamide Step A: 6-Fluoro-2-methyl-3-(N-(propylsulfonyl)propylsulfonamido)-N-(1H-pyrrolo[2,3-b]pyridin-5-yl)benzamide was prepared according to the general procedure for Example 1, substituting 6-fluoro-2-methyl-3-(N-(propylsulfonyl)propylsulfonamido)benzoic acid for 2,6-difluoro-3-(propylsulfonamido)benzoic acid.

Step B: 6-Fluoro-2-methyl-3-(propylsulfonamido)-N-(1H-pyrrolo[2,3-b]pyridin-5-yl)benzamide (47%, 2 steps) was prepared according to the general procedure of Example 112, Step B, substituting 6-fluoro-2-methyl-3-(N-(propylsulfonyl)propylsulfonamido)-N-(1H-pyrrolo[2,3-b]pyridin-5-yl)benzamide for 2,6-difluoro-3-(N-(propylsulfonyl)propylsulfonamido)-N-(1H-pyrrolo[2,3-b]pyridin-5-yl)benzamide. $^1$H NMR (400 MHz, DMSO-d$_6$) δ 11.62 (br s, 1H), 10.65 (s, 1H), 8.38 (br s, 1H), 8.37 (br s, 1H), 7.36-7.40

(m, 1H), 7.17-7.22 (m, 1H), 6.46 (br s, 1H), 3.06-3.10 (m, 2H), 2.33 (s, 3H), 1.74-1.80 (m, 2H), 0.99-1.03 (m, 3H); m/z (APCI-pos) M+1=391.1.

Example 119

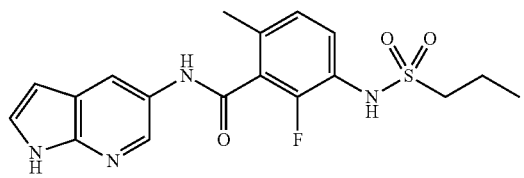

2-fluoro-6-methyl-3-(propylsulfonamido)-N-(1H-pyrrolo[2,3-b]pyridin-5-yl)benzamide Step A: 2-Fluoro-6-methyl-3-(N-(propylsulfonyl)propylsulfonamido)-N-(1H-pyrrolo[2,3-b]pyridin-5-yl)benzamide was prepared according to the general procedure for Example 1, substituting 2-fluoro-6-methyl-3-(N-(propylsulfonyl)propylsulfonamido)benzoic acid for 2,6-difluoro-3-(propylsulfonamido)benzoic acid.

Step B: 2-Fluoro-6-methyl-3-(propylsulfonamido)-N-(1H-pyrrolo[2,3-b]pyridin-5-yl)benzamide (21%, 2 steps) was prepared according to the general procedure of Example 112, Step B, substituting 2-fluoro-6-methyl-3-(N-(propylsulfonyl)propylsulfonamido)-N-(1H-pyrrolo[2,3-b]pyridin-5-yl)benzamide for 2,6-difluoro-3-(N-(propylsulfonyl)propylsulfonamido)-N-(1H-pyrrolo[2,3-b]pyridin-5-yl)benzamide. $^1$H NMR (400 MHz, CD$_3$OD) δ 8.34 (br s, 2H), 7.48-7.52 (m, 1H), 7.42-7.43 (m, 1H), 7.11-7.13 (m, 1H), 6.51-6.52 (m, 1H), 3.08-3.12 (m, 2H), 2.42 (s, 3H), 1.82-1.91 (m, 2H), 1.03-1.07 (m, 3H); m/z (APCI-pos) M+1=391.1.

Example 120

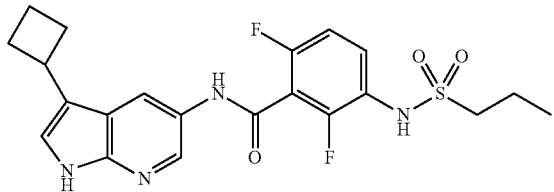

N-(3-cyclobutyl-1H-pyrrolo[2,3-b]pyridin-5-yl)-2,6-difluoro-3-(propylsulfonamido)benzamide Step A: 3-Bromo-1H-pyrrolo[2,3-b]pyridine (7.5 g, 38.07 mmol) was dissolved in dry DMF (190 mL) and chilled to 0° C. Sodium hydride (60% dispersion in mineral oil, 2.13 g, 53.29 mmol) was then added, and the mixture stirred at 0° C. for 30 minutes. Benzenesulfonyl chloride (7.41 g, 41.87 mmol) was then added via syringe and the mixture stirred at 0° C. for 30 minutes. Another lot of benzenesulfonyl chloride (0.5 mL) was then added to consume the starting material. The reaction mixture was then carefully quenched with saturated ammonium chloride, followed by water (200 mL) to precipitate the product. The solids were collected by filtration and dried under vacuum to give 3-bromo-1-(phenylsulfonyl)-1H-pyrrolo[2,3-b]pyridine (11.2 g, 87%) as a solid. $^1$H NMR (400 MHz, CDCl$_3$) δ 8.46-8.49 (m, 1H), 8.19-8.23 (m, 2H), 7.79-7.84 (m, 2H), 7.57-7.62 (m, 1H), 7.47-7.53 (m, 2H), 7.25-7.29 (m, 1H).

Step B: A round bottom flask under a nitrogen atmosphere was charged with magnesium turnings (155 mg, 6.38 mmol) and dry ether (5 mL). Bromocyclobutane (340 mg, 2.52 mmol) was added, followed by 1,2-dibromoethane (50 μL) and refluxing was observed after a few minutes of stirring. This mixture was then warmed back to reflux for 5 hours and then allowed to cool to room temperature. The Grignard reagent was then added to a THF solution (5 mL) of 3-bromo-1-(phenylsulfonyl)-1H-pyrrolo[2,3-b]pyridine (250 mg, 0.74 mmol) and NiCl$_2$(dppf) (10 mg, 0.015 mmol). The mixture was heated at reflux for 16 hours and then allowed to cool to room temperature. The reaction mixture was quenched with saturated ammonium chloride solution and extracted with EtOAc (2×). The extracts were dried over sodium sulfate and concentrated. Flash 40 Biotage (40M cartridge, 3:1 hexane: EtOAc) afforded 3-cyclobutyl-1-(phenylsulfonyl)-1H-pyrrolo[2,3-b]pyridine (45 mg, 19%). m/z (APCI-pos) M+1=313.1.

Step C: Tetrabutylammonium nitrate (88 mg, 0.29 mmol) was dissolved in dichloromethane (0.5 mL) and cooled to 0° C. Trifluoroacetic anhydride (60 μL, 0.288 mmol) was then added, and the mixture was stirred for 30 minutes. This was added to a precooled solution of 3-cyclobutyl-1-(phenylsulfonyl)-1H-pyrrolo[2,3-b]pyridine (45 mg, 0.144 mmol) in dichloromethane (4 mL). This mixture was stirred at 0° C. for 1 hour and then allowed to warm to room temperature and stirred overnight. The mixture was then diluted with DCM, washed with saturated sodium bicarbonate solution, dried over sodium sulfate and concentrated. Sep Pak Purification (10 g cartridge, 3:1 hexane:ethyl acetate) afforded 3-cyclobutyl-5-nitro-1-(phenylsulfonyl)-1H-pyrrolo[2,3-b]pyridine (25 mg, 49%) as a solid. $^1$H NMR (400 MHz, DMSO-d$_6$) δ 9.19-9.21 (m, 1H), 8.79-8.81 (m, 1H), 8.15-8.20 (m, 2H), 7.99 (s, 1H), 7.63-7.78 (m, 3H), 3.71-3.82 (m, 1H), 2.35-2.45 (m, 2H), 2.15-2.27 (m, 2H), 2.00-2.09 (m, 1H), 1.88-1.96 (m, 1H).

Step D: Tin (II) chloride dehydrate (79 mg, 0.35 mmol) was added to a solution of 3-cyclobutyl-5-nitro-1-(phenylsulfonyl)-1H-pyrrolo[2,3-b]pyridine (25 mg, 0.07 mmol) in methanol (1 mL). This mixture was heated to 70° C. for 16 hours and then allowed to cool to room temperature. This mixture was then diluted with EtOAc, washed with saturated sodium bicarbonate solution (1×), dried over sodium sulfate and concentrated to 3-cyclobutyl-1-(phenylsulfonyl)-1H-pyrrolo[2,3-b]pyridin-5-amine (21 mg, 92%). m/z (APCI-pos) M+1=328.1.

Step E: N-(3-Cyclobutyl-1-(phenylsulfonyl)-1H-pyrrolo[2,3-b]pyridin-5-yl)-2,6-difluoro-3-(propylsulfonamido) benzamide was prepared according to the general procedure in Example 1, substituting 3-cyclobutyl-1-(phenylsulfonyl)-1H-pyrrolo[2,3-b]pyridin-5-amine for 1H-pyrrolo[2,3-b]pyridin-5-amine.

Step F: N-(3-Cyclobutyl-1-(phenylsulfonyl)-1H-pyrrolo[2,3-b]pyridin-5-yl)-2,6-difluoro-3-(propylsulfonamido) benzamide was dissolved in methanol (1 mL), and aqueous 2M potassium carbonate (1 mL) was added. The mixture was warmed to 60° C. for 1 hour. The mixture was then diluted with EtOAc, washed with 10% aqueous citric acid (1×), water (1×), dried over sodium sulfate and concentrated. Prep TLC (2×0.5 mm plates, 7% MeOH/DCM as the eluant) afforded N-(3-cyclobutyl-1H-pyrrolo[2,3-b]pyridin-5-yl)-2,6-difluoro-3-(propylsulfonamido)benzamide (15%). $^1$H NMR (400 MHz, DMSO-d$_6$) δ 11.37 (br s, 1H), 10.82 (br s, 1H), 9.78 (br s, 1H), 8.31-8.38 (m, 2H), 7.49-7.58 (m, 1H), 7.20-7.34 (m, 2H), 3.62-3.71 (m, 1H), 3.07-3.14 (m, 2H), 2.30-2.41 (m, 2H), 2.14-2.22 (m, 2H), 1.97-2.08 (m, 1H), 1.85-1.94 (m, 1H), 1.71-1.81 (m, 2H), 0.96-1.02 (m, 3H); m/z (APCI-pos) M+1=449.1.

Example 121

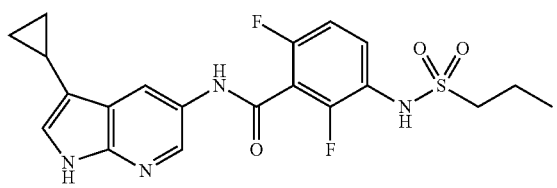

N-3-cyclopropyl-1H-pyrrolo[2,3-b]pyridin-5-yl)-2,6-difluoro-3-(propylsulfonamido)benzamide Step A: 3-Cyclopropyl-1-(phenylsulfonyl)-1H-pyrrolo[2,3-b]pyridine (19%) was prepared according to general procedure in Example 120, Step B, using cyclopropylmagnesium bromide (0.5M solution in THF) in place of the cyclobutylmagnesium bromide. $^1$H NMR (400 MHz, CDCl$_3$) δ 8.40-8.43 (m, 1H), 8.14-8.18 (m, 2H), 7.89-7.93 (m, 1H), 7.52-7.58 (m, 1H), 7.43-7.49 (m, 2H), 7.37 (s, 1H), 7.15-7.20 (m, 1H), 1.79-1.88 (m, 1H), 0.90-0.96 (m, 2H), 0.65-0.71 (m, 2H); m/z (APCI-pos) M+1=299.1.

Step B: 3-Cyclopropyl-5-nitro-1-(phenylsulfonyl)-1H-pyrrolo[2,3-b]pyridine (42%) was prepared according to the general procedure in Example 120, Step C, substituting 3-cyclopropyl-1-(phenylsulfonyl)-1H-pyrrolo[2,3-b]pyridine for 3-cyclobutyl-1-(phenylsulfonyl)-1H-pyrrolo[2,3-b]pyridine. $^1$H NMR (400 MHz, DMSO-d$_6$) δ 9.19-9.21 (m, 1H), 8.92-8.94 (m, 1H), 8.11-8.14 (m, 2H), 7.86 (s, 1H), 7.72-7.77 (m, 1H), 7.62-7.67 (m, 2H), 2.09-2.17 (m, 1H), 0.93-0.99 (m, 2H), 0.80-0.85 (m, 2H).

Step C: 3-Cyclopropyl-1-(phenylsulfonyl)-1H-pyrrolo[2,3-b]pyridin-5-amine (100%) was prepared according to Example 120, Step D, substituting 3-cyclopropyl-5-nitro-1-(phenylsulfonyl)-1H-pyrrolo[2,3-b]pyridine for 3-cyclobutyl-5-nitro-1-(phenylsulfonyl)-1H-pyrrolo[2,3-b]pyridine. m/z (APCI-pos) M+1=314.0.

Step D: N-(3-Cyclopropyl-1H-pyrrolo[2,3-b]pyridin-5-yl)-2,6-difluoro-3-(propylsulfonamido)benzamide (19%) was prepared according to Example 120, Step E, substituting 3-cyclopropyl-1-(phenylsulfonyl)-1H-pyrrolo[2,3-b]pyridin-5-amine for 3-cyclobutyl-1-(phenylsulfonyl)-1H-pyrrolo[2,3-b]pyridin-5-amine. $^1$H NMR (400 MHz, DMSO-d$_6$) δ11.34 (s, 1H), 10.85 (s, 1H), 9.80 (br s, 1H), 8.40-8.43 (m, 1H), 7.50-7.58 (m, 1H), 7.19-7.20 (m, 2H), 3.07-3.16 (m, 2H), 1.87-1.96 (m, 1H), 1.72-1.82 (m, 2H), 0.96-1.03 (m, 2H), 0.81-0.89 (m, 2H), 0.60-0.65 (m, 2H); m/z (APCI-pos) M+1=435.1, m/z (APCI-neg) M+1=433.3.

Example 122

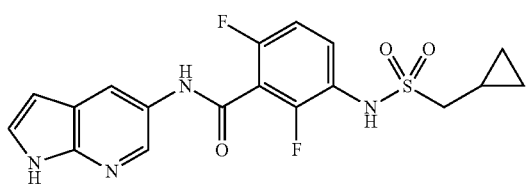

3-(cyclopropylmethylsulfonamido)-2,6-difluoro-N-(1H-pyrrolo[2,3-b]pyridin-5-yl)benzamide 3-(Cyclopropylmethylsulfonamido)-2,6-difluoro-N-(1H-pyrrolo[2,3-b]pyridin-5-yl)benzamide was prepared according to Example 1 substituting 3-(cyclopropylmethylsulfonamido)-2,6-difluorobenzoic acid for 2,6-difluoro-3-(propylsulfonamido)benzoic acid. $^1$H NMR (400 MHz, d$_6$-DMSO) δ 11.65 (s, 1H), 10.84 (s, 1H), 9.82 (s, 1H), 8.38-8.34 (m, 2H), 7.60-7.53 (m, 1H), 7.51-7.48 (m, 1H), 7.28-7.22 (m, 1H), 6.49-6.46 (m, 1H), 3.13 (d, J=7.0 Hz, 2H), 1.12-1.03 (m, 1H), 0.62-0.56 (m, 2H), 0.39-0.34 (m, 2H); m/z (APCI-pos) M+1=407.1.

Example 123

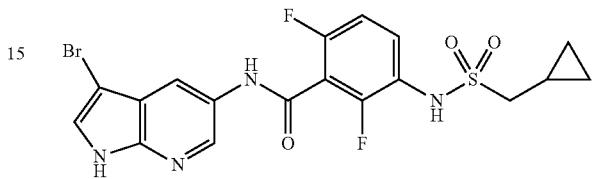

N-(3-bromo-1H-pyrrolo[2,3-b]pyridin-5-yl)-3-(cyclopropylmethylsulfonamido)-2,6-difluorobenzamide N-(3-Bromo-1H-pyrrolo[2,3-b]pyridin-5-yl)-3-(cyclopropylmethylsulfonamido)-2,6-difluorobenzamide was prepared according to Example 2 substituting 3-(cyclopropylmethylsulfonamido)-2,6-difluoro-N-(1H-pyrrolo[2,3-b]pyridin-5-yl)benzamide for 2,6-difluoro-3-(propylsulfonamido)-N-(1H-pyrrolo[2,3-b]pyridin-5-yl)benzamide. $^1$H NMR (400 MHz, d$_6$-DMSO) δ 12.12 (s, 1H), 11.03 (s, 1H), 9.83 (s, 1H), 8.42-8.40 (m, 1H), 8.36-8.34 (m, 1H), 7.77-7.75 (m, 1H), 7.62-7.55 (m, 1H), 7.29-7.23 (m, 1H), 3.13 (d, J=7.1 Hz, 2H), 1.13-1.04 (m, 1H), 0.62-0.56 (m, 2H), 0.39-0.34 (m, 2H); m/z (APCI-pos) M+1=487.0.

Example 124

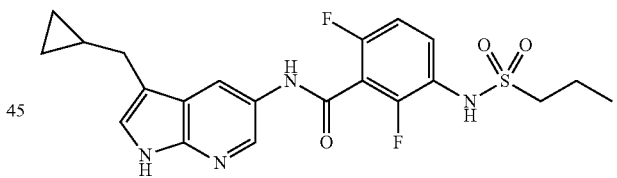

N-(3-(cyclopropylmethyl)-1H-pyrrolo[2,3-b]pyridin-5-yl)-2,6-difluoro-3-(propylsulfonamido)benzamide Step A: 1-(Phenylsulfonyl)-1H-pyrrolo[2,3-b]pyridine-3-carbaldehyde (82%) was prepared according Example 32, Step A, substituting 1H-pyrrolo[2,3-b]pyridine-3-carbaldehyde for 3-iodo-1H-pyrrolo[2,3-b]pyridine. $^1$H NMR (400 MHz, CDCl$_3$) δ 10.06 (s, 1H), 8.50-8.54 (m, 2H), 8.40 (s, 1H), 8.27-8.31 (m, 2H), 7.62-7.68 (m, 1H), 7.52-7.58 (m, 2H), 7.31-7.35 (m, 1H).

Step B: 1-(Phenylsulfonyl)-1H-pyrrolo[2,3-b]pyridine-3-carbaldehyde (0.25 g, 0.87 mmol) was dissolved in dry THF (9 mL) and chilled to 0° C. Cyclopropylmagnesium chloride (2.6 mL of a 0.5M solution in THF, 1.5 eq.) was then added by syringe to the cold reaction mixture and stirred at 0° C. for 30 minutes. The mixture was then quenched with saturated ammonium chloride solution, extracted with EtOAc, extracts dried over sodium sulfate and concentrated to provide cyclopropyl(1-(phenylsulfonyl)-1H-pyrrolo[2,3-b]pyridin-3-yl)methanol (0.285 g, 98%). m/z (APCI-pos) M+1=329.1.

Step C: Cyclopropyl(1-(phenylsulfonyl)-1H-pyrrolo[2,3-b]pyridin-3-yl)methanol (0.285 g, 0.87 mmol) was dissolved in dry dichloromethane (9 mL) and chilled to 0° C. Triethylsilane (1.11 mL, 6.94 mmol, 8 eq.) and TFA (0.201 mL, 2.60 mmol, 3 eq.) were then added. The reaction mixture was stirred at 0° C. for 15 minutes and then allowed to warm to room temperature. After about 1.5 hours, the mixture was quenched with saturated sodium bicarbonate solution and extracted with DCM. The extracts were dried over sodium sulfate and concentrated. Flash 40 Biotage (40M cartridge, DCM to 5% EtOAc/DCM) afforded 3-(cyclopropylmethyl)-1-(phenylsulfonyl)-1H-pyrrolo[2,3-b]pyridine (159 mg, 59%). m/z (APCI-pos) M+1=313.1.

Step D: 3-(Cyclopropylmethyl)-5-nitro-1-(phenylsulfonyl)-1H-pyrrolo[2,3-b]pyridine (41%) was prepared according to Example 32, Step B, substituting 3-(cyclopropylmethyl)-1-(phenylsulfonyl)-1H-pyrrolo[2,3-b]pyridine for 3-iodo-1-(phenylsulfonyl)-1H-pyrrolo[2,3-b]pyridine. $^1$H NMR (400 MHz, CDCl$_3$) δ 9.26-9.28 (m, 1H), 8.64-8.68 (m, 1H), 8.20-8.25 (m, 2H), 7.79 (s, 1H), 7.51-7.65 (m, 3H), 2.61-2.66 (m, 2H), 1.02-1.10 (m, 1H), 0.62-0.69 (m, 2H), 0.23-0.29 (m, 2H).

Step E: 3-(Cyclopropylmethyl)-1-(phenylsulfonyl)-1H-pyrrolo[2,3-b]pyridin-5-amine (89%) was prepared according to Example 32, Step C, substituting 3-(cyclopropylmethyl)-5-nitro-1-(phenylsulfonyl)-1H-pyrrolo[2,3-b]pyridine for 3-iodo-5-nitro-1-(phenylsulfonyl)-1H-pyrrolo[2,3-b]pyridine. m/z (APCI-pos) M+1=328.1.

Step F: N-(3-(Cyclopropylmethyl)-1-(phenylsulfonyl)-1H-pyrrolo[2,3-b]pyridin-5-yl)-2,6-difluoro-3-(propylsulfonamido)benzamide was prepared according to Example 31, Step D, substituting 3-(cyclopropylmethyl)-1-(phenylsulfonyl)-1H-pyrrolo[2,3-b]pyridin-5-amine for 3-iodo-1-(phenylsulfonyl)-1H-pyrrolo[2,3-b]pyridin-5-amine. m/z (APCI-pos) M+1=589.1. This material was then dissolved in methanol (1 mL), and 2M aqueous potassium carbonate (1 mL) was added. The mixture was warmed to 60° C. for one hour. The mixture was then diluted with water and extracted with EtOAc. The extracts were dried over sodium sulfate and concentrated. Preparative TLC (2×0.5 mm plates, 7% MeOH/DCM) afforded N-(3-(cyclopropylmethyl)-1H-pyrrolo[2,3-b]pyridin-5-yl)-2,6-difluoro-3-(propylsulfonamido)benzamide (10 mg, 13%). $^1$H NMR (400 MHz, DMSO-d$_6$) δ1.34-11.38 (br s, 1H), 10.81-10.85 (br s, 1H), 9.75-9.82 (br s, 1H), 8.33-8.39 (m, 2H), 7.20-7.58 (m, 3H), 3.09-3.15 (m, 2H), 2.59-2.63 (m, 2H), 1.71-1.82 (m, 2H), 0.97-1.07 (m, 4H), 0.46-0.53 (m, 2H), 0.17-0.23 (m, 2H); (APCI-pos) M+1=449.1.

The following compounds in Table 5 were prepared following the above procedures.

TABLE 5

| Ex. # | Structure | Name | MS/NMR |
|---|---|---|---|
| 125 | 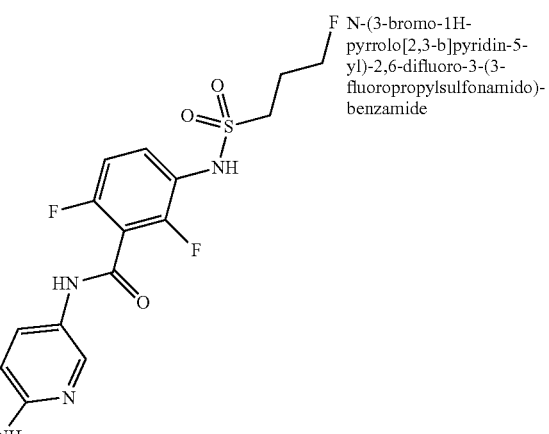 | N-(3-bromo-1H-pyrrolo[2,3-b]pyridin-5-yl)-2,6-difluoro-3-(3-fluoropropylsulfonamido)benzamide | $^1$H NMR (400 MHz, DMSO-d$_6$) ppm 12.14 (s, 1H), 11.06 (s, 1H), 9.96 (s, 1H), 8.40 (d, 1H), 8.35 (d, 1H), 7.76 (d, 1H), 7.59-7.55 (m, 1H), 7.31 (t, 1H), 4.61 (t, 1H), 4.52 (t, 1H) 3.27-3.24 (m, 2H), 2.19-2.08 (m, 2H); MH+ 493.0 |
| 126 | 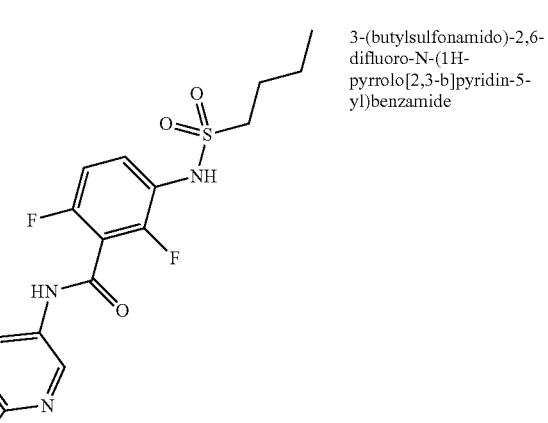 | 3-(butylsulfonamido)-2,6-difluoro-N-(1H-pyrrolo[2,3-b]pyridin-5-yl)benzamide | $^1$H NMR (400 MHz, DMSO-d$_6$) ppm 11.63 (s, 1H), 10.82 (s, 1H), 9.79 (br s, 1H), 8.37-8.34 (m, 2H), 7.56-7.50 (m, 1H), 7.49 (t, 1H), 7.25 (t, 1H), 6.48-6.46 (m, 1H), 3.15-3.11 (m, 2H), 1.73 (qn, 2H) 1.41 (sx, 2H), 0.89 (t, 3H); MH+ 409.2 |

TABLE 5-continued

| Ex. # | Structure | Name | MS/NMR |
|---|---|---|---|
| 127 | 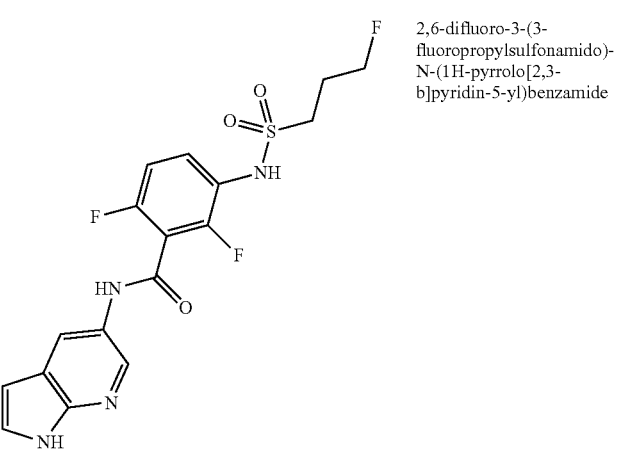 | 2,6-difluoro-3-(3-fluoropropylsulfonamido)-N-(1H-pyrrolo[2,3-b]pyridin-5-yl)benzamide | $^1$H NMR (400 MHz, DMSO-d$_6$) ppm 11.63 (s, 1H), 10.82 (s, 1H), 9.90 (br s, 1H), 8.37-8.34 (m, 2H), 7.57-7.51 (m, 1H), 7.48 (t, 1H), 7.25 (t, 1H), 6.48-6.46 (m, 1H), 4.62 (t, 1H), 4.50 (t, 1H) 3.25-3.22 (m, 2H), 2.19-2.09 (m, 2H); MH+ 413.1 |
| 128 | 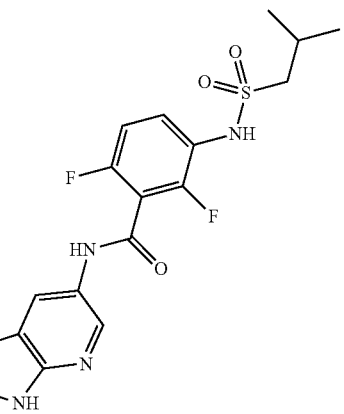 | 2,6-difluoro-3-(2-methylpropylsulfonamido)-N-(1H-pyrrolo[2,3-b]pyridin-5-yl)benzamide | $^1$H NMR (400 MHz, DMSO-d$_6$) ppm 11.63 (s, 1H), 10.83 (s, 1H), 9.77 (s, 1H), 8.36 (dd, 2H), 7.54 (dt, 1H), 7.47 (t, 1H), 7.25 (m, 1H), 6.51-6.42 (m, 1H), 3.05 (d, 2H), 2.20 (m, 1H), 1.04 (d, 6H); MH+ 409.2 |
| 129 | 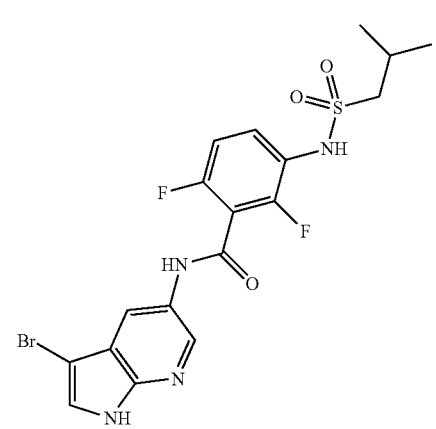 | N-(3-bromo-1H-pyrrolo[2,3-b]pyridin-5-yl)-2,6-difluoro-3-(2-methylpropylsulfonamido)-benzamide | $^1$H NMR (400 MHz, DMSO-d$_6$) ppm 12.1 (d, 1H), 11.17 (d, 1H), 9.80 (d, 1H), 8.41-8.34 (m, 2H), 7.85 (dd, 1H), 7.60-7.52 (m, 1H), 7.31-7.35 (m, 1H), 3.05 (d, 2H), 2.24-2.16 (m, 1H), 1.05 (d, 6H); MH+ 489.0 |

TABLE 5-continued

| Ex. # | Structure | Name | MS/NMR |
|---|---|---|---|
| 130 | 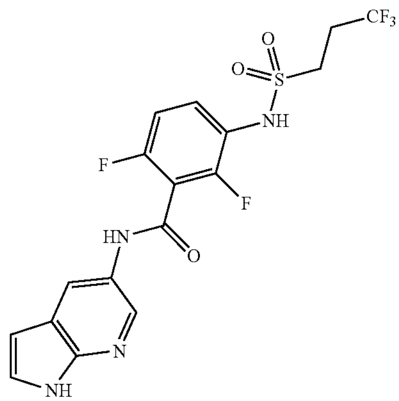 | 2,6-difluoro-N-(1H-pyrrolo[2,3-b]pyridin-5-yl)-3-(3,3,3-trifluoropropylsulfonamido)-benzamide | $^1$H NMR (400 MHz, DMSO-d$_6$) ppm 11.63 (s, 1H), 10.83 (s, 1H), 10.08 (s, 1H), 8.35 (dd, 2H), 7.57 (dt, 1H), 7.49 (t, 1H), 7.29 (m, 1H), 6.47 (dd, 1H), 3.43 (m, 2H), 2.81 (m, 2H); MH+ 449.1 |

Example 131

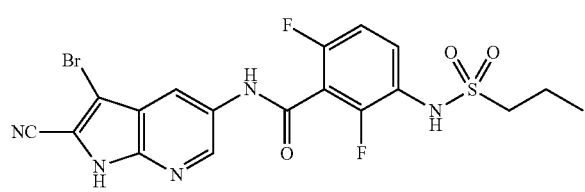

N-(3-bromo-2-cyano-1H-pyrrolo[2,3-b]pyridin-5-yl)-2,6-difluoro-3-(propylsulfonamido)benzamide N-(3-Bromo-2-cyano-1H-pyrrolo[2,3-b]pyridin-5-yl)-2,6-difluoro-3-(propylsulfonamido)benzamide (18%) was prepared according to the general procedure for Example 25, substituting N-(2-cyano-1H-pyrrolo[2,3-b]pyridin-5-yl)-2,6-difluoro-3-(propylsulfonamido)benzamide for 2,6-difluoro-N-(2-phenyl-1H-pyrrolo[2,3-b]pyridin-5-yl)-3-(propylsulfonamido)benzamide and employing DMF as solvent instead of CHCl$_3$. $^1$H NMR (400 MHz, CD$_3$OD) δ 8.64-8.62 (m, 1H), 8.54-8.52 (m, 1H), 7.70-7.63 (m, 1H), 7.18-7.12 (m, 1H), 3.15-3.09 (m, 2H), 1.91-1.83 (m, 2H), 1.09-1.04 (m, 3H); m/z (APCI-neg) M−1=498.1/496.1.

Example 132

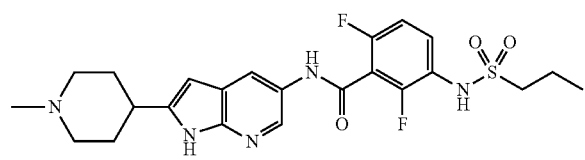

2,6-difluoro-N-(2-(1-methylpiperidin-4-yl)-1H-pyrrolo[2,3-b]pyridin-5-yl)-3-(propylsulfonamido)benzamide 2,6-Difluoro-N-(2-(1-methylpiperidin-4-yl)-1H-pyrrolo[2,3-b]pyridin-5-yl)-3-(propylsulfonamido)benzamide (30%) was prepared according to the general procedure for Example 95, substituting 2,6-difluoro-N-(2-(1-methyl-1,2,3,6-tetrahydropyridin-4-yl)-1H-pyrrolo[2,3-b]pyridin-5-yl)-3-(propylsulfonamido)benzamide for N-(2-(3-(dimethylamino)prop-1-ynyl)-1H-pyrrolo[2,3-b]pyridin-5-yl)-2,6-difluoro-3-(propylsulfonamido)benzamide. $^1$H NMR (400 MHz, CD$_3$OD) δ 8.29 (s, 1H), 7.68-7.61 (m, 1H), 7.16-7.10 (m, 1H), 6.30 (s, 1H), 3.63 (m, 1H), 3.14-3.09 (m, 2H), 3.05-2.94 (m, 2H), 2.84-2.72 (m, 2H), 2.67 (s, 3H), 2.30-2.23 (m, 2H), 2.02-1.82 (m, 4H), 1.08-1.03 (m, 3H); m/z (APCI-pos) M+1=492.2.

Example 133

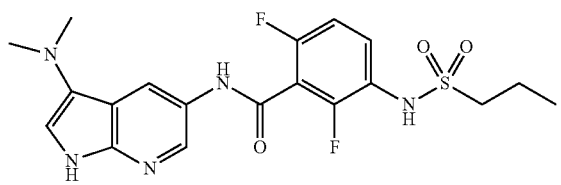

N-(3-(dimethylamino)-1H-pyrrolo[2,3-b]pyridin-5-yl)-2,6-difluoro-3-(propylsulfonamido)benzamide Step A: Sodium hydride (2.13 g, 53.3 mmol, 60% dispersion in mineral oil) was added to 3-bromo-1H-pyrrolo[2,3-b]pyridine (7.5 g, 38.1 mmol) in DMF (190 mL) at 0° C. This mixture was stirred at 0° C. for 30 minutes, and benzene sulfonyl chloride (7.40 g, 41.87 mmol) was then added by syringe. After 30 minutes at 0° C., TLC indicated most of the starting material had been consumed. Benzene sulfonyl chloride (0.5 mL) was added, and the mixture was stirred for another 15 minutes at 0° C. The mixture was then quenched with saturated ammonium chloride solution (100 mL) followed by water (200 mL). A precipitate had formed. The solids were collected by filtration and dried under high vacuum for 16 hours to give 3-bromo-1-(phenylsulfonyl)-1H-pyrrolo[2,3-b]pyridine (11.2 g, 87%) as a solid. $^1$H NMR (400 MHz, CDCl$_3$) δ 8.46-8.49 (m, 1H), 8.19-8.22 (m, 2H), 7.79-7.83 (m, 2H), 7.57-7.62 (m, 1H), 7.47-7.53 (m, 2H), 7.25-7.29 (m, 1H).

Step B: A round bottom flask was charged with dry DCM (5 mL), followed by tetrabutylammonium nitrate (451 mg, 1.48 mmol), and this solution was chilled to 0° C. Trifluoroacetic anhydride (206 mL, 1.48 mmol) was then added by syringe, and the cold mixture stirred for 30 minutes. A DCM solution of 3-bromo-1-(phenylsulfonyl)-1H-pyrrolo[2,3-b] pyridine (250 mg, 0.74 mmol in 2 mL of DCM) was then added, and the mixture was allowed to warm to room temperature over a 16 hour period. The mixture was then quenched with saturated sodium bicarbonate solution and extracted with DCM. The extracts were dried over sodium sulfate and concentrated under reduced pressure. The crude material was put through a 10 g Waters Sep Pak cartridge, eluting with DCM to give 3-bromo-5-nitro-1-(phenylsulfonyl)-1H-pyrrolo[2,3-b]pyridine (131 mg, 41%). $^1$H NMR (400 MHz, CDCl$_3$) δ 9.31-9.33 (m, 2H), 8.66-8.68 (m, 1H), 8.22-8.26 (m, 2H), 8.00 (s, 1H), 7.61-7.70 (m, 1H), 7.54-7.59 (m, 2H).

Step C: 3-Bromo-5-nitro-1-(phenylsulfonyl)-1H-pyrrolo [2,3-b]pyridine (200 mg, 0.523 mmol) and methylamine (1.31 mL, 10.47 mmol, 40% solution in water) were combined with DMF (1 mL) in a microwave vessel and heated to 150° C. in a microwave reactor for one hour. The mixture was then diluted with water, extracted with EtOAc, extracts dried over sodium sulfate and concentrated under reduced pressure. Sep Pak purification (10 g cartridge, 1:1 ethyl acetate:hexanes to 100% ethyl acetate) afforded N,N-dimethyl-5-nitro-1H-pyrrolo[2,3-b]pyridin-3-amine as a solid (55 mg, 51%). $^1$H NMR (400 MHz, d$_6$-DMSO) δ 12.03 (br s, 1H), 8.70-8.72 (m, 1H), 8.20-8.23 (m, 1H), 5.46-5.47 (m, 1H), 2.98 (s, 6H); (APCI-pos) M+1=207.2.

Step D: N,N-Dimethyl-5-nitro-1H-pyrrolo[2,3-b]pyridin-3-amine (50 mg) was taken up in methanol (3 mL) and EtOAc (3 mL). 10% Pd/C (50 mg) was added, and the mixture was hydrogenated under a balloon of hydrogen for one hour. The mixture was then filtered through GF/F filter paper, and the filtrate was concentrated to a solid. This material was purified by preparative TLC (0.5 mm plate, 10% MeOH/DCM/0.5% NH$_4$OH) to give N3,N3-dimethyl-1H-pyrrolo[2,3-b]pyridine-3,5-diamine (17 mg, 40%). (APCI-pos) M+1=177.2.

Step E: N-(3-(Dimethylamino)-1H-pyrrolo[2,3-b]pyridin-5-yl)-2,6-difluoro-3-(propylsulfonamido)benzamide (12%) was prepared following Example 32, Step D, substituting N3,N3-dimethyl-1H-pyrrolo[2,3-b]pyridine-3,5-diamine for 3-iodo-1-(phenylsulfonyl)-1H-pyrrolo[2,3-b]pyridine-5-amine. $^1$H NMR (400 MHz, CD$_3$OD) δ 8.20-8.22 (m, 1H), 8.07-8.09 (m, 1H), 7.59-7.67 (m, 1H), 7.08-7.14 (m, 1H), 3.23 (s, 3H), 3.15 (s, 3H), 3.07-3.13 (m, 2H), 1.82-1.91 (m, 2H), 1.02-1.08 (m, 3H); (APCI-pos) M+1=438.1.

Example 134

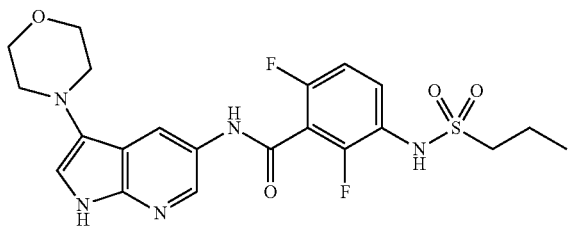

2,6-difluoro-N-(3-morpholino-1H-pyrrolo[2,3-b] pyridin-5-yl)-3-(propylsulfonamido)benzamide Step A: 4-(5-Nitro-1H-pyrrolo[2,3-b]pyridin-3-yl)morpholine (36%) was prepared following Example 133, Step C, substituting morpholine for dimethylamine. (APCI-pos) M+1=249.3.

Step B: 3-Morpholino-1H-pyrrolo[2,3-b]pyridin-5-amine (88%) was prepared following Example 133, Step D, substituting 4-(5-nitro-1H-pyrrolo[2,3-b]pyridin-3-yl)morpholine for N,N-dimethyl-5-nitro-1H-pyrrolo[2,3-b]pyridin-3-amine. (APCI-pos) M+1=219.3.

Step C: 2,6-Difluoro-N-(3-morpholino-1H-pyrrolo[2,3-b] pyridin-5-yl)-3-(propylsulfonamido)benzamide (25%) was prepared following Example 32, Step D, substituting 3-morpholino-1H-pyrrolo[2,3-b]pyridin-5-amine for 3-iodo-1-(phenylsulfonyl)-1H-pyrrolo[2,3-b]pyridine-5-amine. $^1$H NMR (400 MHz, CD$_3$OD) δ 7.97-8.2 (m, 2H), 7.60-7.67 (m, 1H), 7.08-7.15 (m, 1H), 3.77-3.88 (m, 4H), 3.23-3.27 (m, 2H), 3.06-3.14 (m, 2H), 1.82-1.92 (m, 2H), 1.02-1.08 (m, 3H); (APCI-pos) M+1=480.2.

Example 135

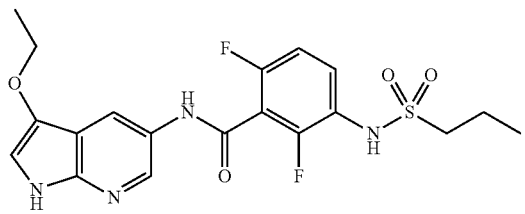

N-(3-ethoxy-1H-pyrrolo[2,3-b]pyridin-5-yl)-2,6-difluoro-3-(propyl sulfonamido)benzamide Step A: 1H-Pyrrolo[2,3-b]pyridine-3-carbaldehyde (16.7 g, 114 mmol) in DMF (150 mL) was added to a chilled (0° C.) mixture of dry DMF (300 mL) and sodium hydride (4.88 g, 122 mmol, 60% dispersion in mineral oil). This was stirred at 0° C. for 30 minutes, and a DMF solution (100 mL) of tosyl chloride (21.8 g, 114 mmol) was then added slowly over a ten minute period. The mixture was then allowed to warm to room temperature and stirred for 3 hours. Water (500 mL) was then added, and the solids were collected to give 1-tosyl-1H-pyrrolo[2,3-b]pyridine-3-carbaldehyde (29.7 g, 87%). $^1$H NMR (400 MHz, d$_6$-DMSO) δ 10.07 (s, 1H), 8.43-8.49 (m, 2H), 8.08-8.13 (m, 2H), 7.44-7.50 (m, 3H), 2.37 (s, 3H).

Step B: 1-Tosyl-1H-pyrrolo[2,3-b]pyridine-3-carbaldehyde (5 g, 16.65 mmol) was dissolved in DCM (165 mL) and chilled to 0° C. m-Chloroperbenzoic acid ("m-CPBA"; 4.85 g, 21.64 mmol, 77% by weight) was added, and the mixture was allowed to gradually warm to room temperature over a 16 hour period. The mixture was then washed with 10% aqueous sodium sulfite solution, dried over sodium sulfate and concentrated. Flash 65 Biotage (5% ethyl acetate/DCM) afforded 1-tosyl-1H-pyrrolo[2,3-b]pyridin-3 (2H)-one (441 mg, 9%). $^1$H NMR (400 MHz, CDCl$_3$) δ 8.61-8.66 (m, 1H), 8.00-8.05 (m, 2H), 7.92-7.97 (m, 1H), 7.29-7.34 (m, 2H), 7.06-7.12 (m, 1H), 4.38 (s, 2H), 2.41 (s, 3H).

Step C: 1-Tosyl-1H-pyrrolo[2,3-b]pyridin-3(2H)-one (234 mg, 0.815 mmol) was dissolved in ethanol (8 mL). A few drops of concentrated sulfuric acid were added, and the mixture was heated at reflux for 5 hours. The mixture was then allowed to cool to room temperature. The mixture was then diluted with EtOAc, washed with saturated sodium bicarbonate solution, dried over sodium sulfate and concentrated. Flash 40 Biotage (40S cartridge, DCM) afforded 3-ethoxy-1-tosyl-1H-pyrrolo[2,3-b]pyridine (126 mg, 49%). $^1$H NMR (400 MHz, CDCl$_3$) δ 8.42-8.45 m, 1H), 7.95-7.99 (m, 2H), 7.83-7.87 (m, 1H), 7.20-7.25 (m, 2H), 7.11-7.17 (m, 1H), 7.06 (s, 1H), 4.03-4.11 (m, 2H), 2.34 (s, 3H), 1.45-1.50 (m, 3H).

Step D: 3-Ethoxy-5-nitro-1-tosyl-1H-pyrrolo[2,3-b]pyridine (32%) was prepared following Example 32, Step B, substituting 3-ethoxy-1-tosyl-1H-pyrrolo[2,3-b]pyridine for 3-bromo-1-(phenylsulfonyl)-1H-pyrrolo[2,3-b]pyridine.

Step E: 3-Ethoxy-1-tosyl-1H-pyrrolo[2,3-b]pyridin-5-amine (32%) was prepared following Example 133, Step D, substituting 3-ethoxy-5-nitro-1-tosyl-1H-pyrrolo[2,3-b]pyridine for N,N-dimethyl-5-nitro-1H-pyrrolo[2,3-b]pyridin-3-amine. (APCI-pos) M+1=332.0.

Step F: N-(3-Ethoxy-1-tosyl-1H-pyrrolo[2,3-b]pyridin-5-yl)-2,6-difluoro-3-(propylsulfonamido)benzamide was prepared following Example 32, Step D, substituting 3-ethoxy-1-tosyl-1H-pyrrolo[2,3-b]pyridin-5-amine for 3-iodo-1-(phenylsulfonyl)-1H-pyrrolo[2,3-b]pyridin-5-amine. N-(3-Ethoxy-1-tosyl-1H-pyrrolo[2,3-b]pyridin-5-yl)-2,6-difluoro-3-(propylsulfonamido)benzamide was then subjected to methanol/aqueous potassium carbonate at 60° C. for 1 hour to give N-(3-ethoxy-1H-pyrrolo[2,3-b]pyridin-5-yl)-2,6-difluoro-3-(propylsulfonamido)benzamide (30%). $^1$H NMR (400 MHz, $d_6$-DMSO) δ 11.03 (s, 1H), 10.83 (s, 1H), 8.31-8.35 (m, 2H), 7.10-7.54 (m, 2H), 7.05 (s, 1H), 4.00-4.06 (m, 2H), 3.00-3.06 (m, 2H), 1.70-1.76 (m, 2H), 1.36-1.40 (m, 3H), 0.94-1.01 (m, 3H); (APCI-pos) M+1=439.1 (APCI-pos) M+1=439.1.

Example 136

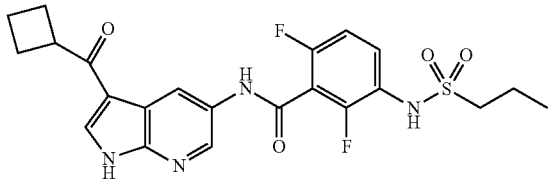

N-(3-(cyclobutanecarbonyl)-1H-pyrrolo[2,3-b]pyridin-5-yl)-2,6-difluoro-3-(propylsulfonamido)benzamide N-(3-(Cyclobutanecarbonyl)-1H-pyrrolo[2,3-b]pyridin-5-yl)-2,6-difluoro-3-(propylsulfonamido)benzamide (10%) was prepared following Example 7, Step A, substituting cyclobutanecarbonyl chloride for chloroacetyl chloride. $^1$H NMR (400 MHz, $d_6$-DMSO) δ 12.48 (br s, 1H), 10.99 (s, 1H), 9.81 (br s, 1H), 8.90-8.93 (m, 1H), 8.52-8.54 (m, 1H), 8.34-8.37 (m, 1H), 7.49-7.58 (m, 1H), 7.21-7.28 (m, 1H), 3.97-4.09 (m, 1H), 3.07-3.13 (m, 2H), 2.16-2.33 (m, 4H), 1.97-2.06 (m, 1H), 1.71-1.87 (m, 3H), 0.97-1.03 (m, 3H); (APCI-pos) M+1=477.1.

Example 137

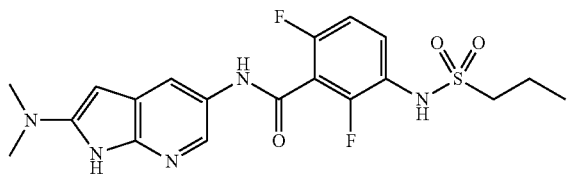

N-(2-(dimethylamino)-1H-pyrrolo[2,3-b]pyridin-5-yl)-2,6-difluoro-3-(propylsulfonamido)benzamide 2,6-Difluoro-N-(2-iodo-1-(phenylsulfonyl)-1H-pyrrolo[2,3-b]pyridin-5-yl)-3-(propylsulfonamido)benzamide (0.050 g, 0.076 mmol) and 7.9M dimethylamine in water (0.240 mL) were combined in 1,4-dioxane (0.500 mL). The solution was heated at 100° C. for 18 hours in a sealed vessel. The reaction mixture was concentrated and purified via reverse phase chromatography to give N-(2-(dimethylamino)-1H-pyrrolo[2,3-b]pyridin-5-yl)-2,6-difluoro-3-(propylsulfonamido)benzamide (5.9 mg, 18% yield) as a solid. $^1$H NMR (400 MHz, $d_6$-DMSO) δ 11.00 (s, 1H), 10.54 (s, 1H), 8.32 (s, 2H), 8.01 (d, 1H), 7.81 (d, 1H), 7.40 (m, 1H), 7.05 (m, 1H), 5.28 (s, 1H), 2.91 (s, 6H), 1.73 (m, 2H), 0.97 (m, 3H). m/z (API-pos) 438.2.

Example 138

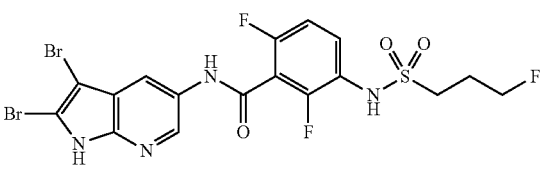

N-(2,3-dibromo-1H-pyrrolo[2,3-b]pyridin-5-yl)-2,6-difluoro-3-(3-fluoropropyl sulfonamido)benzamide N-(2,3-Dibromo-1H-pyrrolo[2,3-b]pyridin-5-yl)-2,6-difluoro-3-(3-fluoropropylsulfonamido)benzamide (24 mg, 0.042 mmol, 22%) was prepared by dissolving 2,6-difluoro-3-(3-fluoropropylsulfonamido)-N-(1H-pyrrolo[2,3-b]pyridin-5-yl)benzamide (0.078 g, 0.19 mmol) in THF (2 mL) and treating with 1,3-dibromo-5,5-dimethylhydantoin (0.06 g, 0.21 mmol) in the dark at room temperature for 30 minutes. The reaction mixture was concentrated and purified by reverse phase chromatography to afford the title compound as a solid. $^1$H NMR (400 MHz, $d_6$-DMSO) δ 11.05 (s, 1H), 8.53-8.18 (m, 2H), 7.55 (td, J=6.0, 9.0, 1H), 7.25 (t, J=8.5, 1H), 4.62 (t, J=6.0, 1H), 4.50 (t, J=6.0, 1H), 3.50-3.20 (m, 2H), 2.28-1.97 (m, 2H); m/z (APCI-pos) M+1=570.9, 573.9.

Example 139

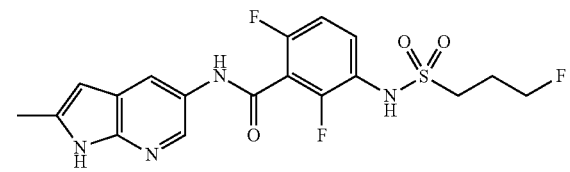

2,6-difluoro-3-(3-fluoropropylsulfonamido)-N-(2-methyl-1H-pyrrolo[2,3-b]pyridin-5-yl)benzamide Step A: 2,6-Difluoro-N-(2-methyl-1-(phenylsulfonyl)-1H-pyrrolo[2,3-b]pyridin-5-yl)-3-(3-fluoropropylsulfonamido)benzamide was prepared according to the general procedure for Example 107, Step C, substituting 2,6-difluoro-3-(3-fluoropropylsulfonamido)benzoic acid for 2,6-difluoro-3-(propylsulfonamido)benzoic acid.

Step B: 2,6-Difluoro-3-(3-fluoropropylsulfonamido)-N-(2-methyl-1H-pyrrolo[2,3-b]pyridin-5-yl)benzamide was prepared according to the general procedure for Example 107, step D, substituting 2,6-difluoro-3-(3-fluoropropylsulfonamido)-N-(2-methyl-1-(phenylsulfonyl)-1H-pyrrolo[2, 3-b]pyridin-5-yl)benzamide for 2,6-difluoro-N-(2-methyl-1-(phenylsulfonyl)-1H-pyrrolo[2,3-b]pyridin-5-yl)-3-(propylsulfonamido)benzamide. $^1$H NMR (400 MHz, d$_6$-DMSO) δ 11.43 (s, 1H), 10.71 (s, 1H), 10.51-10.06 (m, 1H), 8.25 (d, J=2.3, 1H), 8.18 (s, 1H), 7.50 (dd, J=9.0, 15.0, 1H), 7.18 (t, J=8.6, 1H), 6.15 (s, 1H), 4.65 (d, J=6.0, 1H), 4.52 (d, J=6.0, 1H), 3.78-2.85 (m, 2H), 2.12 (s, 3H), 2.25-1.94 (m, 2H); m/z (APCI-pos) M+1=427.1.

Example 140

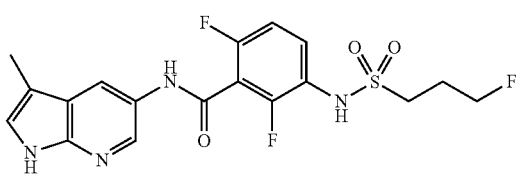

2,6-difluoro-3-(3-fluoropropylsulfonamido)-N-(3-methyl-1H-pyrrolo[2,3-b]pyridin-5-yl)benzamide Step A: 2,6-Difluoro-3-(3-fluoropropylsulfonamido)-N-(3-methyl-1-(phenylsulfonyl)-1H-pyrrolo[2,3-b]pyridin-5-yl)benzamide was prepared according to the general procedure for Example 108, Step D, substituting 2,6-difluoro-3-(3-fluoropropylsulfonamido)benzoic acid for 2,6-difluoro-3-(propylsulfonamido)benzoic acid.

Step B: 2,6-Difluoro-3-(3-fluoropropylsulfonamido)-N-(3-methyl-1H-pyrrolo[2,3-b]pyridin-5-yl)benzamide was prepared according to the general procedure for Example 108, Step E, substituting 2,6-difluoro-3-(3-fluoropropylsulfonamido)-N-(3-methyl-1-(phenylsulfonyl)-1H-pyrrolo[2,3-b]pyridin-5-yl)benzamide for 2,6-difluoro-N-(3-methyl-1-(phenylsulfonyl)-1H-pyrrolo[2,3-b]pyridin-5-yl)-3-(propylsulfonamido)benzamide. $^1$H NMR (400 MHz, d$_6$-DMSO) δ 11.33 (s, 1H), 10.85 (s, 1H), 10.39-9.82 (br s, 1H), 8.48-8.17 (m, 2H), 7.66-7.42 (m, 1H), 7.41-7.18 (m, 2H), 4.62 (t, J=6.0, 1H), 4.50 (t, J=6.0, 1H), 3.25-3.15 (m, 2H), 2.25 (s, 3H), 2.20-2.05 (m, 2H). m/z (APCI-pos) M+1=427.1.

Example 141

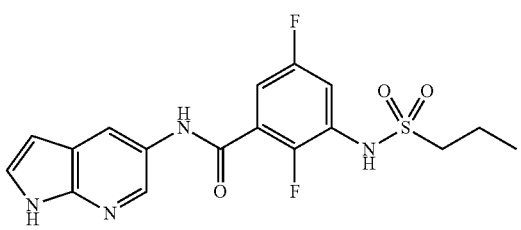

2,5-difluoro-3-(propylsulfonamido)-N-(1H-pyrrolo[2,3-b]pyridin-5-yl)benzamide 2,5-Difluoro-3-(propylsulfonamido)-N-(1H-pyrrolo[2,3-b]pyridin-5-yl)benzamide was prepared according to the general procedure of Example 1, substituting 2,5-difluoro-3-(propylsulfonamido)benzoic acid for 2,6-difluoro-3-(propylsulfonamido)benzoic acid. $^1$H NMR (400 MHz, d$_6$-DMSO) δ 11.63 (br s, 1H), 10.55 (s, 1H), 10.12 (br s, 1H), 8.39 (br s, 1H), 8.34 (br s, 1H), 7.35-7.44 (m, 2H), 6.46-6.48 (m, 1H), 3.22-3.26 (m, 2H), 1.74-1.79 (m, 2H), 0.98-1.02 (m, 3H); m/z (APCI-pos) M+1=395.1.

Example 142

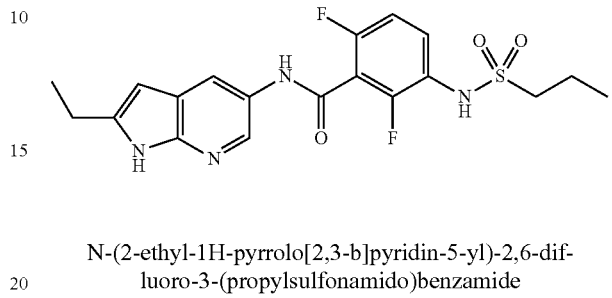

N-(2-ethyl-1H-pyrrolo[2,3-b]pyridin-5-yl)-2,6-difluoro-3-(propylsulfonamido)benzamide Step A: n-Butyllithium (2.03 mL, 3.25 mmol, 1.6M in hexanes) was added to a solution of 1-(phenylsulfonyl)-1H-pyrrolo[2,3-b]pyridine (0.60 g, 2.32 mmol) in THF (9.0 mL) at −78° C. The reaction mixture was stirred at −78° C. for 30 minutes, and then iodoethane (0.557 mL, 6.97 mmol) was added. The reaction mixture was warmed up to 0° C. and stirred for 2 hours, after which more iodoethane (0.278 mL, 3.48 mmol) was added. The reaction mixture was warmed up to room temperature and stirred overnight. Saturated aqueous ammonium chloride and ethyl acetate were then added, and the layers were separated. The aqueous layer was extracted with ethyl acetate. The combined organic layers were dried with sodium sulfate, filtered and concentrated in vacuo. The crude product was purified by flash chromatography to afford 2-ethyl-1-(phenylsulfonyl)-1H-pyrrolo[2,3-b]pyridine (0.25 g, 23% yield).

Step B: Trifluoroacetic anhydride (0.187 mL, 1.33 mmol) was added to a solution of tetrabutylammonium nitrate (0.404 g, 1.33 mmol) in dichloromethane (8 mL) cooled to 0° C. in an ice bath. After 10 minutes, a solution of 2-ethyl-1-(phenylsulfonyl)-1H-pyrrolo[2,3-b]pyridine (253 mg, 0.884 mmol) in DCM (3 mL) was added dropwise. The resulting solution was stirred at room temperature overnight. The reaction mixture was treated with saturated aqueous sodium bicarbonate, and the layers were separated. The aqueous layer was extracted with dichloromethane. The combined organic layers were washed with saturated aqueous sodium bicarbonate, dried over sodium sulfate, filtered, and evaporated. The crude product was purified by column chromatography to afford 2-ethyl-5-nitro-1-(phenylsulfonyl)-1H-pyrrolo[2,3-b]pyridine (0.25 g, 63%).

Step C: Potassium carbonate (1.02 g, 7.394 mmol) was added to a solution of 2-ethyl-5-nitro-1-(phenylsulfonyl)-1H-pyrrolo[2,3-b]pyridine (0.245 g, 0.739 mmol) in methanol (6.5 mL) and water (2.2 mL). The reaction mixture was heated at 80° C. overnight. The reaction mixture was then cooled down and treated with water and ethyl acetate. The layers were then separated. The organic layers were washed twice with water, dried over sodium sulfate, filtered, and evaporated to afford 2-ethyl-5-nitro-1H-pyrrolo[2,3-b]pyridine (0.14 g, 74% yield).

Step D: 2-Ethyl-1H-pyrrolo[2,3-b]pyridin-5-amine (0.10 g, 85%) was prepared according to Example 111, Step B, substituting 2-ethyl-5-nitro-1H-pyrrolo[2,3-b]pyridine for 2,6-difluoro-5-nitro-(3H-imidazo[4,5-b]pyridin-6-yl)benzamide.

Step E: 2-Ethyl-1H-pyrrolo[2,3-b]pyridin-5-amine (0.100 g, 0.62 mmol), 2,6-difluoro-3-(propylsulfonamido)benzoic acid (0.182 g, 0.65 mmol), EDCI (0.125 g, 0.65 mmol) and HOBt (0.084 g, 0.65 mmol) were dissolved in DMF (1.5 mL) and stirred at room temperature overnight. The solution was then directly purified by reverse phase HPLC to afford N-(2-ethyl-1H-pyrrolo[2,3-b]pyridin-5-yl)-2,6-difluoro-3-(propylsulfonamido)benzamide (0.061 g, 23% yield). $^1$H NMR (400 MHz, d$_6$-DMSO) δ 11.46 (s, 1H), 10.75 (s, 1H), 9.79 (br s, 1H), 8.26-8.25 (m, 1H), 8.19-8.18 (m, 1H), 7.56-7.50 (m, 1H), 7.24 (t, 1H), 6.18-6.17 (m, 1H), 3.13-3.09 (m, 2H), 2.74 (q, 2H), 1.77 (sx, 2H), 1.28 (t, 3H), 0.99 (t, 3H); m/z (ES-MS) 423.2 (100.0%) [M+1].

Example 143

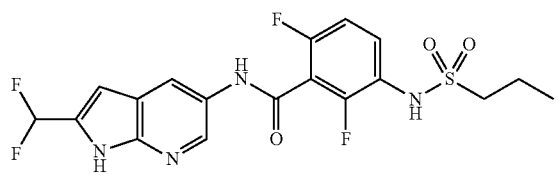

N-(2-(difluoromethyl)-1H-pyrrolo[2,3-b]pyridin-5-yl)-2,6-difluoro-3-(propylsulfonamido)benzamide Step A: n-Butyllithium (11.9 mL, 19.0 mmol, 1.6M in hexanes) was added to a solution of 1-(phenylsulfonyl)-1H-pyrrolo[2,3-b]pyridine (3.50 g, 13.6 mmol) in THF (53 mL) at −78° C. The reaction mixture was stirred at −78° C. for 30 minutes, and then DMF (4.2 mL, 54.2 mmol) was added. The reaction mixture was warmed up to 0° C. and stirred for 3 hours. It was then treated with saturated aqueous ammonium chloride and ethyl acetate, and the layers were separated. The aqueous layer was extracted with ethyl acetate. The organic layer was dried with sodium sulfate, filtered and concentrated in vacuo. The crude product was purified by flash chromatography to afford 1-(phenylsulfonyl)-1H-pyrrolo[2,3-b]pyridine-2-carbaldehyde (2.4 g, 62%) as a solid.

Step B: 5-Nitro-1-(phenylsulfonyl)-1H-pyrrolo[2,3-b]pyridine-2-carbaldehyde (1.60 g, 40% yield) was prepared according to Example 142, Step B, substituting 1-(phenylsulfonyl)-1H-pyrrolo[2,3-b]pyridine-2-carbaldehyde for 2-ethyl-1-(phenylsulfonyl)-1H-pyrrolo[2,3-b]pyridine.

Step C: Diethylaminosulfur trifluoride ("DAST"; 0.112 mL, 0.845 mmol) was added to a solution of 5-nitro-1-(phenylsulfonyl)-1H-pyrrolo[2,3-b]pyridine-2-carbaldehyde (0.140 g, 0.423 mmol) in DCM (3.8 mL) at 0° C. The reaction mixture was stirred at room temperature overnight. The reaction mixture was then treated with saturated aqueous NaHCO$_3$, and the layers were separated. The aqueous layer was extracted with dichloromethane. The combined organic layers were dried with sodium sulfate, filtered and concentrated in vacuo. The crude product was purified by flash chromatography to afford 2-(difluoromethyl)-5-nitro-1-(phenylsulfonyl)-1H-pyrrolo[2,3-b]pyridine (0.11 g, 83% yield) as a solid.

Step D: Potassium carbonate (0.25 g, 1.76 mmol) was added to a solution of 2-(difluoromethyl)-5-nitro-1-(phenylsulfonyl)-1H-pyrrolo[2,3-b]pyridine (0.089 g, 0.252 mmol) in methanol (2.2 mL) and water (0.7 mL). The reaction mixture was heated at 40° C. for 30 minutes. The reaction mixture was then cooled down and treated with water and ethyl acetate. The layers were separated. The combined organic layers were washed twice with water, dried over sodium sulfate, filtered, and evaporated to afford 2-(difluoromethyl)-5-nitro-1H-pyrrolo[2,3-b]pyridine (0.032 g, 49%).

Step E: 2-(Difluoromethyl)-1H-pyrrolo[2,3-b]pyridin-5-amine (0.017 g, 62%) was prepared according to Example 111, Step B, substituting 2-(difluoromethyl)-5-nitro-1H-pyrrolo[2,3-b]pyridine for 2,6-difluoro-5-nitro-(3H-imidazo[4,5-b]pyridin-6-yl)benzamide.

Step F: N-(2-(Difluoromethyl)-1H-pyrrolo[2,3-b]pyridin-5-yl)-2,6-difluoro-3-(propylsulfonamido)benzamide (0.017 g, 41% yield) was prepared according to Example 142, Step E, substituting 2-(difluoromethyl)-1H-pyrrolo[2,3-b]pyridin-5-amine for 2-ethyl-1H-pyrrolo[2,3-b]pyridin-5-amine. $^1$H NMR (400 MHz, d$_6$-DMSO) δ 12.38 (s, 1H), 10.93 (s, 1H), 9.80 (br s, 1H), 8.49-8.48 (m, 2H), 7.57-7.51 (m, 1H), 7.25 (t, 1H), 7.22 (t, 1H), 6.84-6.83 (m, 1H), 3.13-3.10 (m, 2H), 1.77 (sx, 2H), 1.00 (t, 3H); m/z (ES-MS) 445.1 (100.0%) [M+1].

Example 144

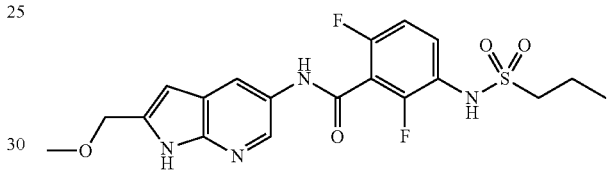

2,6-difluoro-N-(2-(methoxymethyl)-1H-pyrrolo[2,3-b]pyridin-5-yl)-3-(propylsulfonamido)benzamide Step A: NaBH$_4$ (0.084 g, 2.21 mmol) was added to a solution of 5-nitro-1-(phenylsulfonyl)-1H-pyrrolo[2,3-b]pyridine-2-carbaldehyde (611 mg, 1.844 mmol) in THF (18.3 mL) and methanol (1.8 mL) at 0° C. The reaction mixture was stirred for 1 hour. It was then treated with water and ethyl acetate, and the layers were separated. The aqueous layer was extracted with ethyl acetate. The combined organic layers were dried with sodium sulfate, filtered and concentrated in vacuo. The crude product was purified by flash chromatography to afford (5-nitro-1-(phenylsulfonyl)-1H-pyrrolo[2,3-b]pyridin-2-yl)methanol (0.26 g, 42% yield).

Step B: N,N,N',N'-Tetramethyl-1,8-naphthalenediamine (0.212 g, 0.99 mmol) and trimethyloxonium tetrafluoroborate (0.146 g, 0.99 mmol) were added to a solution of (5-nitro-1-(phenylsulfonyl)-1H-pyrrolo[2,3-b]pyridin-2-yl)methanol (0.11 g, 0.33 mmol) in DCM (3.3 mL). The reaction mixture was stirred at room temperature for 1 hour. It was then treated with saturated aqueous NaHCO$_3$, and the layers were separated. The aqueous layer was extracted with DCM. The combined organic layers were dried with sodium sulfate, filtered and concentrated in vacuo. The crude product was purified by flash chromatography to afford 2-(methoxymethyl)-5-nitro-1-(phenylsulfonyl)-1H-pyrrolo[2,3-b]pyridine (0.11 g, 96%).

Step C: Potassium carbonate (0.306 g, 2.22 mmol) was added to a solution of 2-(methoxymethyl)-5-nitro-1-(phenylsulfonyl)-1H-pyrrolo[2,3-b]pyridine (0.11 g, 0.317 mmol) in methanol (3.3 mL) and water (0.9 mL). The reaction mixture was heated at 60° C. for 90 minutes. The reaction mixture was then cooled down. The mixture was treated with water and ethyl acetate, and the layers were separated. The organic layers were washed twice with water, dried over sodium sulfate, filtered, and evaporated to afford 2-(methoxymethyl)-5-nitro-1H-pyrrolo[2,3-b]pyridine (70 mg, quantitative yield).

Step D: 2-(Methoxymethyl)-1H-pyrrolo[2,3-b]pyridin-5-amine was prepared in quantitative yield according to Example 111, Step B, substituting 2-(methoxymethyl)-5-nitro-1H-pyrrolo[2,3-b]pyridine for 2,6-difluoro-5-nitro-(3H-imidazo[4,5-b]pyridin-6-yl)benzamide.

Step E: 2,6-Difluoro-N-(2-(methoxymethyl)-1H-pyrrolo[2,3-b]pyridin-5-yl)-3-(propylsulfonamido)benzamide was prepared in 42% yield according to Example 142, Step E, substituting 2-(methoxymethyl)-1H-pyrrolo[2,3-b]pyridin-5-amine for 2-ethyl-1H-pyrrolo[2,3-b]pyridin-5-amine. $^1$H NMR (400 MHz, d$_6$-DMSO) δ 11.71 (s, 1H), 10.82 (s, 1H), 9.76 (br s, 1H), 8.33-8.30 (m, 2H), 7.57-7.51 (m, 1H), 7.25 (t, 1H), 6.43-6.42 (m, 1H), 4.53 (s, 2H), 3.31 (s, 3H), 3.14-3.10 (m, 2H), 1.77 (sx, 2H), 1.00 (t, 3H); m/z (ES-MS) 439.2 (94.5%) [M+1].

Example 145

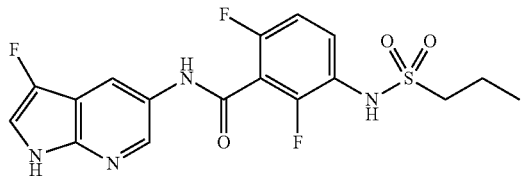

2,6-difluoro-N-(3-fluoro-1H-pyrrolo[2,3-b]pyridin-5-yl)-3-(propylsulfonamido)benzamide 1-Fluoro-2,6-dichloropyridinium triflate (31 mg, 0.1 mmol) was added to 2,6-difluoro-N-(1H-pyrrolo[2,3-b]pyridin-5-yl)-3-(propylsulfonamido)benzamide (39 mg, 0.1 mmol) in MeCN (4 mL). The mixture was heated at 60° C. for 18 hours and then cooled to room temperature. The mixture was then diluted with EtOAc, washed with brine, dried over MgSO$_4$ and concentrated. The crude product was purified using silica gel chromatography (ISCO) using 5% MeOH in CH$_2$Cl$_2$ as eluent, and subsequently reverse phase HPLC to give 2,6-difluoro-N-(3-fluoro-1H-pyrrolo[2,3-b]pyridin-5-yl)-3-(propylsulfonamido)benzamide (10.7 mg, 26%). $^1$H NMR (400 MHz, d$_6$-DMSO) δ 11.51 (s, 3H), 10.97 (s, 3H), 9.77 (s, 3H), 8.41 (s, 6H), 7.70-7.38 (m, 6H), 7.26 (t, J=8.5, 3H), 3.45-2.96 (m, 32H), 2.50 (s, 57H), 2.36-2.09 (m, 1H), 1.77 (dd, J=7.5, 15.1, 6H), 1.00 (t, J=7.4, 9H); m/z (LC-MS) M+1=413.4.

Example 146

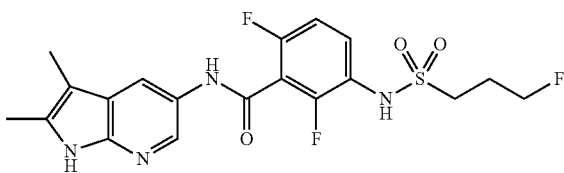

N-(2,3-dimethyl-1H-pyrrolo[2,3-b]pyridin-5-yl)-2,6-difluoro-3-(3-fluoropropylsulfonamido)benzamide Step A: Lithium diisopropylamide (0.88 mL, 1.52 mmol, 1.8M in heptane/THF/ethylbenzene) was added to a solution of 3-methyl-1-(phenylsulfonyl)-1H-pyrrolo[2,3-b]pyridine (0.20 g, 0.734 mmol) in THF (4.0 mL) at −78° C. The slurry was stirred at −78° C. for 30 minutes, and then methyl iodide (0.059 mL, 0.952 mmol) was added. The reaction mixture was allowed to warm up to room temperature and stirred for 2 hours. Water was then added to the mixture followed by dichloromethane. The layers were separated. The aqueous layer was extracted twice with dichloromethane. The organic layers were dried with sodium sulfate, filtered and concentrated in vacuo. The crude was purified by flash chromatography to afford 2,3-dimethyl-1-(phenylsulfonyl)-1H-pyrrolo[2,3-b]pyridine (0.17 g, 99%) as a solid (purity 80%).

Step B: 2,3-Dimethyl-5-nitro-1-(phenylsulfonyl)-1H-pyrrolo[2,3-b]pyridine (0.22 g, 68%) was prepared according to Example 142, Step B, substituting 2,3-dimethyl-1-(phenylsulfonyl)-1H-pyrrolo[2,3-b]pyridine for 2-ethyl-1-(phenylsulfonyl)-1H-pyrrolo[2,3-b]pyridine.

Step C: 2,3-Dimethyl-5-nitro-1H-pyrrolo[2,3-b]pyridine (0.11 g, 90%) was prepared according to Example 142, Step C, substituting 2,3-dimethyl-5-nitro-1-(phenylsulfonyl)-1H-pyrrolo[2,3-b]pyridine for 2-ethyl-5-nitro-1-(phenylsulfonyl)-1H-pyrrolo[2,3-b]pyridine.

Step D: 2,3-Dimethyl-5-nitro-1H-pyrrolo[2,3-b]pyridine (0.11 g, 0.596 mmol), iron (0.40 g, 7.16 mmol) and ammonium chloride (0.13 g, 2.39 mmol) were combined with ethanol (2.8 mL) and water (0.65 mL) in a microwave vessel and heated in a microwave reactor to 110° C. for 15 minutes. The reaction mixture was filtered, saturated aqueous sodium bicarbonate was added, and the layers were separated. The aqueous layer was extracted once with ethyl acetate. The organic layers were dried with sodium sulfate, filtered and concentrated in vacuo to afford 2,3-dimethyl-1H-pyrrolo[2,3-b]pyridin-5-amine (0.096 g, 100%), which was carried to the next step without further purification.

Step E: 2,3-Dimethyl-1H-pyrrolo[2,3-b]pyridin-5-amine (0.048 g, 0.298 mmol), 2,6-difluoro-3-(3-fluoropropylsulfonamido)benzoic acid (0.097 g, 0.328 mmol), EDCI (0.063 g, 0.328 mmol) and HOBt (0.040 g, 0.298 mmol) were dissolved in DMF (1.6 mL) and stirred at room temperature for 16 hours. The reaction mixture was directly purified by reverse phase HPLC to give N-(2,3-dimethyl-1H-pyrrolo[2,3-b]pyridin-5-yl)-2,6-difluoro-3-(3-fluoropropylsulfonamido)benzamide (0.043 g, 33%) as a solid. $^1$H NMR (400 MHz, d$_6$-DMSO) δ 11.24 (s, 1H), 10.80 (s, 1H), 9.93 (br s, 1H), 8.18 (d, 2H), 7.61-7.46 (m, 1H), 7.35-7.19 (m, 1H), 4.68-4.56 (m, 1H), 4.56-4.44 (m, 1H), 3.29-3.16 (m, 2H), 2.32 (s, 3H), 2.23-2.04 (m, 5H); m/z (ES-MS) 441.1 (98.2%) [M+1]. One methyl peak was hidden under solvent signal.

Example 147

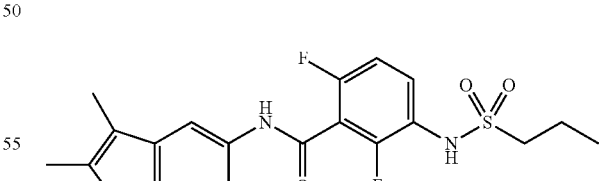

N-(2,3-dimethyl-1H-pyrrolo[2,3-b]pyridin-5-yl)-2,6-difluoro-3-(propylsulfonamido)benzamide 2,3-Dimethyl-1H-pyrrolo[2,3-b]pyridin-5-amine (0.048 g, 0.298 mmol), 2,6-difluoro-3-(3-propylsulfonamido)benzoic acid (0.092 g, 0.328 mmol), EDCI (0.063 g, 0.328 mmol) and HOBt (0.040 g, 0.298 mmol) were dissolved in DMF (1.6 mL) and stirred at room temperature for 16 hours. The reaction mixture was directly purified by reverse phase HPLC to give N-(2,3-dimethyl-1H-pyrrolo[2,3-b]pyridin-5-yl)-2,6-difluoro-3-(propylsulfonamido)benzamide (0.059 g, 47%) as a solid. $^1$H NMR (400 MHz, d$_6$-DMSO) 11.23 (s, 1H), 10.77 (s, 1H), 9.19 (br s, 1H), 8.27-8.09 (m, 2H), 7.59-7.39 (m, 1H), 7.28-7.10 (m, 1H), 3.17-2.95 (m, 2H), 2.32 (s, 3H), 2.15 (s, 3H), 1.84-1.65 (m, 2H), 0.98 (s, 3H); m/z (ES-MS) 423.2 (96.1%) [M+1].

Example 148

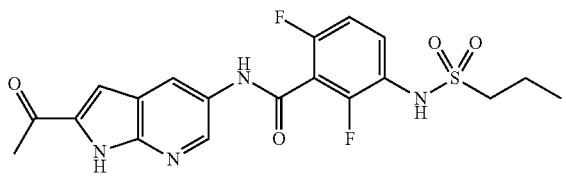

N-(2-acetyl-1H-pyrrolo[2,3-b]pyridin-5-yl)-2,6-difluoro-3-(propylsulfonamido)benzamide Step A: Lithium diisopropylamide (19.4 mL, 35.0 mmol, 1.8M in heptane/THF/ethylbenzene) was added to a solution of 1-(phenylsulfonyl)-1H-pyrrolo[2,3-b]pyridine (4.50 g, 17.4 mmol) in THF (100 mL) at −78° C. The reaction mixture was stirred at −78° C. for 30 minutes, and then acetic anhydride (6.6 mL, 69.7 mmol) was added. The reaction mixture was warmed up to room temperature and stirred for 40 minutes. The reaction mixture was treated with water and dichloromethane, and the layers were separated. The aqueous layer was extracted once with dichloromethane. The organic layers were dried with sodium sulfate, filtered and concentrated in vacuo. The crude material was purified by flash chromatography to afford 1-(1-(phenylsulfonyl)-1H-pyrrolo[2,3-b]pyridin-2-yl)ethanone (2.15 g, 41%).

Step B: 1-(5-Nitro-1-(phenylsulfonyl)-1H-pyrrolo[2,3-b]pyridin-2-yl)ethanone (1.37 g, 66%) was prepared according to Example 142, Step B, substituting 141-(phenylsulfonyl)-1H-pyrrolo[2,3-b]pyridin-2-yl)ethanone for 2-ethyl-1-(phenylsulfonyl)-1H-pyrrolo[2,3-b]pyridine.

Step C: Potassium carbonate (1.20 g, 8.69 mmol) was added to a solution of 1-(5-nitro-1-(phenylsulfonyl)-1H-pyrrolo[2,3-b]pyridin-2-yl)ethanone (0.50 g, 1.45 mmol) in methanol (13 mL) and water (4.3 mL). The reaction mixture was heated at 40° C. for 30 minutes. The reaction mixture was then cooled down and treated with water and ethyl acetate. The layers were then separated. The organic layers were washed twice with water, dried over sodium sulfate, filtered, and evaporated to afford 1-(5-nitro-1H-pyrrolo[2,3-b]pyridin-2-yl)ethanone (0.30 g, quantitative yield).

Step D: 1-(5-Amino-1H-pyrrolo[2,3-b]pyridin-2-yl)ethanone (0.047 g, 55%) was prepared according to Example 146, Step D, substituting 1-(5-nitro-1H-pyrrolo[2,3-b]pyridin-2-yl)ethanone for 2,3-dimethyl-5-nitro-1H-pyrrolo[2,3-b]pyridine.

Step E: N-(2-Acetyl-1H-pyrrolo[2,3-b]pyridin-5-yl)-2,6-difluoro-3-(propylsulfonamido)benzamide (0.015 g, 22%) was prepared according to Example 147, substituting 1-(5-amino-1H-pyrrolo[2,3-b]pyridin-2-yl)ethanone for 2,3-dimethyl-1H-pyrrolo[2,3-b]pyridin-5-amine. $^1$H NMR (400 MHz, d$_6$-DMSO) δ 12.35 (s, 1H), 11.03 (s, 1H), 9.86 (br s, 1H), 8.59 (d, 1H), 8.54 (d, 1H), 7.55 (dd, 1H), 7.40 (d, 1H), 7.27 (t, 1H), 3.16-3.08 (m, 2H), 2.57 (s, 3H), 1.77 (m, 2H), 0.99 (t, 3H); m/z (ES-MS) 437.1 (99.3%) [M+1].

Example 149

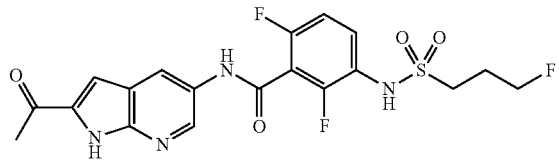

N-(2-acetyl-1H-pyrrolo[2,3-b]pyridin-5-yl)-2,6-difluoro-3-(3-fluoropropylsulfonamido)benzamide N-(2-Acetyl-1H-pyrrolo[2,3-b]pyridin-5-yl)-2,6-difluoro-3-(3-fluoropropylsulfonamido)benzamide (0.022 g, 18%) was prepared according to Example 146, Step E, substituting 1-(5-amino-1H-pyrrolo[2,3-b]pyridin-2-yl)ethanone for 2,3-dimethyl-1H-pyrrolo[2,3-b]pyridin-5-amine. $^1$H NMR (400 MHz, d$_6$-DMSO) δ 12.36 (s, 1H), 11.03 (s, 1H), 9.94 (br s, 1H), 8.59 (d, 1H), 8.54 (d, 1H), 7.56 (dd, 1H), 7.40 (d, 1H), 7.28 (t, 1H), 4.62 (t, 1H), 4.50 (t, 1H), 3.28-3.16 (m, 2H), 2.57 (s, 3H), 2.25-2.01 (m, 3H); m/z (ES-MS) 455.1 (98.0%) [M+1].

Example 150

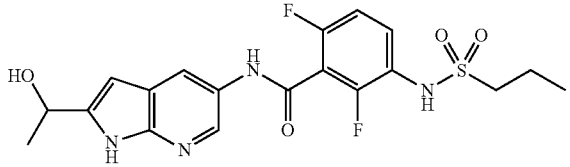

2,6-difluoro-N-(2-(1-hydroxyethyl)-1H-pyrrolo[2,3-b]pyridin-5-yl)-3-(propylsulfonamido)benzamide Step A: Sodium tetrahydroborate (0.15 g, 4.10 mmol) was added to a solution of 1-(5-nitro-1H-pyrrolo[2,3-b]pyridin-2-yl)ethanone (0.28 g, 1.37 mmol) in THF (8.7 mL) and methanol (0.90 mL) at 0° C., after which the reaction mixture was warmed up to room temperature and stirred for 1 hour. The reaction mixture was then treated with water and ethyl acetate, and the layers were separated. The aqueous layer was extracted once with ethyl acetate. The organic layers were dried with sodium sulfate, filtered and concentrated in vacuo. The crude material was purified by flash chromatography to afford 1-(5-nitro-1H-pyrrolo[2,3-b]pyridin-2-yl)ethanol (0.12 g, 41%).

Step B: 1-(5-Amino-1H-pyrrolo[2,3-b]pyridin-2-yl)ethanol (0.100 g, quantitative yield) was prepared according to Example 146, Step D, substituting 1-(5-nitro-1H-pyrrolo[2,3-b]pyridin-2-yl)ethanol for 2,3-dimethyl-5-nitro-1H-pyrrolo[2,3-b]pyridine.

Step C: 2,6-Difluoro-N-(2-(1-hydroxyethyl)-1H-pyrrolo[2,3-b]pyridin-5-yl)-3-(propylsulfonamido)benzamide (0.057 g, 58%) was prepared according to Example 147, substituting 1-(5-amino-1H-pyrrolo[2,3-b]pyridin-2-yl)ethanol for 2,3-dimethyl-1H-pyrrolo[2,3-b]pyridin-5-amine. $^1$H NMR (400 MHz, d$_6$-DMSO) δ 11.52 (s, 1H), 10.81 (s, 1H), 9.87 (br s, 1H), 8.29 (d, 1H), 8.26 (d, 1H), 7.53 (dd, 1H), 7.25 (t, 1H), 6.30 (d, 1H), 5.35 (d, 1H), 4.91-4.81 (m, 1H), 3.17-3.04 (m, 2H), 1.76 (m, 2H), 1.47 (d, 3H), 0.99 (t, 3H); m/z (ES-MS) 439.1 (92.3%) [M+1].

Example 151

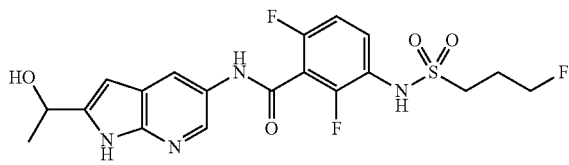

2,6-difluoro-3-(3-fluoropropylsulfonamido)-N-(2-(1-hydroxyethyl)-1H-pyrrolo[2,3-b]pyridin-5-yl)benzamide 2,6-Difluoro-3-(3-fluoropropylsulfonamido)-N-(2-(1-hydroxyethyl)-1H-pyrrolo[2,3-b]pyridin-5-yl)benzamide (0.036 g, 55%) was prepared according to Example 146, Step E, substituting 1-(5-amino-1H-pyrrolo[2,3-b]pyridin-2-yl)ethanol for 2,3-dimethyl-1H-pyrrolo[2,3-b]pyridin-5-amine. $^1$H NMR (400 MHz, d$_6$-DMSO) δ 11.52 (s, 1H), 10.82 (s, 1H), 9.98 (br s, 1H), 8.29 (d, 1H), 8.26 (d, 1H), 7.54 (dd, 1H), 7.26 (t, 1H), 6.30 (d, 1H), 5.35 (d, 1H), 4.93-4.80 (m, 1H), 4.62 (t, 1H), 4.50 (t, 1H), 3.28-3.16 (m, 2H), 2.24-2.03 (m, 2H), 1.47 (d, 3H); m/z (ES-MS) 457.1 (93.2%) [M+1].

Example 152

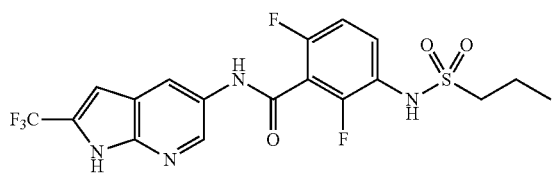

2,6-difluoro-3-(propylsulfonamido)-N-(2-(trifluoromethyl)-1H-pyrrolo[2,3-b]pyridin-5-yl)benzamide Step A: Lithium hexamethyldisilazide (3.6 mL, 3.6 mmol, 1M in THF) was added to a solution of 2-(trifluoromethyl)-1H-pyrrolo[2,3-b]pyridine (0.57 g, 3.04 mmol; see WO 2008/034860) in THF (20 mL) at −78° C. The reaction mixture was stirred at −78° C. for 5 minutes, then warmed up to 0° C. for 30 minutes, and finally warmed to room temperature for another 30 minutes. The mixture was cooled back to −78° C. where methyl chloroformate (0.35 mL, 4.55 mmol) was added dropwise. The mixture was slowly warmed up to room temperature and stirred for 16 hours. Water was then added, followed by dichloromethane. The layers were separated. The aqueous layer was extracted twice with dichloromethane. The organic layers were dried with sodium sulfate, filtered and concentrated in vacuo. The crude was purified by flash chromatography to afford methyl 2-(trifluoromethyl)-1H-pyrrolo[2,3-b]pyridine-1-carboxylate (0.45 g, 61%).

Step B: Methyl 5-nitro-2-(trifluoromethyl)-1H-pyrrolo[2,3-b]pyridine-1-carboxylate (0.35 g, 64%) was prepared according to Example 142, Step B, substituting methyl 2-(trifluoromethyl)-1H-pyrrolo[2,3-b]pyridine-1-carboxylate for 2-ethyl-1-(phenylsulfonyl)-1H-pyrrolo[2,3-b]pyridine.

Step C: Sodium hydroxide (4.2 mL, 4.2 mmol, 1M in water) was added to a solution of methyl 5-nitro-2-(trifluoromethyl)-1H-pyrrolo[2,3-b]pyridine-1-carboxylate (0.35 g, 1.19 mmol) in THF (6.9 mL) and methanol (1.7 mL) at room temperature. The reaction mixture was heated at 40° C. for 30 minutes. The reaction mixture was then cooled down and treated with water and ethyl acetate. The layers were then separated. The organic layers were washed twice with water, dried over sodium sulfate, filtered, and evaporated to afford 5-nitro-2-(trifluoromethyl)-1H-pyrrolo[2,3-b]pyridine (0.24 g, 86%), which was carried to the next step without further purification.

Step D: 2-(Trifluoromethyl)-1H-pyrrolo[2,3-b]pyridin-5-amine (0.190 g, 93%) was prepared according to Example 146, Step D, substituting 5-nitro-2-(trifluoromethyl)-1H-pyrrolo[2,3-b]pyridine for 2,3-dimethyl-5-nitro-1H-pyrrolo[2,3-b]pyridine.

Step E: 2,6-Difluoro-3-(propylsulfonamido)-N-(2-(trifluoromethyl)-1H-pyrrolo[2,3-b]pyridin-5-yl)benzamide (0.048 g, 52%) was prepared according to Example 147, substituting 2-(trifluoromethyl)-1H-pyrrolo[2,3-b]pyridin-5-amine for 2,3-dimethyl-1H-pyrrolo[2,3-b]pyridin-5-amine. $^1$H NMR (400 MHz, d$_6$-DMSO) δ 12.91 (s, 1H), 11.01 (s, 1H), 9.79 (br s, 1H), 8.58 (d, 1H), 8.55 (d, 1H), 7.55 (dd, 1H), 7.26 (t, 1H), 7.10 (s, 1H), 3.16-3.05 (m, 2H), 1.77 (m, 2H), 1.00 (t, 3H); m/z (ES-MS) 463.1 (100.0%) [M+1].

Example 153

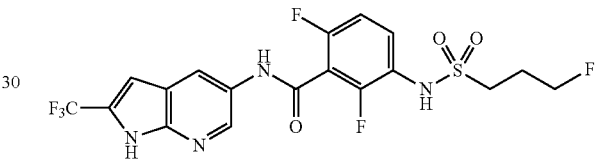

2,6-difluoro-3-(3-fluoropropylsulfonamido)-N-(2-(trifluoromethyl)-1H-pyrrolo[2,3-b]pyridin-5-yl)benzamide 2,6-Difluoro-3-(3-fluoropropylsulfonamido)-N-(2-(trifluoromethyl)-1H-pyrrolo[2,3-b]pyridin-5-yl)benzamide (0.037 g, 52%) was prepared according to Example 146, Step E, substituting 2-(trifluoromethyl)-1H-pyrrolo[2,3-b]pyridin-5-amine for 2,3-dimethyl-1H-pyrrolo[2,3-b]pyridin-5-amine. $^1$H NMR (400 MHz, d$_6$-DMSO) δ 12.91 (s, 1H), 11.02 (s, 1H), 9.91 (s, 1H), 8.60-8.52 (m, 2H), 7.57 (dd, 1H), 7.29 (t, 1H), 7.10 (s, 1H), 4.62 (t, 1H), 4.51 (t, 1H), 3.30-3.21 (m, 2H), 2.24-2.08 (m, 2H). m/z (ES-MS) 481.1 (100.0%) [M+1].

Example 154

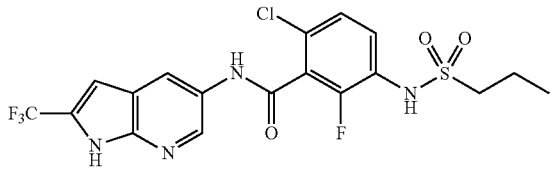

6-chloro-2-fluoro-3-(propylsulfonamido)-N-(2-(trifluoromethyl)-1H-pyrrolo[2,3-b]pyridin-5-yl)benzamide 2-(Trifluoromethyl)-1H-pyrrolo[2,3-b]pyridin-5-amine (0.040 g, 0.199 mmol), 6-chloro-2-fluoro-3-(propylsulfonamido)benzoic acid (0.064 g, 0.219 mmol), EDCI (0.042 g, 0.219 mmol) and HOBt (0.027 g, 0.199 mmol) were dissolved in DMF (0.6 mL) and stirred at room temperature for 16 hours. The reaction mixture was directly purified by reverse phase HPLC to give 6-chloro-2-fluoro-3-(propylsulfonamido)-N-(2-(trifluoromethyl)-1H-pyrrolo[2,3-b]pyridin-5-yl)benzamide (0.050 g, 52%) as a solid. $^1$H NMR (400 MHz, $d_6$-DMSO) δ 12.91 (s, 1H), 10.99 (s, 1H), 9.96 (s, 1H), 8.60-8.56 (m, 1H), 8.56-8.52 (m, 1H), 7.54 (t, 1H), 7.44 (d, 1H), 7.10 (s, 1H), 3.21-3.12 (m, 2H), 1.76 (m, 2H), 0.99 (t, 3H); m/z (ES-MS) 479.1 (100.0%) [M+1].

Example 155

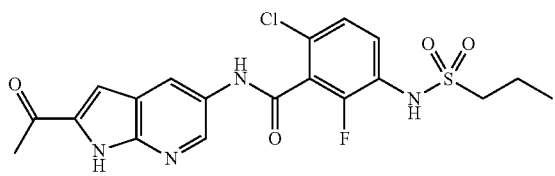

N-(2-acetyl-1H-pyrrolo[2,3-b]pyridin-5-yl)-6-chloro-2-fluoro-3-(propylsulfonamido)benzamide N-(2-Acetyl-1H-pyrrolo[2,3-b]pyridin-5-yl)-6-chloro-2-fluoro-3-(propylsulfonamido)benzamide (0.024 g, 7%) was prepared according to Example 154, substituting 1-(5-amino-1H-pyrrolo[2,3-b]pyridin-2-yl)ethanone for 2-(trifluoromethyl)-1H-pyrrolo[2,3-b]pyridin-5-amine. $^1$H NMR (400 MHz, $d_6$-DMSO) δ 12.31 (s, 1H), 10.95 (s, 1H), 10.03 (br s, 1H), 8.57 (d, 1H), 8.54 (d, 1H), 7.53 (t, 1H), 7.40 (dd, 2H), 3.19-3.07 (m, 2H), 2.57 (s, 3H), 1.76 (m, 2H), 0.99 (t, 3H); m/z (ES-MS) 453.1 (100.0%) [M+1].

Example 156

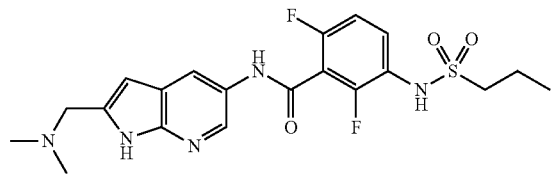

N-(2-((dimethylamino)methyl)-1H-pyrrolo[2,3-b]pyridin-5-yl)-2,6-difluoro-3-(propylsulfonamido)benzamide Step A: A round-bottom flask was charged with 5-nitro-1-(phenylsulfonyl)-1H-pyrrolo[2,3-b]pyridine-2-carbaldehyde (0.30 g, 0.91 mmol), dimethylamine hydrochloride salt (0.10 g, 1.27 mmol), trimethoxymethane (0.99 mL, 9.1 mmol), sodium triacetoxyborohydride (0.25 g, 1.18 mmol), sodium acetate (0.10 g, 1.27 mmol) and 1,2-dichloroethane (9.0 mL). The mixture was stirred at room temperature for 24 hours, after which saturated aqueous sodium bicarbonate was added, then dichloromethane. The layers were separated. The aqueous layer was extracted twice with dichloromethane. The organic layers were dried with sodium sulfate, filtered and concentrated in vacuo. The crude was purified by flash chromatography to afford N,N-dimethyl-1-(5-nitro-1-(phenylsulfonyl)-1H-pyrrolo[2,3-b]pyridin-2-yl)methanamine (0.16 g, 49%).

Step B: Sodium hydroxide (1.11 mL, 1.11 mmol, 1M in water) was added to a solution of N,N-dimethyl-1-(5-nitro-1-(phenylsulfonyl)-1H-pyrrolo[2,3-b]pyridin-2-yl)methanamine (0.10 g, 0.28 mmol) in THF (1.5 mL). The reaction mixture was heated at 70° C. for 16 hours. The reaction mixture was then cooled down and treated with water and ethyl acetate. The layers were then separated. The aqueous layer was extracted once with ethyl acetate. The organic layers were dried over sodium sulfate, filtered, and evaporated to afford N,N-dimethyl-1-(5-nitro-1H-pyrrolo[2,3-b]pyridin-2-yl)methanamine (0.05 g, 82%).

Step C: $SnCl_2$ dihydrate (0.11 g, 0.463 mmol) was added to a solution of N,N-dimethyl-1-(5-nitro-1H-pyrrolo[2,3-b]pyridin-2-yl)methanamine (0.017 g, 0.077 mmol) in ethyl acetate (0.8 mL) and methanol (0.2 mL). The mixture was heated at 75° C. for 2 hours, after which saturated aqueous sodium bicarbonate was added. The salts were filtered off, and then the layers were separated. The organic layers were dried over sodium sulfate, filtered, and evaporated to afford 2-((dimethylamino)methyl)-1H-pyrrolo[2,3-b]pyridin-5-amine (0.008 g, 50%).

Step D: N-(2-((dimethylamino)methyl)-1H-pyrrolo[2,3-b]pyridin-5-yl)-2,6-difluoro-3-(propylsulfonamido)benzamide (0.007 g, 40%) was prepared according to Example 147, substituting 2-((dimethylamino)methyl)-1H-pyrrolo[2,3-b]pyridin-5-amine for 2,3-dimethyl-1H-pyrrolo[2,3-b]pyridin-5-amine. $^1$H NMR (500 MHz, $d_6$-DMSO) δ 11.54 (s, 1H), 10.77 (s, 1H), 8.29 (d, 1H), 8.24 (d, 1H), 8.17 (s, 1H), 7.56-7.44 (m, 1H), 7.27-7.15 (m, 1H), 6.31 (s, 1H), 3.55 (s, 2H), 3.14-3.01 (m, 2H), 2.20 (s, 6H), 1.91-1.61 (m, 2H), 0.99 (t, 3H); m/z (ES-MS) 452.1 (100.0%) [M+1].

Example 157

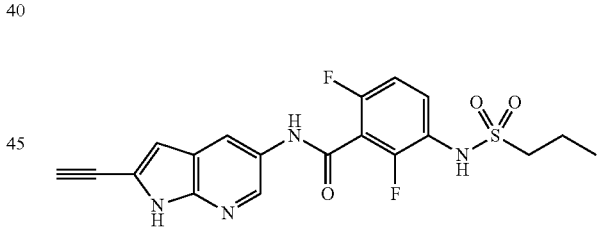

N-(2-ethynyl-1H-pyrrolo[2,3-b]pyridin-5-yl)-2,6-difluoro-3-(propylsulfonamido)benzamide Step A: Potassium carbonate (0.97 g, 6.98 mmol) was added to a suspension of 1-(phenylsulfonyl)-1H-pyrrolo[2,3-b]pyridine-2-carbaldehyde (1.00 g, 3.49 mmol) in methanol (1.0 mL), followed by the addition of a solution of dimethyl 1-diazo-2-oxopropylphosphonate (0.81 g, 4.19 mmol) in methanol (0.2 mL). The reaction mixture was stirred at room temperature for 2 hours, after which water was added, then ethyl acetate. The layers were separated. The aqueous layer was extracted twice with ethyl acetate. The organic layers were dried with sodium sulfate, filtered and concentrated in vacuo. The crude was purified by flash chromatography to afford 2-ethynyl-1-(phenylsulfonyl)-1H-pyrrolo[2,3-b]pyridine (0.40 g, 41%; purity 70%).

Step B: 2-Ethynyl-5-nitro-1-(phenylsulfonyl)-1H-pyrrolo[2,3-b]pyridine (0.032 g, 7%) was prepared according to Example 142, Step B, substituting 2-ethynyl-1-(phenylsulfonyl)-1H-pyrrolo[2,3-b]pyridine for 2-ethyl-1-(phenylsulfonyl)-1H-pyrrolo[2,3-b]pyridine.

Step C: Sodium hydroxide (0.39 mL, 0.39 mmol, 1M in water) was added to a solution of 2-ethynyl-5-nitro-1-(phenylsulfonyl)-1H-pyrrolo[2,3-b]pyridine (0.032 g, 0.10 mmol) in THF (0.5 mL). The reaction mixture was heated at 60° C. for 90 minutes. The reaction mixture was then cooled down and treated with water and ethyl acetate. The layers were then separated. The aqueous layer was extracted once with ethyl acetate. The organic layers were dried over sodium sulfate, filtered, and evaporated to afford 2-ethynyl-5-nitro-1H-pyrrolo[2,3-b]pyridine (0.02 g, quantitative yield).

Step D: 2-Ethynyl-1H-pyrrolo[2,3-b]pyridin-5-amine (0.015 g, 89%) was prepared according to Example 146, Step D, substituting 2-ethynyl-5-nitro-1H-pyrrolo[2,3-b]pyridine for 2,3-dimethyl-5-nitro-1H-pyrrolo[2,3-b]pyridine.

Step E: N-(2-Ethynyl-1H-pyrrolo[2,3-b]pyridin-5-yl)-2,6-difluoro-3-(propylsulfonamido)benzamide (0.015 g, 38%) was prepared according to Example 147, substituting 2-ethynyl-1H-pyrrolo[2,3-b]pyridin-5-amine for 2,3-dimethyl-1H-pyrrolo[2,3-b]pyridin-5-amine. $^1$H NMR (400 MHz, d$_6$-DMSO) δ 12.20 (s, 1H), 10.89 (s, 1H), 9.77 (br s, 1H), 8.43 (d, 1H), 8.37 (d, 1H), 7.54 (dd, 1H), 7.24 (t, 1H), 6.80 (d, 1H), 4.58 (s, 1H), 3.18-3.04 (m, 2H), 1.77 (m, 2H), 0.99 (t, 3H); m/z (ES-MS) 419.1 (98.7%) [M+1].

Example 158

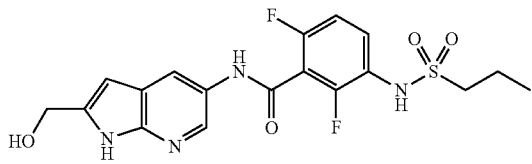

2,6-difluoro-N-(2-(hydroxymethyl)-1H-pyrrolo[2,3-b]pyridin-5-yl)-3-(propylsulfonamido)benzamide Step A: Sodium tetrahydroborate (0.069 g, 1.81 mmol) was added to a solution of 5-nitro-1-(phenylsulfonyl)-1H-pyrrolo[2,3-b]pyridine-2-carbaldehyde (200 mg, 0.60 mmol) in THF (3.8 mL) and methanol (0.4 mL) at −40° C. The mixture was stirred at −40° C. for 30 minutes. The reaction mixture was then treated with water and ethyl acetate, and the layers were separated. The aqueous layer was extracted once with ethyl acetate. The organic layers were dried with sodium sulfate, filtered and concentrated in vacuo. The crude material was purified by flash chromatography to afford (5-nitro-1-(phenylsulfonyl)-1H-pyrrolo[2,3-b]pyridin-2-yl)methanol (0.13 g, 65%).

Step B: (5-Nitro-1H-pyrrolo[2,3-b]pyridin-2-yl)methanol (0.025 g, 39%) was prepared according to Example 157, Step C, substituting (5-nitro-1-(phenylsulfonyl)-1H-pyrrolo[2,3-b]pyridin-2-yl)methanol for 2-ethynyl-5-nitro-1-(phenylsulfonyl)-1H-pyrrolo[2,3-b]pyridine.

Step C: (5-Amino-1H-pyrrolo[2,3-b]pyridin-2-yl)methanol (0.018 g, 85%) was prepared according to Example 156, Step C, substituting (5-nitro-1H-pyrrolo[2,3-b]pyridin-2-yl)methanol for N,N-dimethyl-1-(5-nitro-1H-pyrrolo[2,3-b]pyridin-2-yl)methanamine.

Step D: 2,6-Difluoro-N-(2-(hydroxymethyl)-1H-pyrrolo[2,3-b]pyridin-5-yl)-3-(propylsulfonamido)benzamide (0.005 g, 10%) was prepared according to Example 147, substituting (5-amino-1H-pyrrolo[2,3-b]pyridin-2-yl)methanol for 2,3-dimethyl-1H-pyrrolo[2,3-b]pyridin-5-amine. m/z (ES-MS) 425.1 (100.0%) [M+1].

Example 159

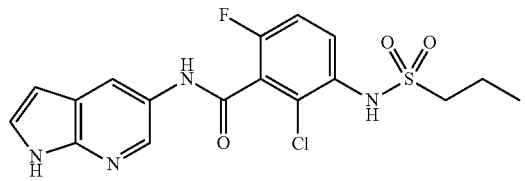

2-chloro-6-fluoro-3-(propylsulfonamido)-N-(1H-pyrrolo[2,3-b]pyridin-5-yl)benzamide 1H-Pyrrolo[2,3-b]pyridin-5-amine (20 mg, 0.150 mmol) in N,N-dimethylformamide (1.5 mL) was sequentially treated with 2-chloro-6-fluoro-3-(propylsulfonamido)benzoic acid (48.9 mg, 0.165 mmol), 1-(3-dimethylaminopropyl)-3-ethylcarbodiimide hydrochloride (31.7 mg, 0.165 mmol), and 1-hydroxybenzotriazole (22.3 mg, 0.165 mmol) at ambient temperature. After 24 hours, the reaction mixture was diluted with ethyl acetate and washed with water (4×), sodium bicarbonate (2×), and brine (1×), dried over sodium sulfate and concentrated. The crude product was triturated with dichloromethane to provide 2-chloro-6-fluoro-3-(propylsulfonamido)-N-(1H-pyrrolo[2,3-b]pyridin-5-yl)benzamide (61.7 mg, 0.0382 mmol, 25.4% yield) as a solid. $^1$H NMR (400 MHz, CD$_3$OD) δ 8.40-8.35 (d, 2H), 7.73-7.67 (q, 1H), 7.45-7.42 (d, 1H), 7.31-7.25 (t, 1H), 6.53-6.50 (d, 1H), 3.15-3.08 (t, 2H), 1.93-1.82 (m, 2H), 1.08-1.02 (t, 3H); MS (APCI-neg) m/z=409.1 (M-H).

Example 160

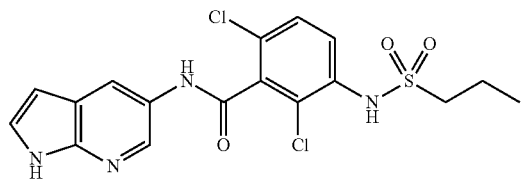

2,6-dichloro-3-(propylsulfonamido)-N-(1H-pyrrolo[2,3-b]pyridin-5-yl)benzamide

1H-Pyrrolo[2,3-b]pyridin-5-amine (192 mg, 1.44 mmol) in N,N-dimethylformamide (7.2 mL) was sequentially treated with 2,6-dichloro-3-(propylsulfonamido)benzoic acid (690.5 mg, 2.212 mmol), 1-(3-dimethylaminopropyl)-3-ethylcarbodiimide hydrochloride (466.4 mg, 2.433 mmol), and 1-hydroxybenzotriazole (328.8 mg, 2.433 mmol) and heated to 60° C. After 24 hours, the reaction mixture was allowed to cool to ambient temperature. The mixture was diluted with ethyl acetate, washed with water (4×), sodium bicarbonate (2×), and brine (1×), dried over sodium sulfate, and concentrated. The crude product was applied directly to a silica gel column and eluted with a gradient (30% to 100%) of ethyl acetate-hexanes to provide 2,6-dichloro-3-(propylsulfonamido)-N-(1H-pyrrolo[2,3-b]pyridin-5-yl)benzamide (10.5 mg, 0.0246 mmol, 3.41% yield) as a solid. $^1$H NMR (400 MHz, d$_6$-DMSO) δ 11.70-11.59 (s, 1H), 10.77-10.68 (s, 1H), 9.88-9.75 (s, 1H), 8.39-8.30 (m, 2H), 7.56-7.47 (m, 3H), 6.49-6.45 (d, 1H), 3.21-3.04 (m, 2H), 1.82-1.70 (m, 2H), 1.03-0.95 (t, 3H); MS (APCI-neg) m/z=425.1 (M-H).

Example 161

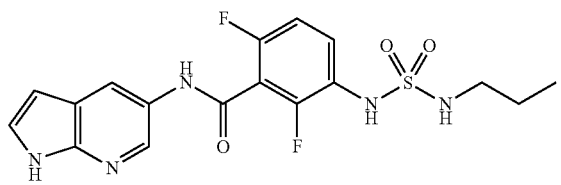

2,6-difluoro-3-(N-propylsulfamoylamino)-N-(1H-pyrrolo[2,3-b]pyridin-5-yl)benzamide Step A: Propylsulfamoyl chloride (0.379 mL, 2.40 mmol) was added to methyl 3-amino-2,6-difluorobenzoate (0.150 mL, 0.802 mmol), TEA (0.335 mL, 2.40 mmol) in DCM (1.5 mL) at 0° C. The solution was allowed to warm to room temperature overnight. The solids were filtered, and the supernate was concentrated to provide crude methyl 2,6-difluoro-3-(N-propylsulfamoylamino)benzoate, which was used directly in next step.

Step B: NaOH (1M, 3.20 mL, 3.20 mmol) was added to methyl 2,6-difluoro-3-(N-propylsulfamoylamino)benzoate (0.24 g, 0.80 mmol) in 2:1 THF:MeOH (3 mL). The solution was stirred at room temperature for 16 hours, and then the solution was stirred at 70° C. for 16 hours. The solution was concentrated under reduced pressure to about half volume and then washed with EtOAc. The pH was adjusted to about 5 and extracted with EtOAc (3×5 mL). The organic layers were dried over sodium sulfate, decanted and concentrated to provide 2,6-difluoro-3-(N-propylsulfamoylamino)benzoic acid.

Step C: 2,6-Difluoro-3-(N-propylsulfamoylamino)benzoic acid (0.095 g, 0.32 mmol), 1H-pyrrolo[2,3-b]pyridin-5-amine (0.043 g, 0.32 mmol), HOBt (0.044 g, 0.32 mmol), and EDCI (0.062 g, 0.32 mmol) were dissolved in DMF (1.6 mL) and stirred at room temperature for 16 hours. The mixture was diluted with EtOAc (30 mL) and washed with a mixture of 1:1:1 water:bicarbonate:brine (3×20 mL). The organic layers were dried over sodium sulfate and concentrated under reduced pressure. The residue was purified via column chromatography eluting with 1:1 then 8:2 EtOAc:hexanes to provide 2,6-difluoro-3-(N-propylsulfamoylamino)-N-(1H-pyrrolo[2,3-b]pyridin-5-yl)benzamide (0.060 g, 0.15 mmol, 45% yield). $^1$H NMR (400 MHz, CD$_3$OD) δ 8.36-8.40 (m, 2H), 7.64-7.72 (m, 1H), 7.41-7.43 (m, 1H), 7.06-7.13 (m, 1H), 6.50-6.52 (m, 1H), 2.96-3.02 (m, 2H), 1.47-1.57 (m, 2H), 0.87-0.93 (m, 3H); m/z (APCI-pos) M+1=410.2.

Example 162

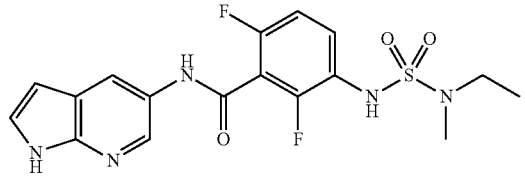

3-(N-ethyl-N-methylsulfamoylamino)-2,6-difluoro-N-(1H-pyrrolo[2,3-b]pyridin-5-yl)benzamide Step A: A solution of triethylamine (0.260 mL, 1.85 mmol) and methyl 3-amino-2,6-difluorobenzoate (0.257 mL, 1.85 mmol) was added dropwise to sulfuryl dichloride (0.156 mL, 1.85 mmol) in DCM (3 mL) at −78° C. After 2 hours, N-methylethanamine (0.304 mL, 3.70 mmol) was added, and the reaction mixture was allowed to warm to room temperature overnight. The solvent was concentrated under reduced pressure, and the residue was taken up in NaOH (2 mL, 1M) and washed with EtOAc. The aqueous pH was lowered to below 3 and extracted with EtOAc (3×5 mL). The combined organic layers were dried over sodium sulfate, decanted and concentrated under reduced pressure. The residue was purified via silica gel chromatography eluting with 7:3 hexane-EtOAc to afford impure methyl 3-(N-ethyl-N-methylsulfamoylamino)-2,6-difluorobenzoate (0.280 g, 49.0% yield).

Step B: NaOH (0.908 mL, 1.82 mmol) was added to methyl 3-(N-ethyl-N-methylsulfamoylamino)-2,6-difluorobenzoate (0.280 g, 0.908 mmol) in THF-MeOH (3:2; 5 mL). The mixture was warmed to 60° C. for 16 hours. The cooled mixture was concentrated under reduced pressure, and the residue was taken up in 1M NaOH (4 mL) and washed with EtOAc. The aqueous pH was lowered to below 3 and extracted with EtOAc (3×6 mL) to provide crude 3-(N-ethyl-N-methylsulfamoylamino)-2,6-difluorobenzoic acid (222 mg, 83% yield).

Step C: HOBt (0.011 g, 0.085 mmol), EDCI (0.036 g, 0.19 mmol), and 1H-pyrrolo[2,3-b]pyridin-5-amine (0.025 g, 0.19 mmol) was added to 3-(N-ethyl-N-methylsulfamoylamino)-2,6-difluorobenzoic acid (0.050 g, 0.17 mmol) in DMF (1 mL). The reaction mixture was stirred at room temperature for 16 hours. The mixture was diluted with EtOAc (6 mL) and washed with brine (3×5 mL). The organic layers were dried over sodium sulfate, decanted, and concentrated under reduced pressure. The residue was purified via silica gel chromatography eluting with 5% MeOH-DCM to afford 3-(N-ethyl-N-methylsulfamoylamino)-2,6-difluoro-N-(1H-pyrrolo[2,3-b]pyridin-5-yl)benzamide (0.005 g, 0.012 mmol, 7.2% yield). m/z (APCI-neg) M−1=408.0.

The following compounds in Table 6 were prepared following the above procedures.

TABLE 6

| Ex. # | Structure | Name | MS/NMR |
|---|---|---|---|
| 163 | 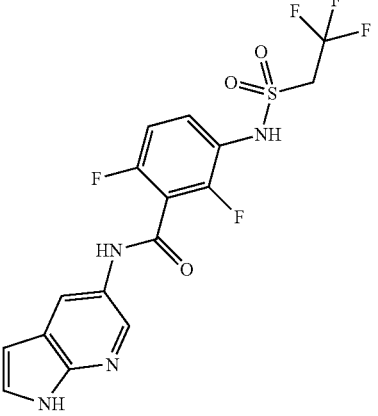 | 2,6-difluoro-N-(1H-pyrrolo[2,3-b]pyridin-5-yl)-3-(2,2,2-trifluoroethyl-sulfonamido)-benzamide | $^1$H NMR (400 MHz, DMSO) δ 11.63 (s, 1H), 10.80 (s, 1H), 10.50 (s, 1H), 8.36 (dd, J = 2.2, 9.9, 2H), 7.65-7.43 (m, 2H), 7.26 (t, J = 8.6, 1H), 6.47 (dd, J = 1.9, 3.3, 1H), 4.53 (q, J = 9.8, 2H), 3.29 (s, 34H), 2.56-2.43 (m, 30H), 2.07 (s, 2H); m/z (LC-MS) M + 1 = 435.3 |
| 164 | 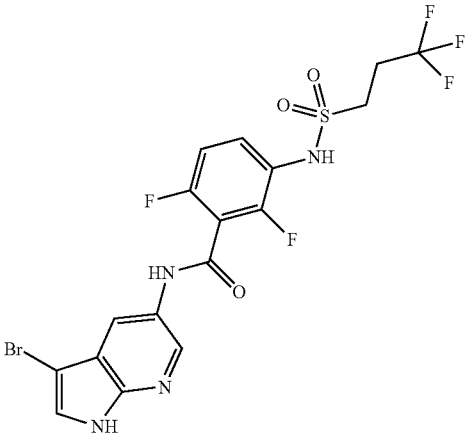 | N-(3-bromo-1H-pyrrolo[2,3-b]pyridin-5-yl)-2,6-difluoro-3-(3,3,3-trifluoropropyl-sulfonamido)-benzamide | $^1$H NMR (400 MHz, DMSO) δ 12.11 (s, 1H), 11.01 (s, 1H), 10.09 (s, 1H), 8.37 (dd, J = 2.2, 25.7, 2H), 7.75 (d, J = 2.7, 1H), 7.68-7.45 (m, 1H), 7.31 (t, J = 8.8, 1H), 3.62-3.04 (m, 43H), 3.01-2.66 (m, 3H), 2.66-2.33 (m, 35H); m/z (LC-MS) M + 1 = 527.3 |
| 165 | 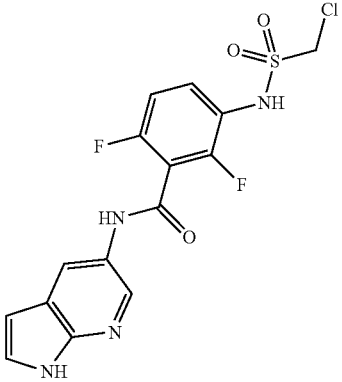 | 3-(chloromethyl-sulfonamido)-2,6-difluoro-N-(1H-pyrrolo[2,3-b]pyridin-5-yl)benzamide | $^1$H NMR (400 MHz, DMSO) δ 11.63 (s, 4H), 10.80 (s, 4H), 10.68-10.01 (m, 3H), 8.36 (dd, J = 2.2, 9.7, 7H), 7.72-7.39 (m, 8H), 7.24 (t, J = 8.7, 4H), 6.47 (dd, J = 1.9, 3.3, 4H), 5.01 (s, 7H), 3.30 (s, 73H), 2.70 (d, J = 25.0, 1H), 2.46 (dd, J = 34.7, 36.4, 69H); m/z (LC-MS) M + 1 = 401.8 |

TABLE 6-continued

| Ex. # | Structure | Name | MS/NMR |
|---|---|---|---|
| 166 | 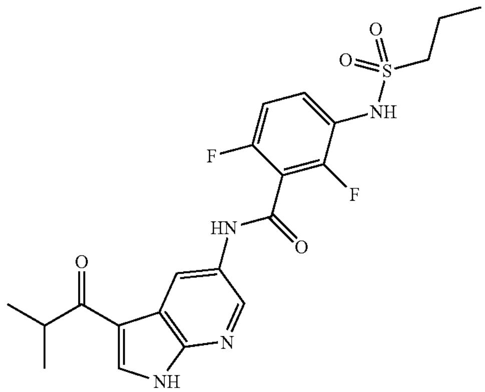 | 2,6-difluoro-N-(3-isobutyryl-1H-pyrrolo[2,3-b]pyridin-5-yl)-3-(propylsulfonamido)-benzamide | $^1$H NMR (400 MHz, MeOH-d$_4$) δ 8.90-8.92 (m, 1H), 8.64-8.66 (m, 1H), 8.36-8.37 (m, 1H), 7.62-7.70 (m, 1H), 7.11-7.17 (m, 1H), 3.46-3.54 (m, 1H), 3.09-3.15 (m, 2H), 1.82-1.94 (m, 2H), 1.23 (d, 6H), 1.04-1.09 (m, 3H) |
| 167 | 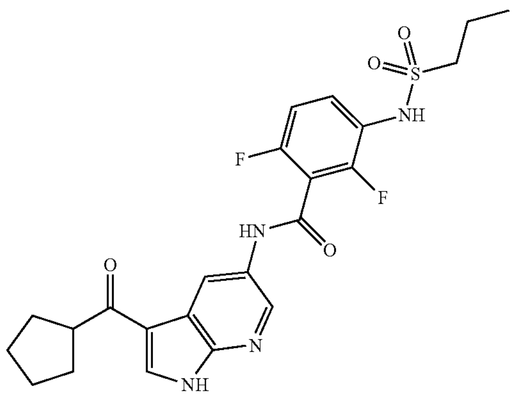 | N-(3-(cyclopentane-carbonyl)-1H-pyrrolo[2,3-b]pyridin-5-yl)-2,6-difluoro-3-(propylsulfonamido)-benzamide | $^1$H NMR (400 MHz, MeOH-d$_4$) δ 8.90-8.92 (m, 1H), 8.63-8.65 (m, 1H), 8.35 (s, 1H), 7.62-7.69 (m, 1H), 7.11-7.17 (m, 1H), 3.65-3.75 (m, 1H), 3.09-3.14 (m, 2H), 1.84-2.2 (m, 6H), 1.64-1.84 (m, 4H), 1.04-1.09 (m, 3H); m/z (APCI-pos) M + 1 = 491.1 |
| 168 | 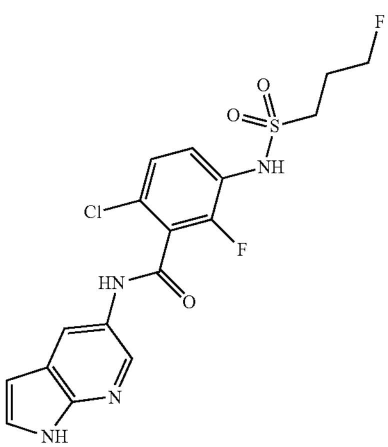 | 6-chloro-2-fluoro-3-(3-fluoropropyl-sulfonamido)-N-(1H-pyrrolo[2,3-b]pyridin-5-yl)benzamide | $^1$H NMR (400 MHz, DMSO-d$_6$) δ 11.7 (br s, 1H), 10.8 (br s, 1H), 10.1 (br s, 1H), 8.3 (m, 2H), 7.5 (m, 3H), 6.5 (m, 1H), 4.6 (m, 1H), 4.5 (m, 1H), 3.3 (m, 2H), 2.2-2.1 (m, 2H); m/z (APCI-pos) M + 1 = 429.1, 431.1 |
| 169 | 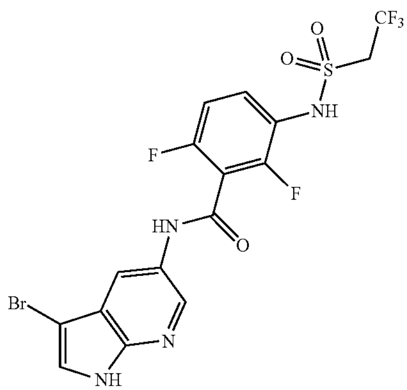 | N-(3-bromo-1H-pyrrolo[2,3-b]pyridin-5-yl)-2,6-difluoro-3-(2,2,2-trifluoroethyl-sulfonamido)-benzamide | $^1$H NMR (400 MHz, DMSO) δ 11.63 (s, 2H), 10.80 (s, 1H), 10.50 (s, 2H), 8.36 (dd, J = 2.2, 9.9, 4H), 7.57 (dd, J = 9.0, 14.9, 2H), 7.37 (dt, J = 5.9, 17.2, 4H), 6.47 (dd, J = 1.9, 3.3, 2H), 4.53 (q, J = 9.8, 4H), 3.67 (s, 1H), 2.07 (s, 3H); m/z (LC-MS) M + 1 = 514.2 |

| Ex. # | Structure | Name | MS/NMR |
|---|---|---|---|
| 170 | 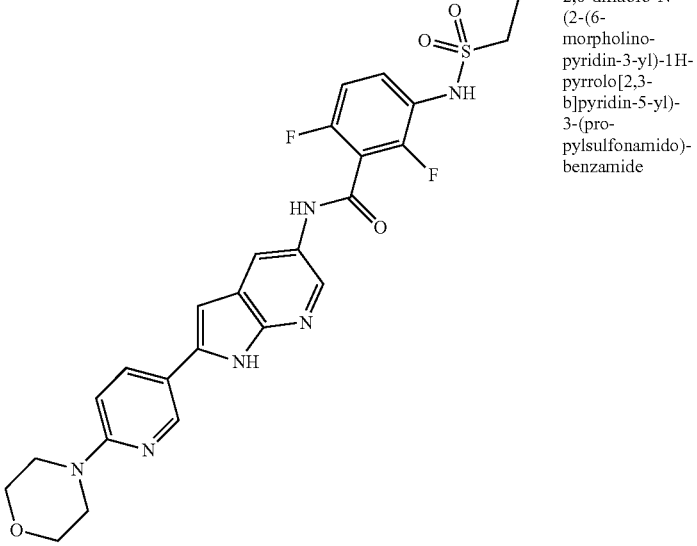 | 2,6-difluoro-N-(2-(6-morpholino-pyridin-3-yl)-1H-pyrrolo[2,3-b]pyridin-5-yl)-3-(pro-pylsulfonamido)-benzamide | $^1$H NMR (400 MHz, DMSO-d$_6$) δ 12.01 (br s, 1H), 10.85 (br s, 1H), 9.77 (br s, 1H), 8.72-8.74 (m, 1H), 8.33-8.35 (m, 1H), 8.27-8.29 (m, 1H), 8.06-8.11 (m, 1H), 7.50-7.59 (m, 1H), 7.23-7.29 (m, 1H), 6.94-9.98 (m, 1H), 6.82-6.84 (m, 1H), 3.70-3.74 (m, 4H), 3.51-3.55 (m, 4H), 3.09-3.15 (m, 2H), 1.74-1.83 (m, 2H), 0.97-1.03 (m, 3H); m/z (APCI-pos) M + 1 = 557.1 |
| 171 | 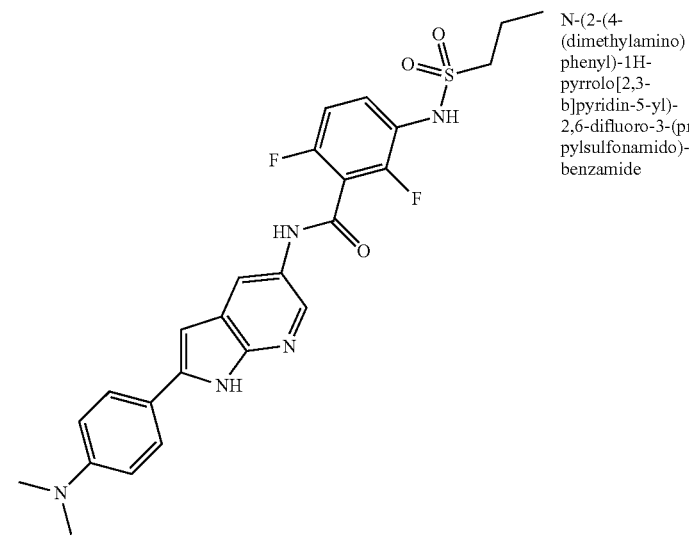 | N-(2-(4-(dimethylamino)phenyl)-1H-pyrrolo[2,3-b]pyridin-5-yl)-2,6-difluoro-3-(pro-pylsulfonamido)-benzamide | $^1$H NMR (400 MHz, MeOH-d$_4$) 8.41-8.42 (m, 1H), 8.34-36 (m, 1H), 8.13-8.17 (m, 1H), 7.82-7.86 (m, 1H), 7.61-7.69 (m, 1H), 7.53-7.58 (m, 1H), 7.43-7.48 (m, 1H), 7.10-7.16 (m, 1H), 6.84 (s, 1H), 3.29-3.32 (br s, coincident with solvent), 3.09-3.14 (m, 2H), 1.83-1.93 (m, 2H), 1.04-1.09 (m, 3H); m/z (APCI-pos) M + 1 = 514.1 |
| 172 | 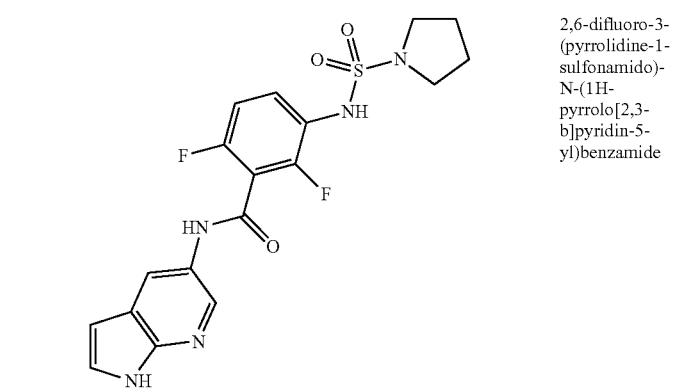 | 2,6-difluoro-3-(pyrrolidine-1-sulfonamido)-N-(1H-pyrrolo[2,3-b]pyridin-5-yl)benzamide | m/z (APCI-neg) M − 1 = 420.0 |

TABLE 6-continued

| Ex. # | Structure | Name | MS/NMR |
|---|---|---|---|
| 173 | 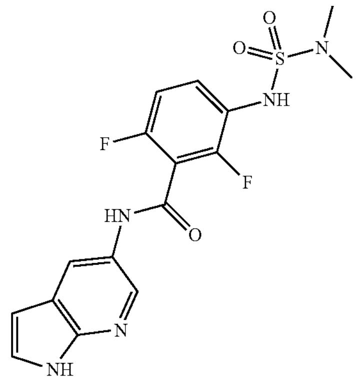 | 3-(N,N-dimethyl-sulfamoylamino)-2,6-difluoro-N-(1H-pyrrolo[2,3-b]pyridin-5-yl)benzamide | m/z (APCI-neg) M − 1 = 394.0 |

While the invention has been described in conjunction with the enumerated embodiments, it will be understood that they are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:
1. A compound selected from Formula I:

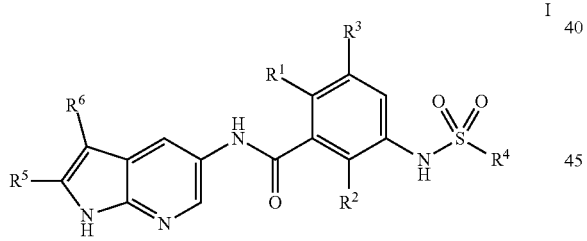

I and stereoisomers, tautomers, and pharmaceutically acceptable salts thereof, wherein:
$R^1$ and $R^2$ are independently selected from hydrogen, halogen, CN, $C_1$-$C_3$ alkyl and $C_1$-$C_3$ alkoxy;
$R^3$ is hydrogen, halogen or $C_1$-$C_3$ alkyl;
$R^4$ is $C_3$-$C_5$ cycloalkyl, $C_1$-$C_6$ alkyl, $C_2$-$C_6$ alkenyl, or $C_2$-$C_6$ alkynyl, phenyl, a 5-6 membered heteroaryl, or $NR^nR^o$, wherein the cycloalkyl, alkyl, alkenyl, alkynyl, phenyl and heteroaryl are optionally substituted with $OR^g$, halogen, phenyl, $C_3$-$C_4$ cycloalkyl, or $C_1$-$C_4$ alkyl optionally substituted with halogen;
$R^5$ is:
hydrogen,
halogen,
CN,
$NR^kR^l$,
$C_1$-$C_6$ alkyl optionally substituted with halogen, oxo, $OR^g$ or $NR^gR^h$,
$C_2$-$C_6$ alkenyl optionally substituted with halogen, $OR^g$ or $NR^gR^h$,
$C_2$-$C_6$ alkynyl optionally substituted with halogen, $OR^g$ or $NR^gR^h$,
a saturated or partially unsaturated $C_3$-$C_6$ cycloalkyl optionally substituted with halogen or $C_1$-$C_4$ alkyl,
a saturated or partially unsaturated 4-6 membered heterocyclyl optionally substituted with $C_1$-$C_4$ alkyl,
a 5-6 membered heteroaryl optionally substituted with $R^c$,
a 9-10 membered bicyclic heterocyclyl optionally substituted with $C_1$-$C_4$ alkyl,
a 9-10 membered bicyclic heteroaryl optionally substituted with $C_1$-$C_4$ alkyl, or phenyl optionally substituted with $R^d$;
$R^6$ is:
hydrogen,
halogen,
CN,
$NR^kR^l$,
a saturated or partially unsaturated $C_3$-$C_6$ cycloalkyl optionally substituted with halogen or $C_1$-$C_4$ alkyl,
a saturated or partially unsaturated 4-6 membered heterocyclyl optionally substituted with $C_1$-$C_4$ alkyl,
phenyl optionally substituted with one to three $R^a$ groups,
a 5-6 membered heteroaryl optionally substituted with $C_1$-$C_4$ alkyl or benzyl,
$C_2$-$C_6$ alkenyl optionally substituted with halogen, $OR^g$ or $NR^gR^h$,
$C_2$-$C_6$ alkynyl optionally substituted with halogen, $OR^g$ or $NR^gR^h$, or
$C_1$-$C_6$ alkyl optionally substituted with one to three $R^h$ groups;
each $R^a$ is independently selected from halogen, CN, $CF_3$, OH, —O($C_1$-$C_4$ alkyl), a 5-6 membered heterocyclyl, or $C_1$-$C_4$ alkyl optionally substituted with $NR^gR^h$ or a 5-6 membered heterocyclyl;
each $R^b$ is independently selected from halogen, OH, $OCH_3$, oxo, —$NR^eR^f$, phenyl optionally substituted with a halogen, $C_3$-$C_6$ cycloalkyl, or a 5-6 membered heterocyclyl optionally substituted with halogen;
$R^c$ is —$NR^hR^j$, $C_1$-$C_4$ alkyl, or a 5-6 membered heterocyclyl optionally substituted by $C_1$-$C_4$ alkyl or —$(CH_2)_p$$C_3$-$C_6$ cycloalkyl;
$R^d$ is halogen, CN, $NR^gR^h$, phenyl, a 5-6 membered heterocyclyl, —O($C_1$-$C_4$ alkyl) or $C_1$-$C_4$ alkyl, wherein the alkyl or alkoxy are optionally substituted with halogen, OH, oxo, —O(C$_1$-C$_3$ alkyl), NR$^g$R$^h$, or a 5-6 membered heterocyclyl optionally substituted with C$_1$-C$_3$ alkyl;

R$^e$ and R$^f$ are independently selected from hydrogen, C$_1$-C$_4$ alkyl or phenyl;

each R$^g$ and R$^h$ are independently selected from hydrogen or C$_1$-C$_4$ alkyl;

R$^j$ is hydrogen or C$_1$-C$_4$ alkyl optionally substituted with a 5-6 membered heterocyclyl;

each R$^k$ and R$^l$ are independently selected from hydrogen or C$_1$-C$_4$ alkyl;

R$^m$ is selected from hydrogen or C$_1$-C$_4$ alkyl;

R$^n$ and R$^o$ are independently selected from hydrogen and C$_1$-C$_5$ alkyl, or R$^n$ and R$^o$ together with the nitrogen to which they are attached form a 4 to 6 membered heterocyclic ring; and p is 0 or 1.

2. A compound of claim 1, wherein R$^1$, R$^2$ and R$^3$ are independently selected from hydrogen, halogen or C$_1$-C$_3$ alkyl.

3. A compound of claim 1, wherein the residue:

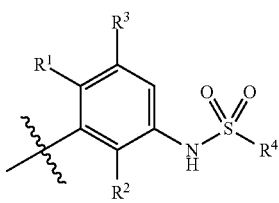

of Formula I, wherein the wavy line represents the point of attachment of the residue in Formula I, is selected from:

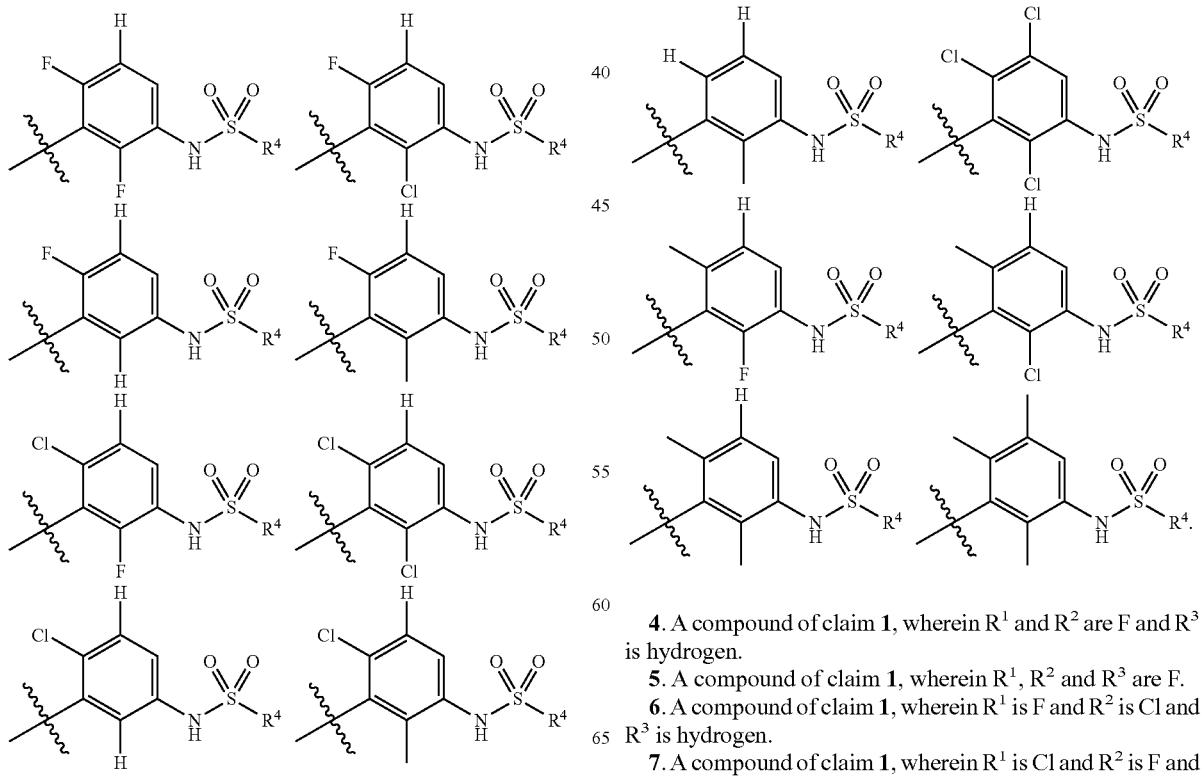

4. A compound of claim 1, wherein R$^1$ and R$^2$ are F and R$^3$ is hydrogen.

5. A compound of claim 1, wherein R$^1$, R$^2$ and R$^3$ are F.

6. A compound of claim 1, wherein R$^1$ is F and R$^2$ is Cl and R$^3$ is hydrogen.

7. A compound of claim 1, wherein R$^1$ is Cl and R$^2$ is F and R$^3$ is hydrogen.

8. A compound of claim 1, wherein $R^1$ is F and $R^2$ is methyl and $R^3$ is hydrogen.

9. A compound of claim 1, wherein $R^1$ is methyl and $R^2$ is F and $R^3$ is hydrogen.

10. A compound of claim 1, wherein $R^1$ is F and $R^2$ and $R^3$ are hydrogen.

11. A compound of claim 1, wherein $R^1$ is Cl and $R^2$ and $R^3$ are hydrogen.

12. A compound of claim 1, wherein $R^2$ is F and $R^1$ and $R^3$ are hydrogen.

13. A compound of claim 1, wherein $R^2$ and $R^3$ are F and $R^1$ is hydrogen.

14. A compound of claim 1, wherein $R^4$ is cyclopropyl, ethyl, propyl, butyl, isobutyl, —$CH_2Cl$, —$CH_2CF_3$, —$CH_2CH_2CH_2F$, —$CH_2CH_2CF_3$, phenylmethyl, cyclopropylmethyl, phenyl, 2-fluorophenyl, 3-fluorophenyl, 4-fluorophenyl, 2,5-difluorophenyl, 4-chloro-3-trifluoromethylphenyl, 1-methyl-1H-imidazol-4-yl, furan-2-yl, pyridin-2-yl, pyridin-3-yl, thiophen-2-yl, —$NHCH_2CH_3$, —$NHCH_2CH_2CH_3$—$N(CH_3)CH_2CH_3$, —$N(CH_3)_2$, or pyrrolidine.

15. A compound of claim 1, wherein $R^4$ is cyclopropyl, propyl, butyl, isobutyl, —$CH_2Cl$, —$CH_2CF_3$, —$CH_2CH_2CH_2F$, —$CH_2CH_2CF_3$, cyclopropylmethyl, —$NHCH_2CH_2CH_3$, —$N(CH_3)CH_2CH_3$, —$N(CH_3)_2$, or pyrrolidine.

16. A compound of claim 1, wherein $R^4$ is propyl, butyl, isobutyl, —$CH_2CH_2CH_2F$, —$CH_2CH_2CF_3$ or cyclopropylmethyl.

17. A compound of claim 1, wherein $R^4$ is propyl.

18. A compound of claim 1, wherein $R^4$ is —$CF_3$, —$CH_2CF_3$, —$CH_2CH_2CH_2F$, —$CH_2CH_2CF_3$, —$CF_2CF_3$ or —$CF_2CF_2CF_3$.

19. A compound of claim 1, wherein $R^6$ is hydrogen.

20. A compound of claim 1, wherein $R^6$ is halogen or CN.

21. A compound of claim 1, wherein $R^6$ is a saturated or partially unsaturated $C_3$-$C_6$ cycloalkyl selected from cyclopropyl, cyclobutyl, cyclopentyl, cyclopentenyl, cyclohexyl and cyclohexenyl.

22. A compound of of claim 1, wherein $R^6$ is $C_1$-$C_6$ alkyl optionally substituted with one to three $R^b$ groups.

23. A compound of claim 22, wherein $R^6$ is $C_1$-$C_4$ alkyl optionally substituted with one to three $R^b$ groups, wherein each $R^b$ is independently selected from halogen, OH, $OCH_3$, oxo, —$NR^eR^f$, phenyl optionally substituted with a halogen, $C_3$-$C_6$ cycloalkyl, and a 5-6 membered heterocyclyl optionally substituted with halogen.

24. A compound of claim 1, wherein $R^6$ is $C_1$-$C_2$ alkyl optionally substituted by one to three groups selected from F, $C_1$-$C_2$ alkyl optionally substituted by oxo and —$NR^eR^f$, $C_1$-$C_2$ alkyl optionally substituted by oxo and phenyl optionally substituted by halogen, $C_1$-$C_2$ alkyl optionally substituted by oxo and $OCH_3$, $C_1$-$C_2$ alkyl optionally substituted by OH and phenyl optionally substituted by halogen, $C_1$-$C_2$ alkyl optionally substituted by oxo and a 5-6 membered heterocyclyl optionally substituted with halogen, or $C_1$-$C_3$ alkyl optionally substituted by $OCH_3$ or OH.

25. A compound of claim 1, wherein $R^6$ is phenyl optionally substituted with one to three $R^a$ groups or a 5-6 membered heteroaryl optionally substituted with $C_1$-$C_4$ alkyl or benzyl.

26. A compound of claim 1, wherein $R^6$ is $NR^kR^l$.

27. A compound of claim 1, wherein $R^6$ is $OR^m$.

28. A compound of claim 1, wherein $R^6$ is a saturated or partially unsaturated 4-6 membered heterocyclyl.

29. A compound of claim 1, wherein $R^6$ is a 5-6 membered heteroaryl optionally substituted with $C_1$-$C_4$ alkyl or benzyl.

30. A compound of claim 1, wherein $R^6$ is $C_2$-$C_4$ alkenyl.

31. A compound of claim 1, wherein $R^6$ is $C_2$-$C_6$ alkynyl optionally substituted with $OR^g$.

32. A compound of claim 1, wherein $R^6$ is selected from hydrogen, Cl, Br, I, CN, cyclohexyl, cyclopentyl, cyclobutyl, cyclopropyl, cyclopentenyl, (2,2-dimethyl-1,3-dioxolan-4-yl)methoxy, phenyl, 2-fluorophenyl, 3-fluorophenyl, 4-fluorophenyl, 3-chlorophenyl, 4-chlorophenyl, 3-methylphenyl, 3-methoxyphenyl, 3-isopropylphenyl, 3-isopropoxyphenyl, 3-trifluoromethylphenyl, 4-trifluoromethylphenyl, 3-morpholinophenyl, 2,5-difluorophenyl, 3,4-difluorophenyl, 3-chloro-4-fluorophenyl, 3,5-difluorophenyl, 3-((dimethylamino)methyl)phenyl, 3-(morpholinomethyl)phenyl, pyridin-3-yl, furan-3-yl, thiopheny-3-yl, 2-methylthiazol-4-yl, 1-methyl-1H-pyrazol-4-yl, 1H-pyrazol-5-yl, 1-benzyl-1H-pyrazol-4-yl, —$CH$=$CH_2$, —$C$≡$CCH_2OH$, —$C$≡$CCH_2OCH_3$, methyl, ethyl, tert-butyl, cyclopropylmethyl, —$CH_2CH_2CH_2OCH_3$, —$CH_2CH_2CH_2OH$, —$CH_2$-4-chlorophenyl, —$C(=O)CH_3$, —$C(=O)CH_2N(CH_3)_2$, —$C(=O)NH(phenyl)$, —$C(=O)NH(CH_3)$, —$C(=O)N(CH_3)_2$, —$C(=O)cyclopropyl$, —$CH(OH)$-4-chlorophenyl, —$C(=O)$-4-chlorophenyl, —$C(=O)$-3,4-dichlorophenyl, —$C(=O)CH_2$-piperidin-1-yl, —$C(=O)CH_2$-3-fluoropiperidin-1-yl, —$C(=O)OCH_3$ and $CF_3$.

33. A compound of claim 1, wherein $R^6$ is selected from hydrogen, Cl, Br, I, CN, cyclohexyl, cyclopentyl, cyclobutyl, cyclopropyl, cyclopentenyl, phenyl, 2-fluorophenyl, 3-fluorophenyl, 4-fluorophenyl, 3-chlorophenyl, 4-chlorophenyl, 3-methylphenyl, 3-methoxyphenyl, 3-isopropylphenyl, 3-isopropoxyphenyl, 3-trifluoromethylphenyl, 4-trifluoromethylphenyl, 3-morpholinophenyl, 2,5-difluorophenyl, 3,4-difluorophenyl, 3-chloro-4-fluorophenyl, 3,5-difluorophenyl, 3-((dimethylamino)methyl)phenyl, 3-(morpholinomethyl)phenyl, pyridin-3-yl, furan-3-yl, thiopheny-3-yl, 2-methylthiazol-4-yl, 1-methyl-1H-pyrazol-4-yl, 1H-pyrazol-5-yl, 1-benzyl-1H-pyrazol-4-yl, —$CH$=$CH_2$, —$C$≡$CCH_2OH$, —$C$≡$CCH_2OCH_3$, methyl, ethyl, tert-butyl, cyclopropylmethyl, —$CH_2CH_2CH_2OCH_3$, —$CH_2CH_2CH_2OH$, —$CH_2$-4-chlorophenyl, —$C(=O)CH_3$, —$C(=O)CH_2N(CH_3)_2$, —$C(=O)NH(phenyl)$, —$C(=O)NH(CH_3)$, —$C(=O)N(CH_3)_2$, —$C(=O)cyclopropyl$, —$CH(OH)$-4-chlorophenyl, —$C(=O)$-4-chlorophenyl, —$C(=O)$-3,4-dichlorophenyl, —$C(=O)CH_2$-piperidin-1-yl, —$C(=O)CH_2$-3-fluoropiperidin-1-yl, —$C(=O)OCH_3$ and $CF_3$.

34. A compound of claim 1, wherein $R^5$ is phenyl optionally substituted halogen, $NR^gR^h$, phenyl, a 5-6 membered heterocyclyl, —$O(C_1$-$C_4$ alkyl) or $C_1$-$C_4$ alkyl, wherein the alkyl or alkoxy are optionally substituted with halogen, OH, oxo, —$O(C_1$-$C_3$ alkyl), $NR^gR^h$, or a 5-6 membered heterocyclyl optionally substituted with $C_1$-$C_3$ alkyl.

35. A compound of claim 1, wherein $R^5$ is a 5-6 membered heteroaryl selected from pyridyl, pyrazolyl and imidazolyl, wherein the heteroaryl is optionally substituted by —$NR^hR^j$, $C_1$-$C_4$ alkyl or a 5-6 membered heterocyclyl optionally substituted by $C_1$-$C_4$ alkyl.

36. A compound of claim 1, wherein $R^5$ is $C_3$-$C_6$ alkynyl optionally substituted with OH or $NR^gR^h$.

37. A compound of claim 1, wherein $R^5$ is $C_1$-$C_4$ alkyl optionally substituted with OH or $NR^gR^h$ or saturated or partially unsaturated $C_3$-$C_6$ cycloalkyl.

38. A compound of claim 1, wherein $R^5$ is $C_1$-$C_6$ alkyl optionally substituted with halogen, $OR^g$ or $NR^gR^h$.

39. A compound of claim 1, wherein $R^5$ is $C_2$-$C_6$ alkynyl optionally substituted with $OR^g$ or $NR^gR^h$.

40. A compound of claim 1, wherein $R^5$ is a 9-10 membered bicyclic heterocyclyl heteroaryl optionally substituted with $C_1$-$C_4$ alkyl or a 9-10 membered bicyclic heteroaryl optionally substituted with $C_1$-$C_4$ alkyl.

41. A compound of claim 40, wherein $R^5$ is a 9-10 membered bicyclic heterocyclyl selected from 2,3-dihydrobenzofuranyl, 1,3-dihydroisobenzofuranyl, 1,3-dihydrobenzo[c]thiophenyl, 1,3-dihydrobenzo[c]thiophenyl, indolinyl and isoindolinyl, wherein the heterocyclyl is optionally substituted with $C_1$-$C_4$ alkyl.

42. A compound of claim 40, wherein $R^5$ is a 9-10 membered bicyclic heteroaryl selected from indolyl, benzofuranyl and benzo[b]thiophenyl, wherein the heteroaryl is optionally substituted with $C_1$-$C_4$ alkyl.

43. A compound of claim 1, wherein $R^5$ is hydrogen.

44. A compound of claim 1, wherein $R^5$ is $NR^kR^l$.

45. A compound of claim 1, wherein $R^5$ is a saturated or partially unsaturated 4-6 membered heterocyclyl optionally substituted with $C_1$-$C_4$ alkyl.

46. A compound of claim 1, wherein $R^5$ is selected from hydrogen, I, CN, methyl, —CH$_2$CH$_2$CH$_2$OH, —CH$_2$CH$_2$CH$_2$N(CH$_3$)$_2$, —C≡CCH$_2$OH, —C≡CCH$_2$N(CH$_3$)$_2$, cyclopropyl, 1-methyl-1,2,3,6-tetrahydropyridin-4-yl, 1-methyl-1H-imidazol-5-yl, pyridin-2-yl, pyridin-3-yl, 6-(dimethylamino)pyridin-3-yl, 6-(piperazin-1-yl)pyridin-3-yl, 6-(4-methylpiperazin-1-yl)pyridin-3-yl, 2-(4-methylpiperazin-1-yl)pyridin-4-yl, 6-aminopyridin-3-yl, 6-(2-morpholinoethylamino)pyridin-3-yl, 6-(4-isopropylpiperazin-1-yl)pyridin-3-yl, 6-(4-(cyclopropylmethyl)piperazin-1-yl)pyridin-3-yl, 1H-pyrazol-4-yl, 1-methyl-1H-pyrazol-4-yl, 2,3-dihydrobenzofuran-5-yl, 1H-indol-5-yl, 1-methyl-1H-indol-5-yl, phenyl, 2-fluorophenyl, 3-fluorophenyl, 4-fluorophenyl, 2-chlorophenyl, 3-chlorophenyl, 4-chlorophenyl, 3-(dimethylamino)phenyl, 3-(OCH$_2$CH$_2$OCH$_2$CH$_3$)phenyl, 3-(OCH$_2$CH(OH)CH$_2$OH)phenyl, 3-(OCH$_2$CH$_2$N(CH$_3$)$_2$)phenyl, 4-(OCH$_2$CH$_2$N(CH$_3$)$_2$)phenyl, 4-morpholinophenyl, 3-((dimethylamino)methyl)phenyl, 3-cyanophenyl, 4-acetylphenyl, biphenyl-4-yl and 4-(4-methylpiperazine-1-carbonyl)phenyl.

47. A compound of claim 1, wherein $R^5$ is selected from hydrogen, Br, I, CN, dimethylamino, methyl, ethyl, difluoromethyl, trifluoromethyl, —CH$_2$OH, —CH$_2$OCH$_3$, —CH$_2$CH$_2$CH$_2$OH, —CH$_2$CH$_2$CH$_2$N(CH$_3$)$_2$, —CH$_2$N(CH$_3$)$_2$, —CH(OH)CH$_3$, —C(=O)CH$_3$, —C≡CH, —C≡CCH$_2$OH, —C≡CCH$_2$N(CH$_3$)$_2$, cyclopropyl, 1-methyl-1,2,3,6-tetrahydropyridin-4-yl, 1-methylpiperidin-4-yl, 1-methyl-1H-imidazol-5-yl, pyridin-2-yl, pyridin-3-yl, 6-(dimethylamino)pyridin-3-yl, 6-(piperazin-1-yl)pyridin-3-yl, 6-(4-methylpiperazin-1-yl)pyridin-3-yl, 2-(4-methylpiperazin-1-yl)pyridin-4-yl, 6-aminopyridin-3-yl, 6-(2-morpholinoethylamino)pyridin-3-yl, 6-(4-isopropylpiperazin-1-yl)pyridin-3-yl, 6-(4-(cyclopropylmethyl)piperazin-1-yl)pyridin-3-yl, 1H-pyrazol-4-yl, 1-methyl-1H-pyrazol-4-yl, 6-morpholinopyridin-3-yl, 2,3-dihydrobenzofuran-5-yl, 1H-indol-5-yl, 1-methyl-1H-indol-5-yl, phenyl, 2-fluorophenyl, 3-fluorophenyl, 4-fluorophenyl, 2-chlorophenyl, 3-chlorophenyl, 4-chlorophenyl, 3-(dimethylamino)phenyl, 3-(OCH$_2$CH$_2$OCH$_2$CH$_3$)phenyl, 3-(OCH$_2$CH(OH)CH$_2$OH)phenyl, 3-((2,2-dimethyl-1,3-dioxolan-4-yl)methoxy)phenyl, 3-(OCH$_2$CH$_2$N(CH$_3$)$_2$)phenyl, 4-(OCH$_2$CH$_2$N(CH$_3$)$_2$)phenyl, 4-morpholinophenyl, 3-((dimethylamino)methyl)phenyl, 4-acetylphenyl, biphenyl-4-yl, 4-(4-methylpiperazine-1-carbonyl)phenyl and 4-(dimethylamino)phenyl.

48. A compound of Formula I as defined in claim 1 and herein having the structure:

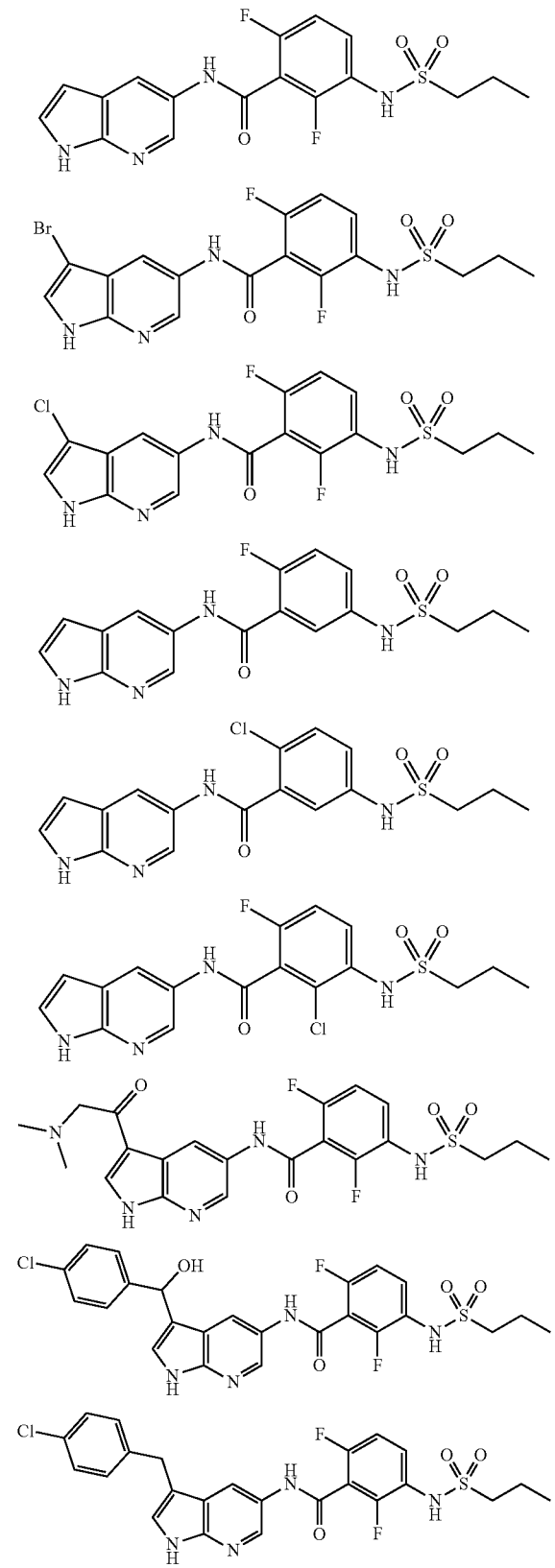

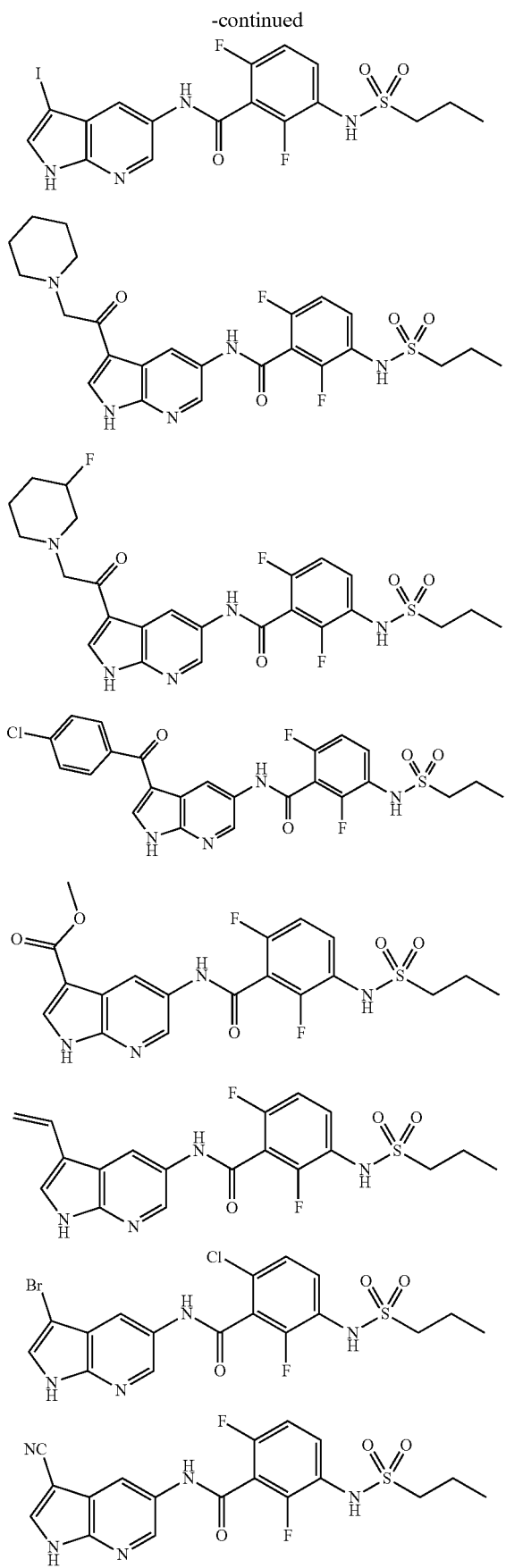
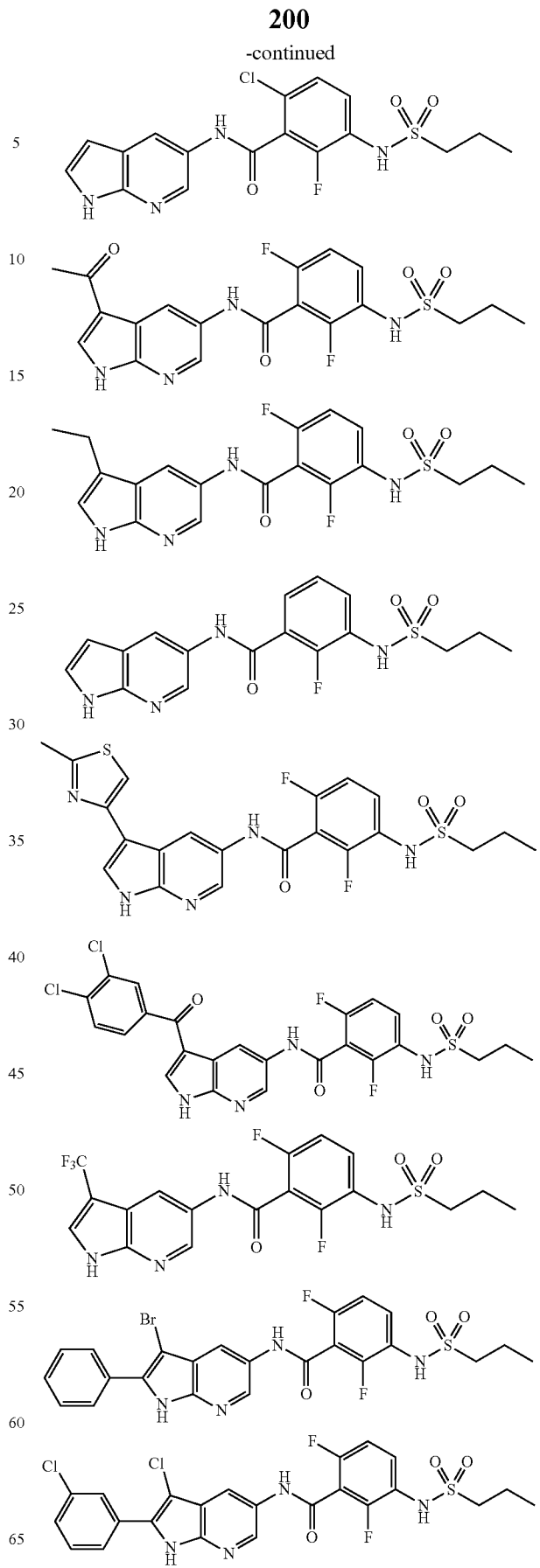

201
-continued
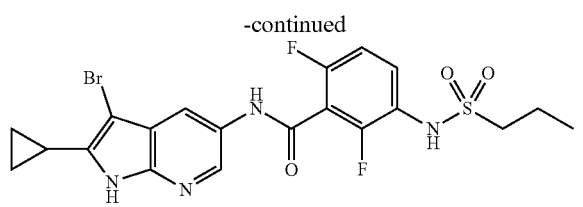
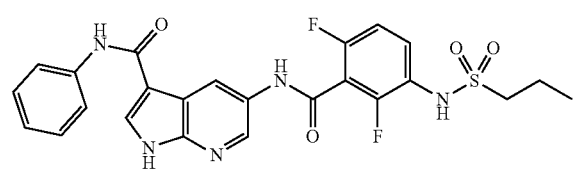
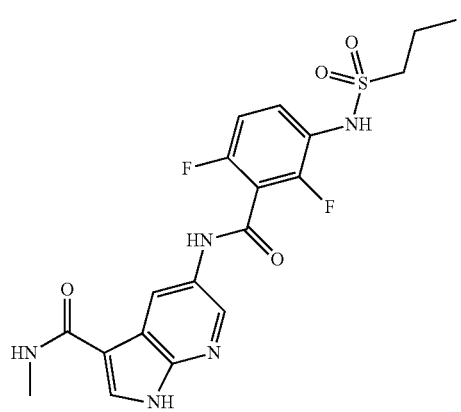
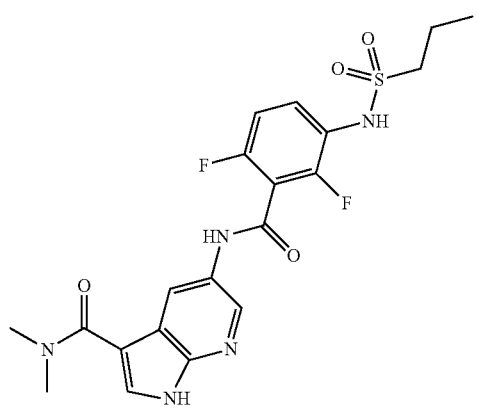
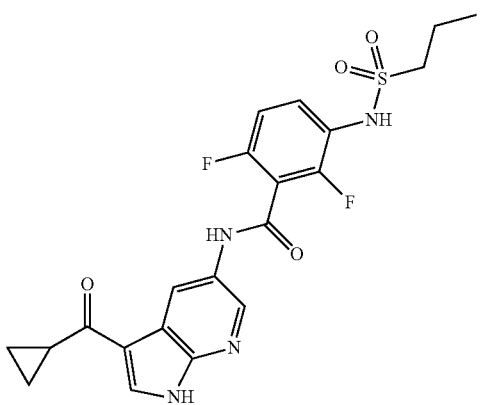
202
-continued
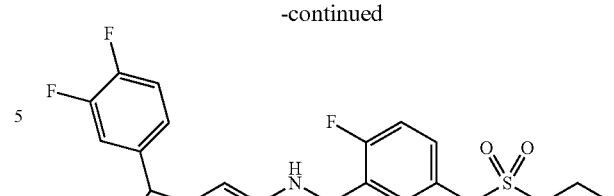
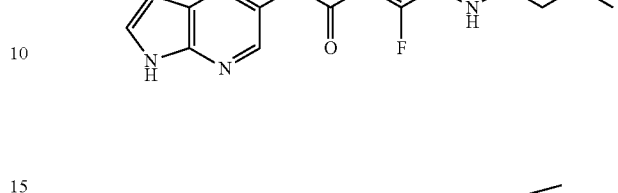
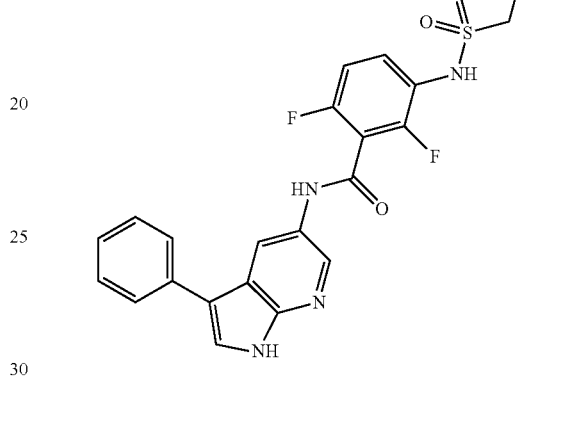
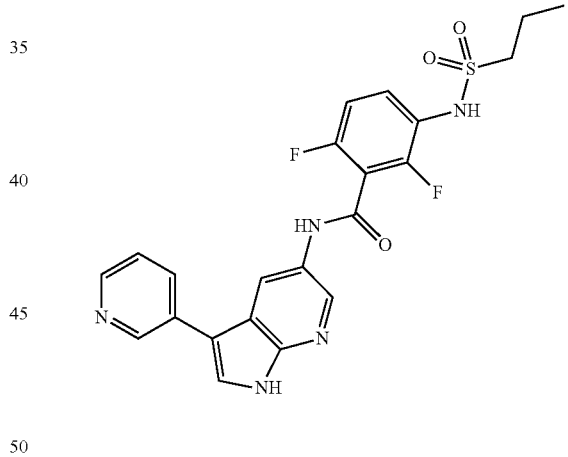
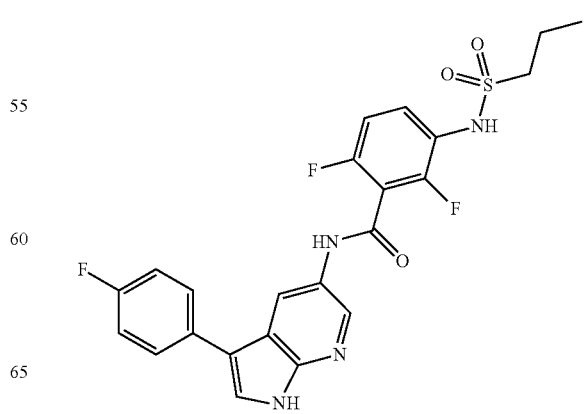

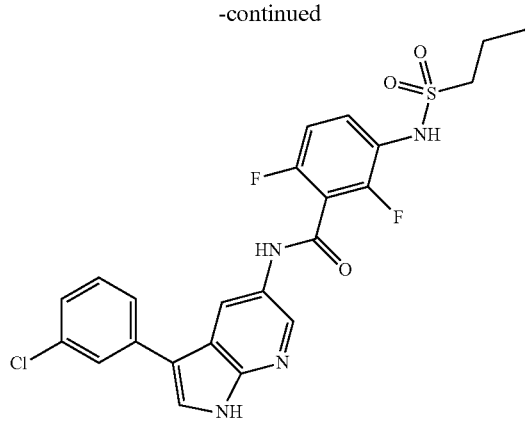
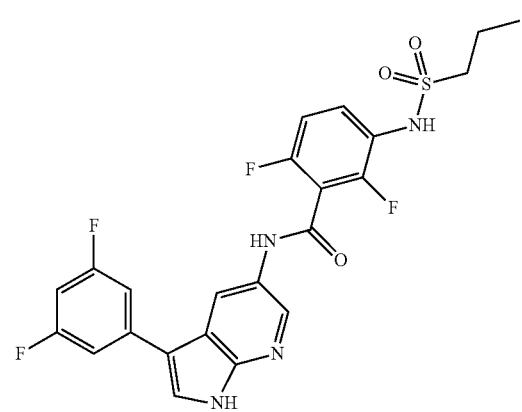
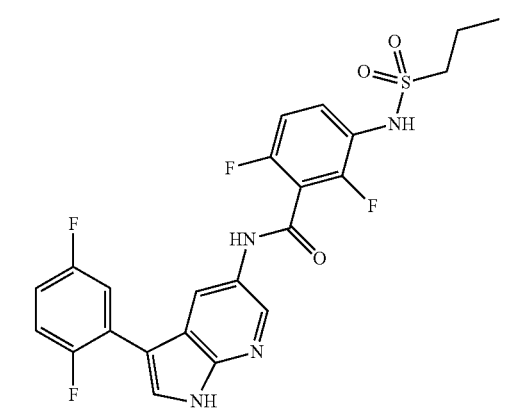
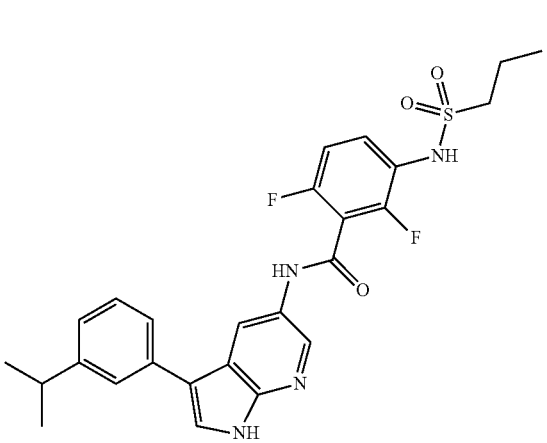
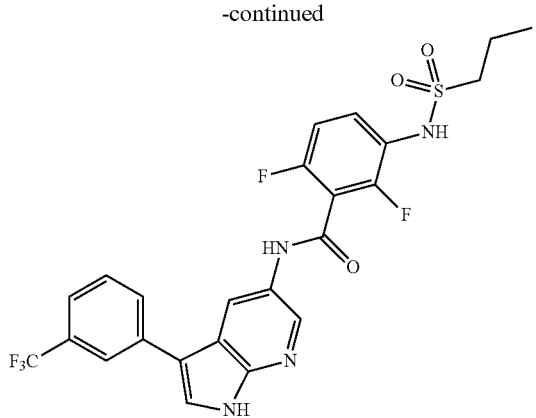
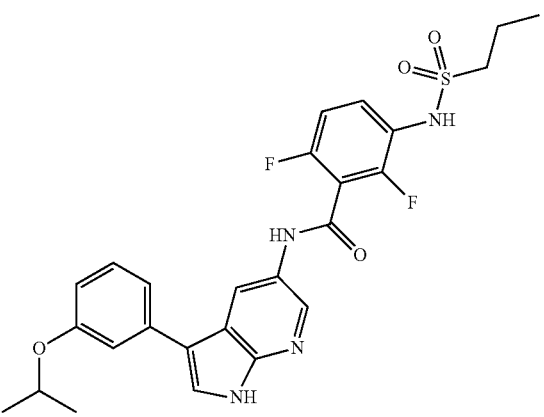
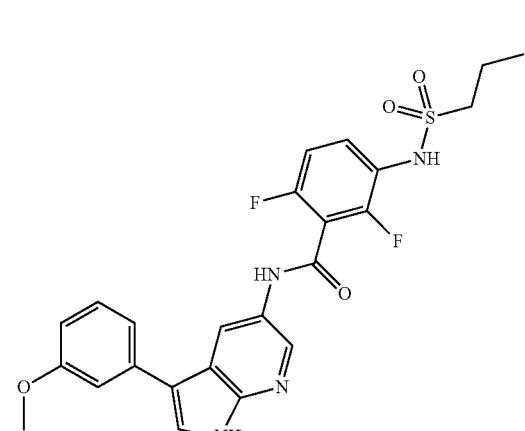
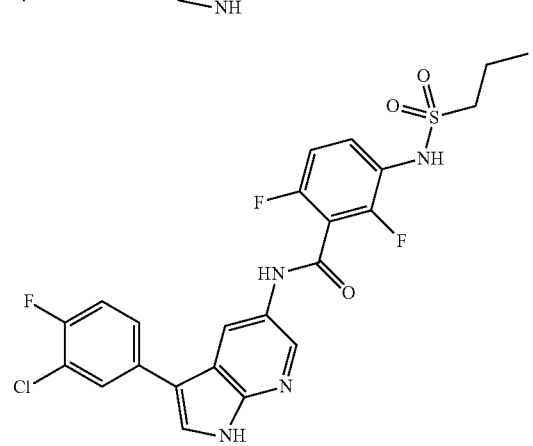

205
-continued
206
-continued
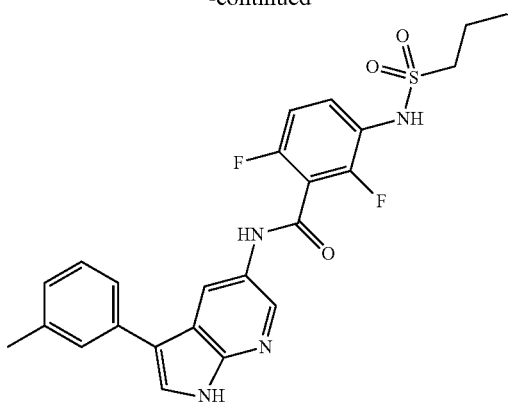
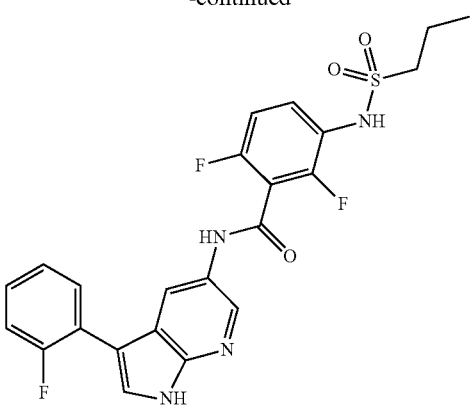

207
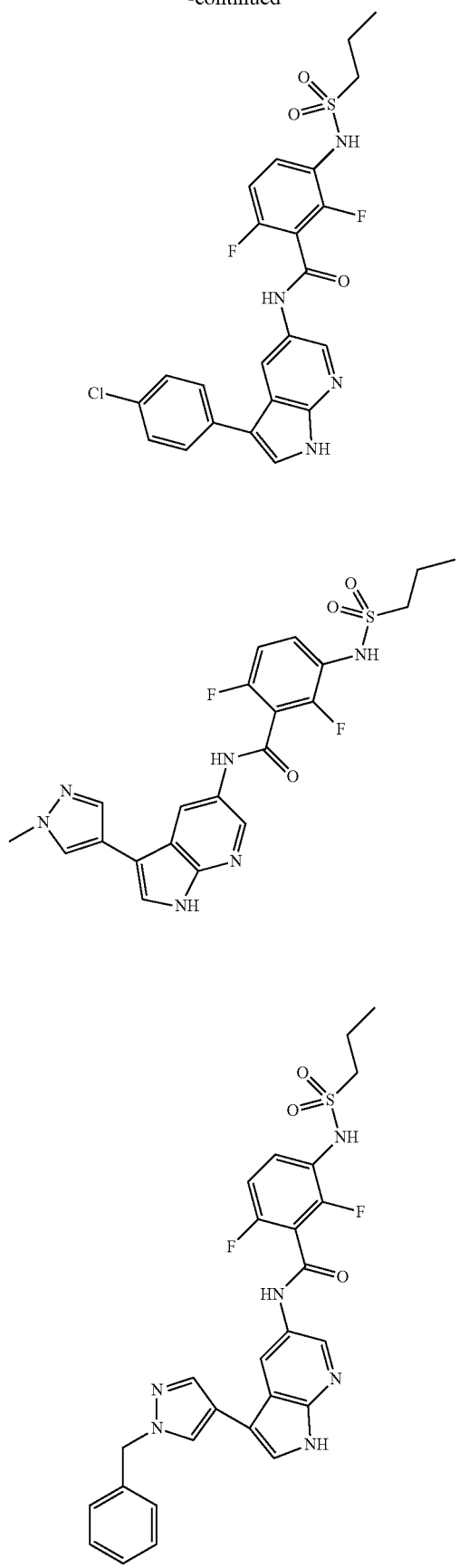
208
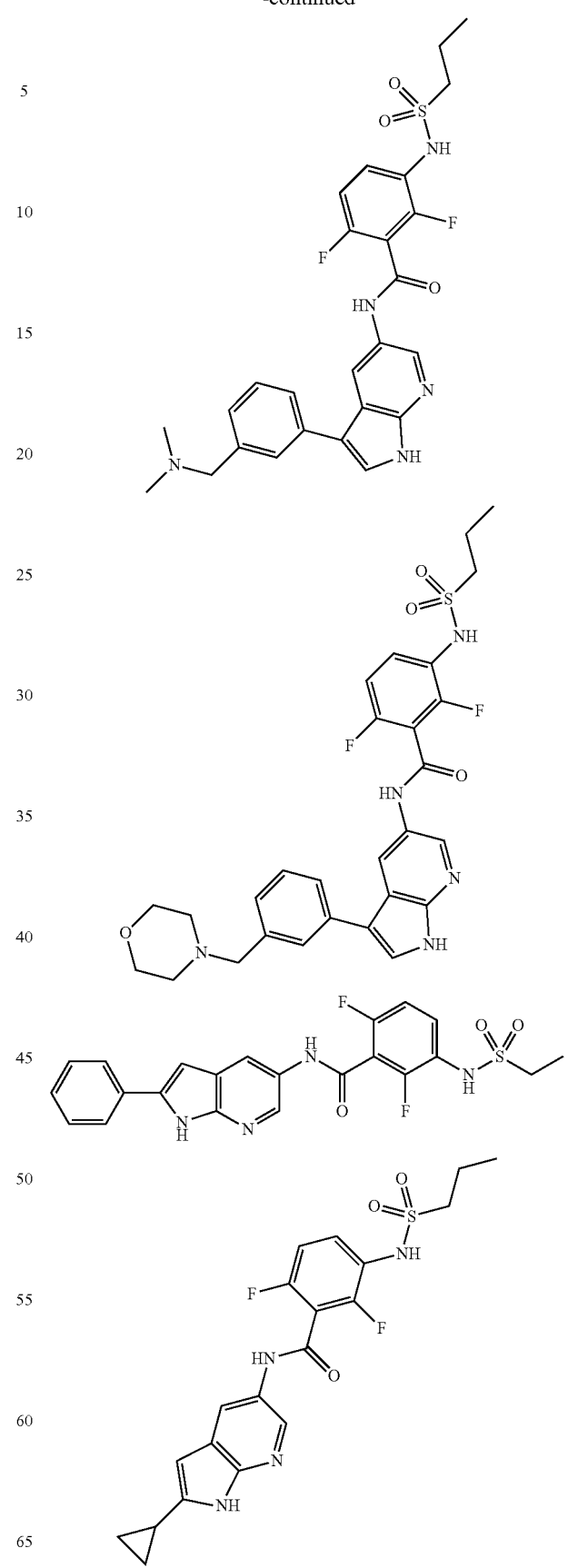

209
-continued
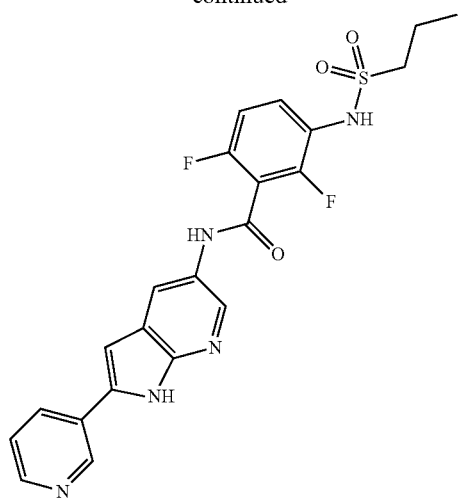
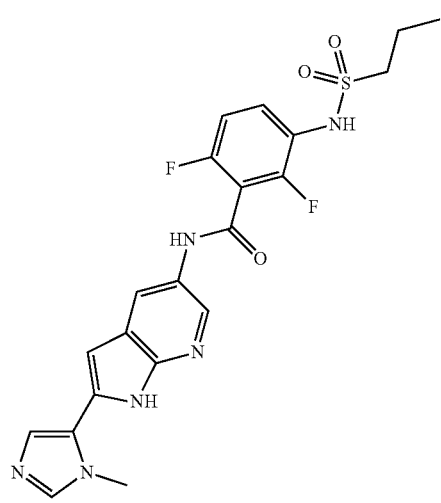
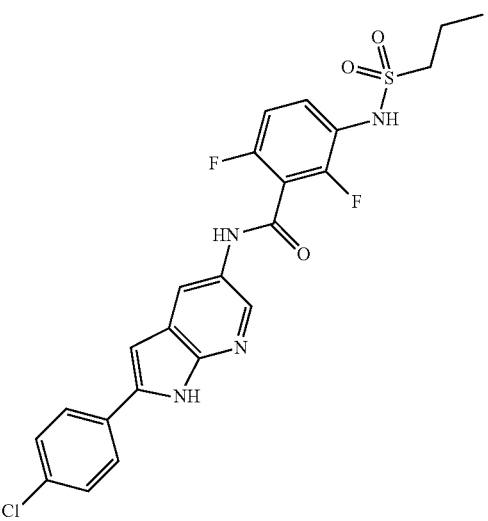
210
-continued
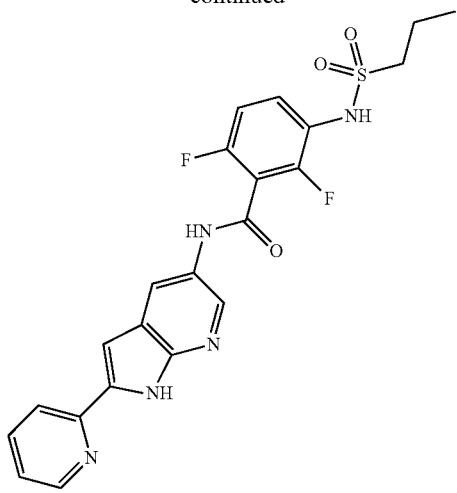
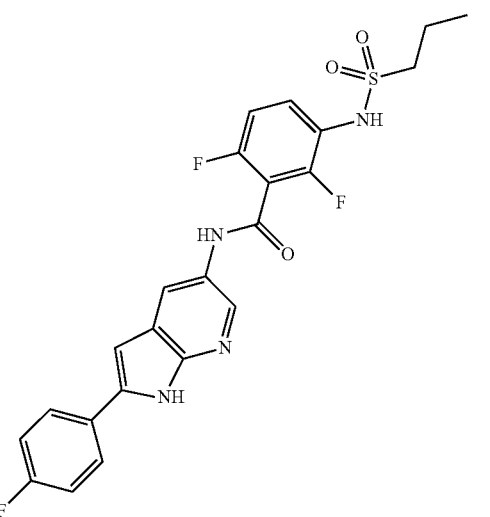

211
-continued
212
-continued
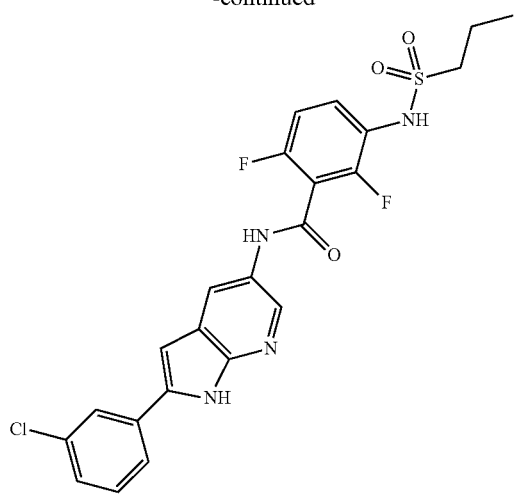
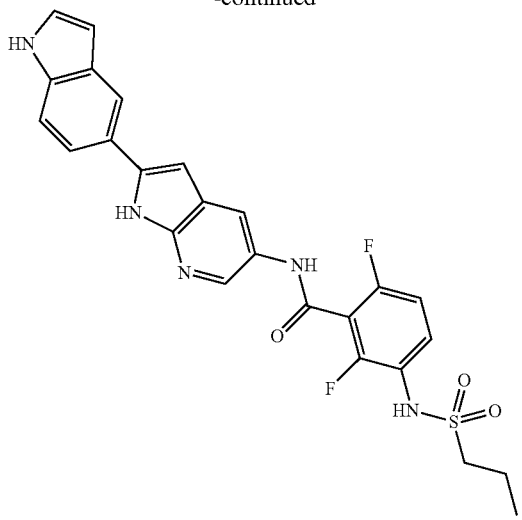
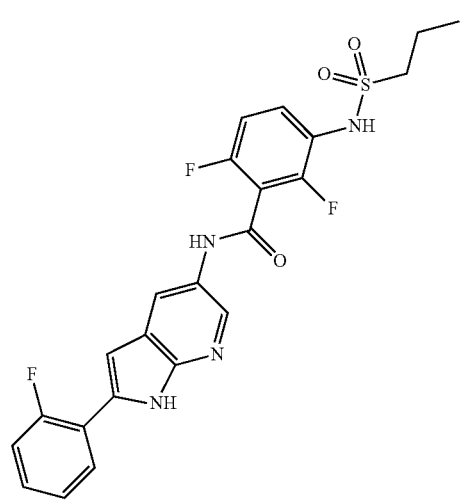
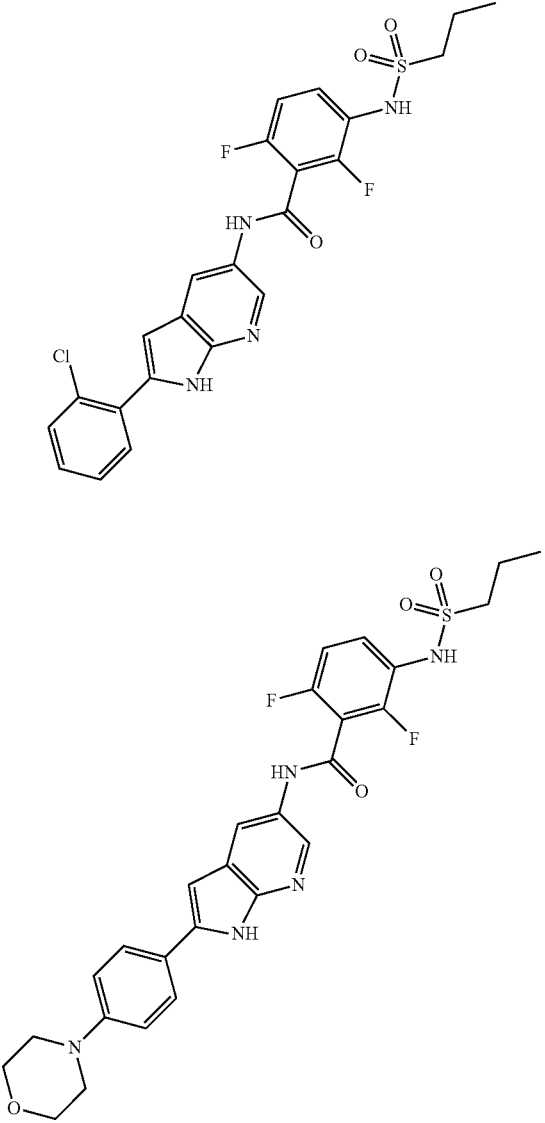

213
-continued
214
-continued
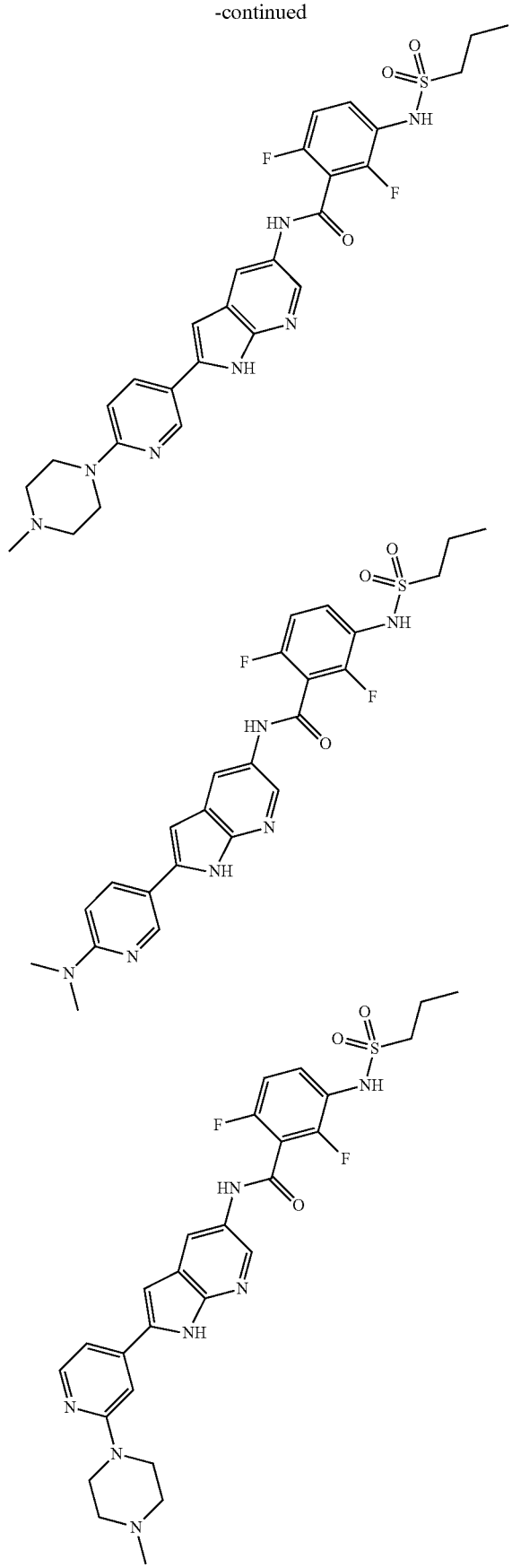
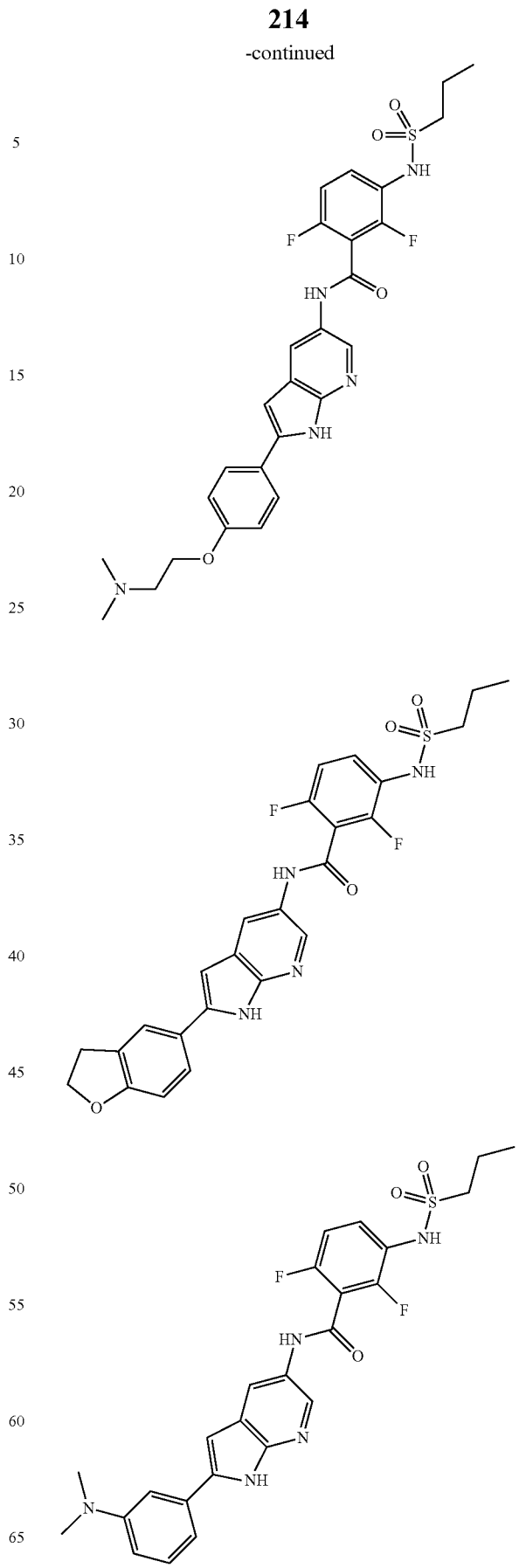

215
-continued
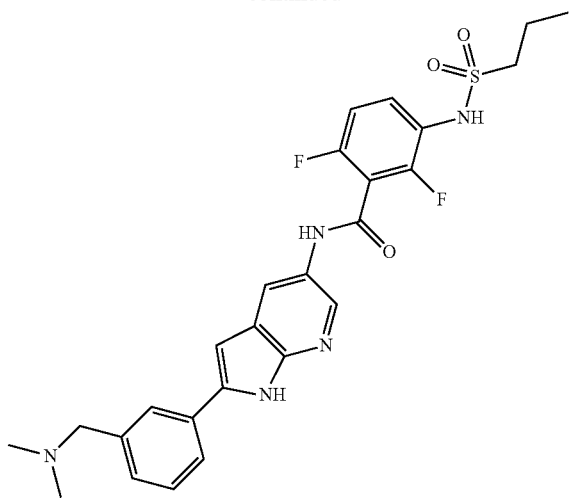
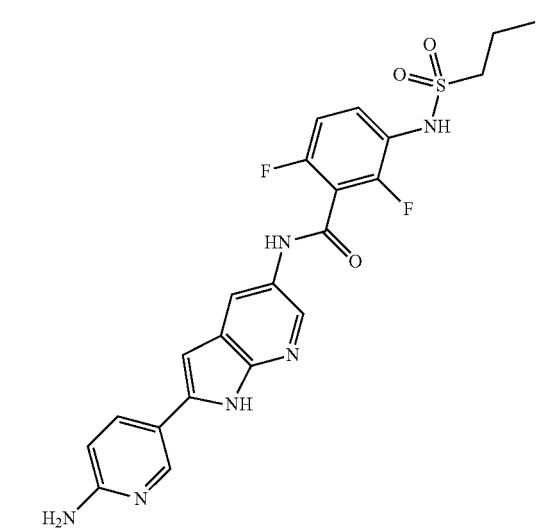
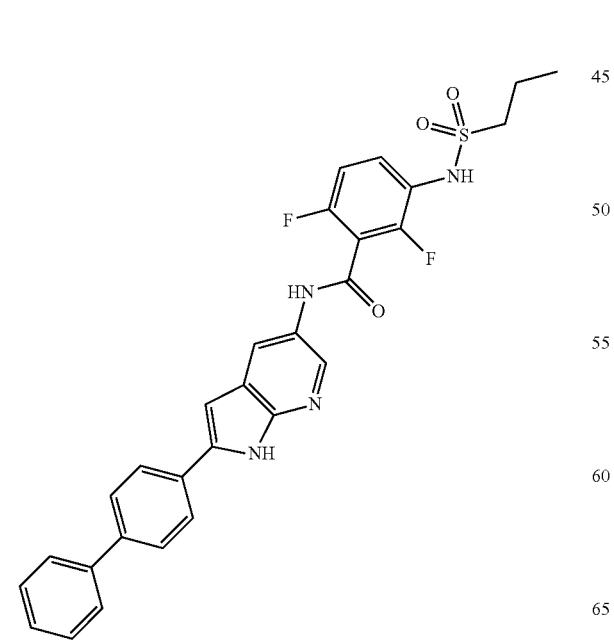
216
-continued
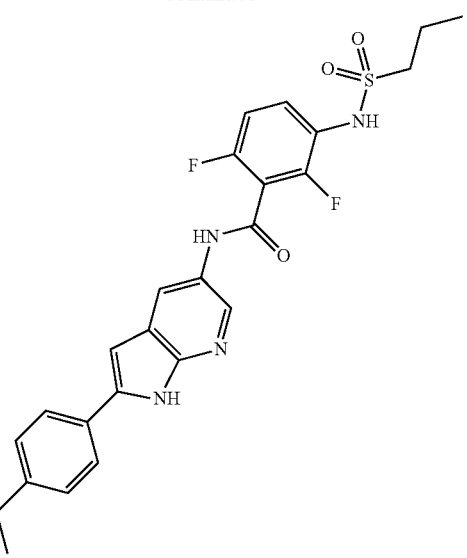
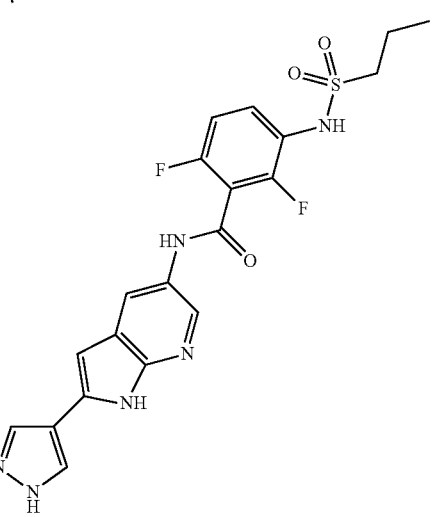
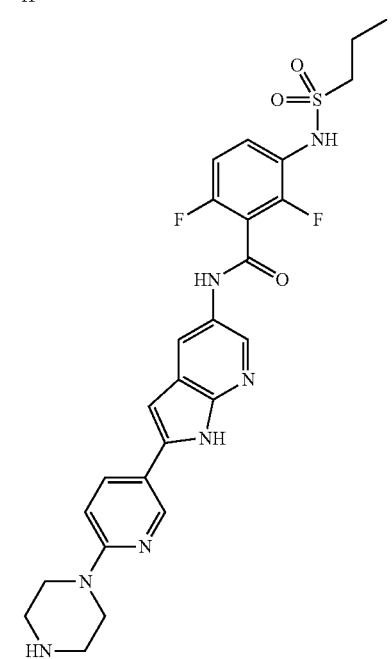

217
-continued
218
-continued
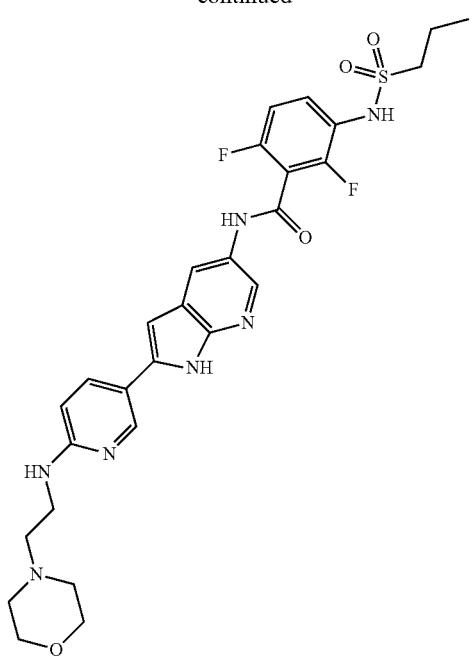
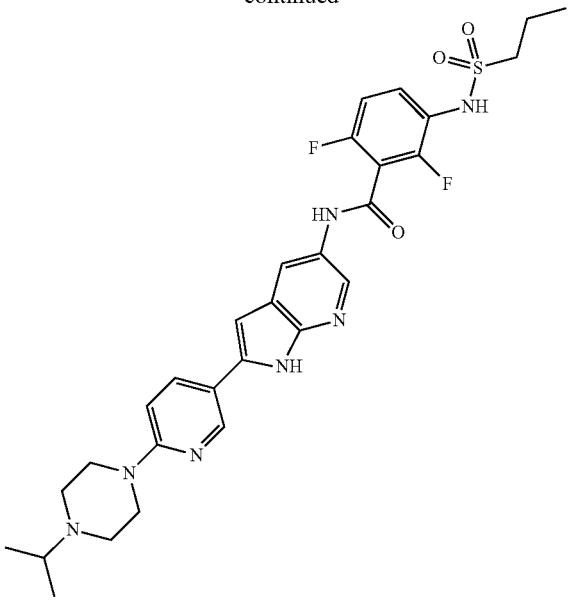

219
-continued
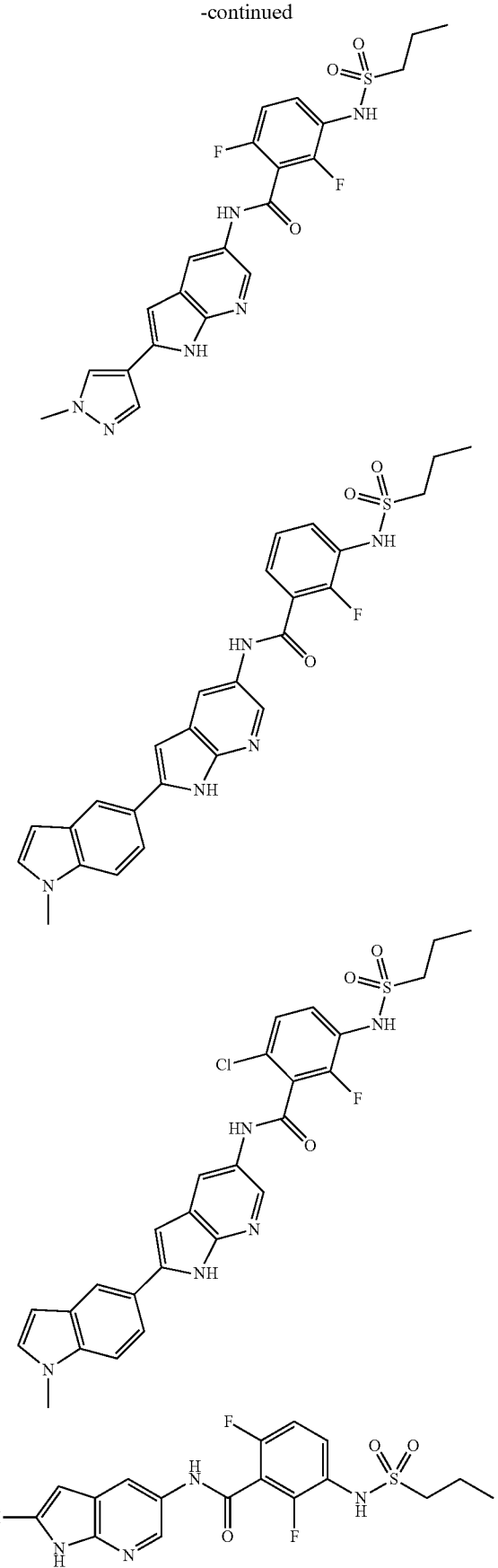
220
-continued
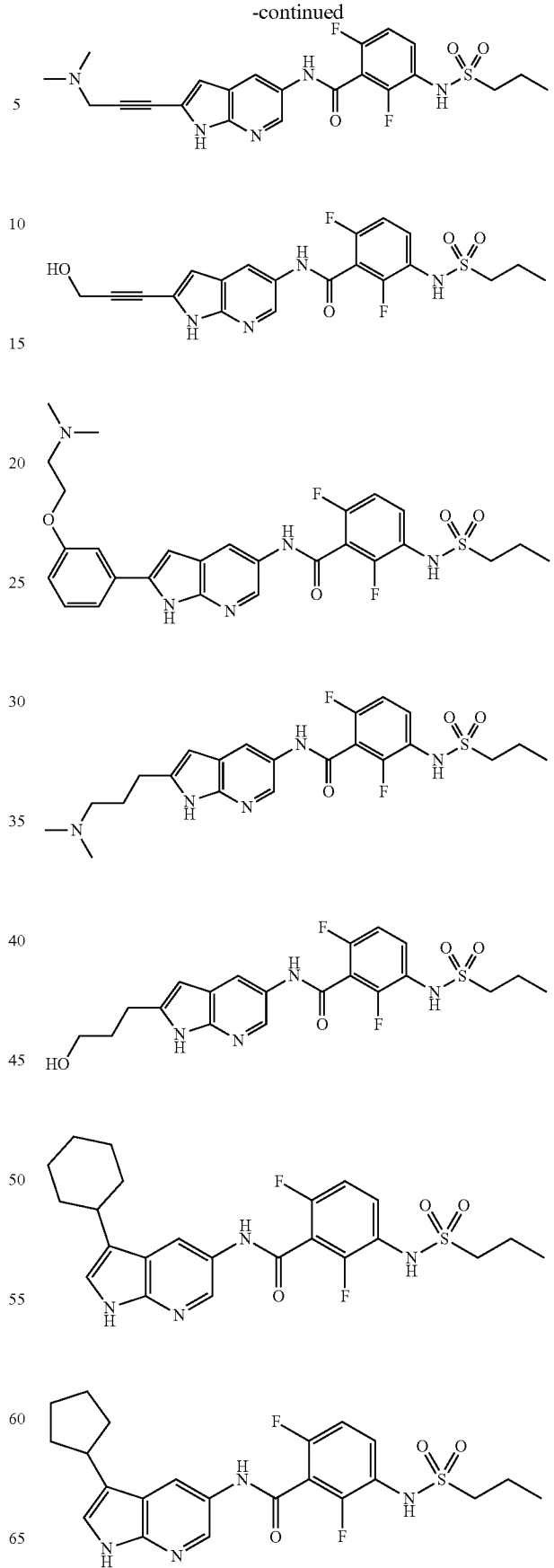

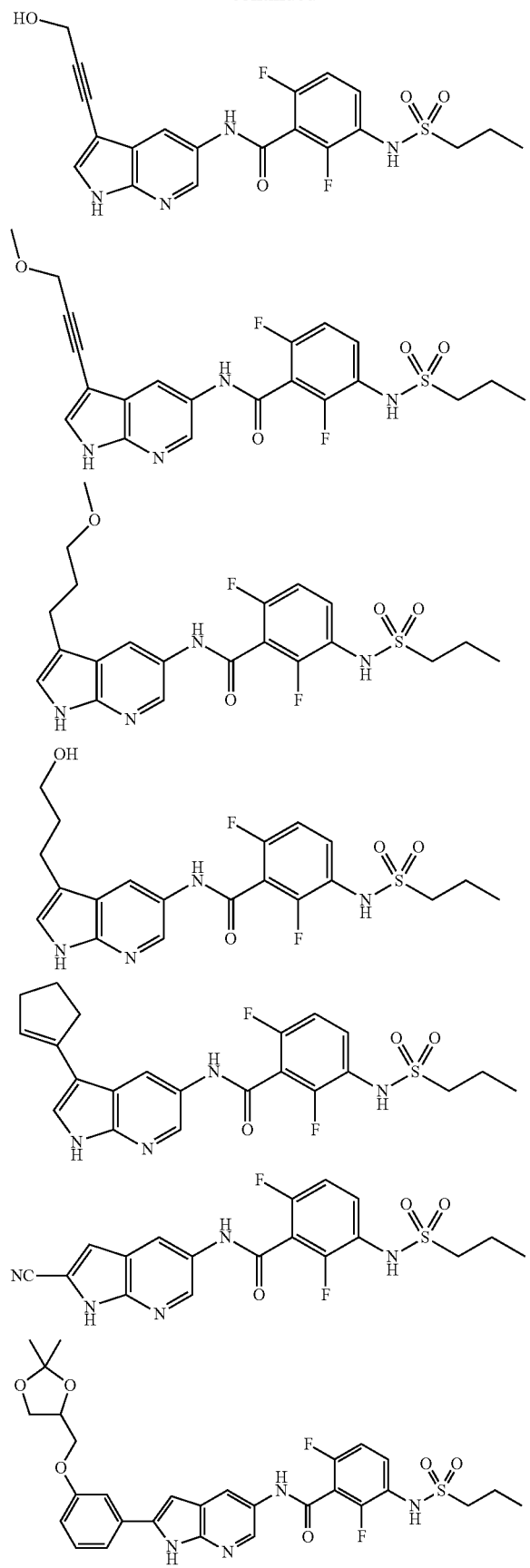
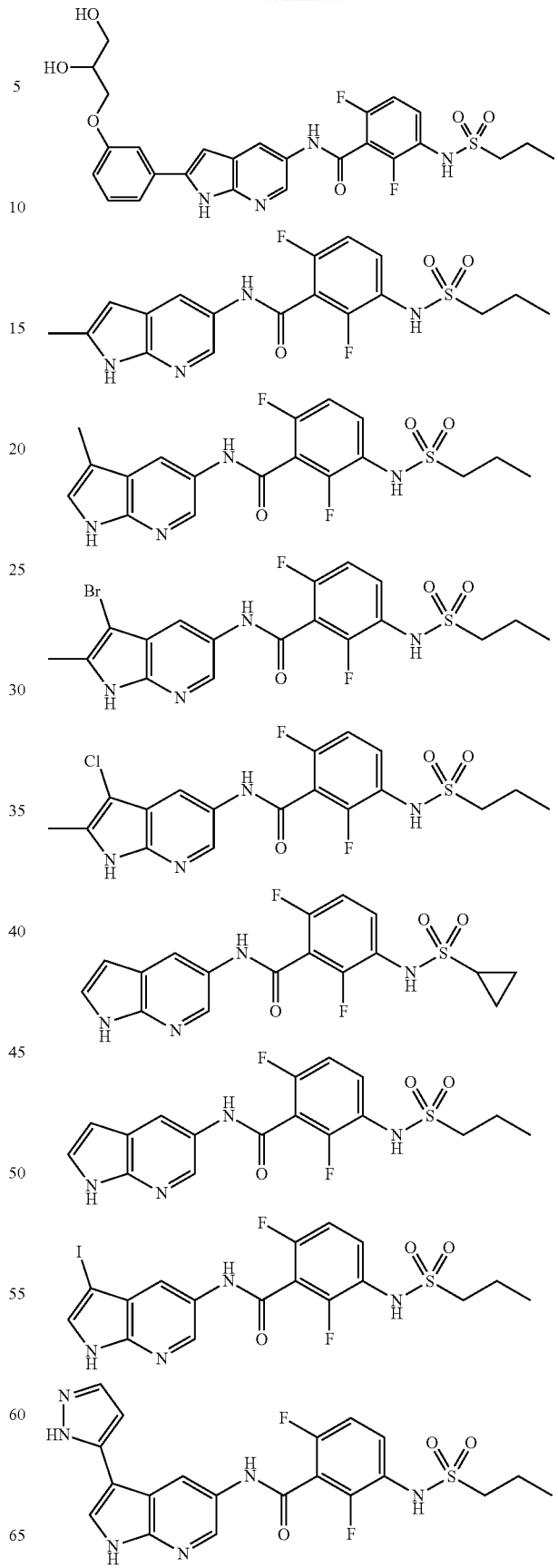

223
-continued
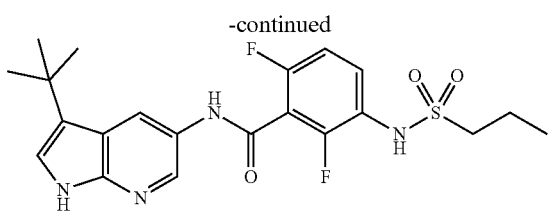
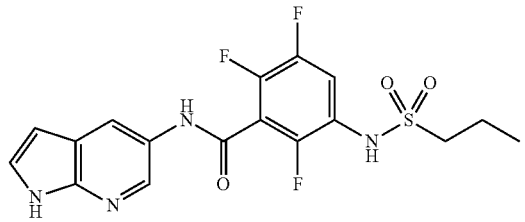
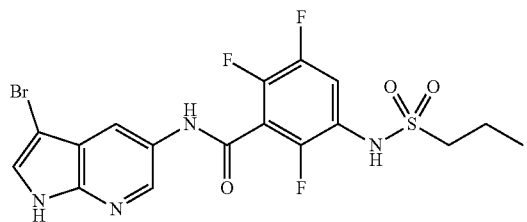
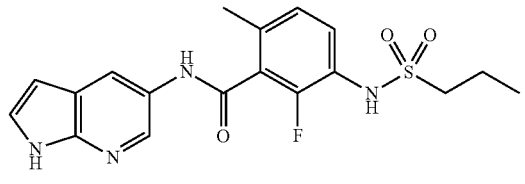
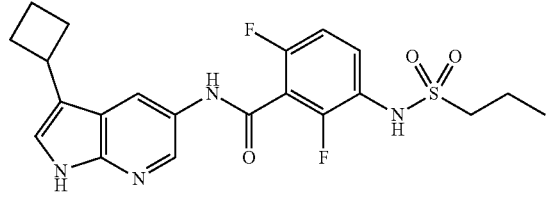
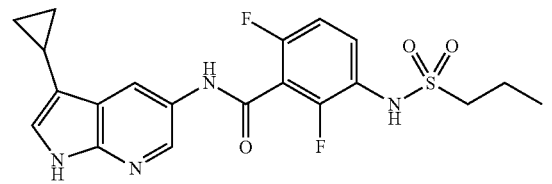
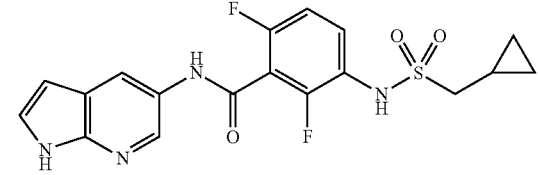
224
-continued
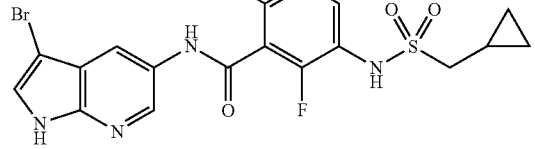
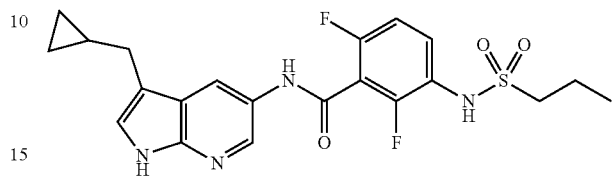
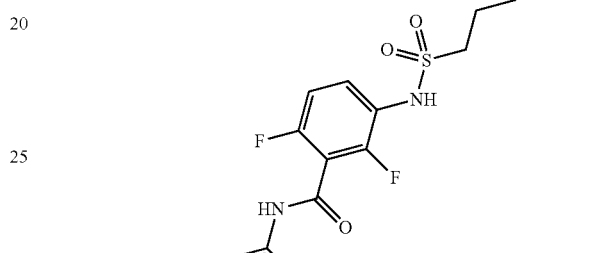
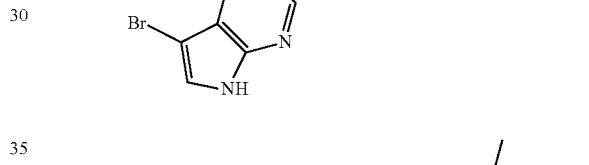
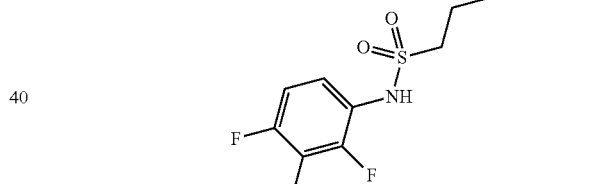
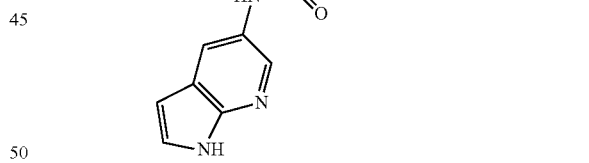
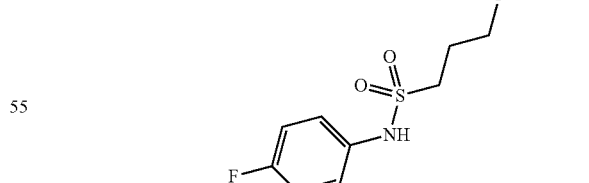
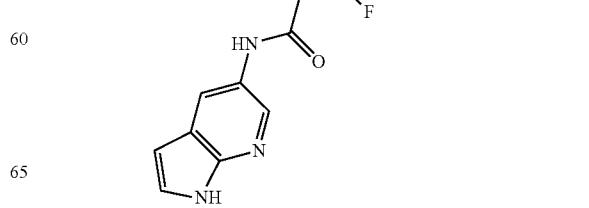

225
-continued
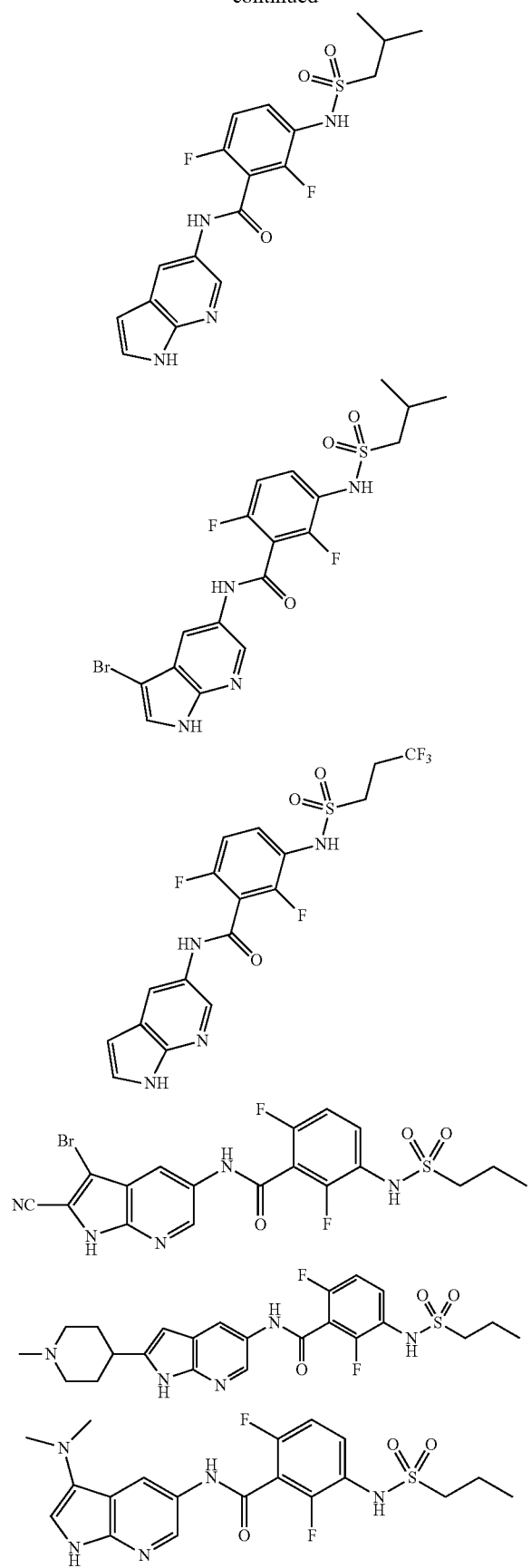
226
-continued
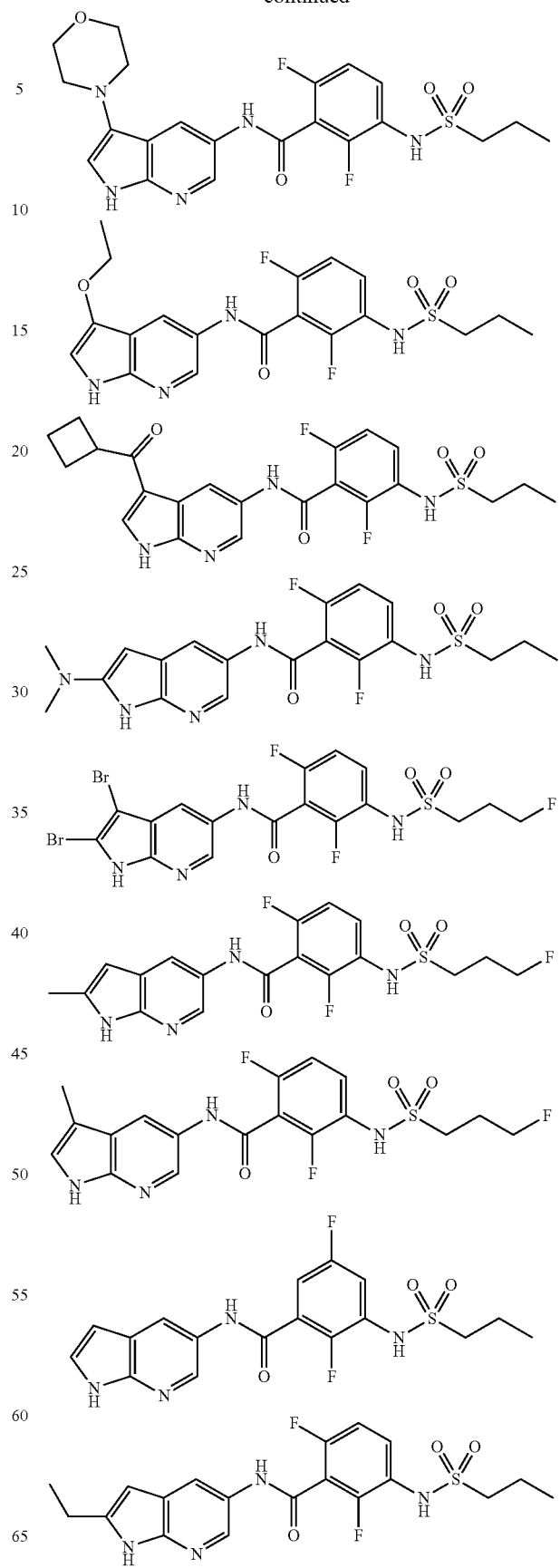

227
-continued
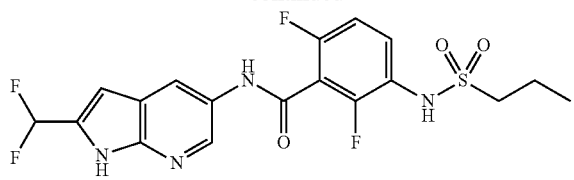
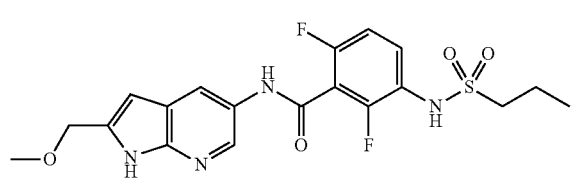
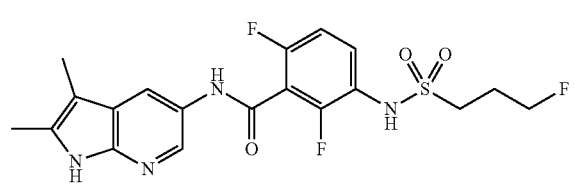
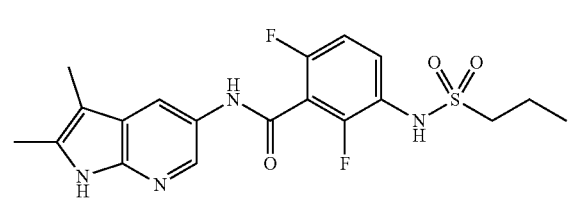
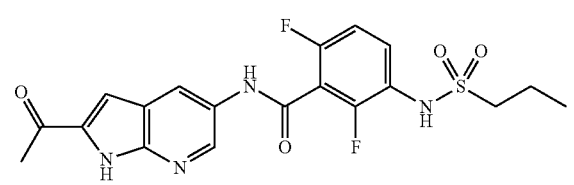
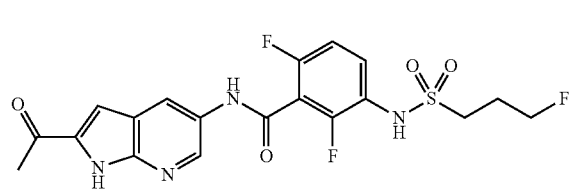
228
-continued
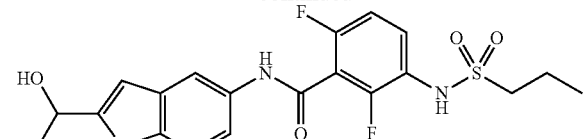
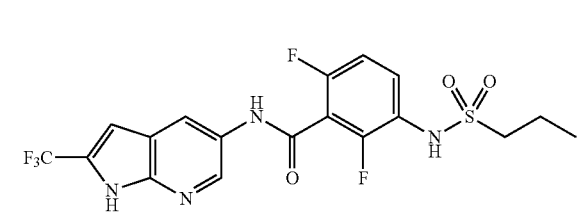
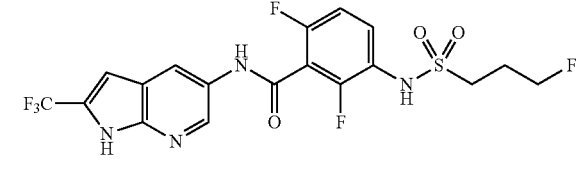
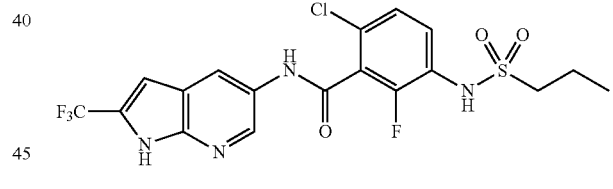
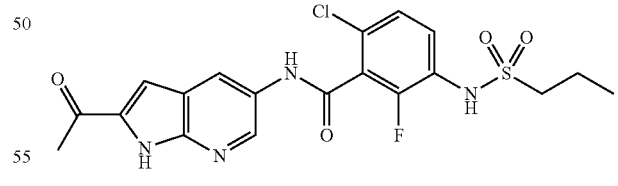
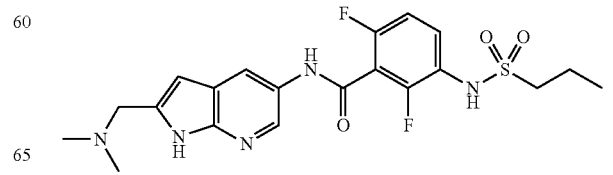

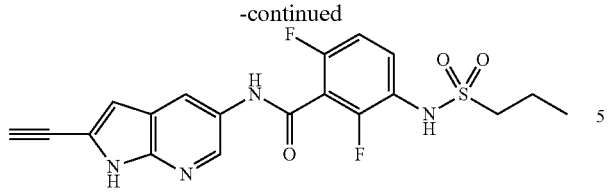
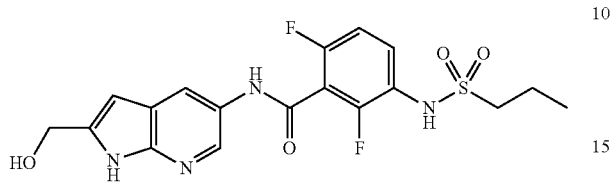
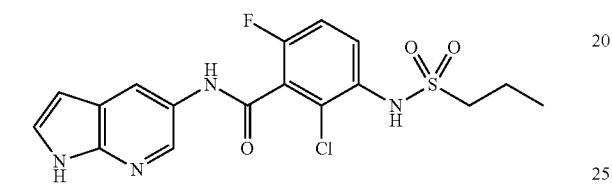
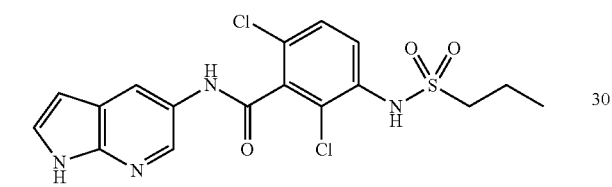
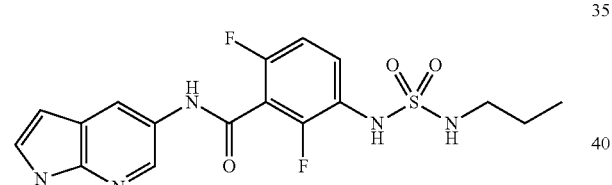
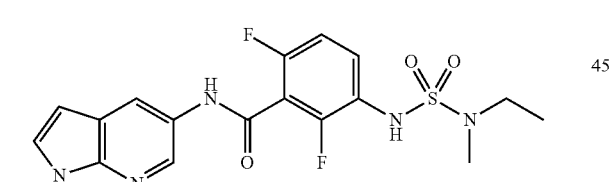
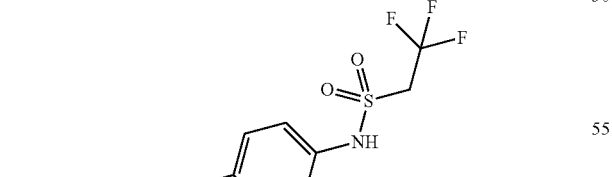
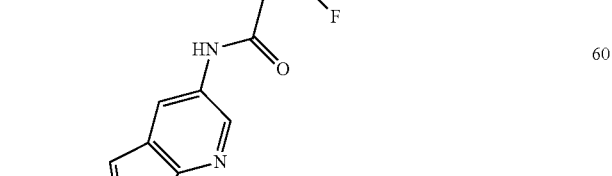
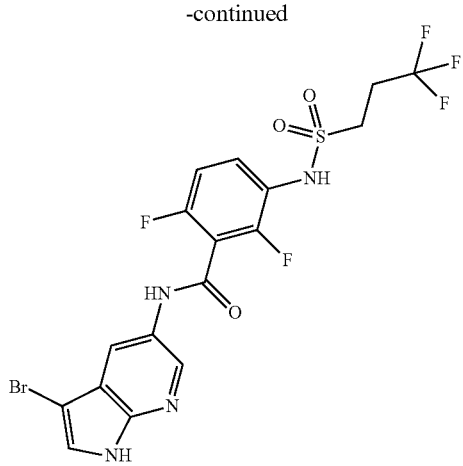
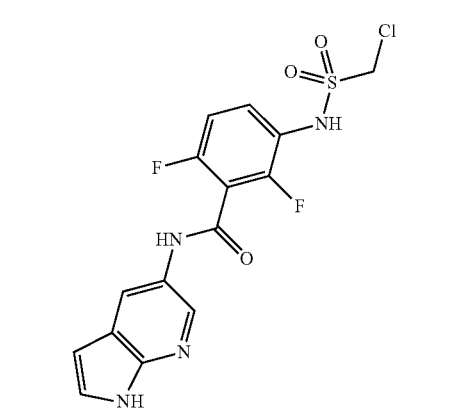
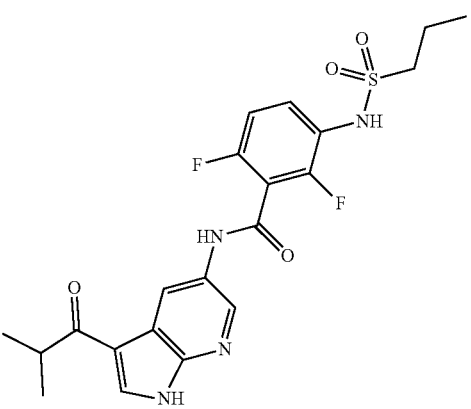
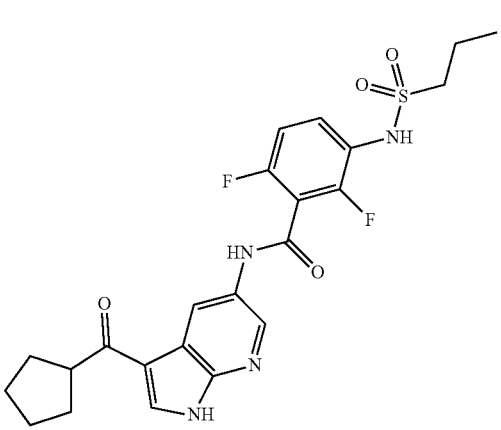

231
-continued
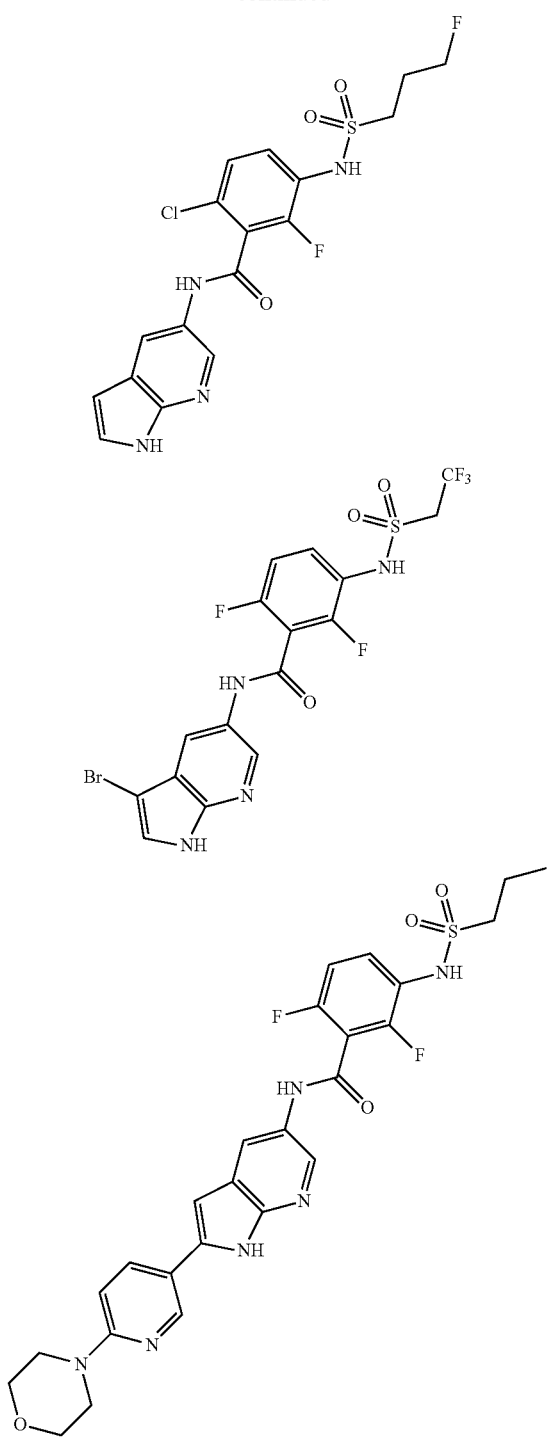
232
-continued
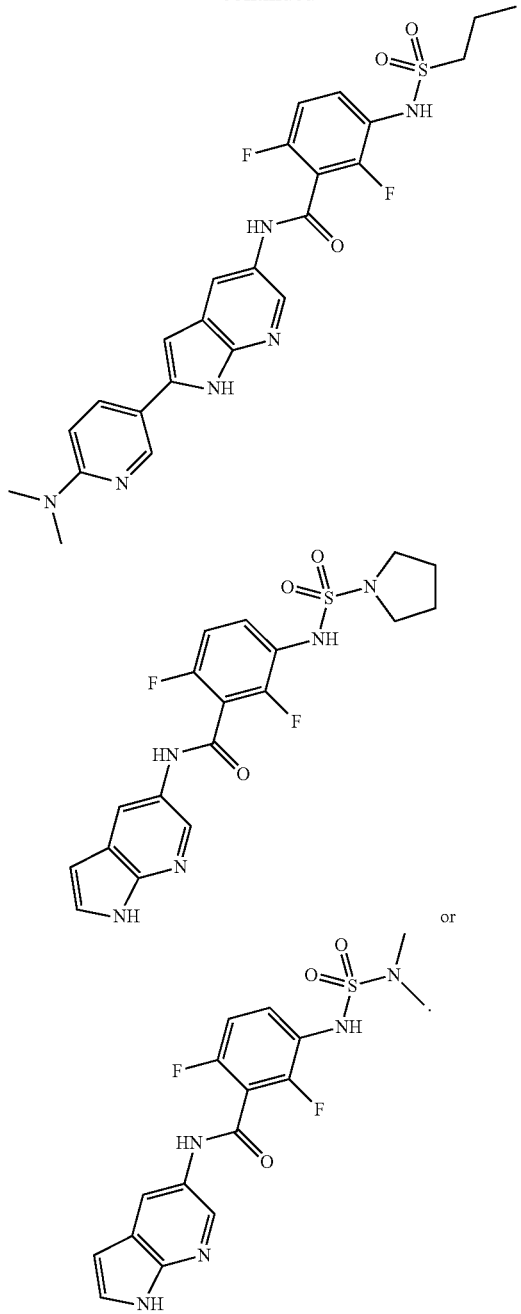
49. A pharmaceutical composition, comprising a compound as claimed in claim 1, and a pharmaceutically acceptable carrier or excipient.
* * * * *